United States Patent
Fox et al.

(10) Patent No.: US 12,201,722 B2
(45) Date of Patent: *Jan. 21, 2025

(54) NANOSTRUCTURED LIPID CARRIERS AND STABLE EMULSIONS AND USES THEREOF

(71) Applicant: ACCESS TO ADVANCED HEALTH INSTITUTE, Seattle, WA (US)

(72) Inventors: Christopher B. Fox, Seattle, WA (US); Amit Praful Khandhar, Issaquah, WA (US); Neal Van Hoeven, Seattle, WA (US); Jesse H. Erasmus, Port Orchard, WA (US); Susan S. Lin, Kirkland, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/470,874

(22) Filed: Sep. 9, 2021

(65) Prior Publication Data
US 2022/0054416 A1 Feb. 24, 2022

Related U.S. Application Data

(63) Continuation of application No. 16/622,908, filed as application No. PCT/US2018/037783 on Jun. 15, 2018, now Pat. No. 11,141,377.
(Continued)

(51) Int. Cl.
*A61K 9/107* (2006.01)
*A61K 9/127* (2006.01)
(Continued)

(52) U.S. Cl.
CPC ............ *A61K 9/1075* (2013.01); *A61K 9/107* (2013.01); *A61K 9/127* (2013.01); *A61K 31/713* (2013.01);
(Continued)

(58) Field of Classification Search
None
See application file for complete search history.

(56) References Cited

U.S. PATENT DOCUMENTS 9,770,463 B2 9/2017 Geall et al.
11,141,377 B2 * 10/2021 Fox ..................... A61K 31/713
(Continued)

FOREIGN PATENT DOCUMENTS

JP 2016204389 A 12/2016
RU 2606846 C2 1/2017
(Continued)

OTHER PUBLICATIONS

Qianwen Li, Tiange Cai, Yinghong Huang, Xi Xia, Susan P. C. Cole, and Yu Cai. "A Review of the Structure, Preparation, and Application of NLCs, PNPs, and PLNs." Nanomaterials, vol. 7(122), 2017, pp. 1-25. (Year: 2017).*
(Continued)

*Primary Examiner* — Isaac Shomer
(74) *Attorney, Agent, or Firm* — Benjamin Keim; Newport IP, LLC

(57) ABSTRACT

Provided herein are nanostructured lipid carrier compositions, and methods of making and using thereof. The compositions comprise a nanostructured lipid carrier (NLC), where the NLC comprises an oil core comprising a mixture of a liquid phase lipid and a solid phase lipid, a cationic lipid, a sorbitan ester, and a hydrophilic surfactant, and optionally a bioactive agent. The bioactive agent can be associated with the NLC. The compositions are capable of delivery of a biomolecule to a cell for the generation of an immune response, for example, for vaccine, therapeutic, or diagnostic uses. Compositions and methods related to making the
(Continued)

compositions and using the compositions for stimulating an immune response are also provided.

49 Claims, 90 Drawing Sheets
Specification includes a Sequence Listing.

Related U.S. Application Data

(60) Provisional application No. 62/680,454, filed on Jun. 4, 2018, provisional application No. 62/677,336, filed on May 29, 2018, provisional application No. 62/669,262, filed on May 9, 2018, provisional application No. 62/622,755, filed on Jan. 26, 2018, provisional application No. 62/622,748, filed on Jan. 26, 2018, provisional application No. 62/582,859, filed on Nov. 7, 2017, provisional application No. 62/563,544, filed on Sep. 26, 2017, provisional application No. 62/556,291, filed on Sep. 8, 2017, provisional application No. 62/540,973, filed on Aug. 3, 2017, provisional application No. 62/520,204, filed on Jun. 15, 2017.

(51) Int. Cl.
| | | |
|---|---|---|
| A61K 31/713 | (2006.01) | |
| A61K 39/39 | (2006.01) | |
| A61K 47/10 | (2017.01) | |
| A61K 47/26 | (2006.01) | |
| C07K 16/10 | (2006.01) | |
| A61K 45/06 | (2006.01) | |

(52) U.S. Cl.
CPC .............. *A61K 39/39* (2013.01); *A61K 47/10* (2013.01); *A61K 47/26* (2013.01); *C07K 16/10* (2013.01); *A61K 45/06* (2013.01); *Y10S 977/773* (2013.01)

(56) References Cited

U.S. PATENT DOCUMENTS

| | | | | |
|---|---|---|---|---|
| 2012/0156251 | A1* | 6/2012 | Brito | A61P 37/04 424/193.1 |
| 2013/0243848 | A1* | 9/2013 | Lobovkina | A61K 9/5123 424/490 |
| 2014/0141070 | A1* | 5/2014 | Geall | A61K 39/12 424/218.1 |

FOREIGN PATENT DOCUMENTS

| | | | |
|---|---|---|---|
| WO | 20090677334 | A1 | 6/2009 |
| WO | 2012006380 | A2 | 1/2012 |
| WO | 2013006834 | A1 | 1/2013 |
| WO | 20130006837 | A1 | 1/2013 |
| WO | WO-2017201340 | A2 * | 11/2017 ......... A61K 31/7105 |

OTHER PUBLICATIONS

Neda Naseri Hadi Valizadeh, and Parvin Zakeri-Milani. "Solid Lipid Nanoparticles and Nanostructured Lipid Carriers: Structure, Preparation and Application." Advanced Pharmaceutical Bulletin, https://www.ncbi.nlm.nih.gov/pmc/articles/PMC4616893/?report=printable, originally published 2015. (Year: 2015).*
ICI Americas Inc. "The HLB System—A Time-Saving Guide to Emulsifier Selection." ICI Americas Inc., Wilmington, Delaware, pp. 1-22, Revised Mar. 1980. (Year: 1980).*
Japanese Patent Application No. 2019-569758, Office Action, mailed Apr. 21, 2022, 7 pages. (with English translation).
Thomas Courant, et al., "Tailoring nanostructured lipid carriers for the delivery of protein antigens: Physicochemical properties versus immunogenicity studies", Biomaterials, 2017, 15 pages.
Neelam Poonia, et al., "Nanostructured lipid carriers: versatile oral delivery vehicle", Future Science OA, 2016, 25 pages.
BR 12 2022 008824-4—Unfavorable Opinion, mailed Jul. 19, 2022, 7 pages, with English translation.
MX MX/a/2019/015076—Office Action, mailed Jul. 12, 2022, 10 pages, with English translation.
CN 201880050697.X—Decision of Rejection, mailed Apr. 24, 2022, 17 pages. (with English translation).
CN 201880050697.X—Second Office Action mailed Jan. 7, 2022, 26 pages. (with English translation).
BR 112019026615-1—Unfavorable Opinion, mailed Nov. 19, 2021, 7 pages.
BR 112019026615-1—Office Action, mailed Mar. 10, 2022, 10 pages. (with machine translation).
RU 2019142632/10—Office Action, mailed Nov. 2, 2021, 16 pages. (with machine translation).
RU 2019142632/10—Second Office Action, mailed Mar. 29, 2022, 22 pages. (with machine translation).
EP 18 742 621.8, Communication pursuant to Article 94(3), EPC, mailed Oct. 27, 2021, 3 pages.
Office Action from related Japan Patent Application No. 2019-569758, mailed Dec. 6, 2022, 7 pages (with translation attached).
Office Action from related Mexico Application No. 2019-015076, mailed Mar. 29, 2023, 7 pages (with translation attached).
Office Action from related Mexico Application No. 2019-015076, mailed Jan. 5, 2023, 7 pages (with translation attached).
Office Action from related Korean Application No. 10-2020-7001253, mailed Aug. 1, 2023, 8 pages (with translation).
Office Action from related Russian Federation Application No. 2019142632, mailed Jun. 20, 2023, 9 pages (with translation attached).
Canada IPO Office Action for related matter application No. 3,067,224, mailed Oct. 17, 2023, 5 pages.
EP Communication per Article 94(3) EPC for related matter application No. 18742621.8, mailed Oct. 26, 2023, 4 pages.
JP Office Action for related matter application 2019-569758, mailed Aug. 29, 2023, 7 pages (translation attached).
Notice Before Acceptance for related patent application in Israel, Application No. 271384, mailed Jun. 6, 2024, 3 pages.
Office Action for related patent application in Mexico, Application No. MX/a/2021/00661, mailed Jun. 7, 2024, 6 pages.
Office Action for related patent application in Republic of Korea, Application No. 10-2024-7018651, mailed Jul. 19, 2024, 5 pages.
Related foreign application Republic of Korea Patent Application No. 10-2020-7001253 Notice of Allowance, issued Mar. 18, 2024, 5 pages.
Related foreign application Mexico Patent Application No. MX/a/2022/013320 Office Action, mailed May 22, 2024, 4 pages.
Related foreign application Mexico Patent Application No. MX/a/2022/013322 Office Action, mailed May 22, 2024, 4 pages.
Related foreign application Russian Federation Patent Application No. 2019142632/10 Notice of Allowance, dated Feb. 8, 2024, 9 pages.
Bahari, et al., "The Impact of Variables on Particle Size of Solid Lipid Nanoparticles and Nanostructured Lipid Carriers; A Comparative Literature Review," Adv Pharm Bull, 2016, 6(2), 143-151.
Related patent application Australian Office Action, Application No. 2018285694, mailed Oct. 2, 2024, 3 pages.
Related patent application Canadian Office Action, Application No. 3,067,224, mailed Aug. 8, 2024, 4 pages.
Office Action for related application MX/a/2021/006661 dated Sep. 18, 2024, 9 pages.

\* cited by examiner

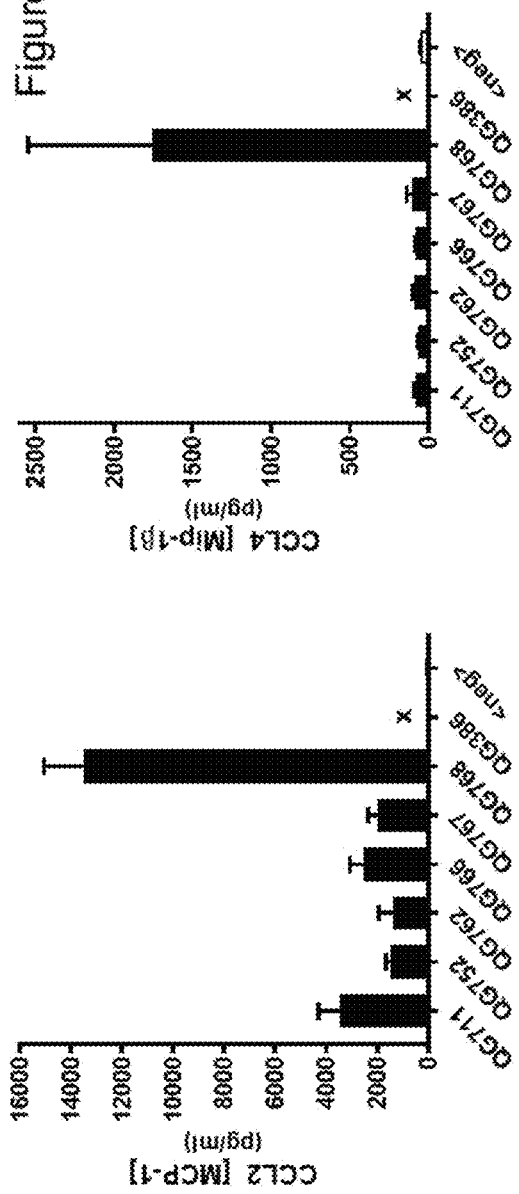
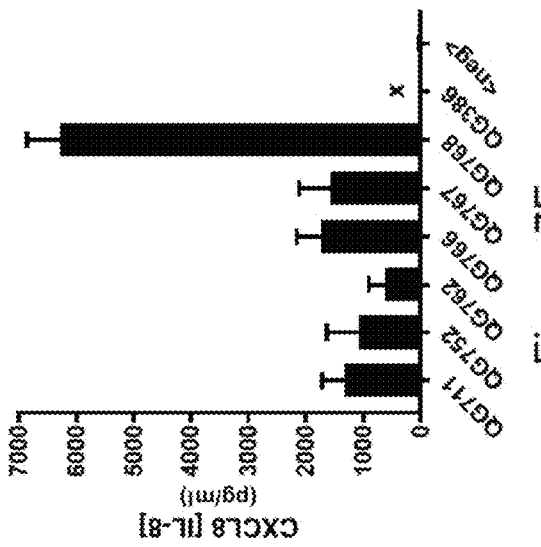
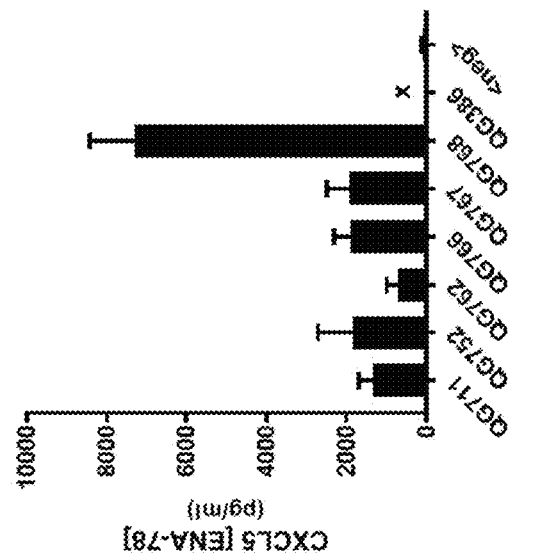
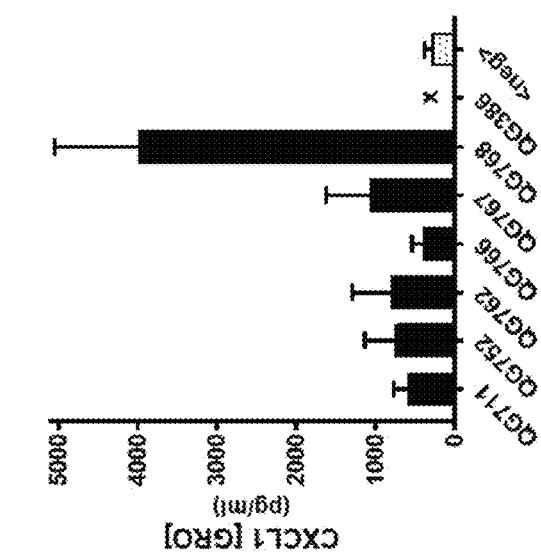
Figure 7A, Figure 7B, Figure 7C, Figure 7D, Figure 7E Figure 18A
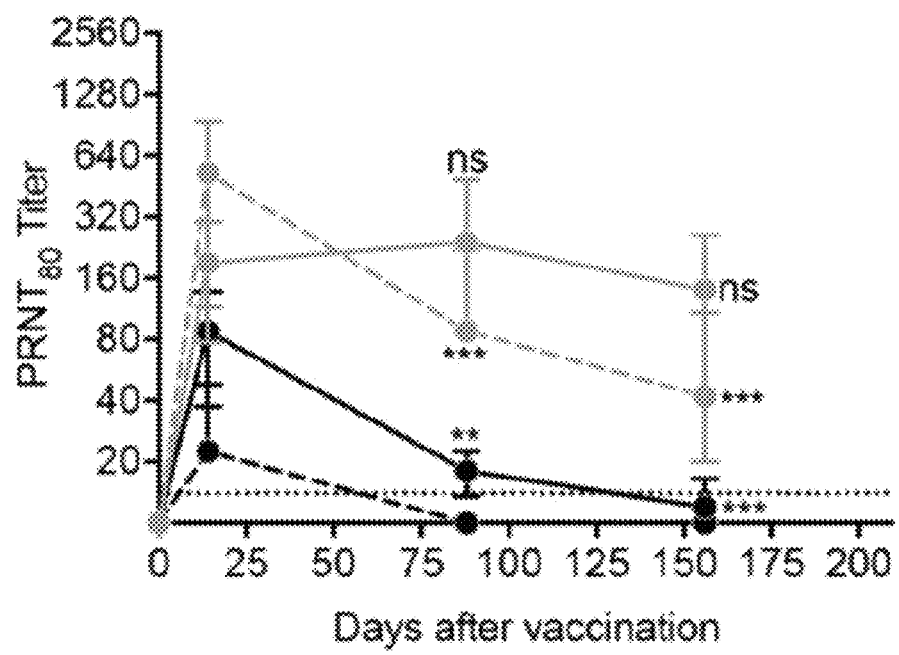
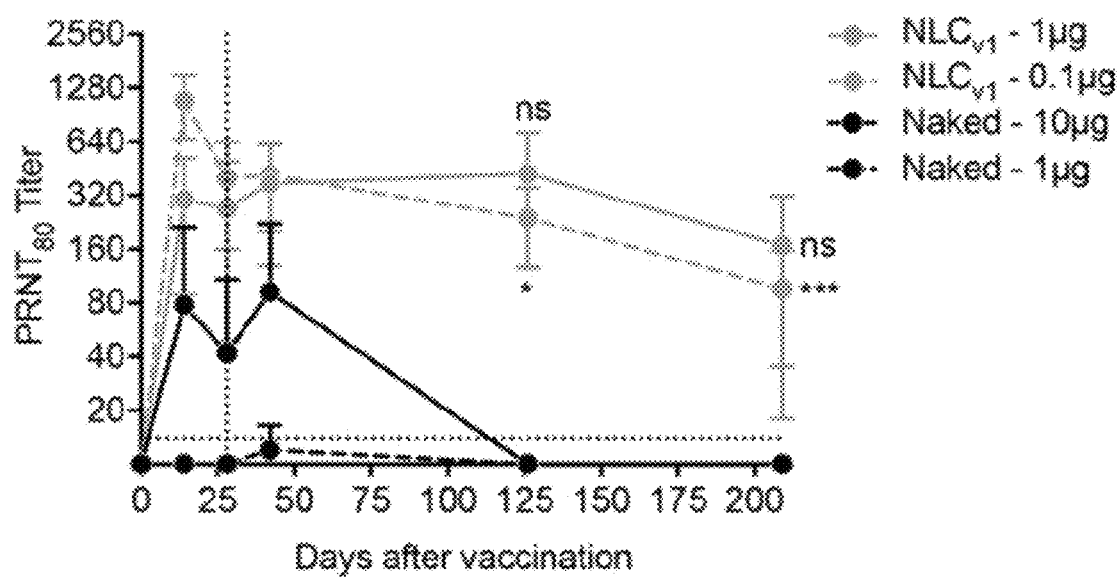
Figure 18B

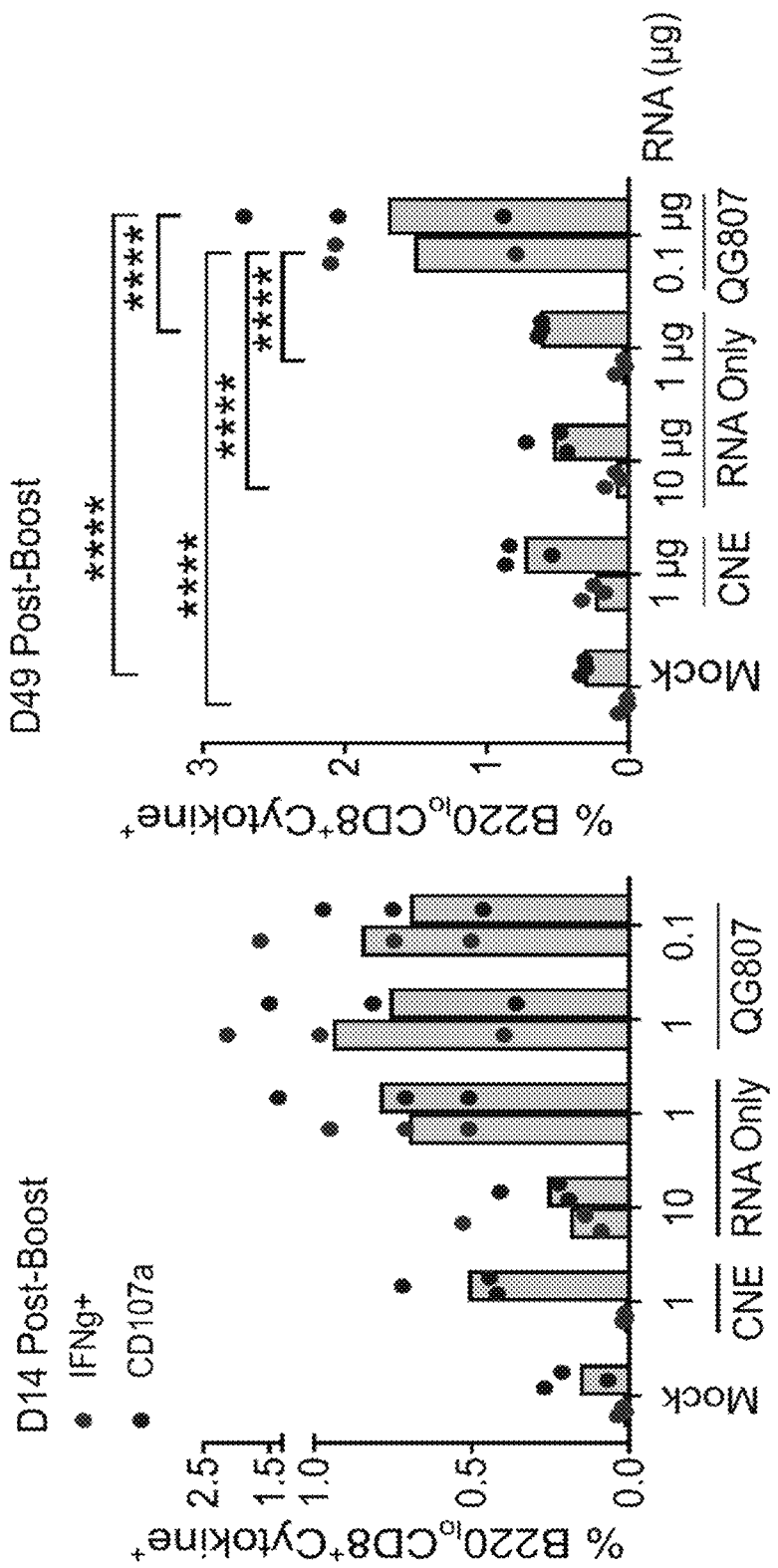

Figure 21A
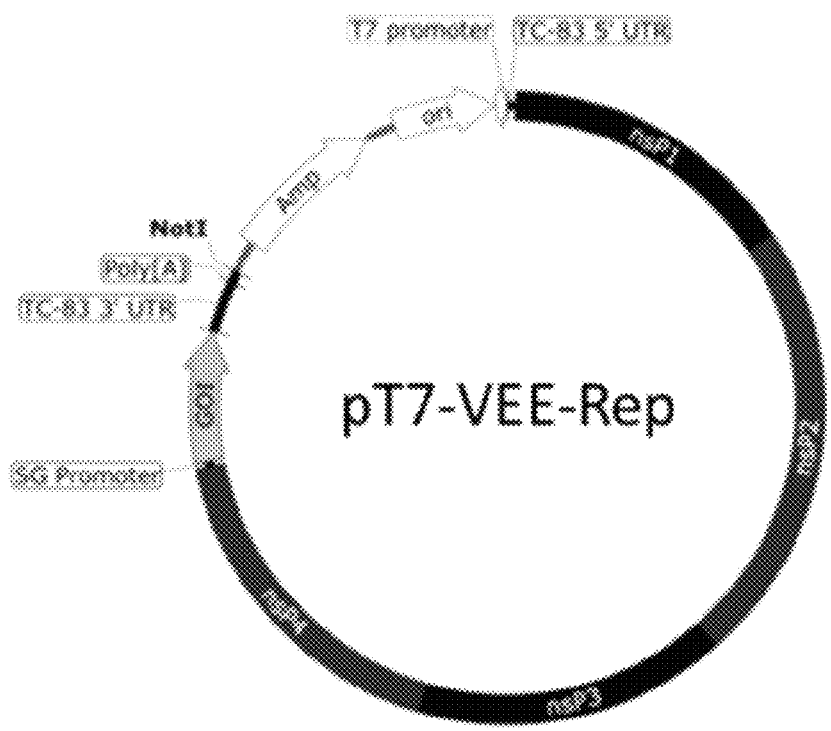
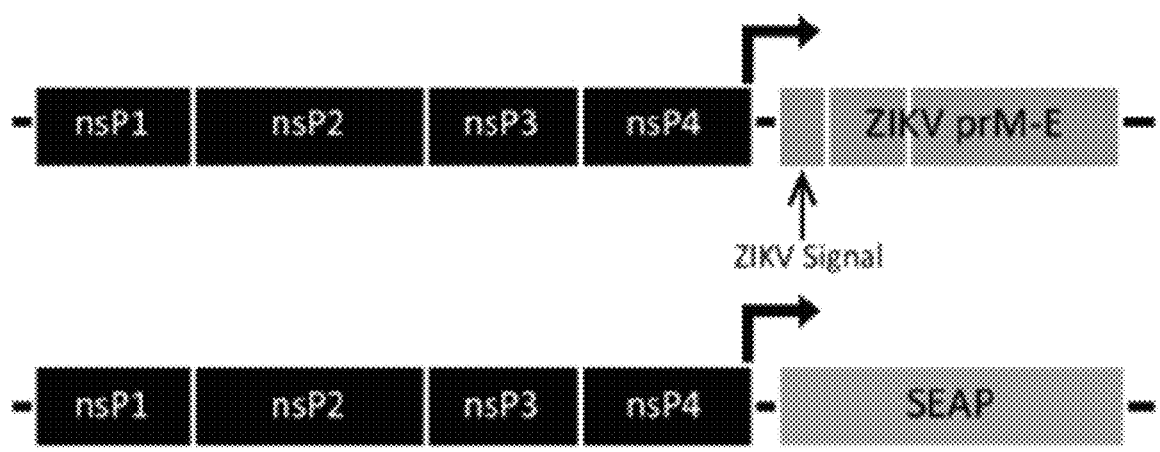
Figure 21B

Figure 21C
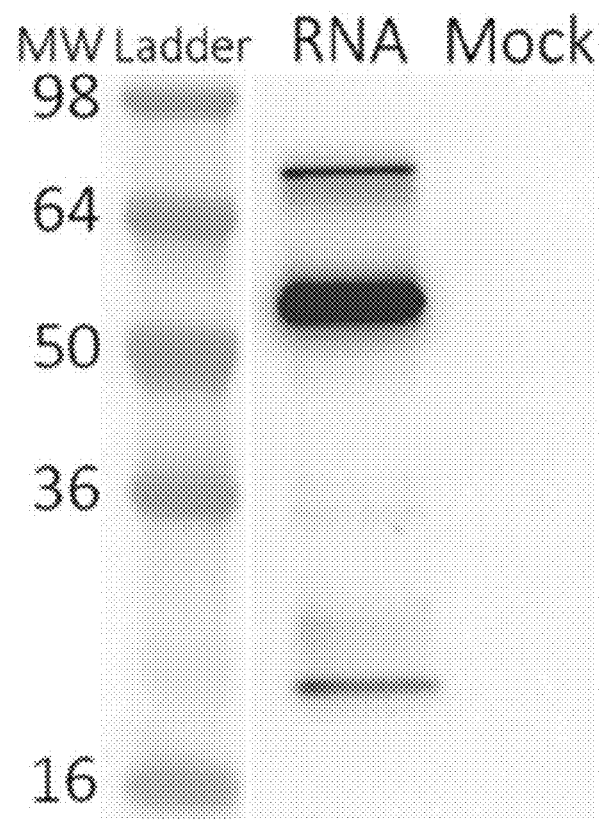
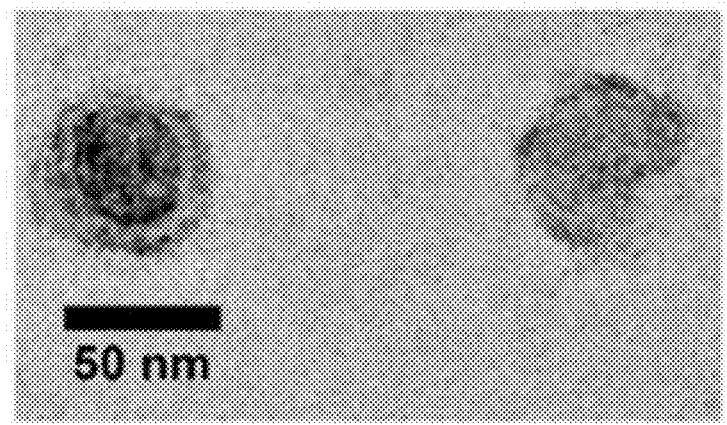
Figure 21D

Figure 28A
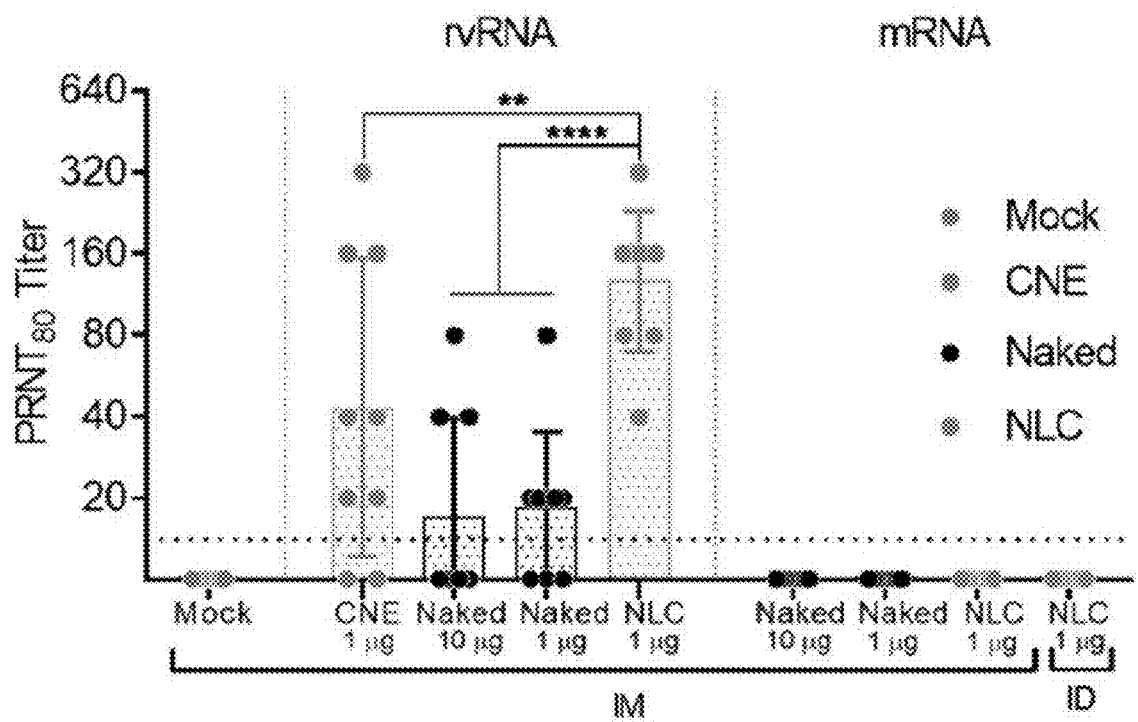
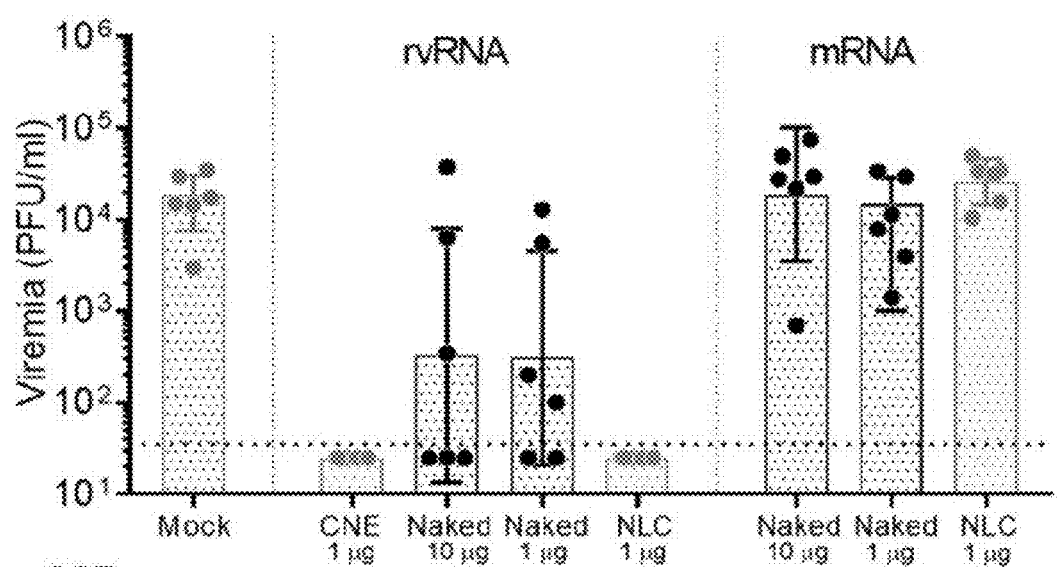
Figure 28B

Figure 28C
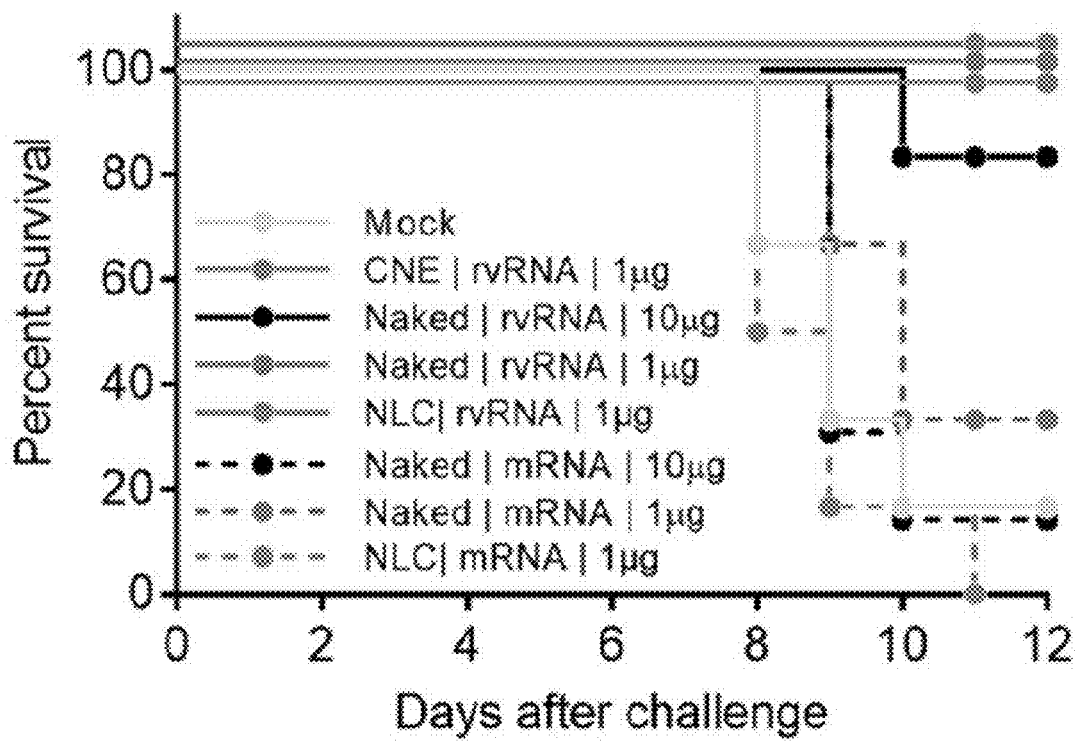
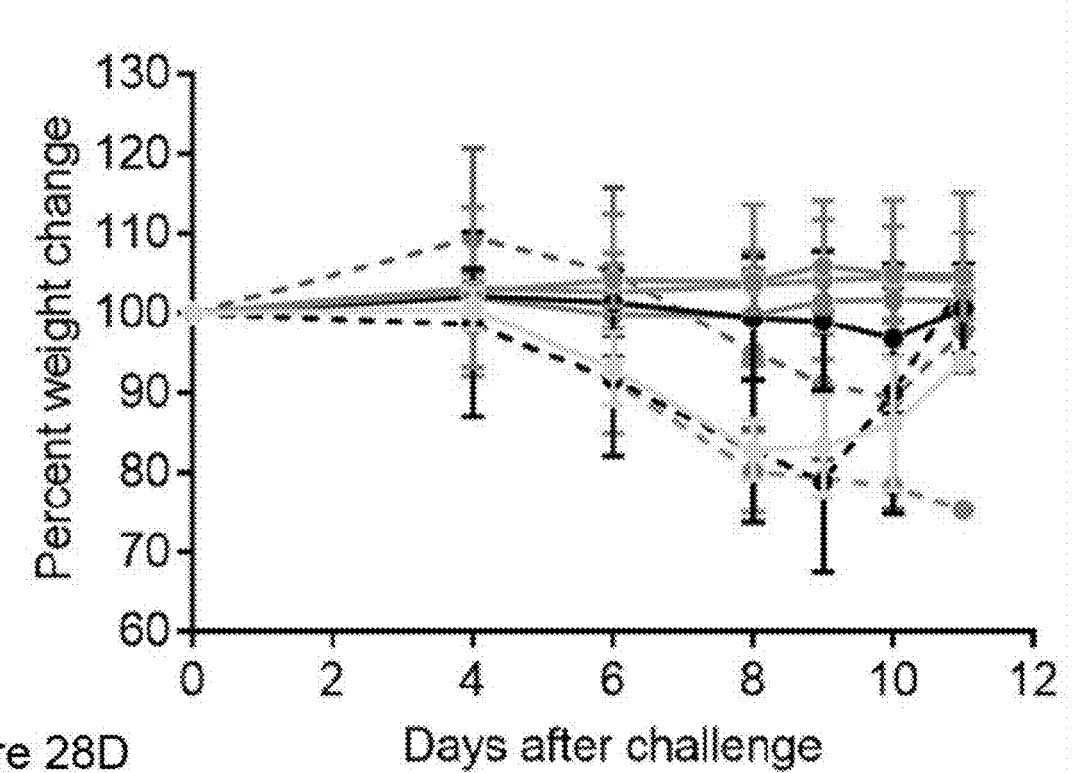
Figure 28D

Figure 28E
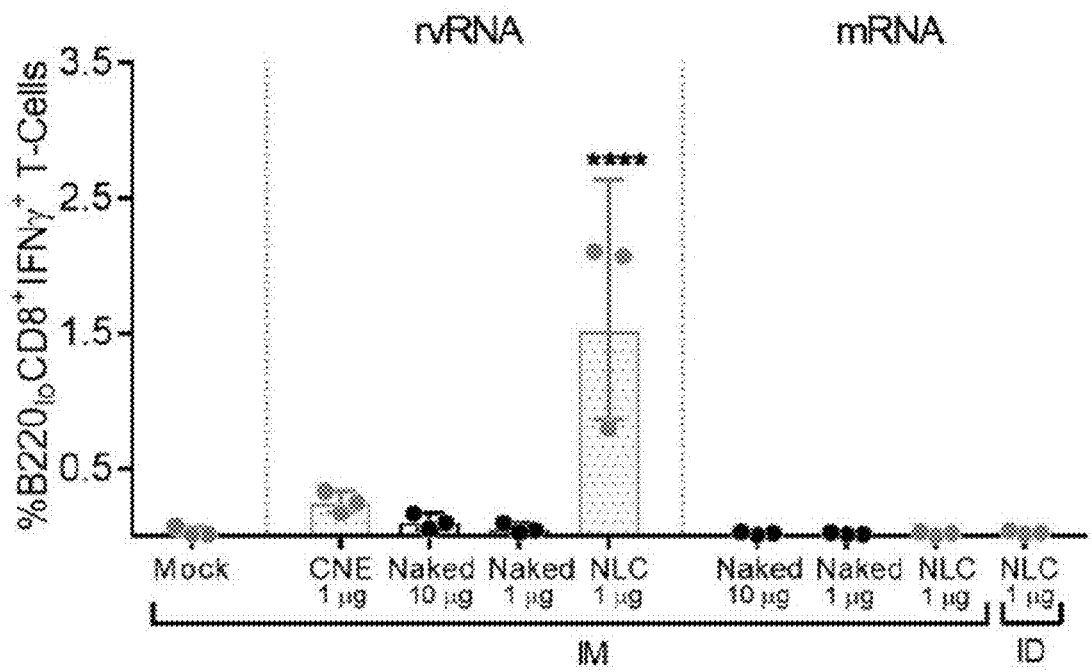
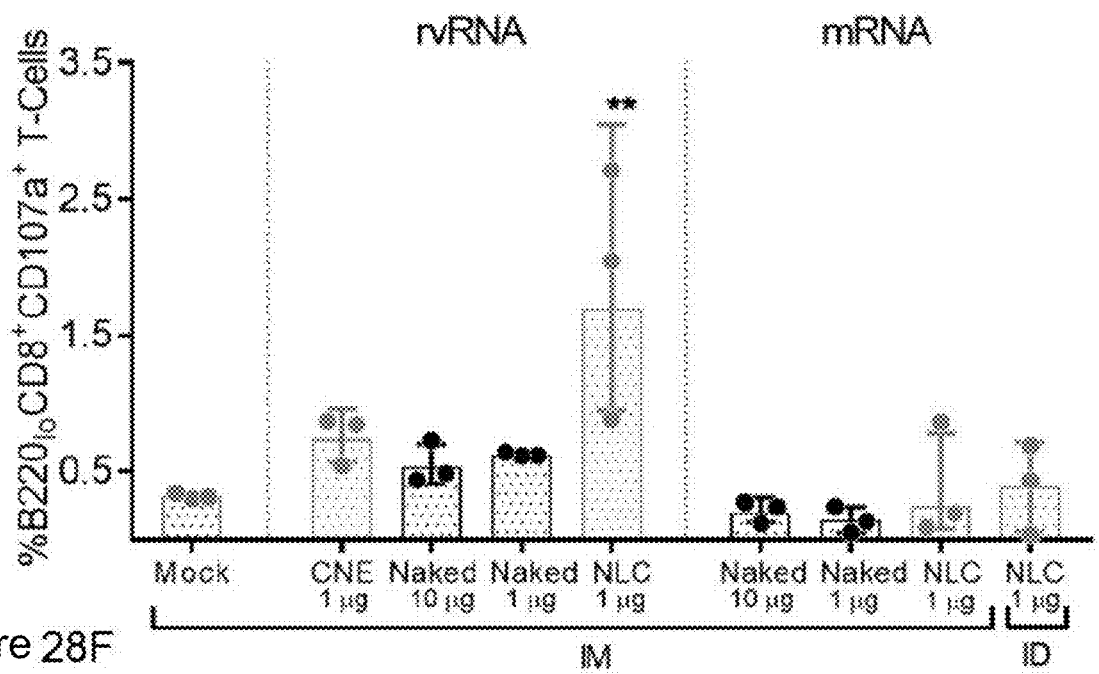
Figure 28F

Figure 31C
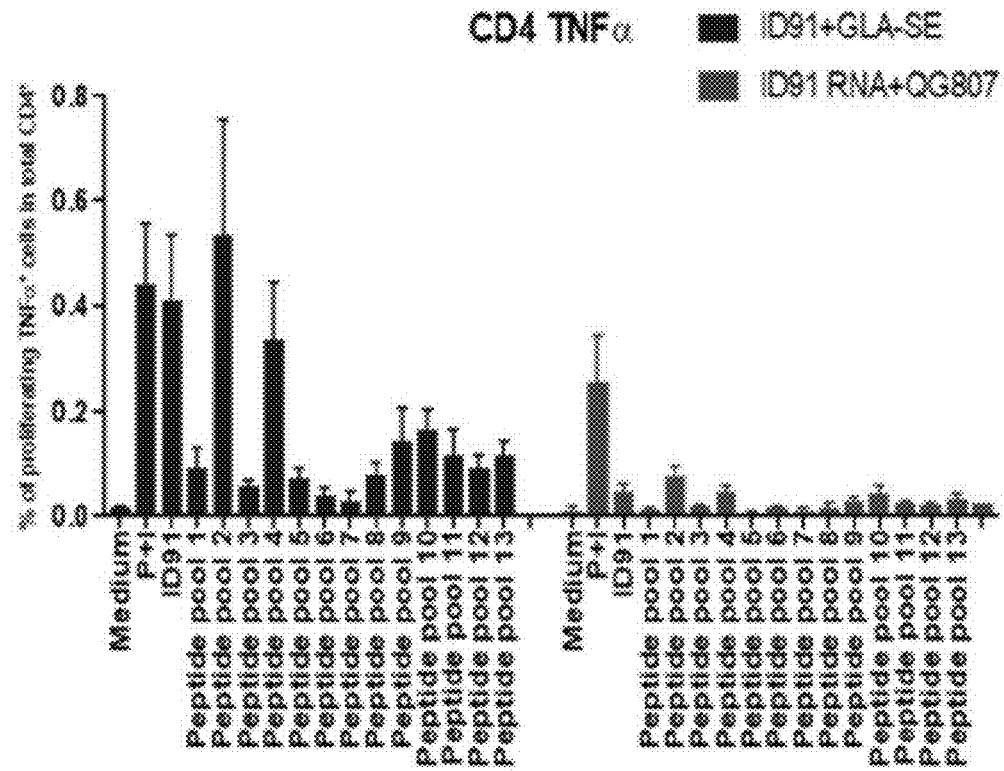
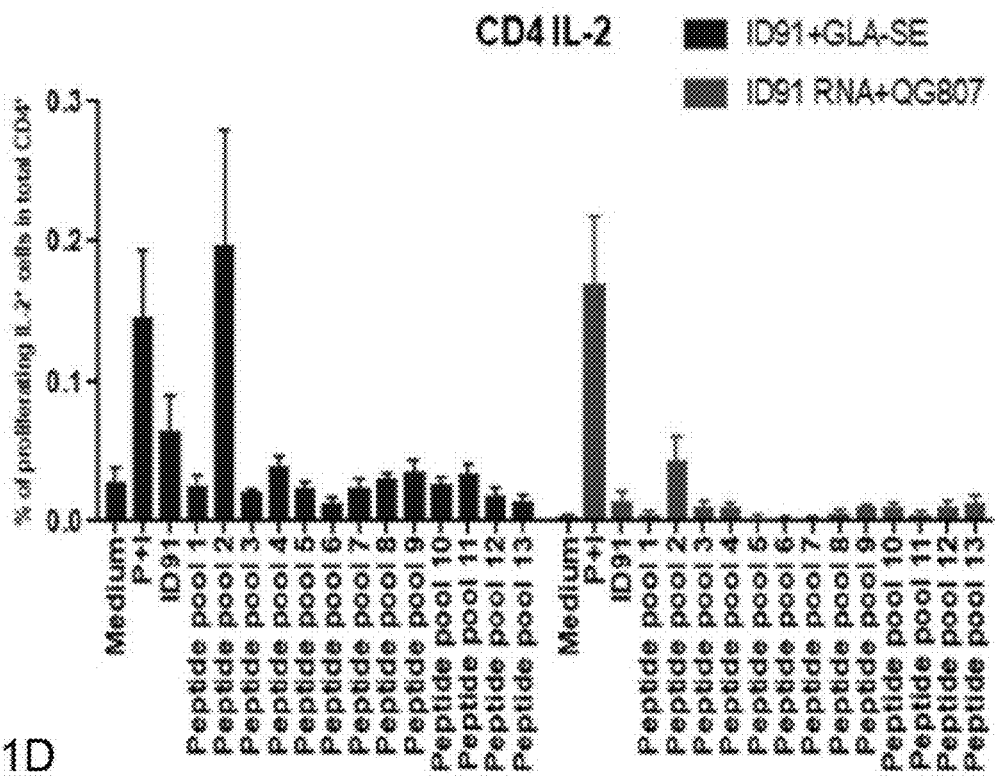
Figure 31D

Figure 32C
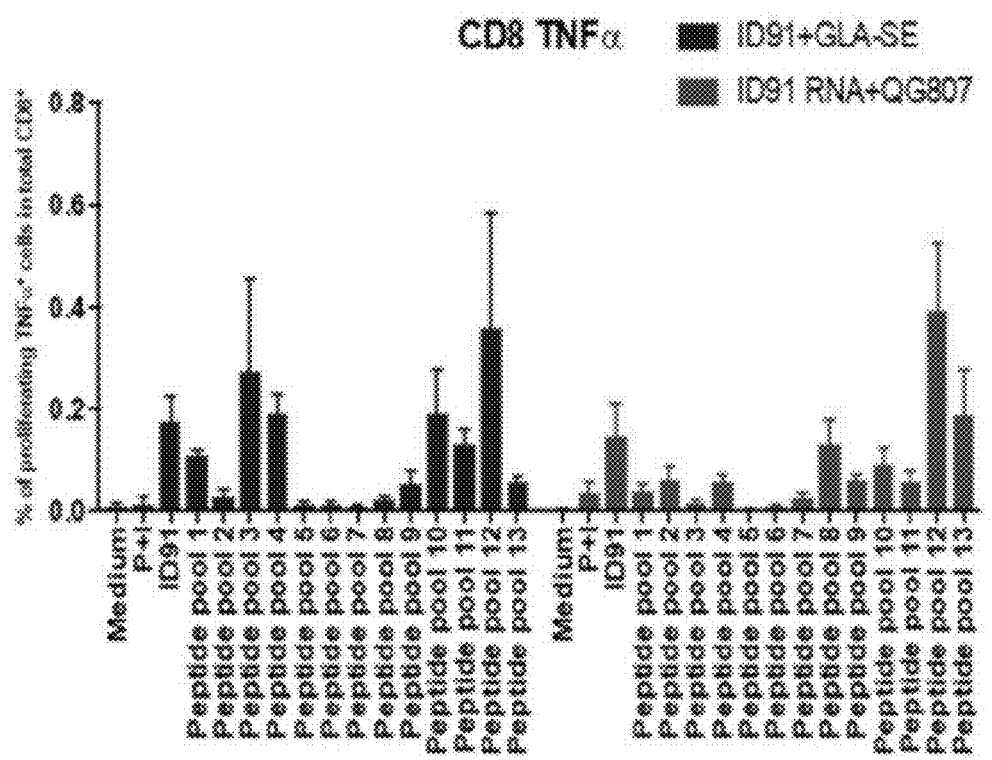
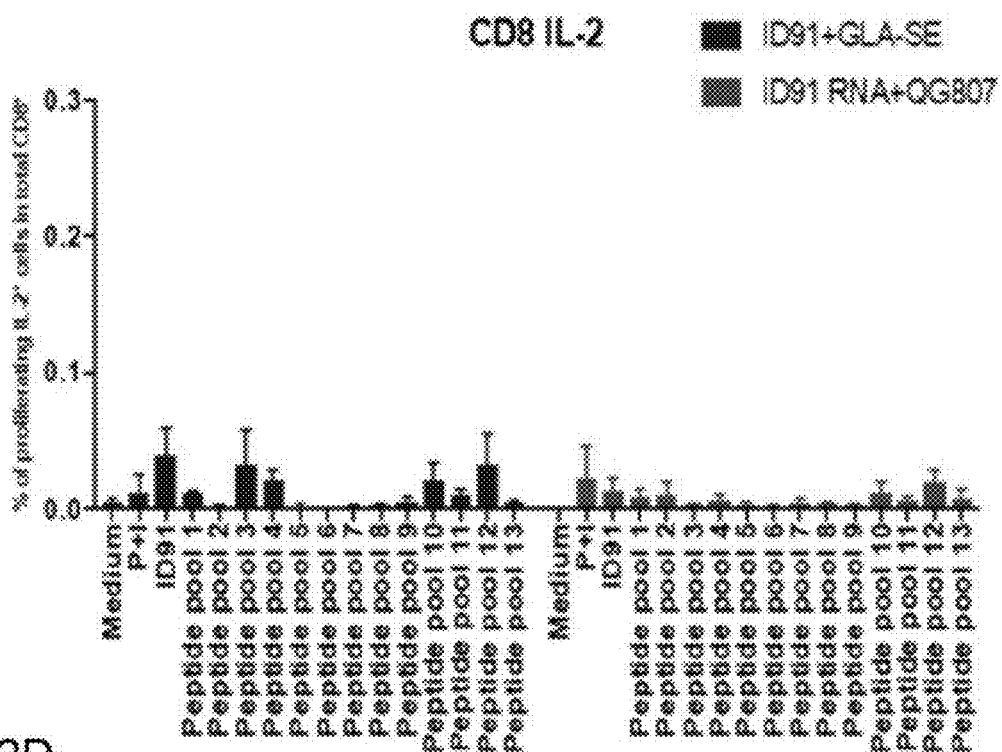
Figure 32D

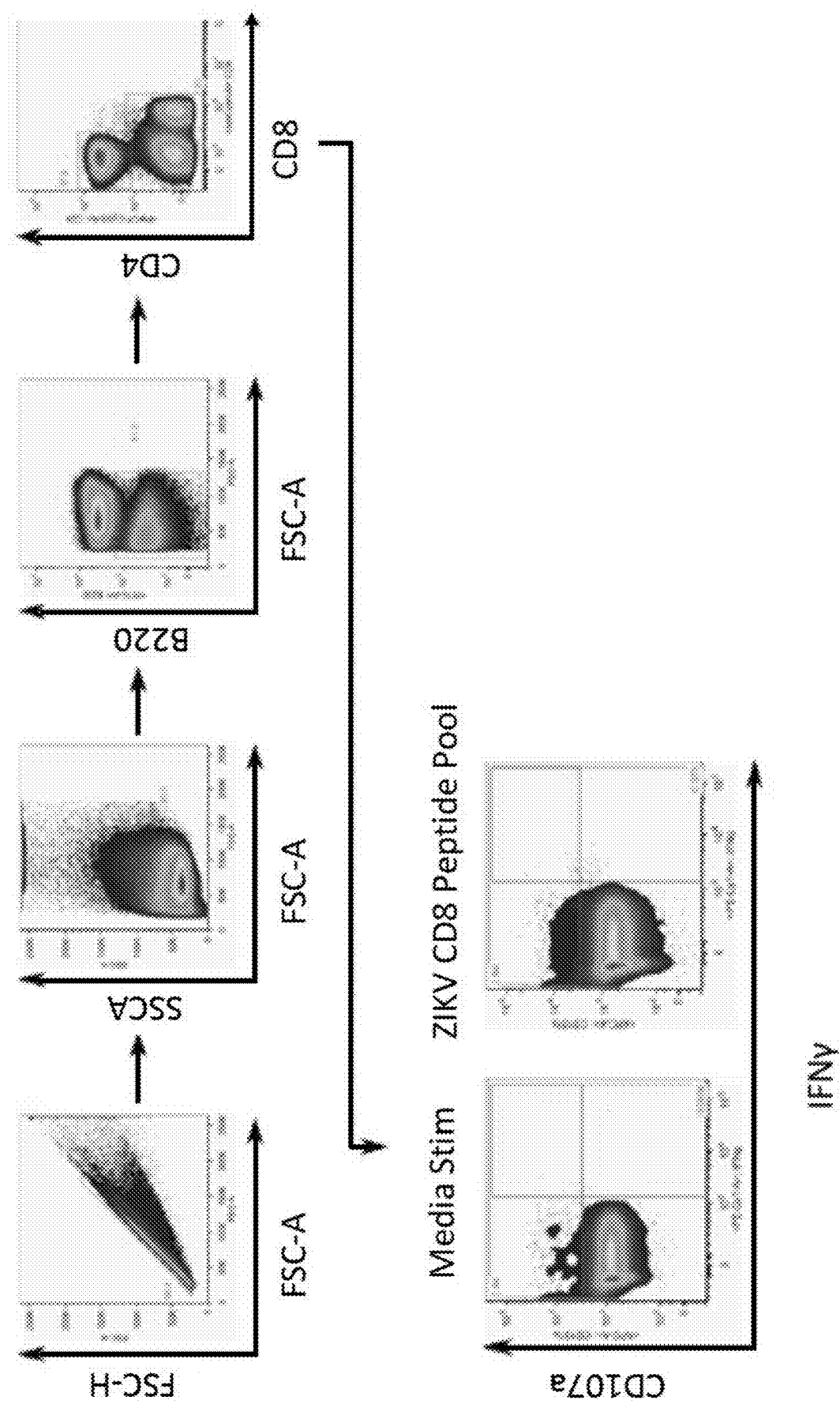

Figure 45

NANOSTRUCTURED LIPID CARRIERS AND STABLE EMULSIONS AND USES THEREOF

CROSS REFERENCE TO RELATED APPLICATIONS

This application is a continuation of U.S. patent application Ser. No. 16/622,908, filed Dec. 13, 2019, which is a national stage filing of International Application No. PCT/US2018/37783, filed Jun. 15, 2018, which is entitled to priority pursuant to 35 U.S.C. § 119(e) to US Provisional Application Nos. 62/520,204, filed Jun. 15, 2017; 62/540,973 filed Aug. 3, 2017; 62/556,291, filed Sep. 8, 2017; 62/563,544, filed Sep. 26, 2017; 62/582,859, filed Nov. 7, 2017; 62/622,748, filed Jan. 26, 2018; 62/622,755, filed Jan. 26, 2018; 62/669,262, filed May 9, 2018; 62/677,336, filed May 29, 2018; and 62/680,454, filed Jun. 4, 2018; each of which is incorporated by reference herein in its entirety for any purpose.

STATEMENT REGARDING FEDERALLY SPONSORED RESEARCH OR DEVELOPMENT

This invention was made with government support under Contract No. R21 AI128992 awarded by the National Institutes of Health. The government has certain rights in the invention.

FIELD

The present disclosure relates generally to the fields of pharmaceutical and vaccine formulations.

BACKGROUND

Nucleic acid immunization is an attractive strategy for the rapid development of vaccines to existing or emerging infectious disease threats. Nucleic acid vaccine candidates are easily generated by common synthetic methods and can be constructed within weeks of the emergence of a new infectious disease. In addition, since the biophysical characteristics of a nucleic acid vaccine are independent of the expressed antigen, the new vaccine requires mini side mal antigen-specific process development for manufacturing. Plasmid DNA vaccines are currently in development for select infectious diseases; however, thus far, no DNA based vaccines have been approved for use in humans due to the associated complications (McKay, Cope et al. 2014, Tregoning and Kinnear 2014).

Delivery of antigens using RNA based platforms has been proposed as a promising alternative compared to DNA based platforms. The transient nature of RNA is desirable for antigen delivery; the risk of long term vaccine persistence is reduced relative to DNA, and nuclear translocation of the delivered vaccine is not required for protein production. However, the relative instability of RNA and the limited expression from a single mRNA transcript has made large scale distribution and use of these vaccines difficult in the field and for commercial development. Abundant research on methods to improve RNA stability through modification of RNA structure has provided several solutions to this problem (Tavernier, Andries et al. 2011, Youn and Chung 2015). In particular, self-amplifying RNA based vaccines have demonstrated a potential mechanism to improve the magnitude and duration of antigen expression (Reviewed in (Vander Veen, Harris et al. 2012, Ljungberg and Liljestrom 2015)).

In order to enable a robust immune response, formulations such as liposomes and oil-in-water emulsions are typically employed to enhance the delivery of RNA into cells (Geall, Verma et al. 2012, Ulmer, Mason et al. 2012, Brito, Chan et al. 2014, Bogers, Oostermeijer et al. 2015, Brito, Kommareddy et al. 2015, Geall and Ulmer 2015). In addition, these formulations may also be used to enhance the delivery of drugs or other therapeutics into cells. However, liposomes or oil-in-water emulsions such as cationic lipid emulsions (CNE) can be structurally unstable in physiological environments, increasing the likelihood of toxicity from acute exposure to individual components. The toxic potential of such carriers can also compound or confound toxicity concerns commonly associated with cationic phospholipids required for RNA adsorption (Bertholet et al. 2010). Additionally, there is limited understanding on how the physicochemical makeup of oil-in-water emulsions (e.g. size, surface charge, chemical nature of excipients and their relative ratios) affects RNA binding, delivery, and ultimately antigen expression.

Thus, there is a need for a formulation platform that is both physically and chemically suited to serve as a versatile, stable, and safe system for the delivery of bioactive agents including nucleic acids to cells.

All references cited herein, including patent applications and patent publications are herein incorporated by reference in their entirety, as if each individual reference is specifically and individually indicated to be incorporated by reference.

BRIEF SUMMARY

The present inventors have developed formulations that are surprisingly effective at delivering a bioactive agent to a cell. Accordingly, provided herein, inter alia, are such formulations (also referred to herein as compositions) and their method of use. The formulations are nanostructured lipid carrier (NLC)-based formulations. It will be understood by the skilled practitioner that a NLC is made up of NLC particles. NLCs are described in Beloqui et al., Nanomedicine. NBM 2016; 12:143-161. Exemplary NLC particles of the present invention comprise (a) an oil core comprising a liquid phase lipid and a solid phase lipid, (b) a cationic lipid, (c) a hydrophobic surfactant (preferably a sorbitan ester (e.g., sorbitan monoester, diester or triester), and (d) a hydrophilic surfactant. Exemplary compositions are stable and are capable of the delivery of bioactive agents to cells. Delivery of the bioactive agent can be, for example, for the generation of an immune response and/or for treatment of disease and health conditions in a subject.

These and other aspects of the present invention will become evident upon reference to the following detailed description and attached drawings. In addition, various references are set forth herein which describe in more detail certain aspects of this invention and are therefore incorporated by reference in their entireties.

BRIEF DESCRIPTION OF THE DRAWINGS

(FIG. 1A), 25° C. (FIG. 1B), 37° C. (FIG. 1C) 60° C. (FIG. 1D) and 80° C. (FIG. 1E). Arrows are included merely to assist with distinguishing the lines.

FIGS. 3B-E show an overlay of in vitro SEAP expression (relative luminescence units, RLUs) and RNA-NLC binding curves as a function of N:P values for QG942 (FIG. 3B), QG963 (FIG. 3C), QG807 (FIG. 3D), and QG843 (FIG. 3E) (QG843 is also referred to herein as CNE).

FIG. 7A-E depicts levels of chemokine release from human whole blood cells in the presence of the indicated formulations. Chemokine expression levels were determined by Luminex assay using a multiplex cytokine bead array.

FIG. 11A depicts Four NLC formulations that differ in emulsifier compositions were compared to CNE or diluent for their ability to enhance protein expression following complexation with RNA encoding secreted alkaline phosphatase (SEAP). Three days after one intramuscular (IM) injection of 100 ng (n=3 per group), sera were harvested from mice and SEAP activity was assayed. Each data point is plotted as well as their mean±standard deviation (S.D.) FIG. 11B depicts the same formulations used in FIG. 11A complexed with RNA encoding ZIKV prM and E and neutralizing antibodies were assayed 14 days after a single 100 ng IM injection (n=5 per group). Data was analyzed by one-way ANOVA with Tukey's multiple comparison test (*p<0.05; NLC Span 60 compared to CNE or NLC Span 85,  p<0.008; NLC Span 60 compared to NLC Span 80, * p=0.0007, CNE compared to NLC Span 80 or 85, not significant). FIG. 11C depicts CNE or NLC composed of 2 different hydrophobic surfactants, Span 85 and Span 60, complexed with RNA encoding ZIKV prM and E and neutralizing antibodies and assayed 14 days after a single 100 ng IM injection. Data was analyzed by multiple two-way ANOVA with Tukey's multiple comparison test. ** p<0.0001.

FIGS. 14G-H: Mice (n=6/group) immunized with a single IM administration were challenged at day 30, following blockade of interferon alpha receptors by monoclonal antibody administration, with a lethal dose of ZIKV. Sera were assayed (FIG. 12G) for virus by plaque assay at 4 days after challenge, while survival was monitored (FIG. 12H). $NLC_4$ is QG807.

FIG. 16A depicts an exemplary NLC particle. FIG. 16B depicts intensity weighted size distribution of $NLC_{v1}$ and CNE (QG386). FIG. 16C depicts particle size (z-average diameter) evolution over nine months to evaluate colloidal stability of formulations stored at 25° C. Dynamic light scattering (DLS) particle size (z-average diameter, Malvern Zetasizer Z/ZS) comparison between CNE (QG386) and QG752, a $NLC_{v1}$ formulation. FIG. 16D depicts Rnase protection by NLCs with relatively lower Tween80 fraction in the surfactant phase (35% of total surfactant and cationic lipid mass) protected rvRNA from degradation.

FIGS. 18A-B depict durability of neutralizing antibody responses following two independent experiments with either one or two doses of NLC-formulated ZIKV rvRNA. C57BL/6 mice (n=5/group) were immunized once on day 0 (FIG. 18A) or on day 0 and 28 (FIG. 18B) via the IM route with 1 or 0.1 µg ZIKV rvRNA formulated with $NLC_{v1}$ and neutralizing antibody titers at various time points were compared to mice immunized with 10 or 1 µg unformulated (naked) ZIKV rvRNA. Data is plotted as mean±S.D. of each biological replicate. $Log_{10}$ transform of data in FIGS. 18A-B was analyzed by one-way ANOVA with Tukey's multiple comparison test, comparing the mean $PRNT_{80}$ at each time point within each group to their respective peak titer at day 14. In FIG. 18A, $NLC_{v1}$-1 µg or Naked-10 µg at days 88 and 156 compared to titers at day 14, *p<0.0001, p<0.001; in FIG. 18B, $NLC_{v1}$-1 µg at days 126 and 209 compared to titers at day 14, *p=0.05, ***p=0.0001, respectively.

FIGS. 19A-B. Mice were immunized with an IM injection of NLC-formulated RNA and compared to 10 or 1 µg unformulated RNA and CNE for levels of CD+ T cells at day 14 (FIG. 19A) and day 49 (FIG. 19B).

Figure 20A:
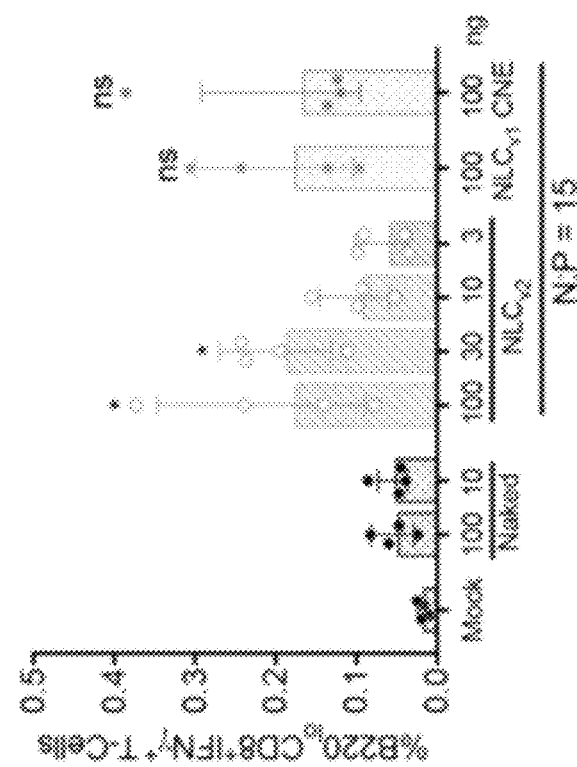
FIGS. 20A-E. Mice were immunized with IM injection of NLC-formulated RNA at the indicated doses. $NLC_{v2}$ (QG942) was complexed with rvRNA encoding ZIKV prM/E at an N:P of 15 and 100, 30, 10, and 3 ng doses were administered to C57BL/6 mice via a single IM injection (n=14/group) and 14 days later, bled to assess neutralizing antibody titers by $PRNT_{80}$ (FIG. 20A) or euthanized (n=4/group) to quantify percent antigen specific $B220_{lo}CD8^+$ $IFNγ^+$ T cells in total splenocytes (FIG. 20B) compared to mock vaccinated mice (vehicle) or 100 or 10 ng naked rvRNA (sucrose) (n=14/group), or 100 ng formulated with $NLC_{v1}$ (n=14) or CNE (n=4) at an N:P of 15 (FIGS. 20A-B). Data are presented as individual values as well as mean±S.D.
Figure 20B:
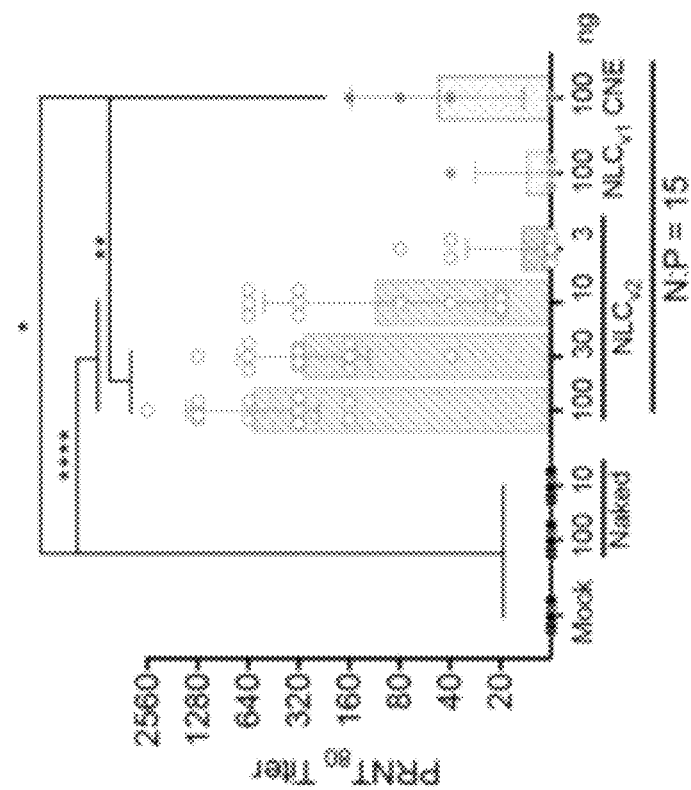
Figure 20C:
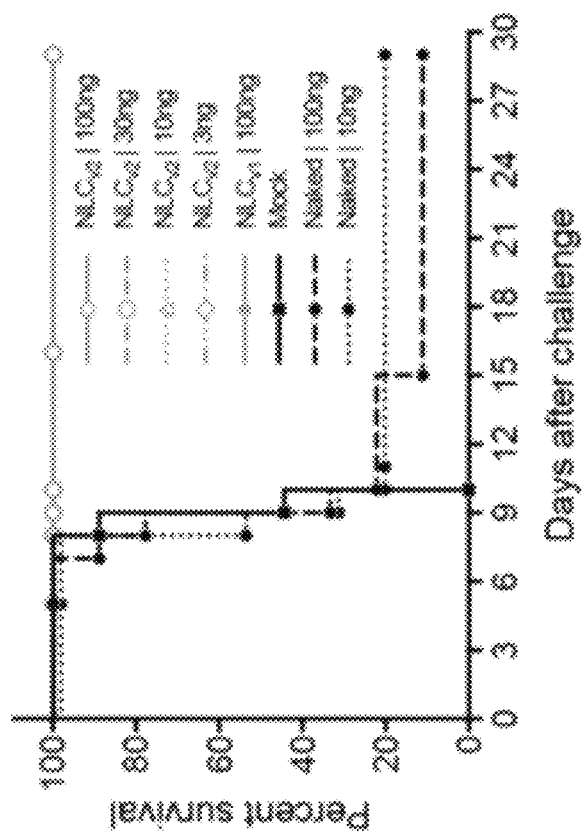
Figure 20D:
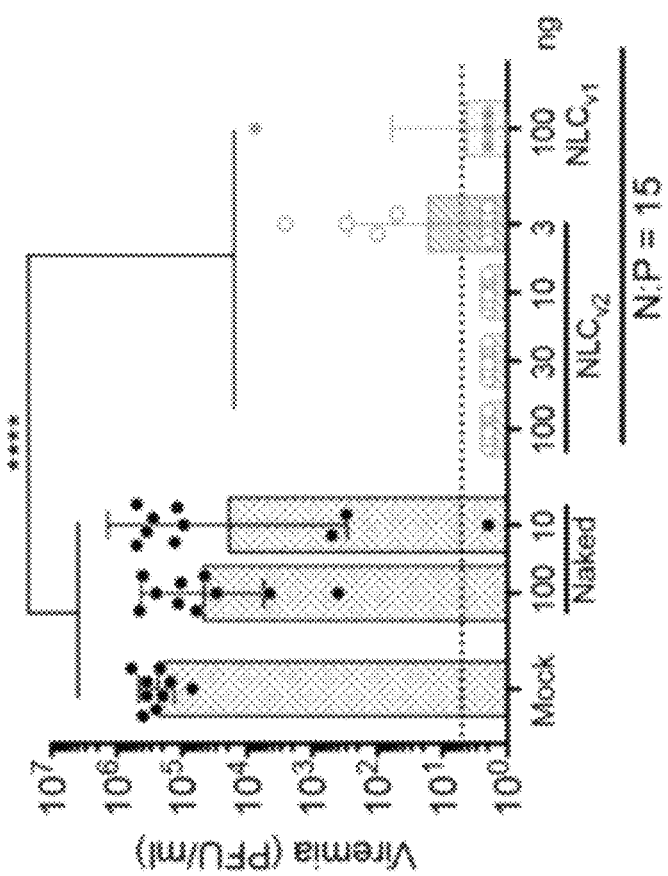
Figure 20E:
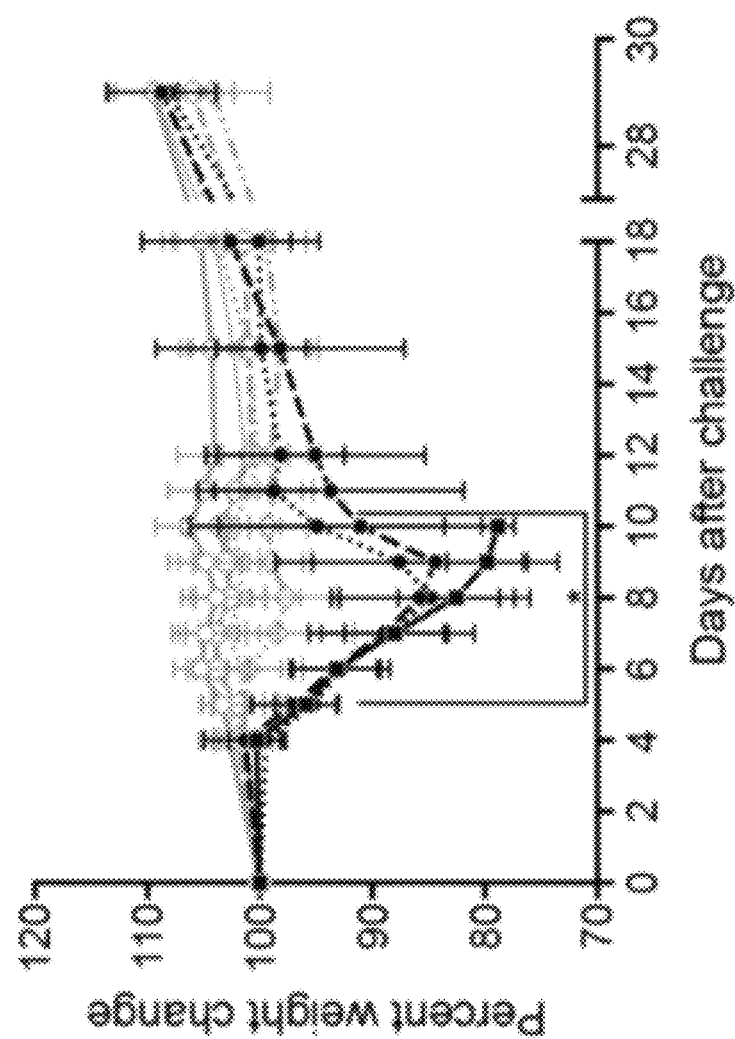
Figure 25:
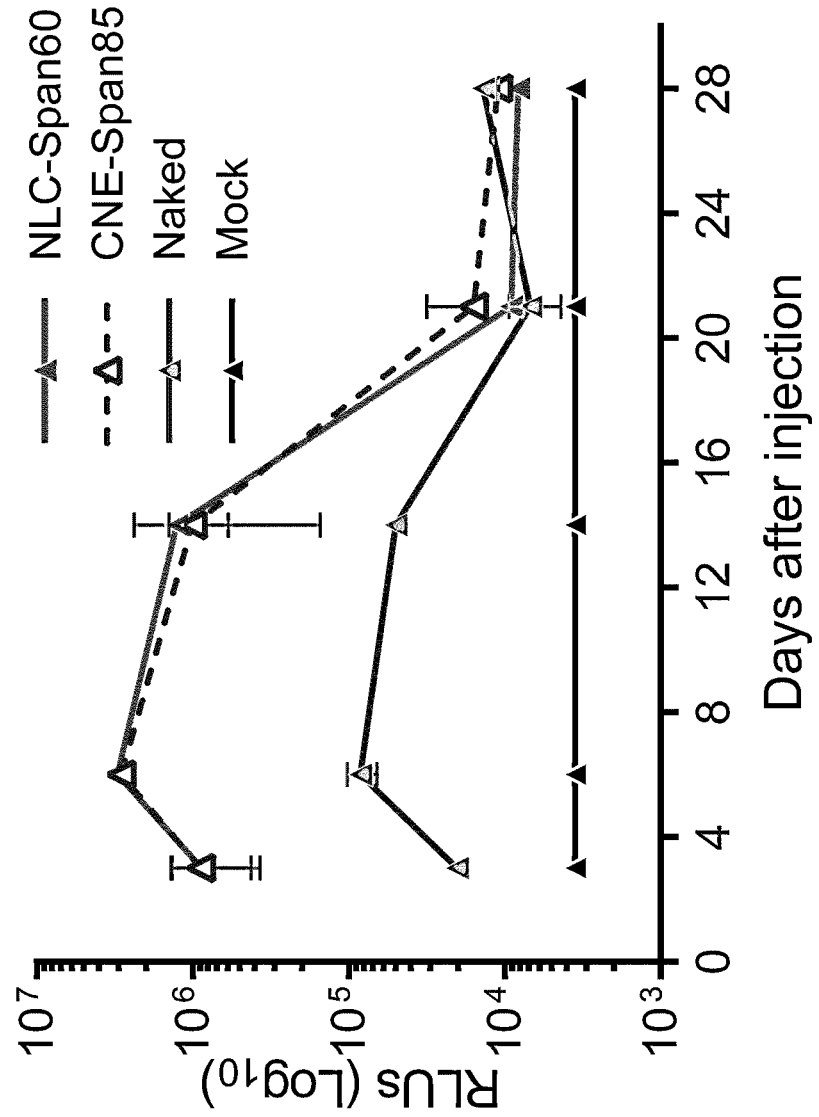

Thirty days after immunization, the remaining 10 mice per group were challenged with 5 $log_{10}$ PFU of ZIKV Dakar strain 41525 following antibody blockade of type I interferon as described in Smith et al., PLoS Negl Trop Dis. 11(1):e0005296 (2017), and bled 4 days later to quantify viremia by plaque assay (FIG. 20C). Data are presented as individual values as well as mean±S.D. Mice were monitored daily for survival (FIG. 20D) and weight loss (FIG. 20E). Data in FIG. 25E are presented as mean±S.D. $Log_{10}$ transform of data in FIGS. 20A and 20C was analyzed by one-way ANOVA with Tukey's multiple comparison test ($PRNT_{80}$ titers in FIG. 25A between control groups—mock, unformulated 100 and 10 ng doses, and $NLC_{v2}$ formulated 100, 30, and 10 ng doses, ****p<0.0001, or CNE formulated 100 ng, *p=0.04; between $NLC_{v2}$ formulated 100 and 30 ng doses and CNE formulated 100 ng, p=0.006; viremia titers in FIG. 20C between control groups—mock, unformulated 100 and 10 ng doses, and all $NLC_{v2}$- or $NLC_{v1}$- formulated doses, **p<0.0001). Data in FIG. 20E was analyzed by two-way ANOVA with Tukey's multiple comparison test (on days 5-10 the percent weight change between control groups—mock, or 100 and 10 ng naked rvRNA, and all formulated groups, *p<0.05). Data in FIGS. 20A-C are representative of two independent experiments.

FIGS. 21A-D depict design and qualification of ZIKV rvRNA. FIG. 21A depicts plasmid DNA encoding a Venezuelan Equine Encephalitis replicon derived from the vaccine strain, TC-83, under the control of a T7 RNA polymerase promoter. Untranslated region (UTR), subgenomic (SG), gene of interest (GOI). FIG. 21B depicts the design of replicating viral RNAs encoding premembrane (prM) and envelope (E) genes of ZIKV strain H/PF/2013 or secreted human embryonic alkaline phosphatase (SEAP). 293T cell supernatants transfected with ZIKV or SEAP rvRNA were analyzed following sedimentation through 30% sucrose by FIG. 21C western blot using polyclonal antibodies against ZIKV and/or FIG. 21D transmission electron microscopy.

Figures 22A, 22B, 22C, 22D:
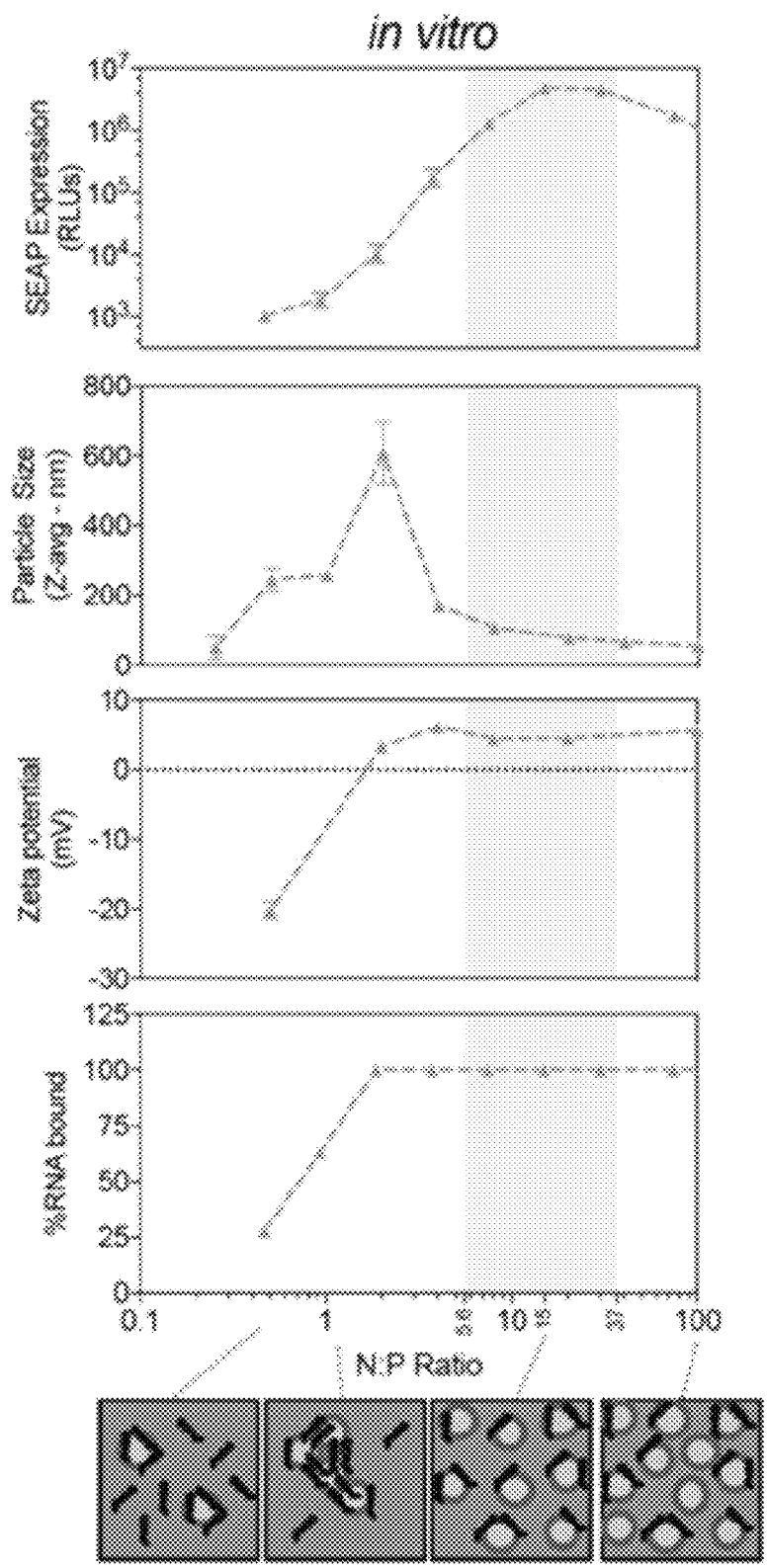
Figures 22E, 22F, 22G, 22H:
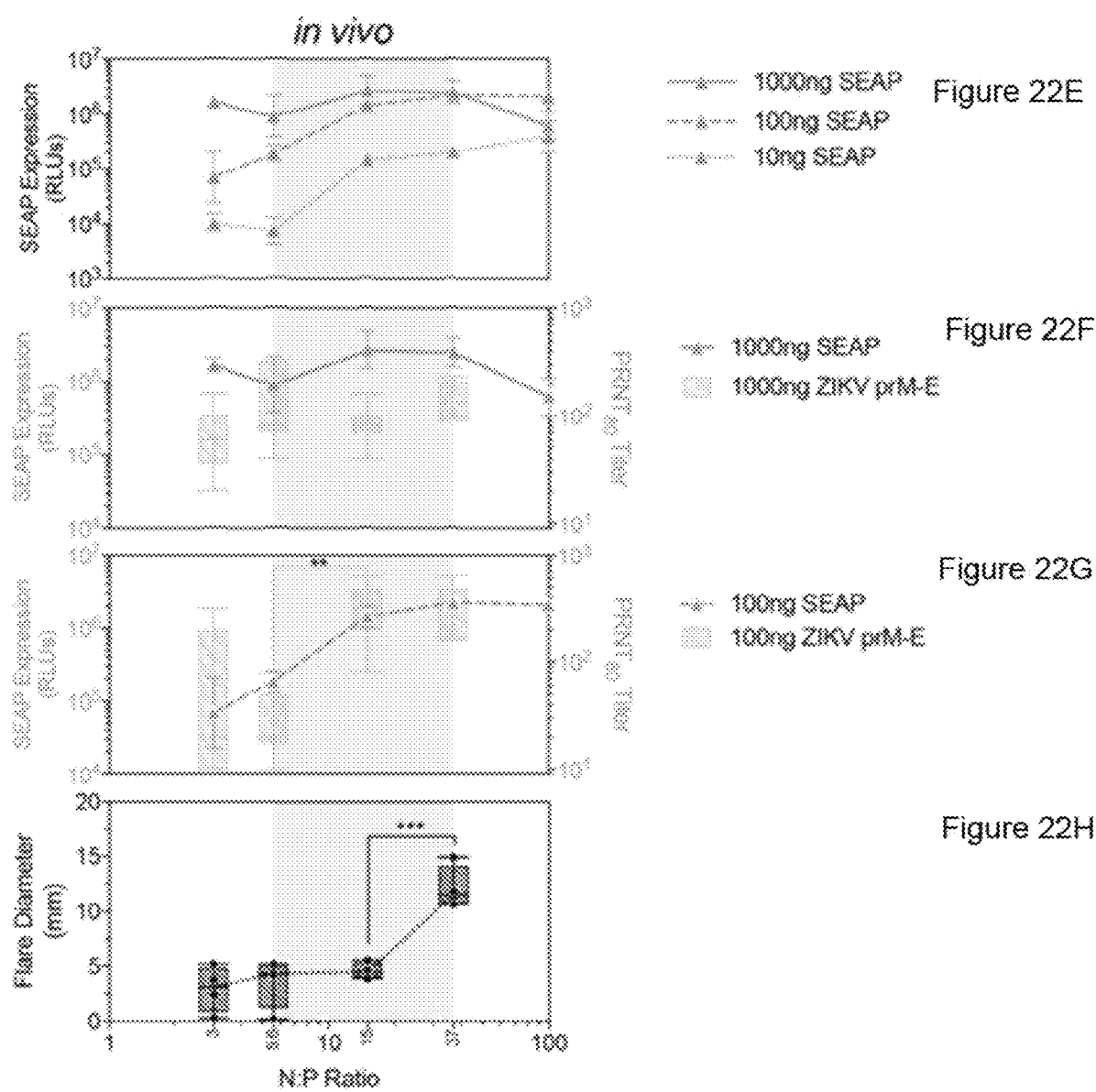

FIGS. 22A-H depicts mapping the physical relationship between $NLC_{v2}$ and rvRNA with biological responses, including gene expression, immunogenicity, and reactogenicity. For in vitro experiments (FIGS. 22A-D) $NLC_{v2}$ was complexed with SEAP rvRNA at various N:P ratios and gene expression (FIG. 11A) was measured by SEAP assay as described above, particle size (FIG. 11B) and zeta potential (FIG. 22C) were measured by dynamic light scattering, and percent RNA binding (FIG. 22D) was measured by densitometry following gel electrophoresis. Data in FIGS. 22A-D are presented as mean±S.D. and are representative of at least 3 independent experiments. For in vivo experiments involving C57BL/6 mice (FIGS. 22E-G), $NLC_{v2}$ was complexed with ZIKV or SEAP rvRNA at N:Ps of 3, 5.6, 15, and 37 and mice (n=3/group for SEAP, or n=5/group for ZIKV) were injected via IM route with 1000, 100, or 10 ng of SEAP rvRNA or 1000 or 100 ng of ZIKV rvRNA. SEAP expression was determined by SEAP assay 3 days after injection (FIGS. 22E-G) while ZIKV neutralizing antibody titers were determined by $PRNT_{80}$ 14 days after injection (FIGS. 22F-G). To determine reactogenicity (FIG. 22H), guinea pigs (n=4/group) were injected via ID route with 50 µg ZIKV rvRNA complexed with $NLC_{v2}$ at N:Ps of 3, 5.6, 15, and 37, and flare diameter was measured 24 hours later. SEAP Data in FIGS. 22E-G are presented as mean±S.D. and are from a single experiment while $PRNT_{80}$ data in FIGS. 22F and G are presented as mean±S.D. and min/max box-whisker plots and are representative of 3 independent experiments. Data in FIG. 22H was from a single experiment and is presented as individual biological replicates with mean±S.D. and min/max box-whisker plots. $Log_{10}$ transform of $PRNT_{80}$ data in FIG. 22G was analyzed by one-way ANOVA with Tukey's multiple comparison test (titers between N:P of 37 and 15, not significant; titers between N:P of 15 and 5.6, p=0.0033). Data in FIG. 22H were analyzed by one-way ANOVA with Tukey's multiple comparison test (flare diameter between N:P of 37 and 15, *p=0.0004; between N:P of 15 and 5.6 or 3, not significant). A cartoon depicting a hypothesized model of the physical interaction between NLC and rvRNA supported by the data is presented with FIG. 22D.

Figure 23B:
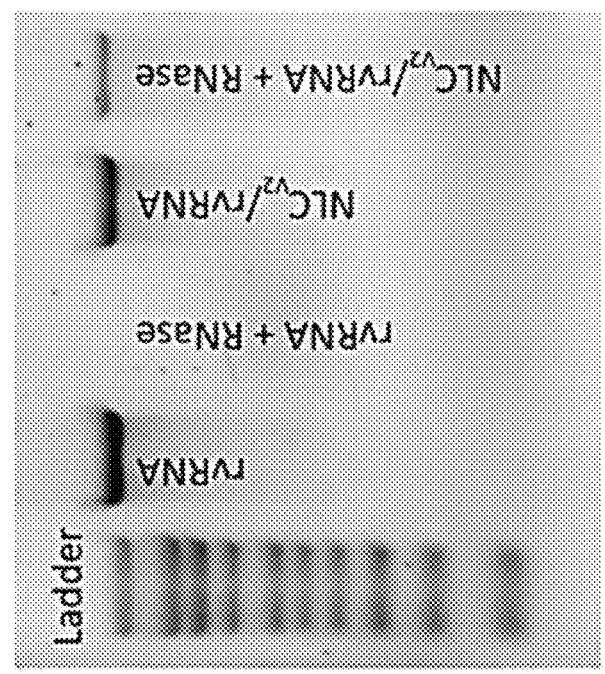
Figure 23A:
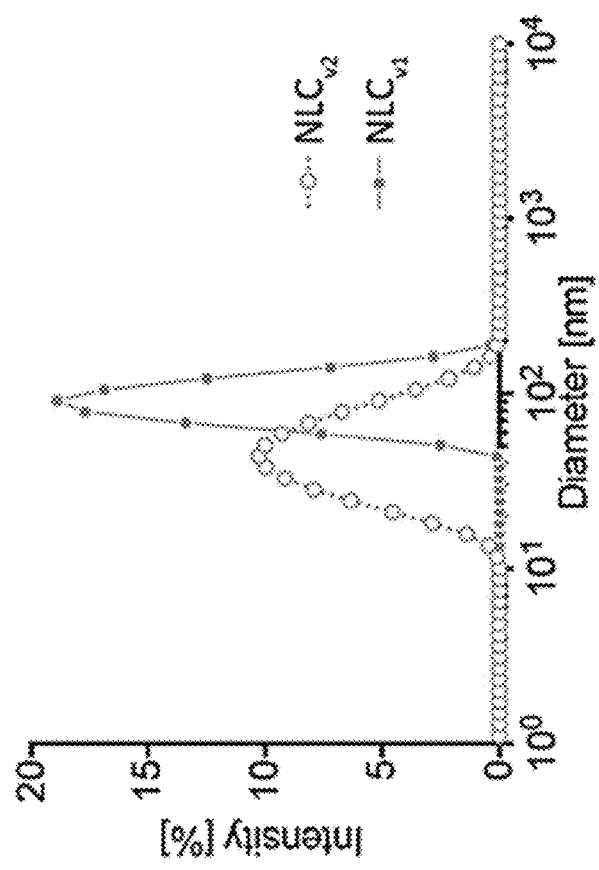
Figure 23D:
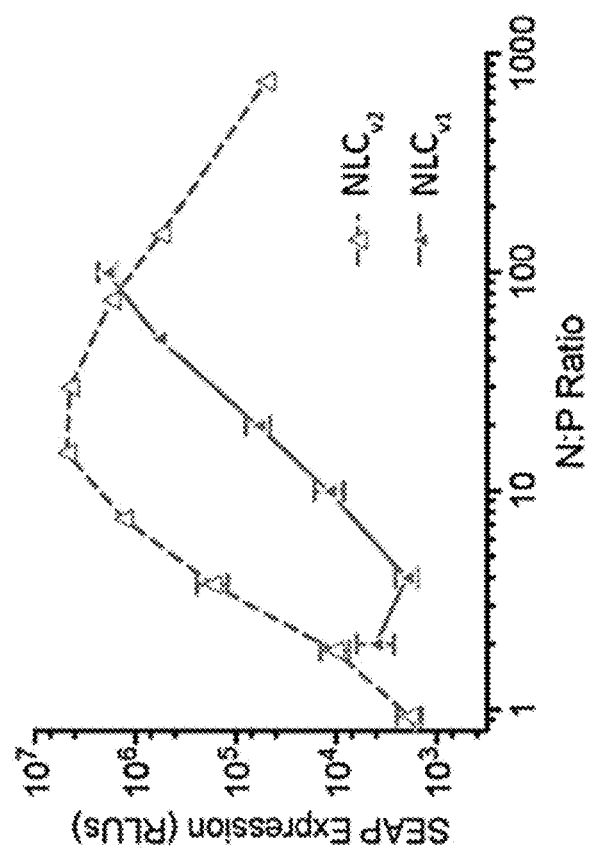
Figure 23C:
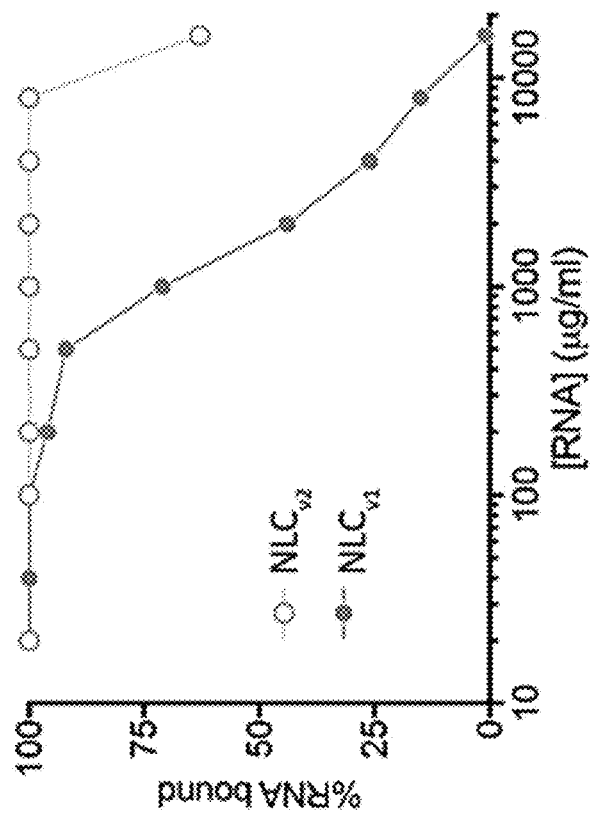
Figure 23E:
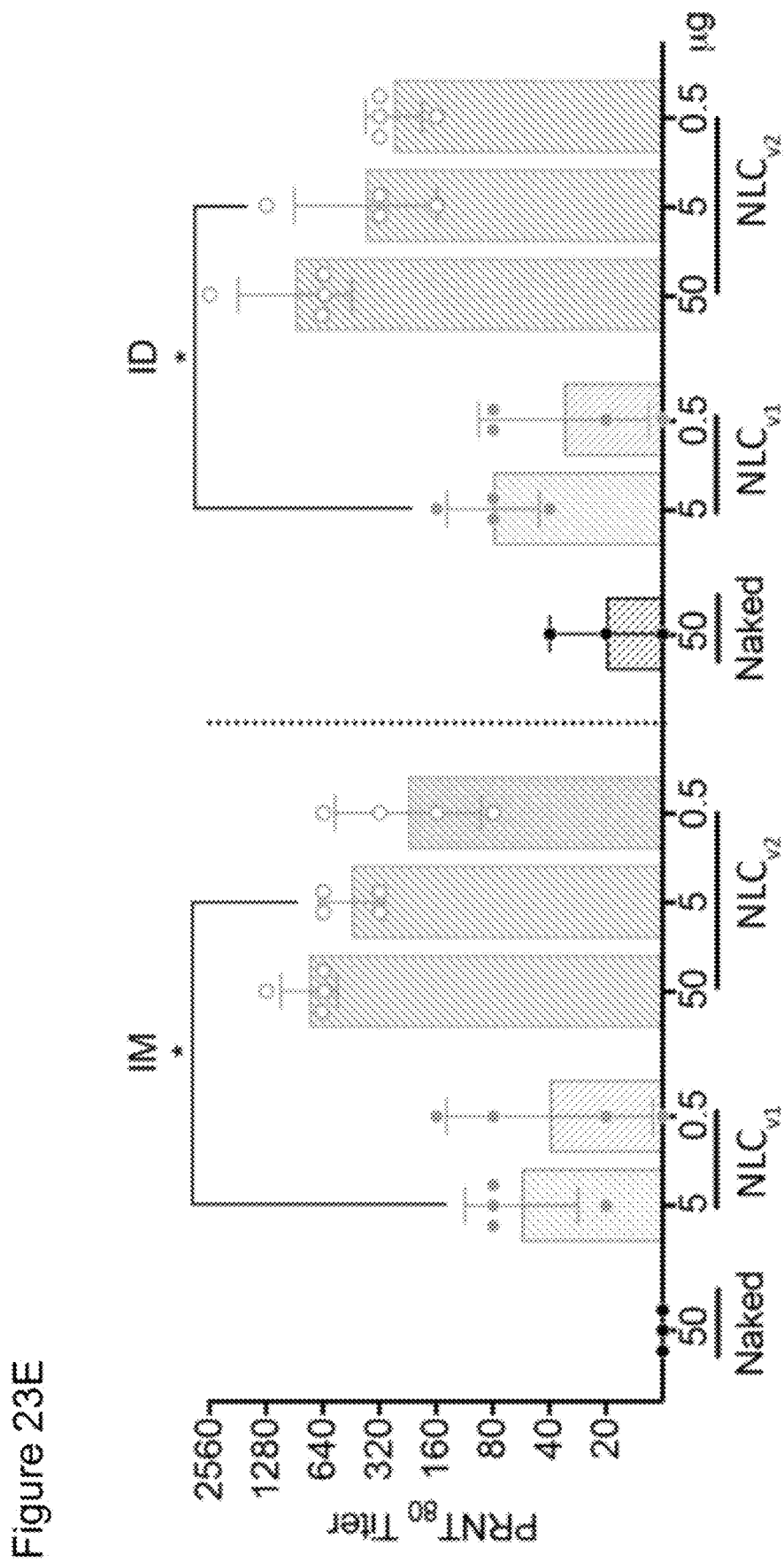
Figure 24A:
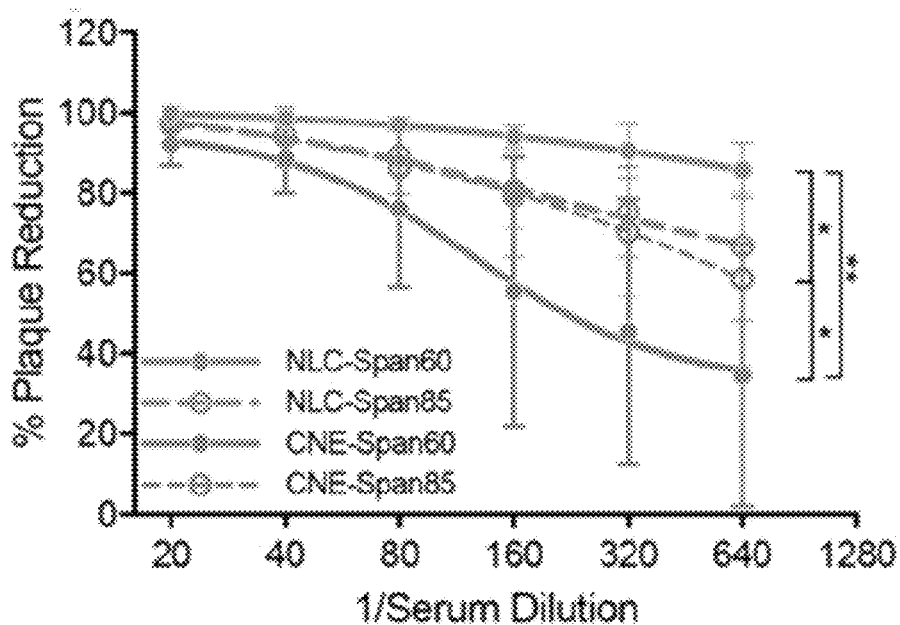
Figure 24B:
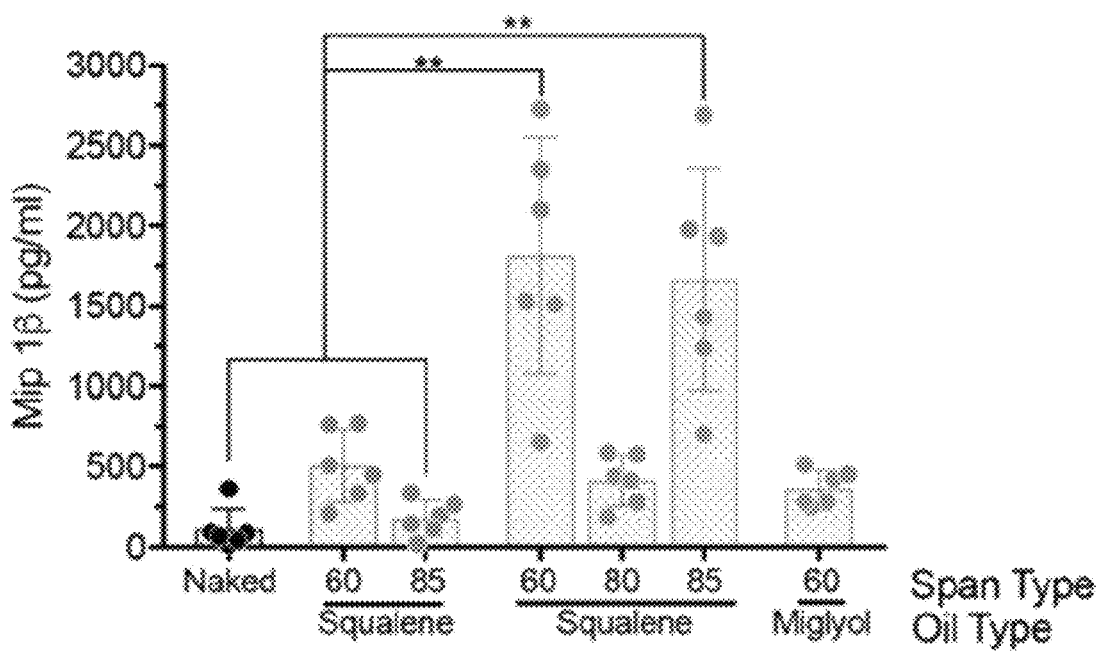

FIGS. 23A-E depict characteristics of $NLC_{v2}$ with enhanced RNA loading capacity. FIG. 23A depicts particle size as measured by DLS. Data are reported as Z-average. FIG. 22B depicts denaturing RNA agarose gel electrophoresis of untreated rvRNA (lane 2) and $NLC_{v2}$ rvRNA (lane 4) or Rnase-treated rvRNA (lane 3) and $NLC_{v2}$ rvRNA (lane 5). Data is representative of 3 independent trials. FIG. 23C depicts percent of RNA bound to $NLC_{v1}$ or $NLC_{v2}$ as measured by densitometry analysis following denaturing agarose gel electrophoresis of $NLC_{v1}$ or $NLC_{v2}$ complexed with increasing concentrations of rvRNA. Data is representative of 3 independent experiments. FIG. 23D depicts SEAP expression in BHK cell supernatant 24 hours after incubation with $NLC_{v1}$ or $NLC_{v2}$ complexed at various N:P ratios with SEAP rvRNA. Data is represented as mean±S.D. of three biological replicates and is representative of results from 3 independent experiments. $NLC_{v1}$ data reproduced from FIG. 23E for comparison purposes. For FIG. 23E, guinea pigs (n=4/group) were immunized with a single 50

μg dose of unformulated ZIKV rvRNA or 5, or 0.5 μg of $NLC_{v1}$-formulated ZIKV rvRNA, or with 50, 5, or 0.5 μg of $NLC_{v2}$ formulated ZIKV rvRNA via the IM or ID routes and serum neutralizing antibody titers, as measured by $PRNT_{80}$, were assayed 28 days later. Each data point is reported as well as mean±S.D. Log 10 transform of data were analyzed by one-way ANOVA with Tukey's multiple comparison test (5 μg doses between $NLC_{v1}$ and $NLC_{v2}$ formulations via IM, *p=0.05, or ID, *p=0.04).

FIGS. 24A-B. FIG. 24A depicts ZIKV neutralization in vitro with serial dilutions of serum harvested in FIG. 11C above. Each serum dilution was plotted as mean±S.D. and a curve was fitted using a sigmoidal non-linear regression model. Data was analyzed by multiple two-way ANOVA with Tukey's multiple comparison test (at 1/640 serum dilution NLC Span 60 vs CNE Span 85 and CNE Span 60 vs CNE Span 85, *p<0.05; NLC Span 60 vs CNE Span 60, p<0.0001). FIG. 24B depicts Mip-1β concentration, as determined by ELISA, in supernatants of human peripheral blood mononuclear cells (n=6 donors) harvested 24 hours after incubation with 40 ng ZIKV rvRNA unformulated (naked) or complexed at an N:P of 15 with CNE containing SPAN 60 or 85 in a squalene emulsion or with NLCs containing Span 60, 80, or 85 and squalene/dynasan, or NLC containing Span 60 and Miglyol®/dynasan emulsion. Two technical ELISA replicates per donor were performed and the mean of each donor is plotted along with the mean±S.D. of the 6 donors. Data was analyzed by multiple one-way ANOVA with Tukey's multiple comparison test (NLC-Span60-Squalene or NLC-Span85-Squalene compared to either Naked or CNE-Span 85,  p<0.005).

FIG. 25 depicts kinetics of protein expression following in vivo delivery of rvRNA formulated with $NLC_{v1}$ or CNE. rvRNA encoding SEAP was formulated with either $NLC_{v1}$, CNE, or 10% sucrose (naked) and 100 ng was administered via the IM route to C57BL/6 mice (n=3/group). Mice mock injected with 10% sucrose alone were used as a negative control. Mice were bled on days 3, 7, 14, 21, and 28 and serum SEAP activity was measured by SEAP assay.

FIG. 26 depicts optimization of rvRNA loading capacity of $NLC_{v1}$. rvRNA encoding SEAP was diluted in 10% sucrose to final concentrations of 400, 300, 200, 100, and 40 μg/ml and complexed 1:1 with $NLC_{v1}$ by gentle pipetting. CNE was complexed 1:1 with 40 μg/ml of rvRNA. Complexed or unformulated rvRNA was then diluted in 10% sucrose for dosing such that each 50 μl injection IM resulted in a 100 ng dose. Mice were then bled 3 days later and serum SEAP activity was measured by SEAP assay and compared to mock-injected mice.

FIG. 27 depicts the effect of decreasing squalene concentration in high-capacity NLCs on serum SEAP activity. High-capacity NLCs (containing 3% w/v DOTAP) manufactured with 30, 15, 7.5, and 3.75% w/v squalene were complexed 1:1 with rvRNA encoding SEAP at an N:P of 37 and 100 ng was administered via IM route in C57BL/6 mice (n=3/group) and serum SEAP activity was measured 3 days later and compared to unformulated rvRNA- or mock-injected mice.

FIGS. 28A-G depict immunogenicity and efficacy of $NLC_{v1}$/rvRNA complexes in C57BL/6 mice. $NLC_{v1}$ was complexed with rvRNA or mRNA encoding ZIKV prM/E at an N:P of 50 and a single 1 μg dose was administered to C57BL/6 mice via IM injection (n=9/group) and 14 days later, bled to assess neutralizing antibody titers by $PRNT_{80}$ (FIG. 28A) compared to mock vaccinated mice or 10 or 1 μg naked rvRNA or mRNA (n=9/group), or 1 μg rvRNA formulated with CNE at an N:P of 50. Data are presented as individual values as well as mean±S.D. Thirty days after immunization, 6 mice per group were challenged with 5 $log_{10}$ PFU of ZIKV Dakar strain 41525 following antibody blockade of type I interferon, as described in Smith et al. PLoS Negl Trop Dis 11(1):e0005296 (2017), and bled 4 days later to quantify viremia by plaque assay (FIG. 28B). Mice were monitored daily for survival (FIG. 28C) and weight loss (FIG. 28D). The remaining 3 mice per group were administered a second immunization on day 30 to assess post-boost $CD8^+$ T-cell responses. Fourteen days later, mice were euthanized and splenocytes were isolated, stained, and % $B220_{lo}CD8^+$ T cells that were $IFN\gamma^+$ (FIG. 28E), $CD107a^+$ (FIG. 28F), or $TNF\alpha^+$ (FIG. 28G) were quantified by flow cytometry (FIG. 37).

FIG. 29 depicts an exemplary fusion protein, ID91 comprising four Mtb antigens/proteins: Rv3619, Rv2389, Rv3478, and Rv1886 (top) and an alpha virus replicon design that encodes ID91. The replicon construct contains a *Gaussia* luciferase signal as a reporter gene.

FIGS. 30A-B depict the percent of TH1 cytokine-secreting CD4+/CD44+ (FIG. 30A) or CD8+/CD44+ T cells (FIG. 30B) from protein or RNA based ID91 vaccines. Statistical significance of P<0.05 was analyzed using two-way ANOVA and is denoted by an asterisk.

FIGS. 31A-D depict data from proliferating or cytokine-producing CD4+ population. Splenocytes from mice immunized with ID91 protein/GLA-SE (blue) or ID91 RNA/QG807 (red) were stimulated with medium, ID91 whole protein 13 peptide pool of 10 peptides-pooled ID91 overlapping peptides.

FIGS. 32A-D depict data from proliferating or cytokine-producing CD8+ population. Splenocytes from mice immunized with ID91 protein/GLA-SE (blue) or ID91 RNA/QG807 (red) were stimulated with medium, ID91 whole protein 13 peptide pool of 10 peptides-pooled ID91 overlapping peptides.

FIGS. 33A-B depict the observation the immunizations with ID91 RNA were prophylactically protective and induced differential CD8+ T cell epitopes when compared to ID91 protein. Cohorts of mice were immunized twice, three weeks apart with either ID91 protein+GLA-SE or Alpha virus RNA encoding ID91 antigens, spleenocytes were isolated and restimulated in vitro using ID91 peptides. Intensity scale of heat map indicates percent of CD4+ (red) and CD8+ (blue) T cell proliferation and cytokine responses in response to each pool (FIG. 30A). In FIG. 33A, M=medium only, ID91=ID91 only, and PP1-PP13 refer to peptide pools 1-13. Scales on the right side indicate the percent of proliferating or cytokine+cells from CD4+ or CD8+ population. FIG. 33B depicts bacterial burden assessed from lung homogenates 3 weeks post challenge with Mtb H37Rv. Cohorts of mice were immunized once 3 weeks pre-challenge with either saline, ID91 protein+GLA-SE, or Alpha virus RNA encoding ID91 antigens in the RNA formulation. Significance of P<0.05 compared to saline by one-way ANOVA with Dunnetts multiple comparisons test is denoted by an asterisk.

FIGS. 34A-B compare signal sequences derived from Zika (ZIKV) or Japanese Encephalitis (JEV) Viruses. FIG. 34A depicts design of rvRNAs encoding ZIKV prM/E with a ZIKV or JEV signal sequence upstream of prM. FIG. 34B depicts rvRNAs encoding ZIKV prM/E with ZIKV or JEV signal sequences were formulated in 10% sucrose (naked) or with cationic nanoemulsion (CNE) and 10 μg of the former or 1 μg of the latter were injected via IM route into C57BL/6 mice (n=5/group) and PRNT80 titers were measured in the serum 21 days later. Mice were then boosted with a second immunization and PRNT80 titers were measured an additional 21 days later.

FIG. 35 depicts the effect of surfactant to oil molar ratio on NLC particle size (Z-average (nm)). The surfactant to oil ratio was changed by varying the amount of total surfactant while holding the amount of oil constant. Experimental data was fit to a one-phase exponential decay equation (R-square=0.972). All formulations were microfluidized under identical conditions (10 passes at 30,000 psi).

Figure 36A:
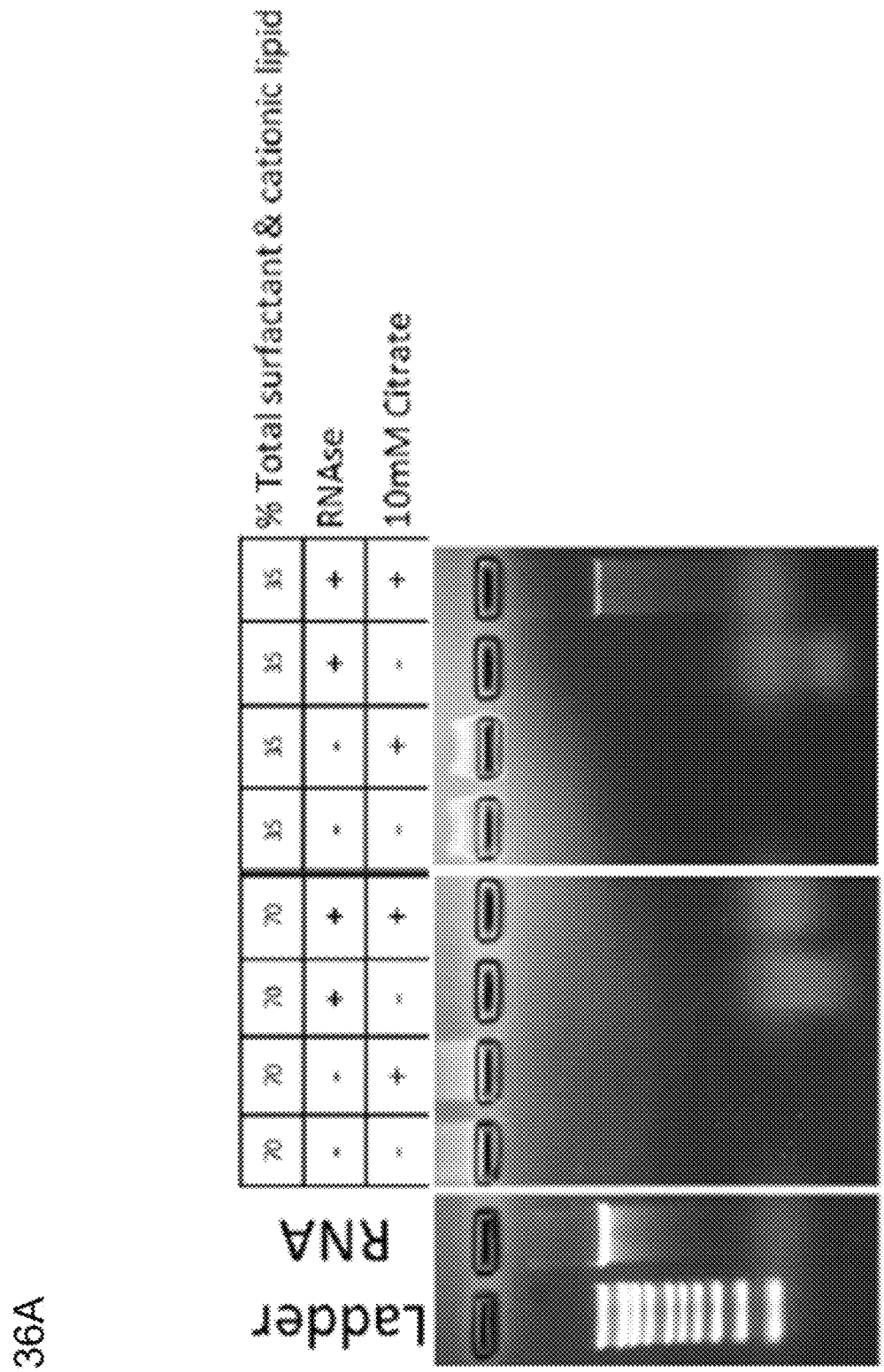
Figure 36B:
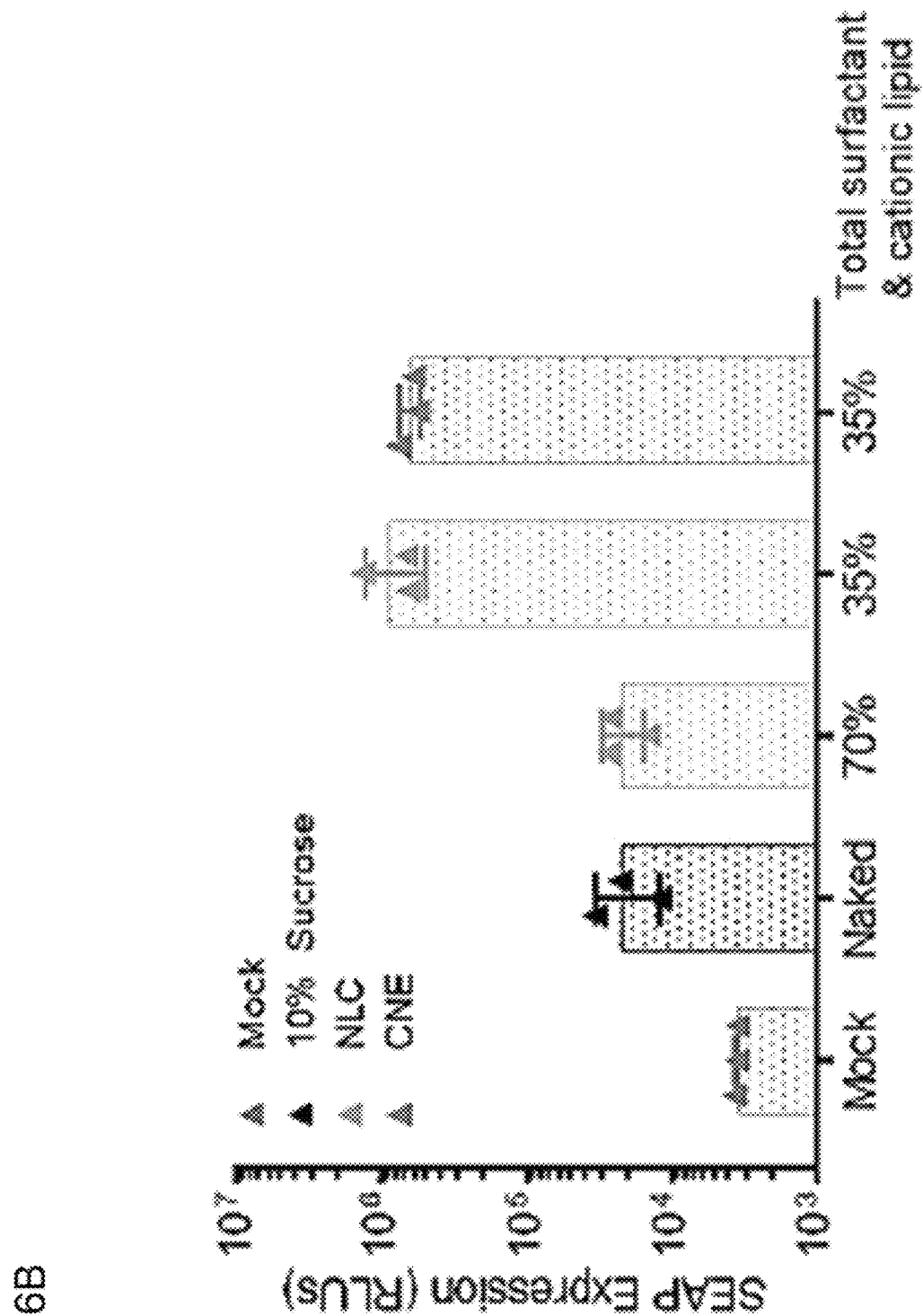

FIG. 36A-B depict the effect of hydrophilic surfactant on protection from RNase challenge and delivery of SEAP expressing rvRNA in vivo. rvRNA was complexed with variations of NLCs made with 70% or 35% total surfactant & cationic lipid manufactured with or without 10 mM citrate buffer and assessed for their ability to protect rvRNA from RNase challenge (FIG. 36A). C57BL/6 mice (n=3/group) were administered rvRNA encoding SEAP complexed with 10% sucrose (naked) or with NLCs made with 70% or 35% total surfactant & cationic lipid, or with CNE, and serum SEAP activity was measured 3 days later (FIG. 36B).

FIG. 37 depicts an exemplary flow cytometry gaiting strategy.

Figure 38A:
Figure 38B:
Figure 39A:
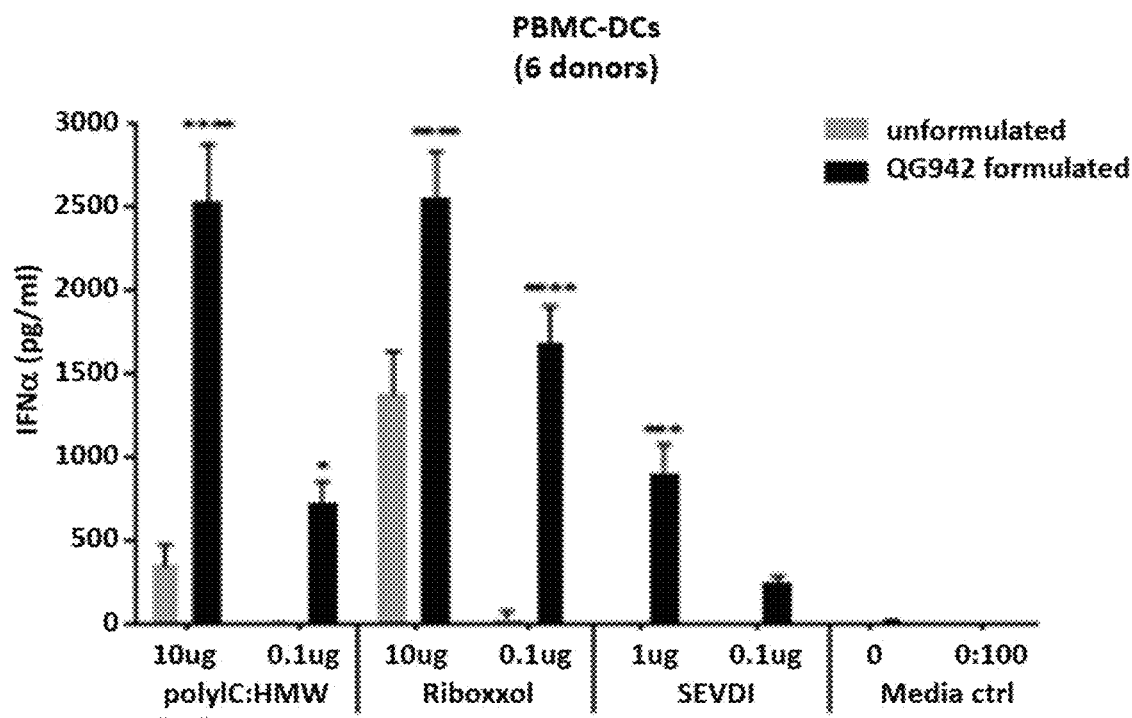
Figure 39B:
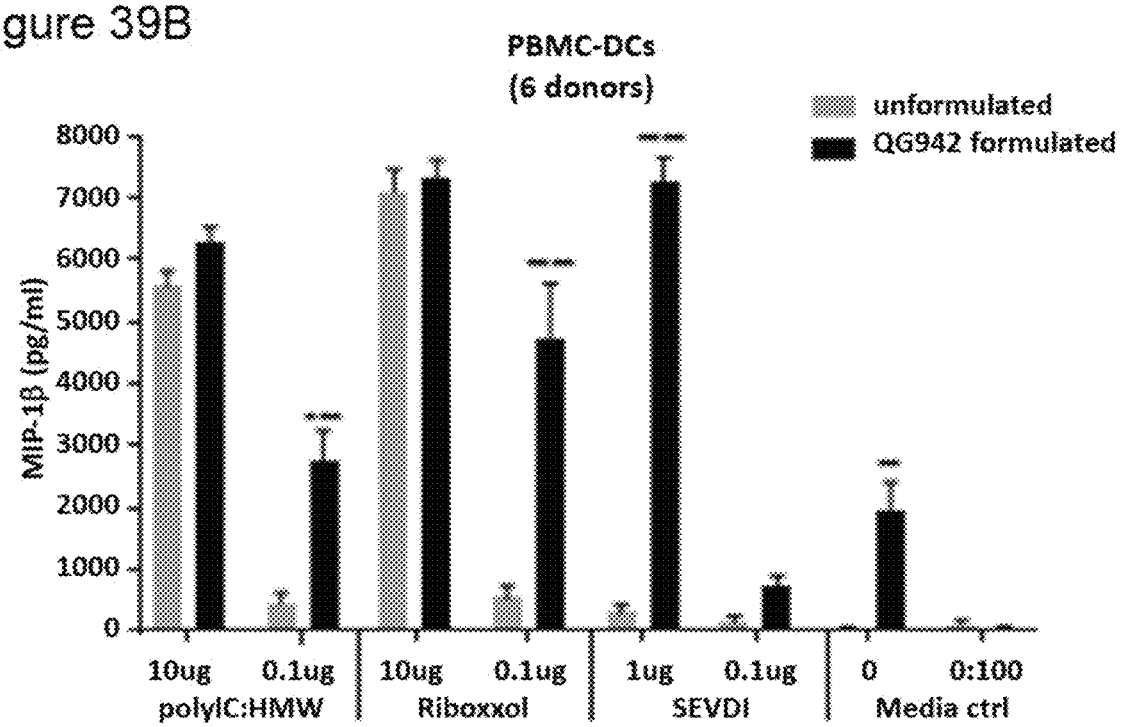
Figure 39C:
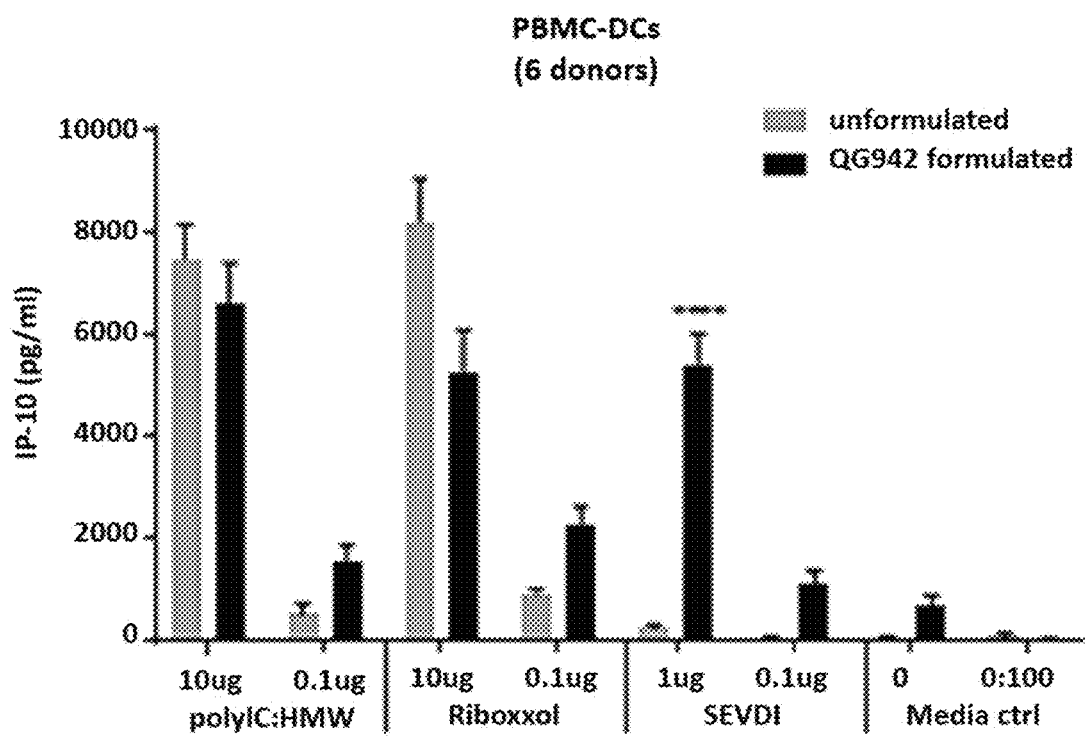
Figure 39D:
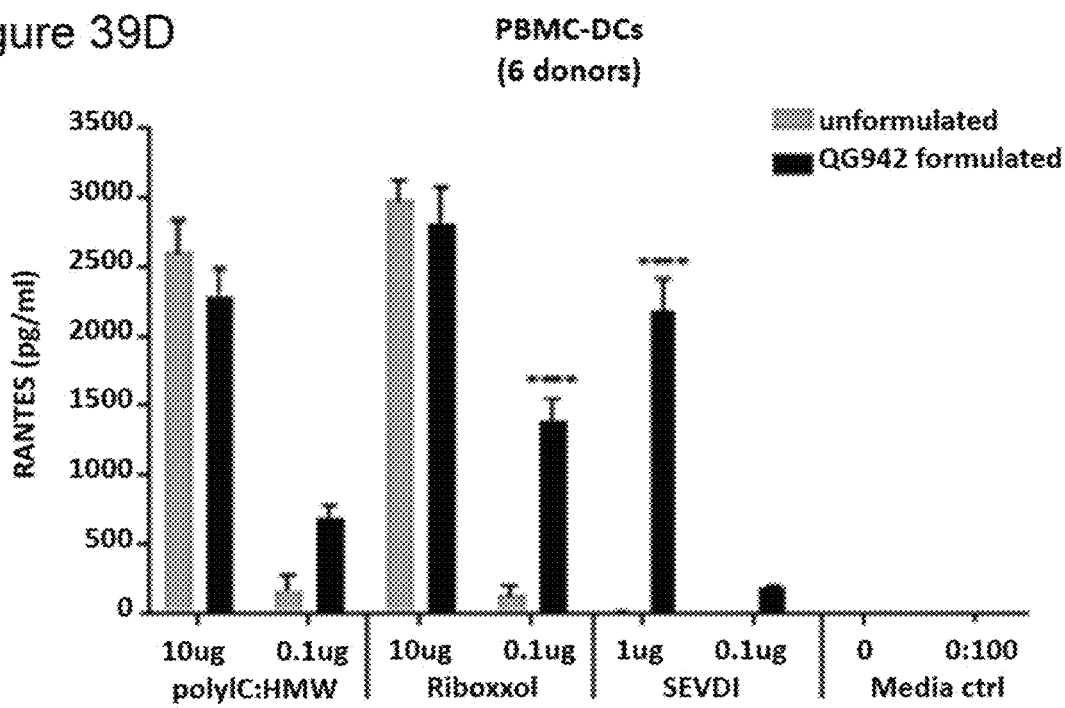
Figure 39E:
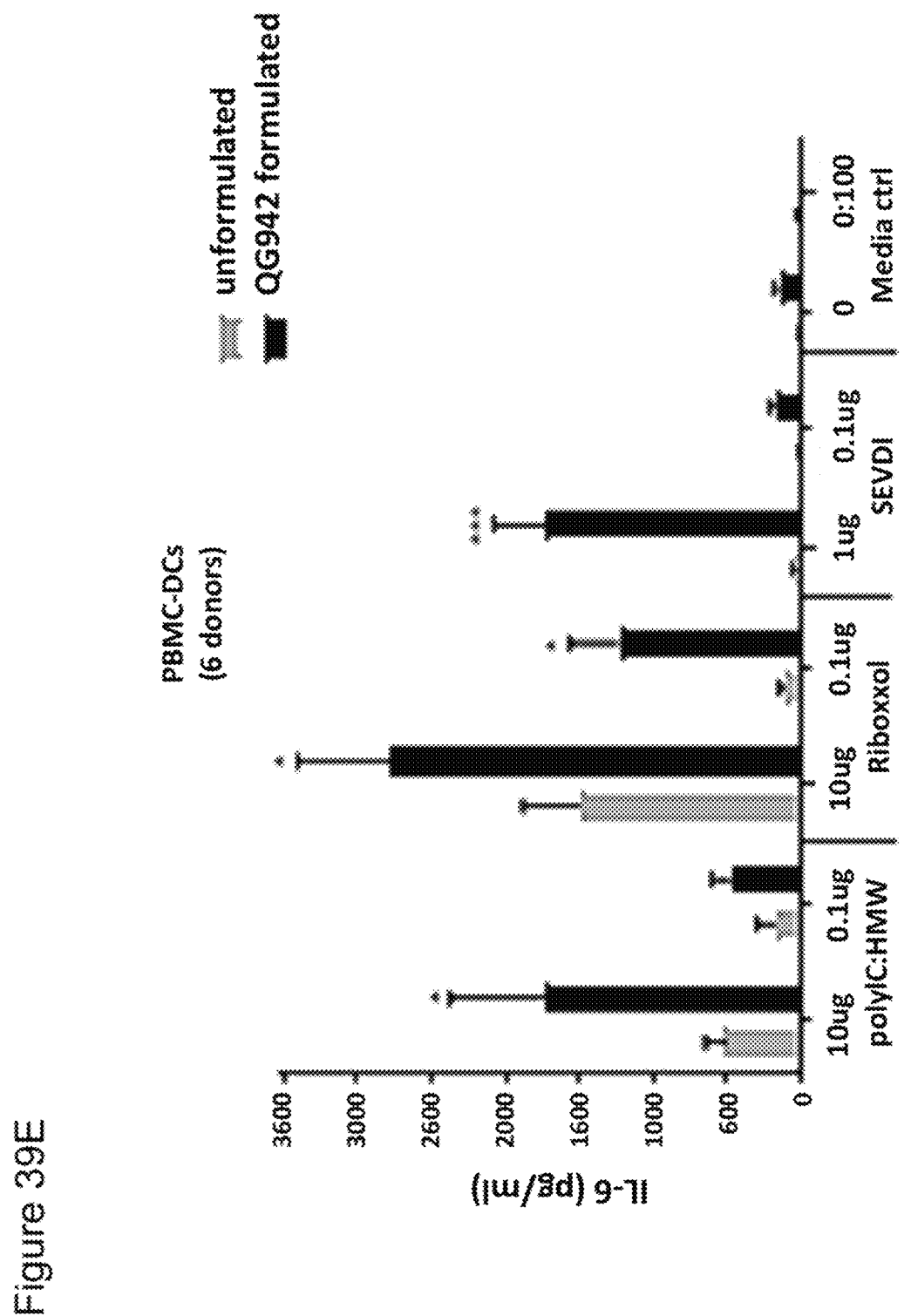

FIGS. 38A-B depict examples of ID91 modified with restriction enzymes. FIG. 38 A depicts vector pET29, and FIG. 38B depicts vector pET28.

FIGS. 39A-E depict innate immune signaling in human PBMC-derived DCs after stimulation with TLR3 (Roboxxol, pIC:HMW) and RIG-I (SEVDI) agonists, with and without NLC formulation. PBMC-DCs from six human donors were stimulated with polyIC:HMW, Riboxxol or SEVDI, either formulated with NLC ("QG942 formulated") or naked ("unformulated"). Formulation-only control is labeled "media ctrl." After 24 hours incubation at 37° C. and 5% CO2 atmosphere, supernatants were assayed for concentration of innate immune markers using commercially available ELISA kits. Statistical analysis was performed by 2-way ANOVA with Sidak's multiple comparisons test. P-values: * $p<0.05$,  $p<0.005$, * $p<0.0005$, **** $p<0.0001$.

Figure 40:
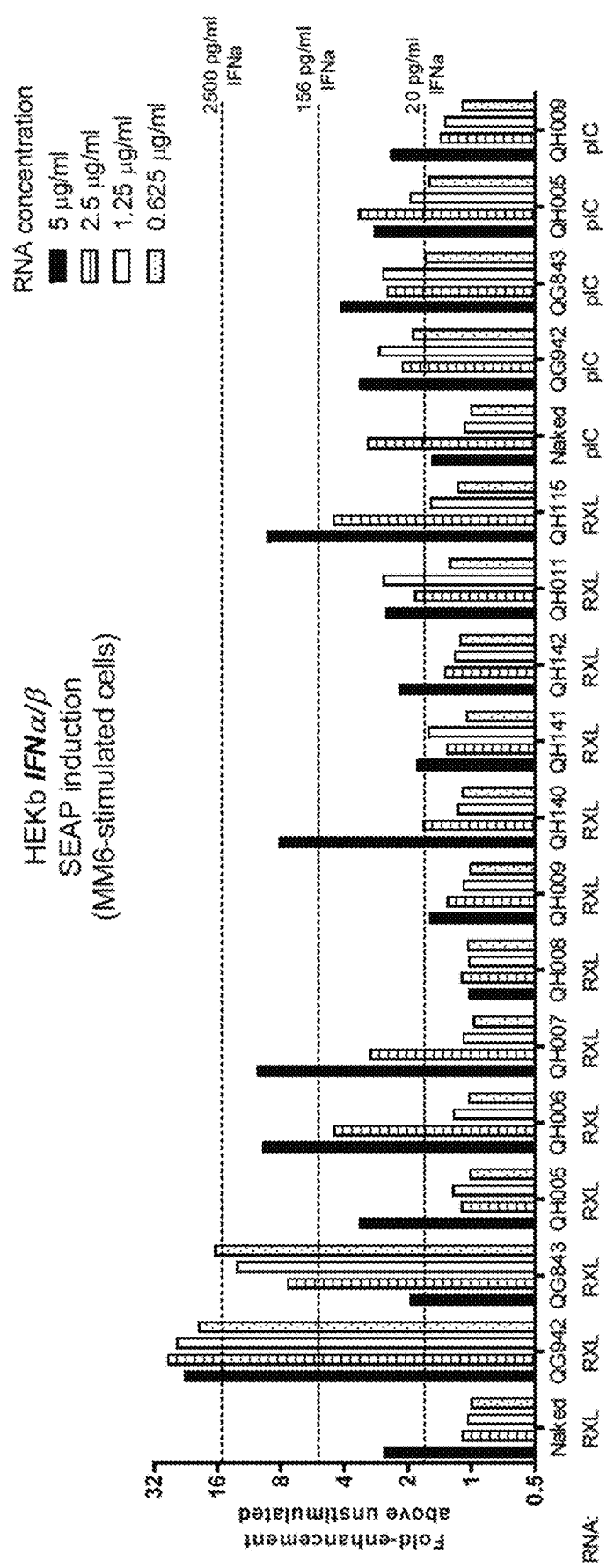

FIG. 40 depicts induction of IFNα/β in MM6 cells stimulated with Riboxxol or pIC:HMW adjuvant. Cells were stimulated with either naked or formulated RNA; formulation compositions provided in Tables 2 and 7. IFNα/R from supernatants of stimulated MM6 cells was measured relative to unstimulated MM6 cells and determined using a HEK-blue IFNα/R SEAP reporter cell line. Dashed lines correspond to relative stimulation as measured after addition of nown IFNα concentration.

Figure 41:
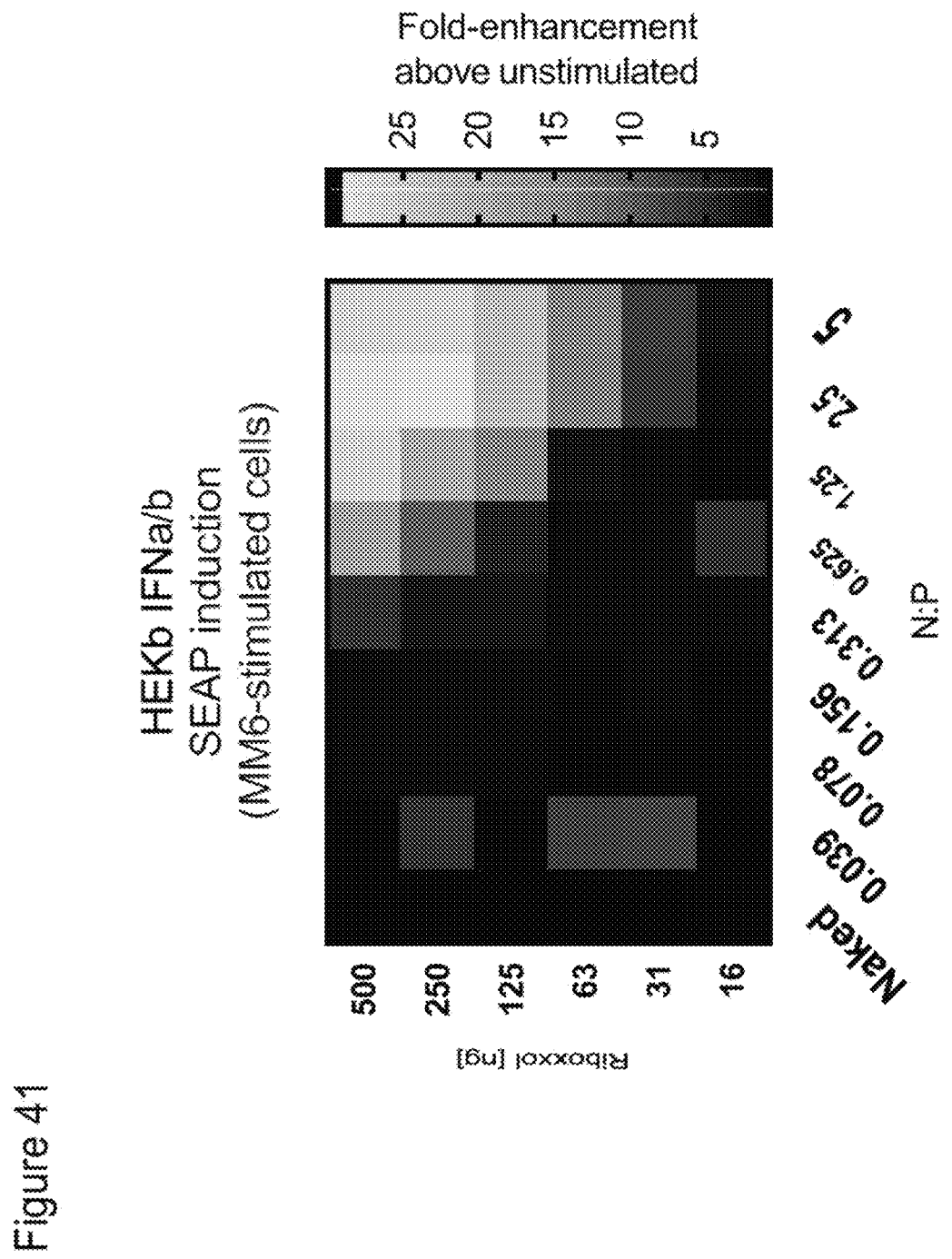
Figure 42A:
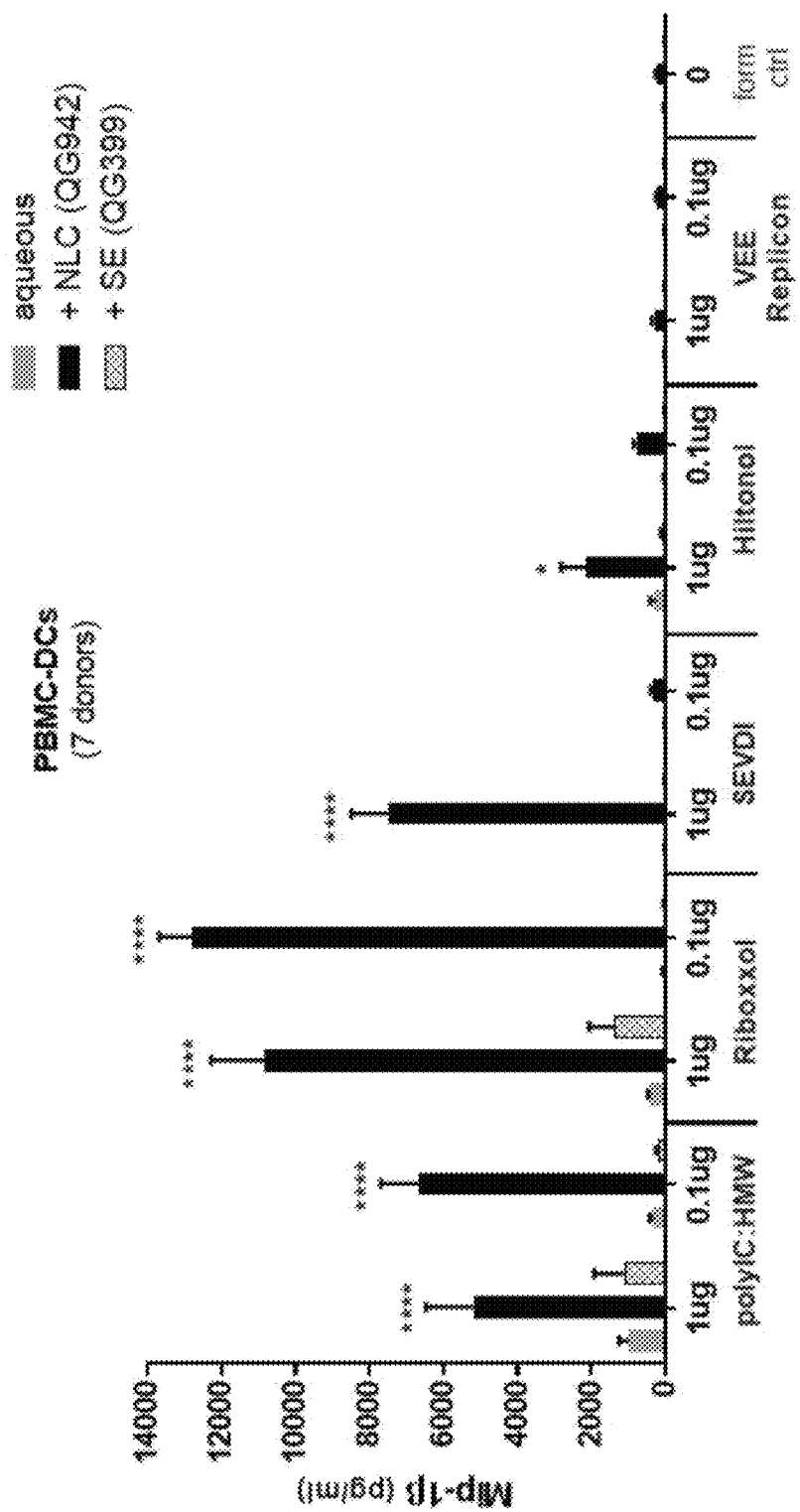
Figure 42B:
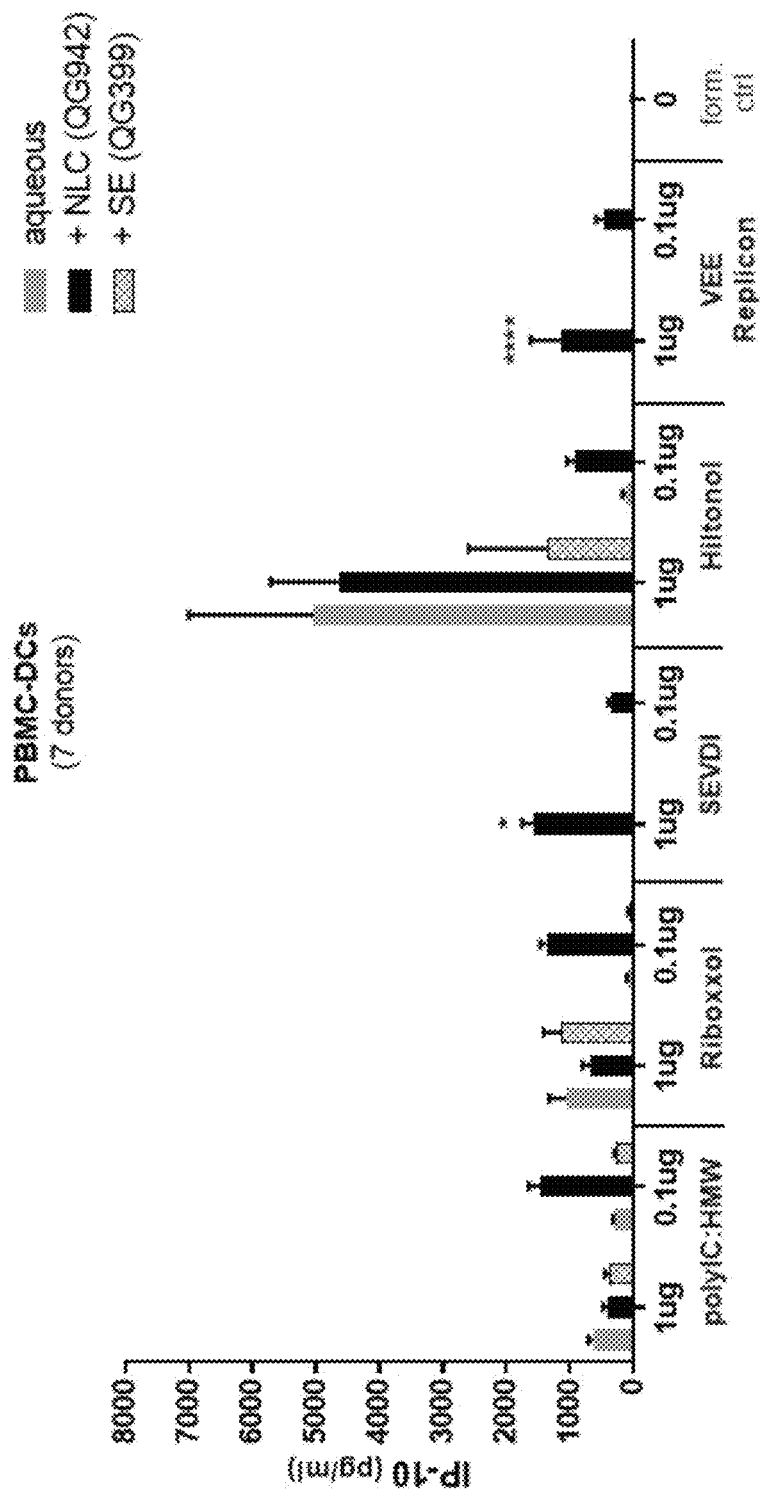
Figure 42C:
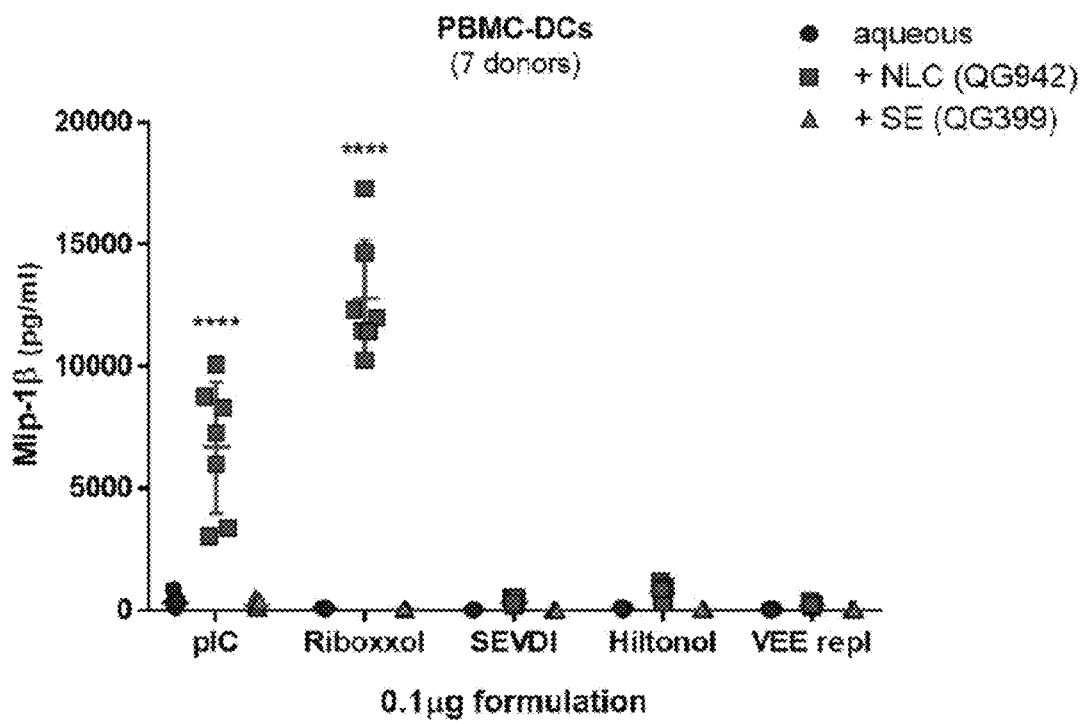
Figure 42D:
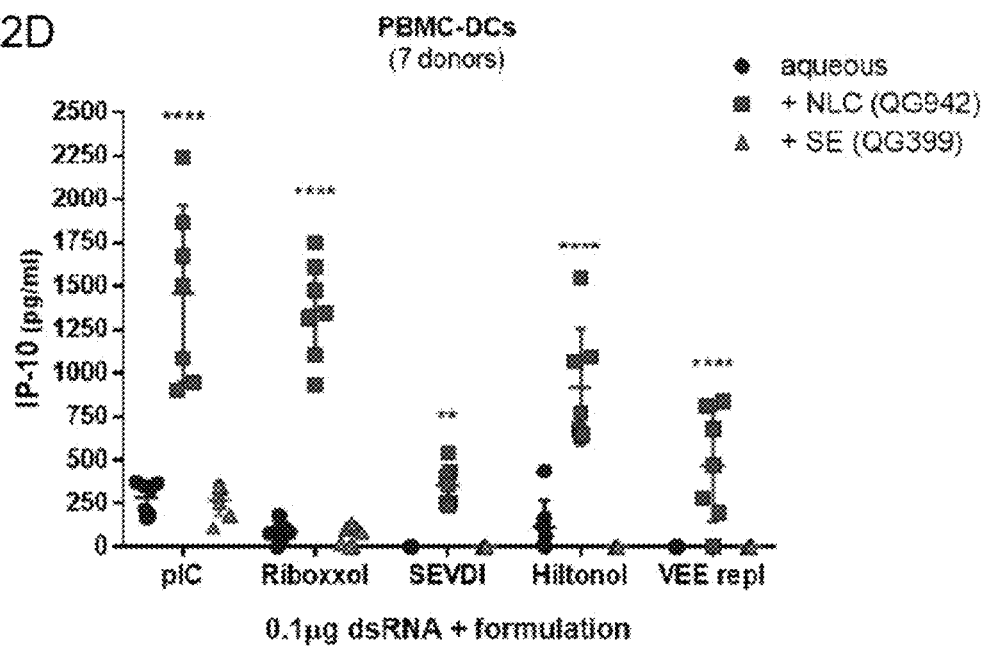

FIG. 41 depicts a heat map summarizing IFNα/R induction as a function of N:P molar ratio and riboxxol dose.

FIGS. 42A-D depict cytokine expression after administration of dsRNA adjuvants formulated with NLC or SE.

Figure 43:
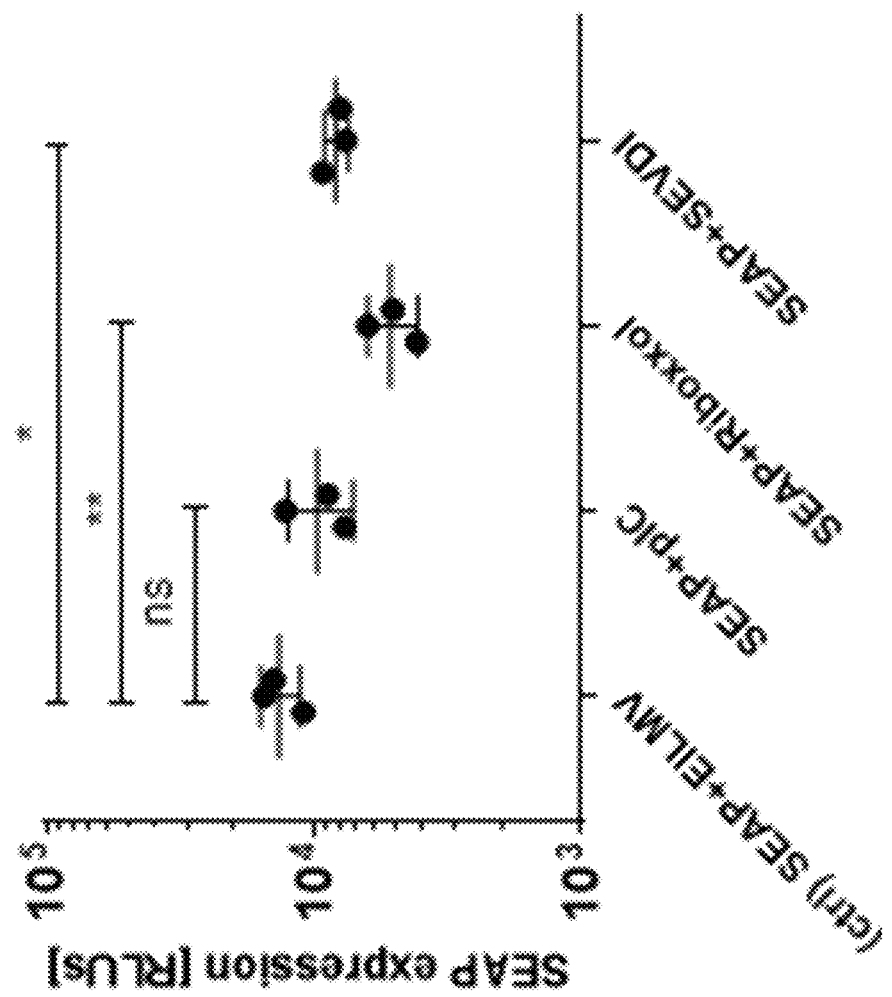

FIG. 43 depicts decreased SEAP expression after administration of SEAP formulated with dsRNA adjuvants (TLR3 ligand) and NLC.

Figure 44A:
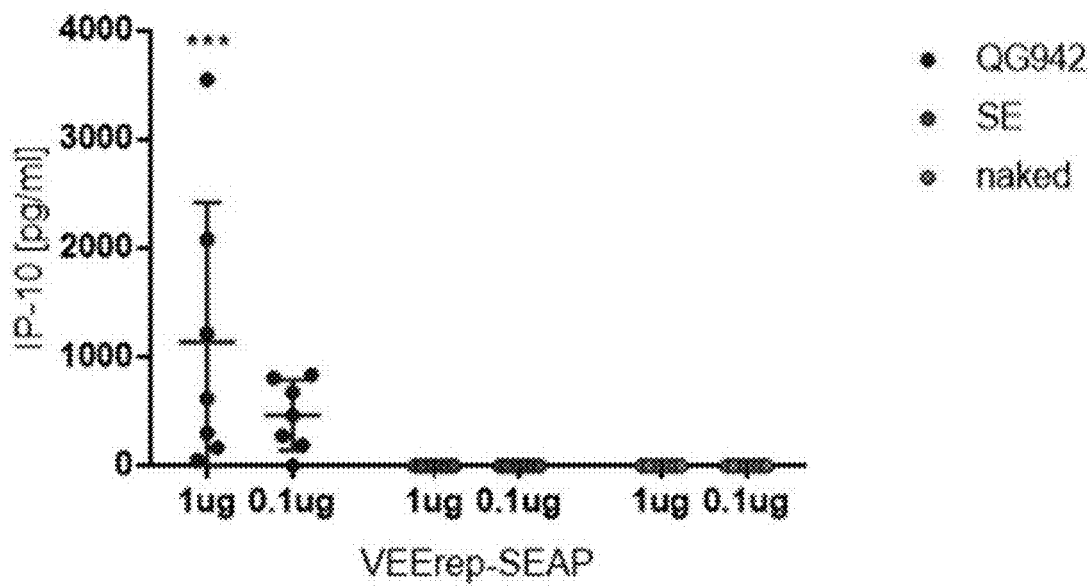
Figure 44B:
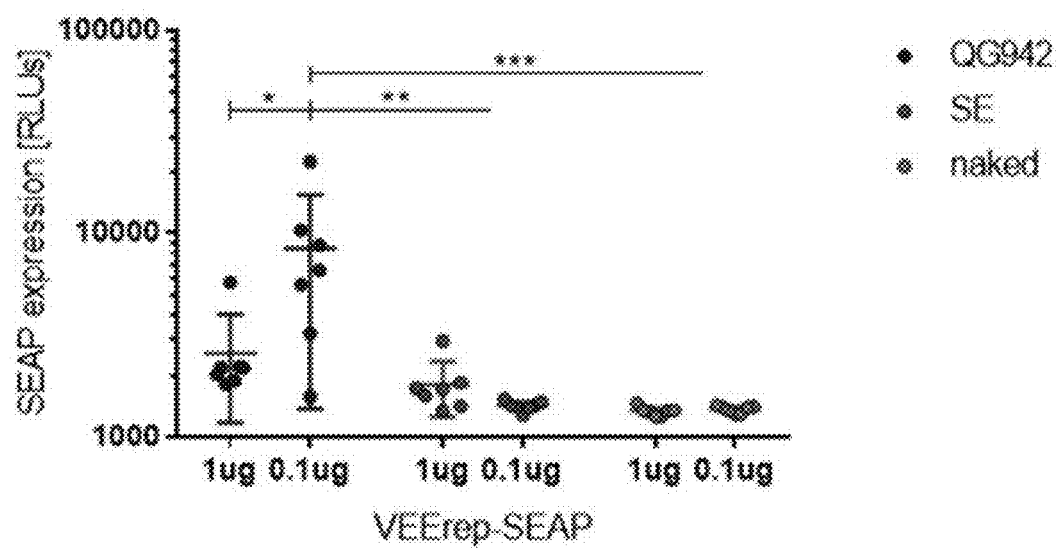

FIGS. 44A-B depict IP-10 (FIG. 44A) and SEAP expression (FIG. 44B) after administration of VEErep-SEAP formulated with NLC, SE, or control. In FIG. 44A ***=statistical significance of 1 μg+QG942 vs. 1 μg naked. In FIG. 44B *=statistical significance of 1 μg+QG942 vs. 0.1 μg+QG942, =statistical significance of 0.1 μg+QG942 vs. 0.1 μg SE or naked, *=statistical significance of 0.1 μg+QG942 vs. 0.1 μg naked.

Figure 45:
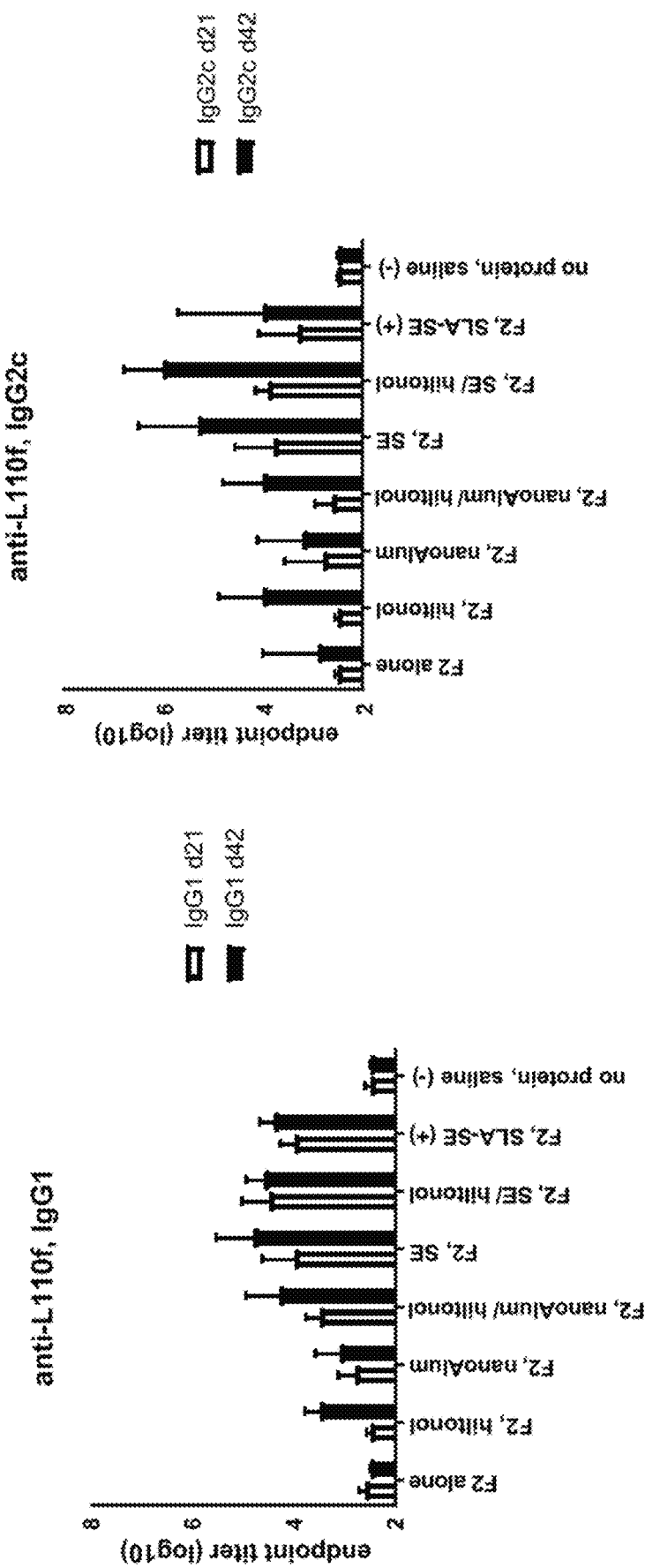

FIG. 45 depicts antigen-specific antibody responses. C57BL/6 mice were injected a total of 2 times, at a 3 week interval, with 1 μg LEISH-F2 protein mixed with the indicated adjuvant formulation. Sera were collected a day 21 (before booster immunization) and day 42 then antigen-specific IgG, IgG1 and IgG2c endpoint titers determined by ELISA. Data are shown as the mean and SD, 5 mice per group.

Figure 46B:
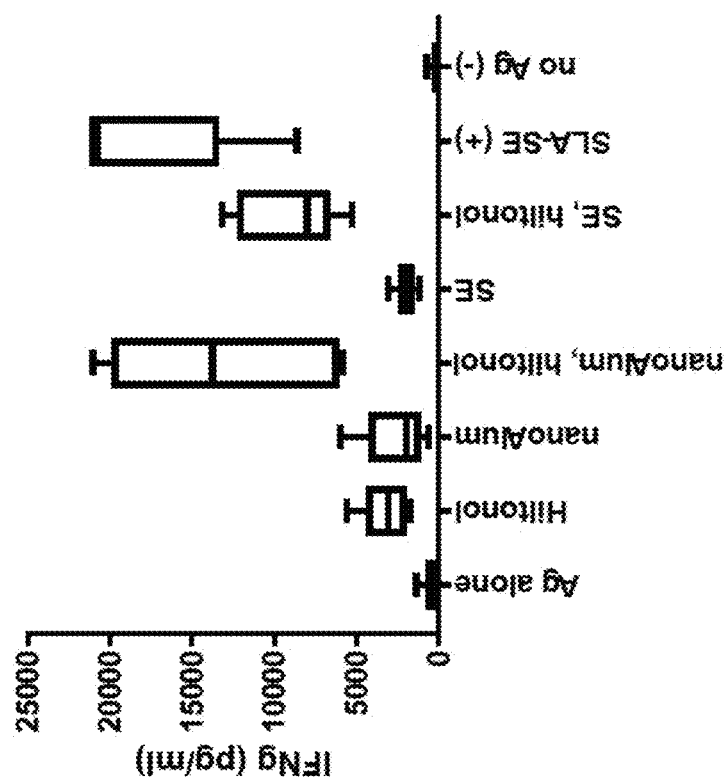
Figure 46A:
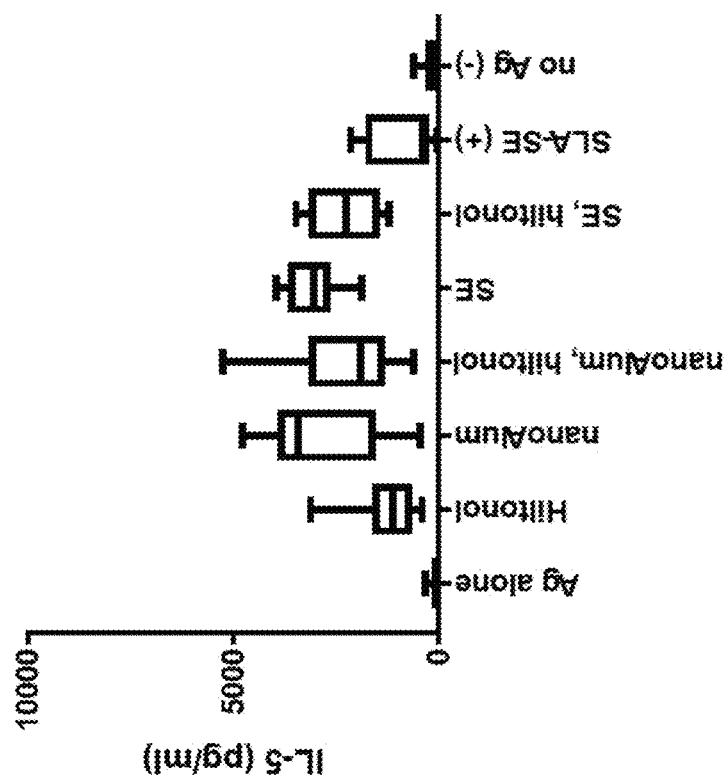

FIGS. 46A-B depict the effects of Hiltonol® formulation on T cell responses. C57BL/6 mice were injected a total of 2 times, at a 3 week interval, with 1 μg LEISH-F2 protein mixed with the indicated adjuvant formulation. Three weeks after the final immunization spleens were removed to prepare single cells suspensions cells were incubated with LEISH-F2 antigen then cytokine content in the culture supernatant determined by ELISA. Data are shown as minimum and maximum, with the box depicting the $25^{th}$ and $75^{th}$ percentiles and the mean indicated by the horizontal bar within the box, 5 mice per group.

FIGS. 47A-E depict the effects of Hiltonol® formulation on T cell responses. C57BL/6 mice were injected a total of 2 times, at a 3 week interval, with 1 μg LEISH-F2 protein mixed with the indicated adjuvant formulation. Three weeks after the final immunization spleens were removed to prepare single cells suspensions cells were incubated with F2 antigen then cell phenotypes determined by flow cytometry. Data are shown as individual points for each mouse, with the mean and SEM indicated by the horizontal and vertical bars, respectively. N=5 mice per group.

Figure 48:
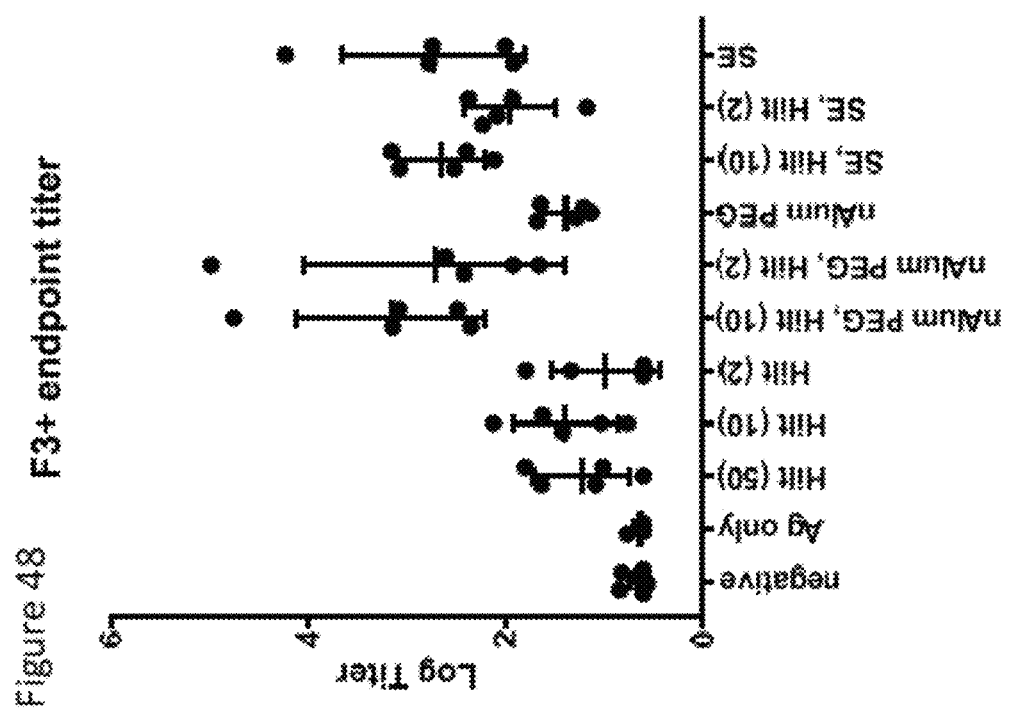

FIG. 48 depicts the effects of Hiltonol® formulation on antigen-specific antibody responses. C57BL/6 mice were injected once with 1 mg LEISH-F3+ protein mixed with the indicated adjuvant formulation. Four weeks after the immunization sera were collected and antigen-specific IgG endpoint titers determined by ELISA. Data are shown as individual points for each animal, along with the mean and SEM. N=5 mice per group.

Figure 49A:
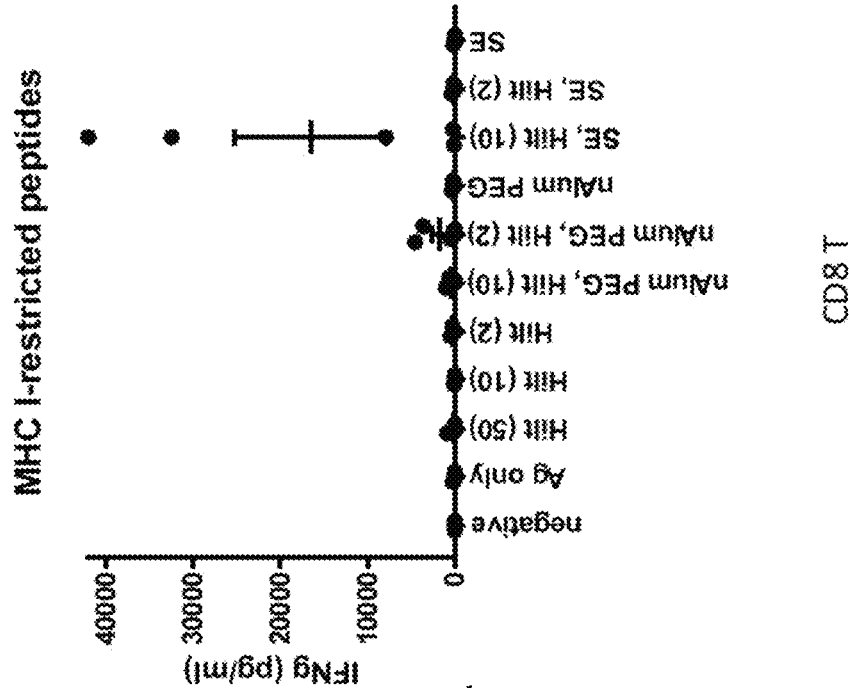
Figure 49B:
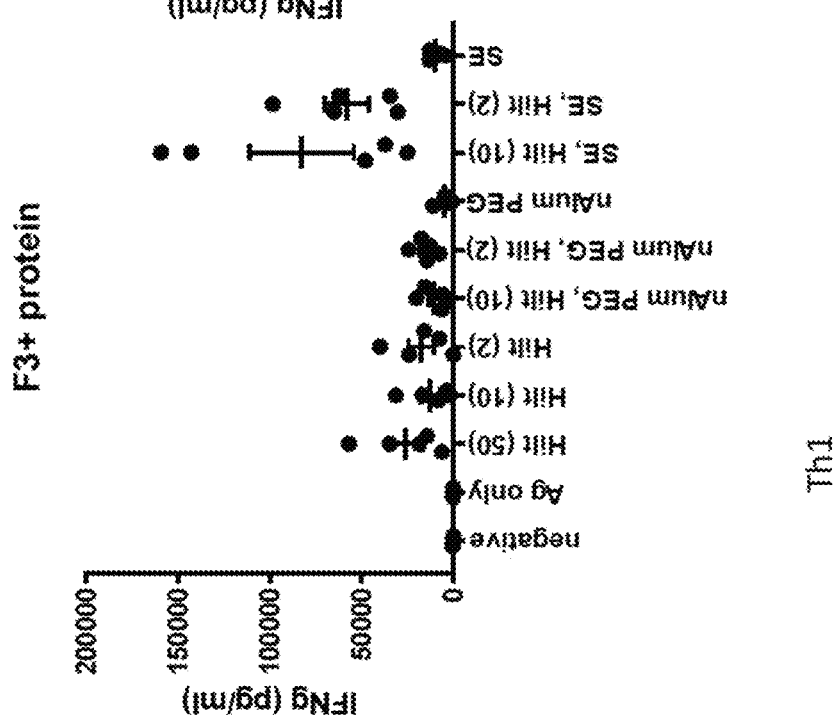
Figure 49C:
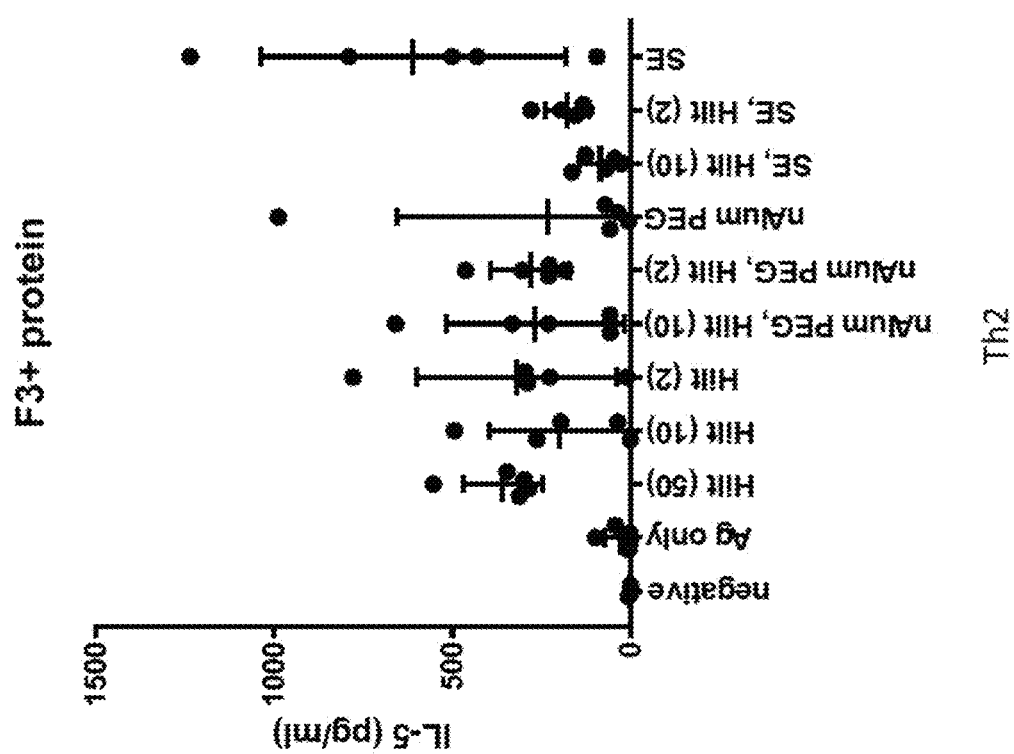
Figure 50A:
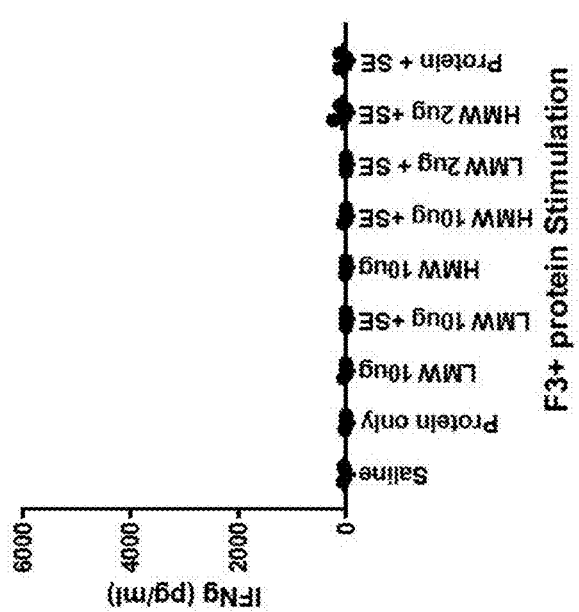
Figure 50B:
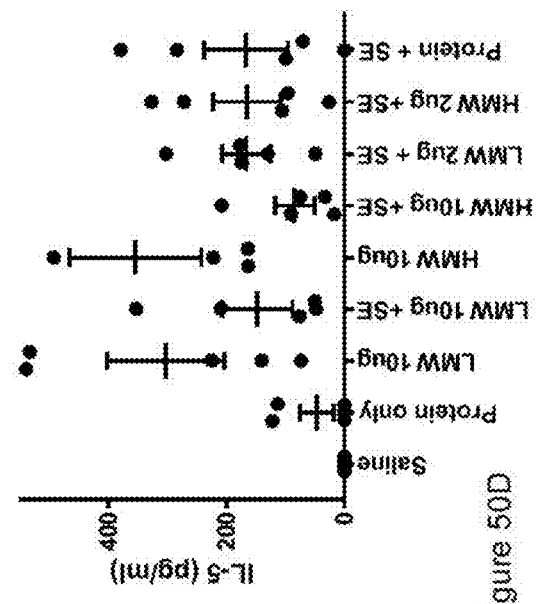
Figure 50C:
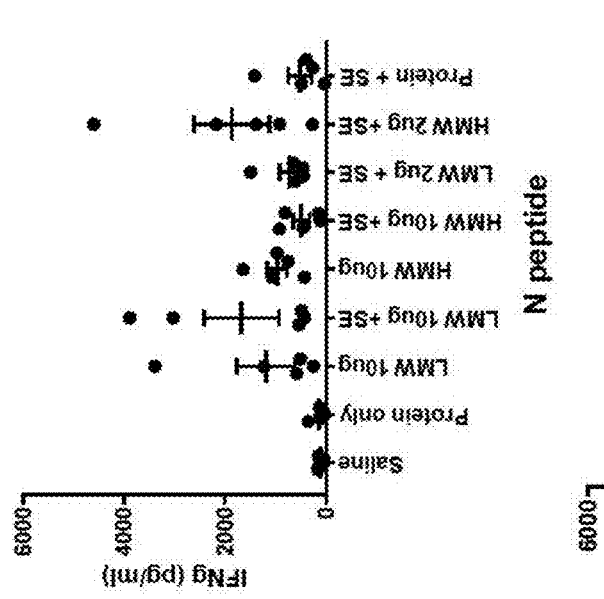
Figure 50D:
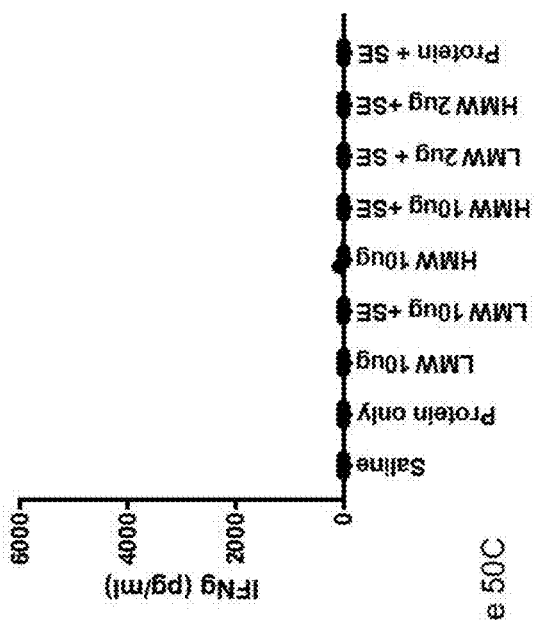
Figure 50G:
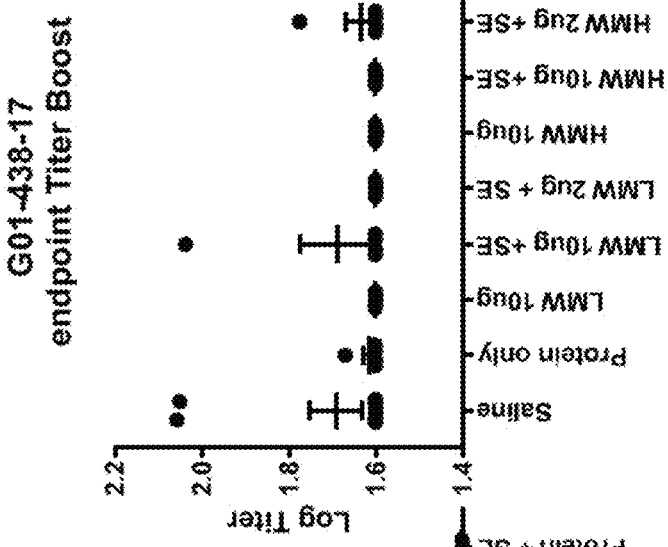
Figure 50F:
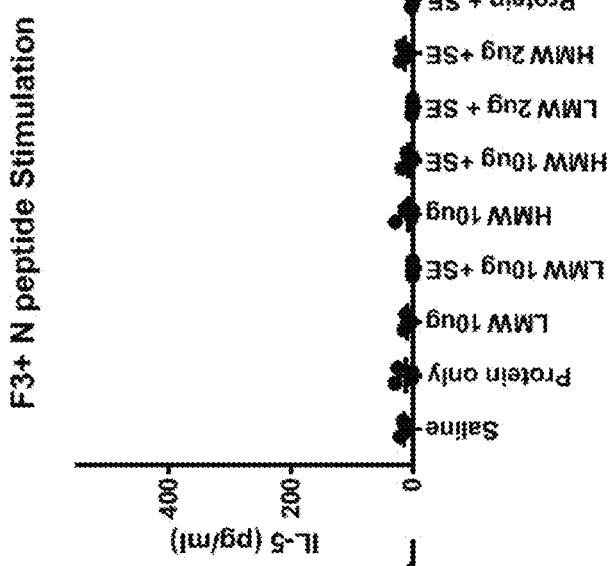
Figure 50E:
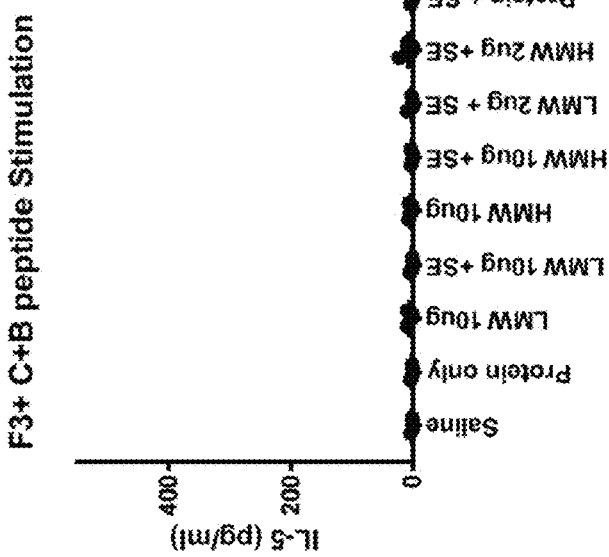

FIGS. 49A-C depict the effects of Hiltonol® formulation on T cell responses. C57BL/6 mice were injected once with 1 μg LEISH-F3+ protein mixed with the indicated adjuvant formulation. Four weeks after the immunization spleens were removed to prepare single cells suspensions cells were incubated with F3+ protein or MHCI-restricted peptides (CD8 T cell epitopes) then cytokine content in the culture supernatant determined by ELISA. Data are shown as individual points for each mouse, with the mean and SEM indicated by the horizontal and vertical bars, respectively. N=5 mice per group.

FIGS. 50A-G depict the impact of antigen vaccine delivery on immunogenic responses with different formulations.

Figure 51A:
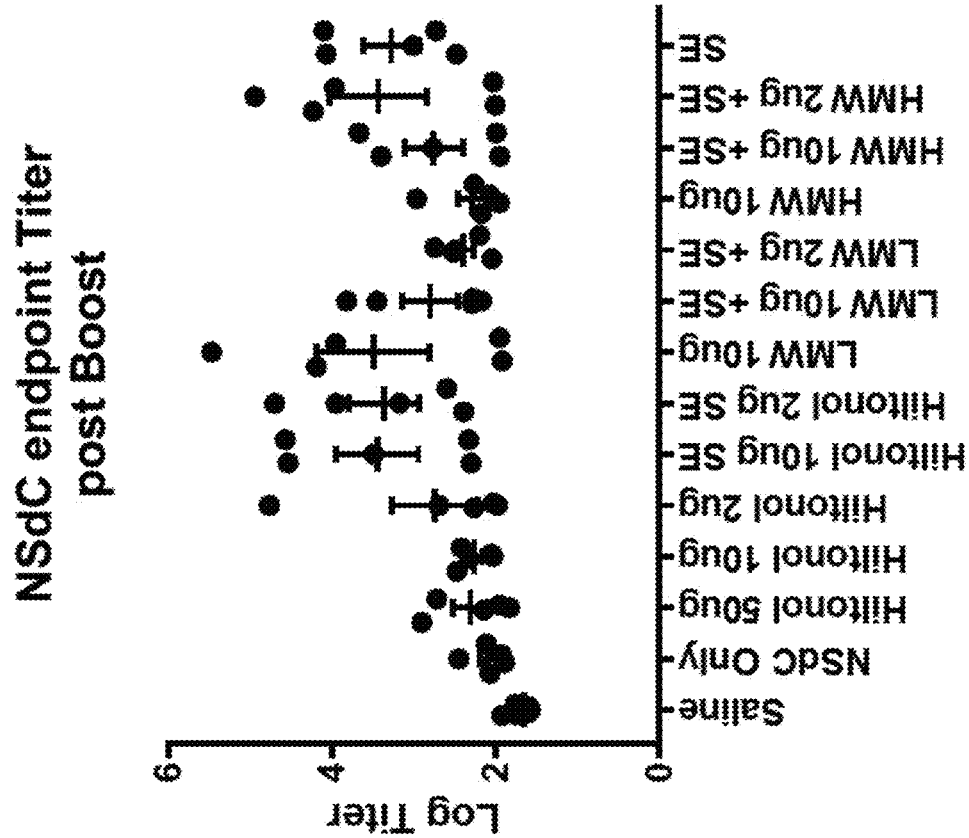
Figure 51B:
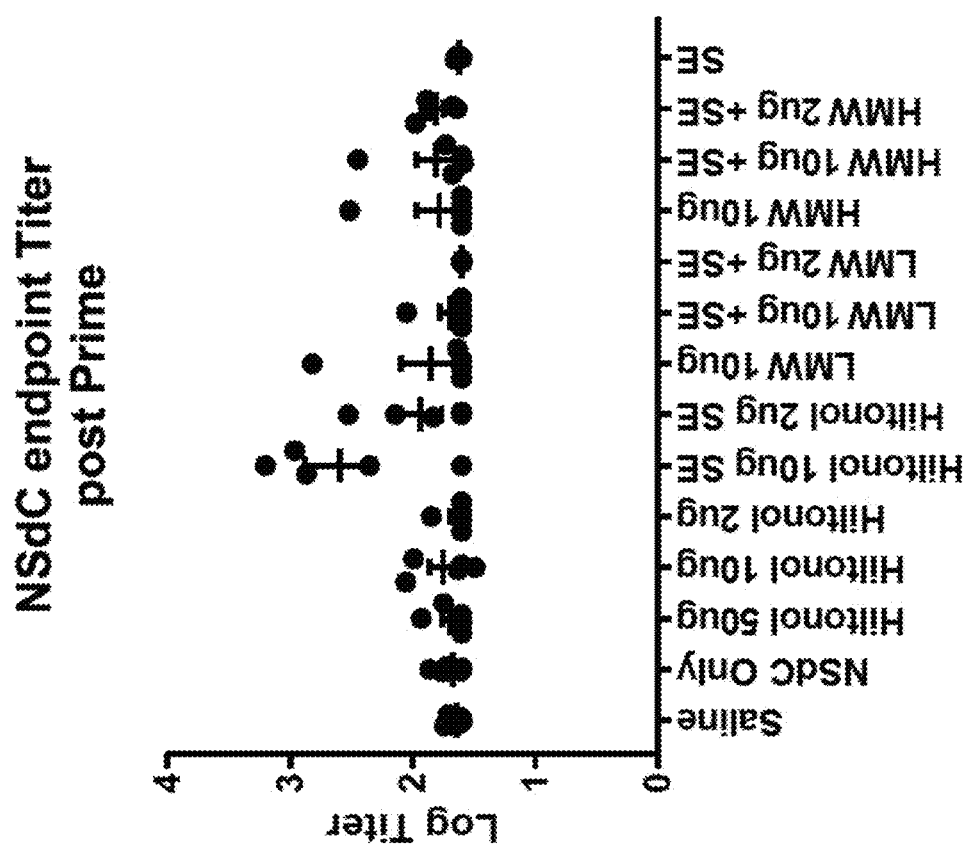
Figure 52A:
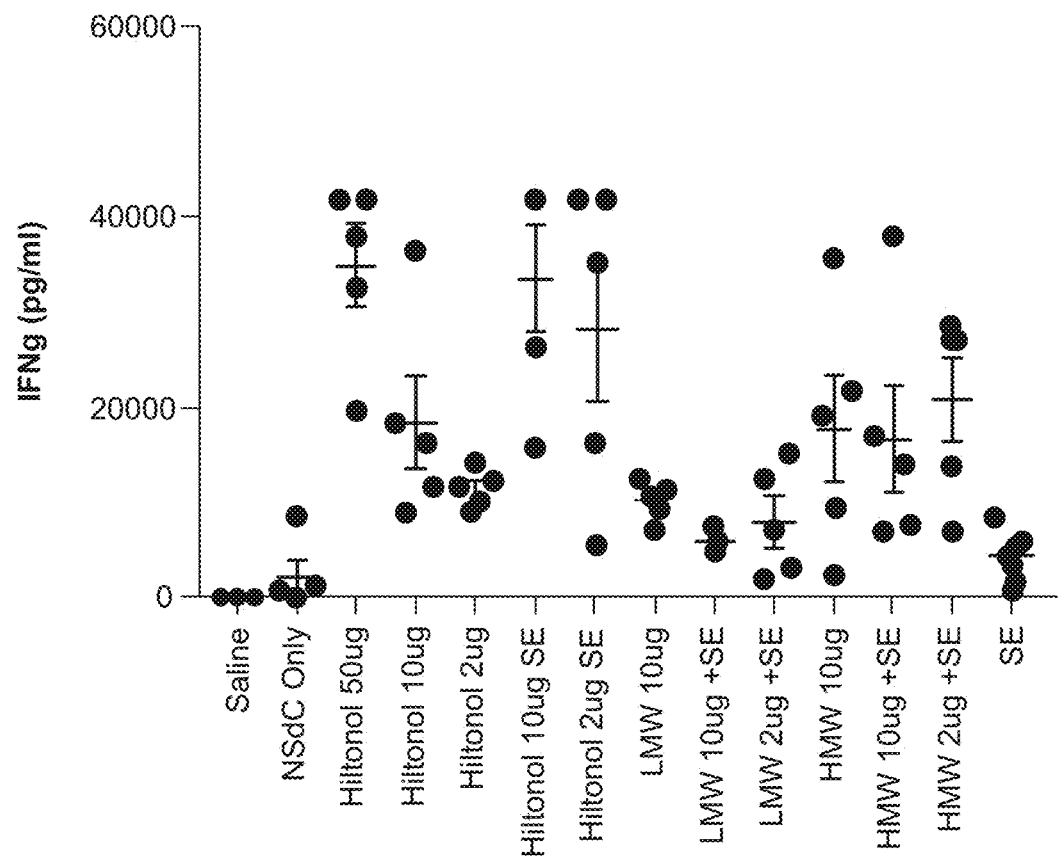
Figure 52B:
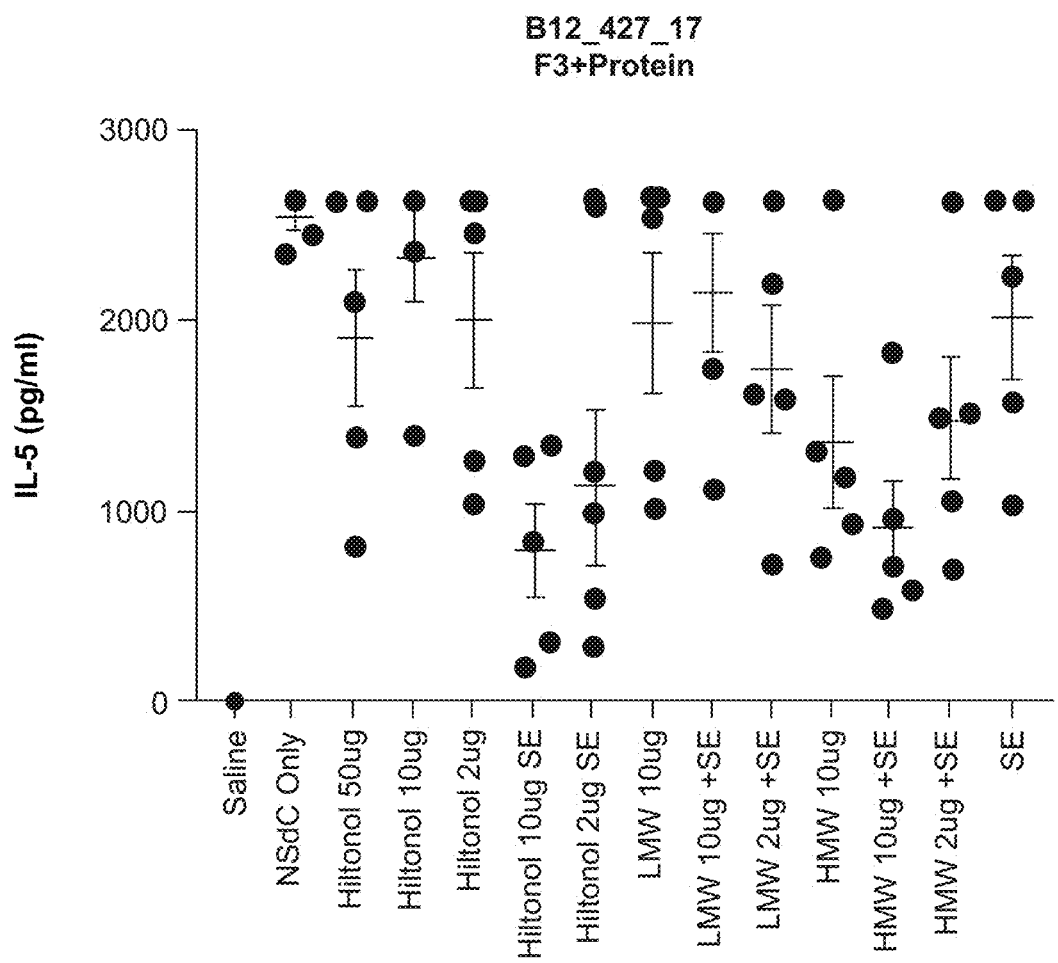
Figure 52C:
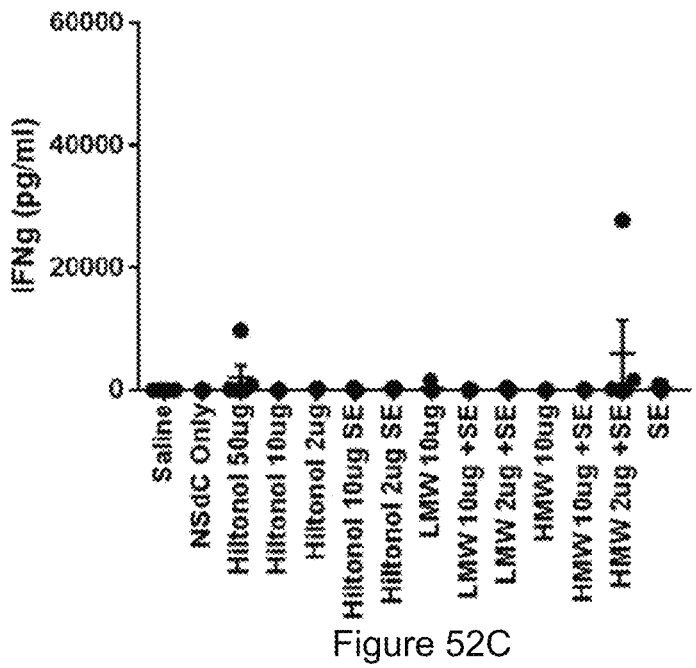
Figure 52D:
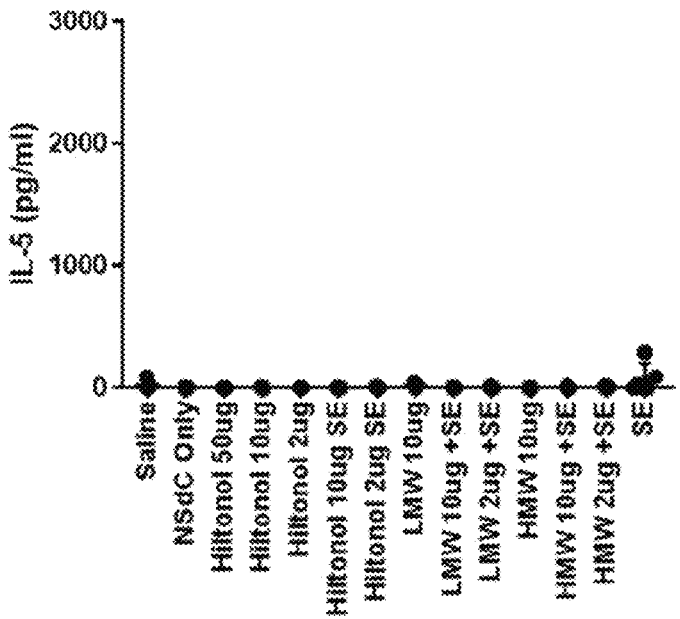
Figure 52E:
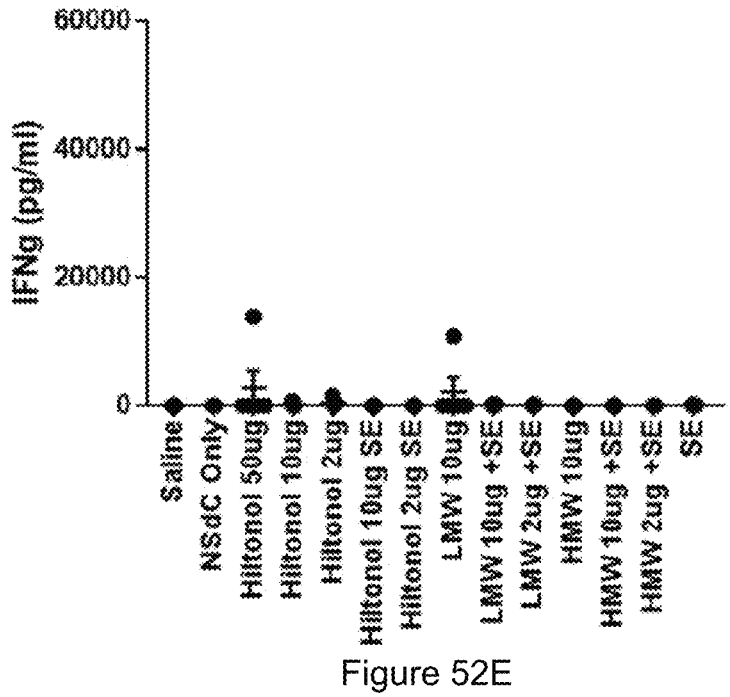
Figure 52F:
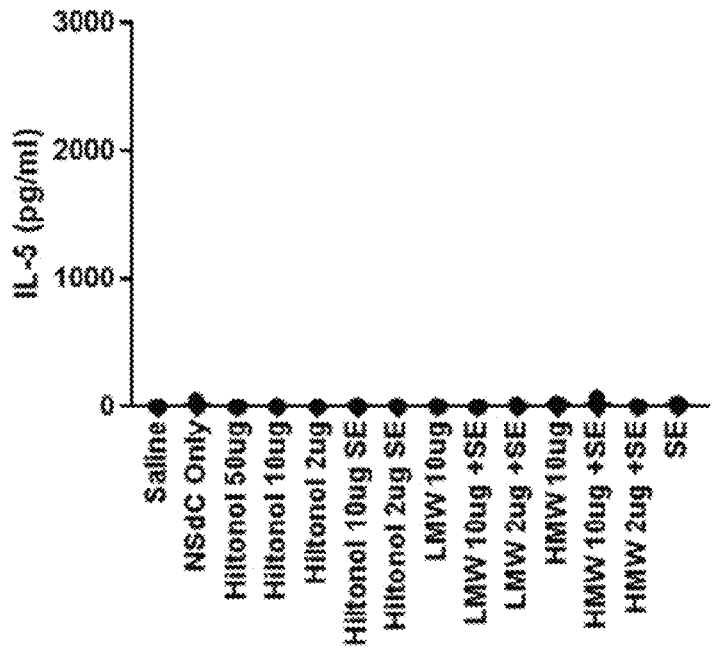

FIGS. 51A-B depict the impact of antigen vaccine delivery on immunogenic responses with different formulations.

FIGS. 52A-F depict the impact of antigen vaccine delivery on immunogenic responses with different formulations.

DESCRIPTION OF THE SEQUENCES

Table 1 provides a listing of certain sequences referenced herein.

TABLE 1

Table 1 provides a listing of certain sequences referenced herein.
Description of the Sequences

| Description | Sequences | SEQ ID NO |
|---|---|---|
| ID91 | MTINYQFGDVDAHGAMIRAQAGSLEAEHQAIISDVLTASDFWGGAGSAAC QGFITQLGRNFQVIYEQANAHGQKVQAAGNNMAQTDSAVGSSWADDID WDAIAQCESGGNWAANTGNGLYGGLQISQATWDSNGGVGSPAAASPQ QQIEVADNIMKTQGPGAWPKCSSCSQGDAPLGSLTHILTFLAAETGGCSG | 1 |

TABLE 1-continued

Table 1 provides a listing of certain sequences referenced herein.
Description of the Sequences

| Description | Sequences | SEQ ID NO |
|---|---|---|
| | SRDDVVDFGALPPEINSARMYAGPGSASLVAAAKMWDSVASDLFSAASA<br>FQSVVWGLTVGSWIGSSAGLMAAAASPYVAWMSVTAGQAQLTAAQVRV<br>AAAAYETAYRLTVPPPVIAENRTELMTLTATNLLGQNTPAIEANQAAYSQM<br>WGQDAEAMYGYAATAATATEALLPFEDAPLITNPGGLLEQAVAVEEAIDT<br>AAANQLMNNVPQALQQLAQPAQGVVPSSKLGGLWTAVSPHLSPLSNVSS<br>IANNHMSMMGIGVSMTNTLHSMLKGLAPAAAQAVETAAENGVWAMSSL<br>GSQLGSSLGSSGLGAGVAANLGRAASVGSLSVPPAWAAANQAVTPAAR<br>ALPLTSLTSAAQTAPGHMLGGLPLGHSVNAGSGINNALRVPARAYAIPRTP<br>AAGFSRPGLPVEYLQVPSPSMGRDIKVQFQSGGNNSPAVYLLDGLRAQD<br>DYNGWDINTPAFEWYYQSGLSIVMPVGGQSSFYSDWYSPACGKAGCQT<br>YKWETFLTSELPQWLSANRAVKPTGSAAIGLSMAGSSAMILAAYHPQQFI<br>YAGSLSALLDPSQGMGPSLIGLAMGDAGGYKAADMWGPSSDPAWERND<br>PTQQIPKLVANNTRLWVYCGNGTPNELGGANIPAEFLENFVRSSNLKFQD<br>AYNAAGGHNAVFNFPPNGTHSWEYWGAQLNAMKGDLQSSLGAG | |
| Rv3619 | MTINYQFGDVDAHGAMIRAQAGSLEAEHQAIISDVLTASDFWGGAGSAAC<br>QGFITQLGRNFQVIYEQANAHGQKVQAAGNNMAQTDSAVGSSWA | 2 |
| Rv2389 | DDIDWDAIAQCESGGNWAANTGNGLYGGLQISQATWDSNGGVGSPAAA<br>SPQQQIEVADNIMKTQGPGAWPKCSSCSQGDAPLGSLTHILTFLAAETGG<br>CSGSRDD | 3 |
| Rv3478 | VVDFGALPPEINSARMYAGPGSASLVAAAKMWDSVASDLFSAASAFQSV<br>VWGLTVGSWIGSSAGLMAAAASPYVAWMSVTAGQAQLTAAQVRVAAAA<br>YETAYRLTVPPPVIAENRTELMTLTATNLLGQNTPAIEANQAAYSQMWGQ<br>DAEAMYGYAATAATATEALLPFEDAPLITNPGGLLEQAVAVEEAIDTAAAN<br>QLMNNVPQALQQLAQPAQGVVPSSKLGGLWTAVSPHLSPLSNVSSIANN<br>HMSMMGTGVSMTNTLHSMLKGLAPAAAQAVETAAENGVWAMSSLGSQL<br>GSSLGSSGLGAGVAANLGRAASVGSLSVPPAWAAANQAVTPAARALPLT<br>SLTSAAQTAPGHMLGGLPLGHSVNAGSGINNALRVPARAYAIPRTPAAG | 4 |
| Rv1886 | FSRPGLPVEYLQVPSPSMGRDIKVQFQSGGNNSPAVYLLDGLRAQDDYN<br>GWDINTPAFEWYYQSGLSIVMPVGGQSSFYSDWYSPACGKAGCQTYKW<br>ETFLTSELPQWLSANRAVKPTGSAAIGLSMAGSSAMILAAYHPQQFIYAGS<br>LSALLDPSQGMGPSLIGLAMGDAGGYKAADMWGPSSDPAWERNDPTQQ<br>IPKLVANNTRLWVYCGNGTPNELGGANIPAEFLENFVRSSNLKFQDAYNA<br>AGGHNAVFNFPPNGTHSWEYWGAQLNAMKGDLQSSLGAG | 5 |
| pET29 vector | HMTINYQFGDVDAHGAMIRAQAGSLEAEHQAIISDVLTASDFWGGAGSAA<br>CQGFITQLGRNFQVIYEQANAHGQKVQAAGNNMAQTDSAVGSSWADDID<br>WDAIAQCESGGNWAANTGNGLYGGLQISQATWDSNGGVGSPAAASPQ<br>QQIEVADNIMKTQGPGAWPKCSSCSQGDAPLGSLTHILTFLAAETGGCSG<br>SRDDVVDFGALPPEINSARMYAGPGSASLVAAAKMWDSVASDLFSAASA<br>FQSVVWGLTVGSWIGSSAGLMAAAASPYVAWMSVTAGQAQLTAAQVRV<br>AAAAYETAYRLTVPPPVIAENRTELMTLTATNLLGQNTPAIEANQAAYSQM<br>WGQDAEAMYGYAATAATATEALLPFEDAPLITNPGGLLEQAVAVEEAIDT<br>AAANQLMNNVPQALQQLAQPAQGVVPSSKLGGLWTAVSPHLSPLSNVSS<br>IANNHMSMMGTGVSMTNTLHSMLKGLAPAAAQAVETAAENGVWAMSSL<br>GSQLGSSLGSSGLGAGVAANLGRAASVGSLSVPPAWAAANQAVTPAAR<br>ALPLTSLTSAAQTAPGHMLGGLPLGHSVNAGSGINNALRVPARAYAIPRTP<br>AAGFSRPGLPVEYLQVPSPSMGRDIKVQFQSGGNNSPAVYLLDGLRAQD<br>DYNGWDINTPAFEWYYQSGLSIVMPVGGQSSFYSDWYSPACGKAGCQT<br>YKWETFLTSELPQWLSANRAVKPTGSAAIGLSMAGSSAMILAAYHPQQFI<br>YAGSLSALLDPSQGMGPSLIGLAMGDAGGYKAADMWGPSSDPAWERND<br>PTQQIPKLVANNTRLWVYCGNGTPNELGGANIPAEFLENFVRSSNLKFQD<br>AYNAAGGHNAVFNFPPNGTHSWEYWGAQLNAMKGDLQSSLGAGKL | 6 |
| ID91 | ACCATCAACTATCAATTCGGGGACGTCGACGCTCACGGCGCCATGATC<br>CGCGCTCAGGCCGGGTCGCTGGAGGCCGAGCATCAGGCCATCATTTC<br>TGATGTGTTGACCGCGAGTGACTTTTGGGGCGGCGCCGGTTCGGCGG<br>CCTGCCAGGGGTTCATTACCCAGCTGGGCCGTAACTTCCAGGTGATCT<br>ACGAGCAGGCCAACGCCCACGGGCAGAAGGTGCAGGCTGCCGGCAA<br>CAACATGGCACAAACCGACAGCGCCGTCGGCTCCAGCTGGGCCGAC<br>GACATCGATTGGGACGCCATCGCGCAATGCGAATCCGGCGGCAATTG<br>GGCGGCCAACACCGGTAACGGGTTATACGGTGGTCTGCAGATCAGCC<br>AGGCGACGTGGGATTCCAACGGTGGTGTCGGGTCGCCGGCGGCCGC<br>GAGTCCCCAGCAACAGATCGAGGTCGCAGACAACATTATGAAACCCA<br>AGGCCCGGGTGCGTGGCCGAAATGTAGTTCTTGTAGTCAGGGAGACG<br>CACCGCTGGGCTCGCTCACCCACATCCTGACGTTCCTCGCCGAGACG<br>ACTGGAGGTTGTTCGGGGAGCAGGGACGATGTGGTGGATTTCGGGGC<br>GTTACCACCGGAGATCAACTCCGCGAGGATGTACGCCGGCCCGGGTT<br>CGGCCTCGCTGGTGGCCGCCGCGAAGATGTGGGACAGCGTGGCGAG<br>TGACCTGTTTTCGGCCGCGTCGGCGTTTCAGTCGGTGGTCTGGGGTC<br>TGACGGTGGGGTCGTGGATAGGTTCGTCGGCGGGTCTGATGGCGGC | 7 |

TABLE 1-continued

Table 1 provides a listing of certain sequences referenced herein.
Description of the Sequences

| Description | Sequences | SEQ ID NO |
|---|---|---|
| | GGCGGCCTCGCCGTATGTGGCGTGGATGAGCGTCACCGCGGGCAG<br>GCCCAGCTGACCGCCGCCCAGGTCCGGGTTGCTGCGGCGGCCTACG<br>AGACAGCGTATAGGCTGACGGTGCCCCCGCCGGTGATCGCCGAGAAC<br>CGTACCGAACTGATGACGCTGACCGCGACCAACCTCTTGGGGCAAAA<br>CACGCCGGCGATCGAGGCCAATCAGGCCGCATACAGCCAGATGTGG<br>GGCCAAGACGCGGAGGCGATGTATGGCTACGCCGCCACGGCGGCGA<br>CGGCGACCGAGGCGTTGCTGCCGTTCGAGGACGCCCCACTGATCACC<br>AACCCCGGCGGGCTCCTTGAGCAGGCCGTCGCGGTCGAGGAGGCCA<br>TCGACACCGCCGCGGCGAACCAGTTGATGAACAATGTGCCCCAAGCG<br>CTGCAACAGCTGGCCCAGCCAGCGCAGGGCGTCGTACCTTCTTCCAA<br>GCTGGGTGGGCTGTGGACGGCGGTCTCGCCGCATCTGTCGCCGCTC<br>AGCAACGTCAGTTCGATAGCCAACAACCACATGTCGATGATGGGCACG<br>GGTGTGTCGATGACCAACACCTTGCACTCGATGTTGAAGGGCTTAGCT<br>CCGGCGGCGGCTCAGGCCGTGGAAACCGCGGCGGAAAACGGGGTCT<br>GGGCGATGAGCTCGCTGGGCAGCCAGCTGGGTTCGTCGCTGGGTTCT<br>TCGGGTCTGGGCGCTGGGGTGGCCGCCAACTTGGGTCGGGCGGCCT<br>CGGTCGGTTCGTTGTCGGTGCCGCCAGCATGGGCCGCGGCCAACCA<br>GGCGGTCACCCCGGCGGCGCGGGCGCTGCCGCTGACCAGCCTGACC<br>AGCGCCGCCCAAACCGCCCCCGGACACATGCTGGGCGGGCTACCGC<br>TGGGGCACTCGGTCAACGCCGGCAGCGGTATCAACAATGCGCTGCGG<br>GTGCCGGCACGGGCCTACGCGATACCCCGCACACCGGCCGCCGGAT<br>TCTCCCGGCCGGGGCTGCCGGTCGAGTACCTGCAGGTGCCGTCGCC<br>GTCGATGGGCCGCGACATCAAGGTTCAGTTCCAGAGCGGTGGGAACA<br>ACTCACCTGCCGGTTTATCTGCTCGACGGCCTGCGCGCCCAAGACGAC<br>TACAACGGCTGGGATATCAACACCCCGGCGTTCGAGTGGTACTACCA<br>GTCGGGACTGTCGATAGTCATGCCGGTCGGCGGGCAGTCCAGCTTCT<br>ACAGCGACTGGTACAGCCCGGCCTGCGGTAAGGCTGGCTGCCAGACT<br>TACAAGTGGGAAACCTTCCTGACCAGCGAGCTGCCGCAATGGTTGTC<br>CGCCAACAGGGCCGTGAAGCCCACCGGCAGCGCTGCAATCGGCTTGT<br>CGATGGCCGGCTCGTCGGCAATGATCTTGGCCGCCTACCACCCCCAG<br>CAGTTCATCTACGCCGGCTCGCTGTCGGCCCTGCTGGACCCCTCTCA<br>GGGGATGGGGCCTAGCCTGATCGGCCTCGCGATGGGTGACGCCGGC<br>GGTTACAAGGCCGCAGACATGTGGGGTCCCTCGAGTGACCCGGCATG<br>GGAGCGCAACGACCCTACGCAGCAGATCCCCAAGCTGGTCGCAAACA<br>ACACCCGGCTATGGGTTTATTGCGGGAACGGCACCCCGAACGAGTTG<br>GGCGGTGCCAACATACCCGCCGAGTTCTTGGAGAACTTCGTTCGTAG<br>CAGCAACCTGAAGTTCCAGGATGCGTACAACGCCGCGGGCGGGCACA<br>ACGCCGTGTTCAACTTCCCGCCCAACGGCACGCACAGCTGGGAGTAC<br>TGGGGCGCTCAGCTCAACGCCATGAAGGGTGACCTGCAGAGTTCGTT<br>AGGCGCCGGCtgaaagctt | |
| Rv3619 | ACCATCAACTATCAATTCGGGGACGTCGACGCTCACGGCGCCATGATC<br>CGCGCTCAGGCCGGGTCGCTGGAGGCCGAGCATCAGGCCATCATTTC<br>TGATGTGTTGACCGCGAGTGACTTTTGGGGCGGCGCCGGTTCGGCGG<br>CCTGCCAGGGGTTCATTACCCAGCTGGGCCGTAACTTCCAGGTGATCT<br>ACGAGCAGGCCAACGCCCACGGGCAGAAGGTGCAGGCTGCCGGCAA<br>CAACATGGCACAAACCGACAGCGCCGTCGGCTCCAGCTGGGCC | 8 |
| Rv2389 | GACGACATCGATTGGGACGCCATCGCGCAATGCGAATCCGGCGGCAA<br>TTGGGCGGCCAACACCGGTAACGGGTTATACGGTGGTCTGCAGATCA<br>GCCAGGCGACGTGGGATTCCAACGGTGGTGTCGGGTCGCCGGCGGC<br>CGCGAGTCCCCAGCAACAGATCGAGGTCGCAGACAACATTATGAAAA<br>CCCAAGGCCCGGGTGCGTGGCCGAAATGTAGTTCTTGTAGTCAGGGA<br>GACGCACCGCTGGGCTCGCTCACCCACATCCTGACGTTCCTCGCGGC<br>CGAGACTGGAGGTTGTTCGGGGAGCAGGGACGAT | 9 |
| Rv3478 | GTGGTGGATTTCGGGGCGTTACCACCGGAGATCAACTCCGCGAGGAT<br>GTACGCCGGCCCGGGTTCGGCCTCGCTGGTGGCCGCCGCGAAGATG<br>TGGGACAGCGTGGCGAGTGACCTGTTTTCGGCCGCGTCGGCGTTTCA<br>GTCGGTGGTCTGGGGTCTGACGGTGGGGTCGTGGATAGGTTCGTCG<br>GCGGGTCTGATGGCGGCGGCGGCCTCGCCGTATGTGGCGTGGATGA<br>GCGTCACCGCGGGCAGGCCCAGCTGACCGCCGCCCAGGTCCGGGT<br>TGCTGCGGCGGCCTACGAGACAGCGTATAGGCTGACGGTGCCCCCG<br>CCGGTGATCGCCGAGAACCGTACCGAACTGATGACGCTGACCGCGAC<br>CAACCTCTTGGGGCAAAACACGCCGGCGATCGAGGCCAATCAGGCCG<br>CATACAGCCAGATGTGGGGCCAAGACGCGGAGGCGATGTATGGCTAC<br>GCCGCCACGGCGGCGACGGCGACCGAGGCGTTGCTGCCGTTCGAGG<br>ACGCCCCACTGATCACCAACCCCGGCGGGCTCCTTGAGCAGGCCGTC<br>GCGGTCGAGGAGGCCATCGACACCGCCGCGGCGAACCAGTTGATGA<br>ACAATGTGCCCCAAGCGCTGCAACAGCTGGCCCAGCCAGCGCAGGG<br>CGTCGTACCTTCTTCCAAGCTGGGTGGGCTGTGGACGGCGGTCTCGC<br>CGCATCTGTCGCCGCTCAGCAACGTCAGTTCGATAGCCAACAACCACA<br>TGTCGATGATGGGCACGGGTGTGTCGATGACCAACACCTTGCACTCG<br>ATGTTGAAGGGCTTAGCTCCGGCGGCGGCTCAGGCCGTGGAAACCGC | 10 |

TABLE 1-continued

Table 1 provides a listing of certain sequences referenced herein.
Description of the Sequences

| Description | Sequences | SEQ ID NO |
|---|---|---|
| | GGCGGAAAACGGGGTCTGGGCGATGAGCTCGCTGGGCAGCCAGCTG<br>GGTTCGTCGCTGGGTTCTTCGGGTCTGGGCGCTGGGGTGGCCGCCA<br>ACTTGGGTCGGGCGGCCTCGGTCGGTTCGTTGTCGGTGCCGCCAGCA<br>TGGGCCGCGGCCAACCAGGCGGTCACCCCGGCGGCGCGGGCGCTG<br>CCGCTGACCAGCCTGACCAGCGCCGCCCAAACCGCCCCCGGACACAT<br>GCTGGGCGGGCTACCGCTGGGGCACTCGGTCAACGCCGGCAGCGGT<br>ATCAACAATGCGCTGCGGGTGCCGGCACGGGCCTACGCGATACCCCG<br>CACACCGGCCGCCGGA | |
| Rv1886 | TTCTCCCGGCCGGGGCTGCCGGTCGAGTACCTGCAGGTGCCGTCGC<br>CGTCGATGGGCCGCGACATCAAGGTTCAGTTCCAGAGCGGTGGGAAC<br>AACTCACCTGCGGTTTATCTGCTCGACGGCCTGCGCGCCCAAGACGA<br>CTACAACGGCTGGGATATCAACACCCCGGCGTTCGAGTGGTACTACC<br>AGTCGGGACTGTCGATAGTCATGCCGGTCGGCGGGCAGTCCAGCTTC<br>TACAGCGACTGGTACAGCCCGGCCTGCGGTAAGGCTGGCTGCCAGAC<br>TTACAAGTGGGAAACCTTCCTGACCAGCGAGCTGCCGCAATGGTTGTC<br>CGCCAACAGGGCCGTGAAGCCCACCGGCAGCGCTGCAATCGGCTTGT<br>CGATGGCCGGCTCGTCGGCAATGATCTTGGCCGCCTACCACCCCCAG<br>CAGTTCATCTACGCCGGCTCGCTGTCGGCCCTGCTGGACCCCTCTCA<br>GGGGATGGGGCCTAGCCTGATCGGCCTCGCGATGGGTGACGCCGGC<br>GGTTACAAGGCCGCAGACATGTGGGGTCCCTCGAGTGACCCGGCATG<br>GGAGCGCAACGACCCTACGCAGCAGATCCCCAAGCTGGTCGCAAACA<br>ACACCCGGCTATGGGTTTATTGCGGGAACGGCACCCCGAACGAGTTG<br>GGCGGTGCCAACATACCCGCCGAGTTCTTGGAGAACTTCGTTCGTAG<br>CAGCAACCTGAAGTTCCAGGATGCGTACAACGCCGCGGGCGGGCACA<br>ACGCCGTGTTCAACTTCCCGCCCAACGGCACGCACAGCTGGGAGTAC<br>TGGGGCGCTCAGCTCAACGCCATGAAGGGTGACCTGCAGAGTTCGTT<br>AGGCGCCGGC | 11 |
| pET29 vector | catatgACCATCAACTATCAATTCGGGGACGTCGACGCTCACGGCGCCAT<br>GATCCGCGCTCAGGCCGGGTCGCTGGAGGCCGAGCATCAGGCCATC<br>ATTTCTGATGTGTTGACCGCGAGTGACTTTTGGGGCGGCGCCGGTTC<br>GGCGGCCTGCCAGGGGTTCATTACCCAGCTGGGCCGTAACTTCCAGG<br>TGATCTACGAGCAGGCCAACGCCCACGGGCAGAAGGTGCAGGCTGC<br>CGGCAACAACATGGCACAAACCGACAGCGCCGTCGGCTCCAGCTGGG<br>CCGACGACATCGATTGGGACGCCATCGCGCAATGCGAATCGGCGGC<br>AATTGGGCGGCCAACACCGGTAACGGGTTATACGGTGGTCTGCAGAT<br>CAGCCAGGCGACGTGGGATTCCAACGGTGGTGTCGGGTCGCCGGCG<br>GCCGCGAGTCCCCAGCAACAGATCGAGGTCGCAGACAACATTATGAA<br>AACCCAAGGCCCGGGTGCGTGGCCGAAATGTAGTTCTTGTAGTCAGG<br>GAGACGCACCGCTGGGCTCGCTCACCCACATCCTGACGTTCCTCGCG<br>GCCGAGACTGGAGGTTGTTCGGGGAGCAGGGACGATGTGGTGGATTT<br>CGGGGCGTTACCACCGGAGATCAACTCCGCGAGGATGTACGCCGGC<br>CCGGGTTCGGCCTCGCTGGTGGCCGCCGCGAAGATGTGGGACAGCG<br>TGGCGAGTGACCTGTTTTCGGCCGCGTCGGCGTTTCAGTCGGTGGTC<br>TGGGGTCTGACGGTGGGGTCGTGGATAGGTTCGTCGGCGGGTCTGAT<br>GGCGGCGGCGGCCTCGCCGTATGTGGCGTGGATGAGCGTCACCGCG<br>GGGCAGGCCCAGCTGACCGCCGCCCAGGTCCGGGTTGCTGCGGCGG<br>CCTACGAGACAGCGTATAGGCTGACGGTGCCCCCGCCGGTGATCGCC<br>GAGAACCGTACCGAACTGATGACGCTGACCGCGACCAACCTCTTGGG<br>GCAAAAACACGCCGGCGATCGAGGCCAATCAGGCCGCATACAGCCAGA<br>TGTGGGGCCAAGACGCGGAGGCGATGTATGGCTACGCCGCCACGGC<br>GGCGACGGCGACCGAGGCGTTGCTGCCGTTCGAGGACGCCCCACTG<br>ATCACCAACCCCGGCGGGCTCCTTGAGCAGGCCGTCGCGGTCGAGG<br>AGGCCATCGACACCGCCGGCGAACCAGTTGATGAACAATGTGCCC<br>CAAGCGCTGCAACAGCTGGCCCAGCCAGCGCAGGGCGTCGTACCTTC<br>TTCCAAGCTGGGTGGGCTGTGGACGGCGGTCTCGCCGCATCTGTCGC<br>CGCTCAGCAACGTCAGTTCGATAGCCAACAACCACATGTCGATGATGG<br>GCACGGGTGTGTCGATGACCAACACCTTGCACTCGATGTTGAAGGGC<br>TTAGCTCCGGCGGCGGCTCAGGCCGTGGAAACCGCGGCGGAAAACG<br>GGGTCTGGGCGATGAGCTCGCTGGGCAGCCAGCTGGGTTCGTCGCT<br>GGGTTCTTCGGGTCTGGGCGCTGGGGTGGCCGCCAACTTGGGTCGG<br>GCGGCCTCGGTCGGTTCGTTGTCGGTGCCGCCAGCATGGGCCGCGG<br>CCAACCAGGCGGTCACCCCGGCGGCGCGGGCGCTGCCGCTGACCAG<br>CCTGACCAGCGCCGCCCAAACCGCCCCCGGACACATGCTGGGCGGG<br>CTACCGCTGGGGCACTCGGTCAACGCCGGCAGCGGTATCAACAATGC<br>GCTGCGGGTGCCGGCACGGGCCTACGCGATACCCCGCACACCGGCC<br>GCCGGATTCTCCCGGCCGGGGCTGCCGGTCGAGTACCTGCAGGTGC<br>CGTCGCCGTCGATGGGCCGCGACATCAAGGTTCAGTTCCAGAGCGGT<br>GGGAACAACTCACCTGCGGTTTATCTGCTCGACGGCCTGCGCGCCCA<br>AGACGACTACAACGGCTGGGATATCAACACCCCGGCGTTCGAGTGGT<br>ACTACCAGTCGGGACTGTCGATAGTCATGCCGGTCGGCGGGCAGTCC<br>AGCTTCTACAGCGACTGGTACAGCCCGGCCTGCGGTAAGGCTGGCTG<br>CCAGACTTACAAGTGGGAAACCTTCCTGACCAGCGAGCTGCCGCAAT | 12 |

TABLE 1-continued

Table 1 provides a listing of certain sequences referenced herein.
Description of the Sequences

| Description | Sequences | SEQ ID NO |
|---|---|---|
| | GGTTGTCCGCCAACAGGGCCGTGAAGCCCACCGGCAGCGCTGCAATC<br>GGCTTGTCGATGGCCGGCTCGTCGGCAATGATCTTGGCCGCCTACCA<br>CCCCCAGCAGTTCATCTACGCCGGCTCGCTGTCGGCCCTGCTGGACC<br>CCTCTCAGGGGATGGGGCCTAGCCTGATCGGCCTCGCGATGGGTGAC<br>GCCGGCGGTTACAAGGCCGCAGACATGTGGGGTCCCTCGAGTGACC<br>CGGCATGGGAGCGCAACGACCCTACGCAGCAGATCCCCAAGCTGGTC<br>GCAAACAACACCCGGCTATGGGTTTATTGCGGGAACGGCACCCCGAA<br>CGAGTTGGGCGGTGCCAACATACCCGCCGAGTTCTTGGAGAACTTCG<br>TTCGTAGCAGCAACCTGAAGTTCCAGGATGCGTACAACGCCGCGGGC<br>GGGCACAACGCCGTGTTCAACTTCCCGCCCAACGGCACGCACAGCTG<br>GGAGTACTGGGGCGCTCAGCTCAACGCCATGAAGGGTGACCTGCAGA<br>GTTCGTTAGGCGCCGGCtgaaagctt | |
| JEVss-FWD | gctggcctccctggctgtggtcattgcctgcgctggagcaGCCGAGGTGACCAGGAGAGG | 13 |
| JEVss-REV | cacatgattgatccggcactcctcttgcccatggcggcggcGTGAGCTGGCGGCGGGTG | 14 |
| ZIKVss-FWD | ggaatcgtgggcctgctgctgaccacagcaatggcaGCCGAGGTGACCAGGAGAGG | 15 |
| ZIKVss-REV | CACGGATGTGTCTGCTCCTCTCCGCATGGCGGCGGCGTGAGCTGGCG<br>GCGGGTG | 16 |
| ZIKV-prM-E-FWD | AATGGACTACGACATAGTCGCCGCCGCCATG | 17 |
| ZIKV-prM-E-REV | GCGGTTTTTGACAccgcggTCAGGCAGACACGGCG | 18 |
| Id91 epitope 1 | HMTINYQFGDVDAHG | 19 |
| Id91 epitope 2 | FGDVDAHGAMIRAQA | 20 |
| Id91 epitope 3 | GAMIRAQAGSLEAEH | 21 |
| Id91 epitope 4 | AGSLEAEHQAIISDV | 22 |
| Id91 epitope 5 | HQAIISDVLTASDFW | 23 |
| Id91 epitope 6 | VLTASDFWGGAGSAA | 24 |
| Id91 epitope 7 | WGGAGSAACQGFITQ | 25 |
| Id91 epitope 8 | ACQGFITQLGRNFQV | 26 |
| Id91 epitope 9 | QLGRNFQVIYEQANA | 27 |
| Id91 epitope 10 | VIYEQANAHGQKVQA | 28 |
| Id91 epitope 11 | AHGQKVQAAGNNMAQ | 29 |
| Id91 epitope 12 | AAGNNMAQTDSAVGS | 30 |
| Id91 epitope 13 | QTDSAVGSSWADDID | 31 |
| Id91 epitope 14 | SSWADDIDWDAIAQC | 32 |
| Id91 epitope 15 | DWDAIAQCESGGNWA | 33 |
| Id91 epitope 16 | CESGGNWAANTGNGL | 34 |
| Id91 epitope 17 | AANTGNGLYGGLQIS | 35 |
| Id91 epitope 18 | LYGGLQISQATWDSN | 36 |
| Id91 epitope 19 | SQATWDSNGGVGSPA | 37 |
| Id91 epitope 20 | NGGVGSPAAASPQQQ | 38 |
| Id91 epitope 21 | AAASPQQQIEVADNI | 39 |
| Id91 epitope 22 | QIEVADNIMKTQGPG | 40 |
| Id91 epitope 23 | IMKTQGPGAWPKCSS | 41 |
| Id91 epitope 24 | GAWPKCSSCSQGDAP | 42 |

TABLE 1-continued

Table 1 provides a listing of certain sequences referenced herein.
Description of the Sequences

| Description | Sequences | SEQ ID NO |
|---|---|---|
| Id91 epitope 25 | SCSQGDAPLGSLTHI | 43 |
| Id91 epitope 26 | PLGSLTHILTFLAAE | 44 |
| Id91 epitope 27 | ILTFLAAETGGCSGS | 45 |
| Id91 epitope 28 | ETGGCSGSRDDVVDF | 46 |
| Id91 epitope 29 | SRDDVVDFGALPPEI | 47 |
| Id91 epitope 30 | FGALPPEINSARMYA | 48 |
| Id91 epitope 31 | INSARMYAGPGSASL | 49 |
| Id91 epitope 32 | AGPGSASLVAAAKMW | 50 |
| Id91 epitope 33 | LVAAAKMWDSVASDL | 51 |
| Id91 epitope 34 | WDSVASDLFSAASAF | 52 |
| Id91 epitope 35 | LFSAASAFQSVVWGL | 53 |
| Id91 epitope 36 | FQSVVWGLTVGSWIG | 54 |
| Id91 epitope 37 | LTVGSWIGSSAGLMA | 55 |
| Id91 epitope 38 | GSSAGLMAAAASPYV | 56 |
| Id91 epitope 39 | AAAASPYVAWMSVTA | 57 |
| Id91 epitope 40 | VAWMSVTAGQAQLTA | 58 |
| Id91 epitope 41 | AGQAQLTAAQVRVAA | 59 |
| Id91 epitope 42 | AAQVRVAAAAYETAY | 60 |
| Id91 epitope 43 | AAAYETAYRLTVPPP | 61 |
| Id91 epitope 44 | YRLTVPPPVIAENRT | 62 |
| Id91 epitope 45 | PVIAENRTELMTLTA | 63 |
| Id91 epitope 46 | TELMTLTATNLLGQN | 64 |
| Id91 epitope 47 | ATNLLGQNTPAIEAN | 65 |
| Id91 epitope 48 | NTPAIEANQAAYSQM | 66 |
| Id91 epitope 49 | NQAAYSQMWGQDAEA | 67 |
| Id91 epitope 50 | MWGQDAEAMYGYAAT | 68 |
| Id91 epitope 51 | AMYGYAATAATATEA | 69 |
| Id91 epitope 52 | TAATATEALLPFEDA | 70 |
| Id91 epitope 53 | ALLPFEDAPLITNPG | 71 |
| Id91 epitope 54 | APLITNPGGLLEQAV | 72 |
| Id91 epitope 55 | GGLLEQAVAVEEAID | 73 |
| Id91 epitope 56 | VAVEEAIDTAAANQL | 74 |
| Id91 epitope 57 | DTAAANQLMNNVPQA | 75 |
| Id91 epitope 58 | LMNNVPQALQQLAQP | 76 |
| Id91 epitope 59 | ALQQLAQPAQGVVPS | 77 |
| Id91 epitope 60 | PAQGVVPSSKLGGLW | 78 |
| Id91 epitope 61 | SSKLGGLWTAVSPHL | 79 |

TABLE 1-continued

Table 1 provides a listing of certain sequences referenced herein.
Description of the Sequences

| Description | Sequences | SEQ ID NO |
|---|---|---|
| Id91 epitope 62 | WTAVSPHLSPLSNVS | 80 |
| Id91 epitope 63 | LSPLSNVSSIANNHM | 81 |
| Id91 epitope 64 | SSIANNHMSMMGTGV | 82 |
| Id91 epitope 65 | MSMMGTGVSMTNTLH | 83 |
| Id91 epitope 66 | VSMTNTLHSMLKGLA | 84 |
| Id91 epitope 67 | HSMLKGLAPAAAQAVE | 85 |
| Id91 epitope 68 | PAAAQAVETAAENGV | 86 |
| Id91 epitope 69 | ETAAENGVWAMSSLG | 87 |
| Id91 epitope 70 | VWAMSSLGSQLGSSL | 88 |
| Id91 epitope 71 | GSQLGSSLGSSGLGA | 89 |
| Id91 epitope 72 | LGSSGLGAGVAANLG | 90 |
| Id91 epitope 73 | AGVAANLGRAASVGS | 91 |
| Id91 epitope 74 | GRAASVGSLSVPPAW | 92 |
| Id91 epitope 75 | SLSVPPAWAAANQAV | 93 |
| Id91 epitope 76 | WAAANQAVTPAARAL | 94 |
| Id91 epitope 77 | VTPAARALPLTSLTS | 95 |
| Id91 epitope 78 | LPLTSLTSAAQTAPG | 96 |
| Id91 epitope 79 | SAAQTAPGHMLGGLP | 97 |
| Id91 epitope 80 | GHMLGGLPLGHSVNA | 98 |
| Id91 epitope 81 | PLGHSVNAGSGINNA | 99 |
| Id91 epitope 82 | AGSGINNALRVPARA | 100 |
| Id91 epitope 83 | ALRVPARAYAIPRTP | 101 |
| Id91 epitope 84 | AYAIPRTPAAGFSRP | 102 |
| Id91 epitope 85 | PAAGFSRPGLPVEYL | 103 |
| Id91 epitope 86 | PGLPVEYLQVPSPSM | 104 |
| Id91 epitope 87 | LQVPSPSMGRDIKVQ | 105 |
| Id91 epitope 88 | MGRDIKVQFQSGGNN | 106 |
| Id91 epitope 89 | QFQSGGNNSPAVYLL | 107 |
| Id91 epitope 90 | NSPAVYLLDGLRAQD | 108 |
| Id91 epitope 91 | LDGLRAQDDYNGWDI | 109 |
| Id91 epitope 92 | DDYNGWDINTPAFEW | 110 |
| Id91 epitope 93 | INTPAFEWYYQSGLS | 111 |
| Id91 epitope 94 | WYYQSGLSIVMPVGG | 112 |
| Id91 epitope 95 | SIVMPVGGQSSFYSD | 113 |
| Id91 epitope 96 | GQSSFYSDWYSPACG | 114 |
| Id91 epitope 97 | DWYSPACGKAGCQTY | 115 |
| Id91 epitope 98 | GKAGCQTYKWETFLT | 116 |

TABLE 1-continued

Table 1 provides a listing of certain sequences referenced herein.
Description of the Sequences

| Description | Sequences | SEQ ID NO |
|---|---|---|
| Id91 epitope 99 | YKWETFLTSELPQWL | 117 |
| Id91 epitope 100 | TSELPQWLSANRAVK | 118 |
| Id91 epitope 101 | LSANRAVKPIGSAAI | 119 |
| Id91 epitope 102 | KPTGSAAIGLSMAGS | 110 |
| Id91 epitope 103 | IGLSMAGSSAMILAA | 111 |
| Id91 epitope 104 | SSAMILAAYHPQQFI | 112 |
| Id91 epitope 105 | AYHPQQFIYAGSLSA | 113 |
| Id91 epitope 106 | IYAGSLSALLDPSQG | 114 |
| Id91 epitope 107 | ALLDPSQGMGPSLIG | 115 |
| Id91 epitope 108 | GMGPSLIGLAMGDAG | 116 |
| Id91 epitope 109 | GLAMGDAGGYKAADM | 117 |
| Id91 epitope 110 | GGYKAADMWGPSSDP | 118 |
| Id91 epitope 111 | MWGPSSDPAWERNDP | 119 |
| Id91 epitope 112 | PAWERNDPTQQIPKL | 120 |
| Id91 epitope 113 | PTQQIPKLVANNTRL | 121 |
| Id91 epitope 114 | LVANNTRLWVYCGNG | 122 |
| Id91 epitope 115 | LWVYCGNGTPNELGG | 123 |
| Id91 epitope 116 | GTPNELGGANIPAEF | 124 |
| Id91 epitope 117 | GANIPAEFLENFVRS | 125 |
| Id91 epitope 118 | FLENFVRSSNLKFQD | 126 |
| Id91 epitope 119 | SSNLKFQDAYNAAGG | 127 |
| Id91 epitope 120 | DAYNAAGGHNAVFNF | 128 |
| Id91 epitope 121 | GHNAVFNFPPNGTHS | 129 |
| Id91 epitope 122 | FPPNGTHSWEYWGAQ | 130 |
| Id91 epitope 123 | SWEYWGAQLNAMKGD | 131 |
| Id91 epitope 124 | QLNAMKGDLQSSLGA | 132 |
| Id91 epitope 125 | AMKGDLQSSLGAGKL | 133 |

DETAILED DESCRIPTION

Provided herein are compositions for delivering a bioactive agent to a cell and methods of such delivery. NLCs have a core comprising of a combination of liquid-phase and solid-phase lipids. In contrast to solid lipid nanoparticles (LNPs), which have a completely solid crystalline core, the mixed phase core in NLCs provides more versatility to incorporate active molecules of various structures. Without being bound by theory, it is believed that the addition of solid lipids to the composition yields NLC cores with structural integrity and stability. In the NLCs of the present invention, the mixed phase oil core is emulsified with a mixture of surfactants (typically a sorbitan ester and a hydrophilic surfactant) and a cationic component (typically a cationic lipid or phospholipid). Whereas typically, bioactive agents, such as small molecule drugs, have been incorporated in the oil core of the NLCs, the present inventors have synthesized NLCs that can also interact with bioactive agents such as negatively charged molecules (e.g., RNA) at or near their surface (i.e., the bioactive agent is not encapsulated by the NLC). The present inventors have discovered that the stability of the NLC, the ability of the described NLCs to deliver nucleic acid to a cell, and the ability of a nucleic acid bioactive agent and NLC to be manufactured and stored separately and mixed just prior to use, permit the use of these NLCs in a wide variety of applications, including as a rapid response nucleic acid platform technology for the development of multiple prophylactic or therapeutic treatments. The rapid response nucleic acid delivery platform is based on a flexible system utilizing NLC compositions to deliver nucleic acids (e.g., replicating viral RNA (rvRNA)) to drive RNA replication and/or protein expression (e.g., leading to robust and rapid immune responses to diverse viral, bacterial or parasitic antigens). The NLC compositions of the present invention can be manufactured and stockpiled for extended time periods. The stockpiled vehicle can then be combined with nucleic acid (e.g., synthetic rvRNA expressing a protective antigen) during an emerging disease outbreak or other public health event.

In addition to providing NLCs for combination with a bioactive agent, also provided are those NLCs once combined. Accordingly, in some aspects, the bioactive agent is associated with the NLC. The bioactive agent can be delivered to a subject in a time of need by administration of the NLC-bioactive agent composition.

I. DEFINITIONS

The following terms have the following meanings unless otherwise indicated. Any undefined terms have their art recognized meanings.

In the present description, the terms "about" and "consisting essentially of" mean±20% of the indicated range, value, or structure, unless otherwise indicated.

The use of the alternative (e.g., "or") should be understood to mean either one, both, or any combination thereof of the alternatives.

As used herein, the terms "include," "have" and "comprise" are used synonymously, which terms and variants thereof are intended to be construed as non-limiting.

As used herein and in the appended claims, the singular forms "a," "an," and "the" include plural reference unless the context clearly indicates otherwise.

The term "macromolecule" as used herein refers to large molecules exemplified by, but not limited to, peptides, proteins, oligonucleotides and polynucleotides of biological or synthetic origin.

The term "alkyl" means a straight chain or branched, noncyclic or cyclic, unsaturated or saturated aliphatic hydrocarbon containing the indicated number of carbon atoms. Unsaturated alkyls contain at least one double or triple bond between adjacent carbon atoms.

The terms "polypeptide", "peptide", and "protein" are used interchangeably herein to refer to polymers of amino acids of any length. The polymer may be linear or branched, it may comprise modified nucleotides or amino acids, and it may be interrupted by non-nucleotides or non-amino acids. The terms also encompass a nucleotide or amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polynucleotides or polypeptides containing one or more analogs of a nucleotide or an amino acid (including, for example, unnatural amino acids, etc.), as well as other modifications known in the art.

The term "isolated" means the molecule has been removed from its natural environment.

"Purified" means that the molecule has been increased in purity, such that it exists in a form that is more pure than it exists in its natural environment and/or when initially synthesized and/or amplified under laboratory conditions. Purity is a relative term and does not necessarily mean absolute purity.

A "polynucleotide" or "nucleic acid," as used interchangeably herein, refer to polymers of nucleotides of any length, include DNA and RNA. The nucleotides can be, for example, deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

An "individual" or a "subject" is any mammal. Mammals include, but are not limited to humans, primates, farm animals, sport animals, pets (such as cats, dogs, horses), and rodents.

A "replicon" as used herein includes any genetic element, for example, a plasmid, cosmid, bacmid, phage or virus that is capable of replication largely under its own control. A replicon may be either RNA or DNA and may be single or double stranded.

Vitamin E refers to both tocopherols (TCPs) and tocotrienols and can be naturally occurring or synthetic.

Monoacylglycerols are esters of the trihydric alcohol glycerol in which one of the hydroxyl groups is esterified with a long chain fatty acid.

Lauroyl polyoxylglycerides are a mixture of monoesters, diesters, and triesters of glycerol and monoesters and diesters of polyethylene glycols with a mean relative molecular weight typically between about 300 and about 1500.

Capric/caprylic triglyceride is a mixed triester of glycerin and caprylic and capric acids.

The term liquid phase lipid refers to a lipid that, prior to mixing with any other component, is liquid at ambient temperature.

The term solid phase lipid refers to a lipid that, prior to mixing with any other component, is solid at ambient temperature.

Ambient temperature is between 15° C. and 25° C.

Glycerolipid is a fatty molecule composed of glycerol linked esterically to a fatty acid. Glycerolipids include triglycerides and diglycerides.

The term "sorbitan ester" as used herein refers to an ester of sorbitan. Sorbitan is as shown in Formula A

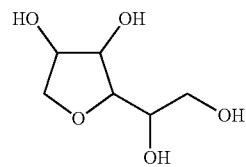

Formula A

Particularly preferred sorbitan esters are sorbitan alkyl esters, wherein the alkyl is a $C_1$-$C_{30}$ alkyl group, preferably a saturated or unsaturated $C_1$-$C_{20}$ alkyl group, more preferably a saturated or unsaturated $C_{10}$-$C_{20}$ alkyl group.

The practice of the present invention will employ, unless otherwise indicated, conventional techniques of molecular biology, recombinant DNA, biochemistry, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide to Molecular Cloning (1984); the treatise, Methods In Enzymology (Academic Press, Inc., N.Y.); and in Ausubel et al., Current Protocols in Molecular Biology, John Wiley and Sons, Baltimore, Md. (1989).

II. NANOSTRUCTURED LIPID CARRIERS

The present disclosure provides, inter alia, NLCs for delivery of a bioactive agent to a cell. The NLC compositions are made up of NLC particles comprising (a) an oil core comprising a liquid phase lipid and a solid phase lipid, (b) a cationic component (preferably, a cationic lipid or phospholipid) (c) a hydrophobic surfactant, preferably a sorbitan ester (e.g., sorbitan monoester, diester, or triester), and (d) a surfactant (preferably, a hydrophilic surfactant). The NLCs of the present invention typically comprise an unstructured or amorphous solid lipid matrix made up of a mixture of blended solid and liquid lipids dispersed in an aqueous phase. One or more of the surfactants can be present in the oil phase, the aqueous phase, or at the interface between the oil and aqueous phase. In certain aspects the sorbitan ester and the cationic lipid are present at the interface between the oil and aqueous phase.

The present inventors have found that the claimed NLCs are particularly effective at delivering protein-encoding nucleic acid, such as RNA. In addition, it has been found that by manipulating certain components of the NLC, the levels of expression of the encoded protein can be increased. Surprisingly, exemplary NLCs are not only capable of effectively delivering RNA, they are also able to improve the immune response to the encoded proteins.

A. Solid-Phase and Liquid-Phase Lipids

NLCs are composed of a blend of solid and liquid lipids. The liquid and solid lipids to be used in the NLCs can be any lipid capable of forming an unstructured or amorphous solid lipid matrix and forming a stable composition. The weight ratio of solid to liquid can vary widely, for example from 0.1:99.9 to 99.9:0.1. In some exemplary embodiments, the solid lipids are mixed with liquid lipids in a solid:liquid lipid weight ratio of from about 70:30 to about 99.9:0.1 or from about 1:10 to about 1:30. In some aspects, the solid lipids are mixed with liquid lipids in a solid:liquid lipid weight of about 1:16.

The total oil core component (solid lipid+liquid oil) of the NLC-based composition or formulation is typically present in an amount from about 0.2% to about 50% (w/v). For example, the NLC may comprise from about 0.2% to about 50% (w/v) oil core component, 0.2% to about 40% (w/v) oil core component, from about 0.2% to about 30% (w/v) oil core component, from about 0.2% to about 20% (w/v) oil core component, from about 0.2% to about 15% (w/v) oil core component, from about 0.2% to about 10% (w/v) oil core component, from about 0.2% to about 9% (w/v) oil core component, from about 0.2% to about 8% (w/v) oil core component, from about 0.2% to about 7% (w/v) oil core component, from about 0.2% to about 6% (w/v) oil core component, from about 0.2% to about 5% (w/v) oil core component, from about 0.2% to about 4.3% (w/v) oil core component, from about 0.3% to about 20% (w/v) oil core component, from about 0.4% to about 20% (w/v) oil core component, from about 0.5% to about 20% (w/v) oil core component, from about 1% to about 20% (w/v) oil core component, from about 2% to about 20% (w/v) oil core component, from about 3% to about 20% (w/v) oil core component, from about 4% to about 20% (w/v) oil core component, from about 5% to about 20% (w/v) oil core component, about 0.5% (w/v) oil core component, about 1% (w/v) oil core component, about 1.5% (w/v) oil core component, about 2% (w/v) oil core component, about 2.5% (w/v) oil core component, about 3% (w/v) oil core component, about 3.5% (w/v) oil core component, about 4% (w/v) oil core component, about 4.3% (w/v) oil core component, about 5% (w/v) oil core component, or about 10% (w/v) oil core component or any other amount or range described herein for the oil core component. Higher or lower w/v percentages are contemplated herein, particularly when considering diluted or concentrated formulations.

The oil core of the NLC comprises a liquid phase lipid. Preferably, although not necessarily, the liquid phase lipid is a metabolizable, non-toxic oil; more preferably one of about 6 to about 30 carbon atoms including, but not limited to, alkanes, alkenes, alkynes, and their corresponding acids and alcohols, the ethers and esters thereof, and mixtures thereof. The oil may be, for example, any vegetable oil, fish oil, animal oil or synthetically prepared oil that can be administered to a subject. In some aspects, the liquid phase lipid will be non-metabolizable.

The oil can be, for example, any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will generally have from about 6 to about 40 or from 6 to about 30 carbon atoms. The moiety may have a straight or branched chain structure. It may be fully saturated or have one or more double or triple bonds. Where mono or poly ester- or ether-based oils are employed, the limitation of about 6 to about 40 carbons applies to the individual fatty acid or fatty alcohol moieties, not the total carbon count.

Any suitable oils from an animal, fish or vegetable source may be used. Sources for vegetable oils include nuts, seeds and grains, and suitable oils include, for example, peanut oil, soybean oil, coconut oil, and olive oil and the like. Other suitable seed oils include safflower oil, cottonseed oil, sunflower seed oil, sesame seed oil and the like. In the grain group, corn oil, and the oil of other cereal grains such as wheat, oats, rye, rice, teff, triticale and the like may also be used. The technology for obtaining vegetable oils is well developed and well known. The compositions of these and other similar oils may be found in, for example, the Merck Index, and source materials on foods, nutrition and food technology.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Naturally occurring or synthetic terpenoids, also referred to as isoprenoids, can be used herein as a liquid phase lipid. Squalene, a branched, unsaturated terpenoid, is particularly preferred herein. A major source of squalene is shark liver oil, although plant oils (primarily vegetable oils), including amaranth seed, rice bran, wheat germ, and olive oils, are also suitable sources. Squalane, the saturated analog to squalene, is also preferred. Oils, including fish oils such as squalene and squalane, are readily available from commercial sources or may be obtained by methods known in the art. Oils to be used herein may also be made using synthetic means, including genetic engineering (e.g., oils made from bioengineered yeast, including squalene.)

Exemplary liquid phase lipids that can be used in the present invention include, for example, castor oil, coconut oil, corn oil, cottonseed oil, evening primrose oil, fish oil, grapeseed oil, jojoba oil, lard oil, linseed oil, olive oil, peanut oil, safflower oil, sesame oil, soybean oil, squalene, squalane, sunflower oil, wheatgerm oil, mineral oil, capric/caprylic triglyceride (e.g., Myglyol®810, Myglyol®812, Labrafac™), vitamin E (e.g., TOS, TPGS), lauroyl polyoxylglycerides (e.g., Gelucire®44/14), monoacylglycerols (e.g., Myverol 18-99 K), soy lecithin (e.g., Epikuron™200), farnesene, or a combination thereof.

The liquid phase lipid can include for example, squalene, sunflower oil, soybean oil, olive oil, grapeseed oil, squalane, capric/caprylic triglyceride, or a combination thereof.

The liquid phase lipid can include for example, squalene, squalene, capric/caprylic triglyceride, or a combination thereof.

The liquid phase lipid can include for example, capric/caprylic triglyceride, vitamin E, lauroyl polyoxylglycerides, monoacylglycerols, soy lecithin, squalene, or squalane or a combination thereof.

The liquid phase lipid can include for example, squalene, squalane, or farnesene or a combination thereof.

The oil core of the NLC comprises a solid phase lipid. A wide variety of solid phase lipids can be used, including for example, glycerolipids. Exemplary solid phase lipids include, for example, glyceryl palmitostearate (Precitol ATO®5), glycerylmonostearate, glyceryl dibehenate (Compritol®888 ATO), cetyl palmitate (Crodamol™ CP), stearic acid, tripalmitin, or a microcrystalline triglyceride. Exemplary microcrystalline triglycerides include those sold under the trade name Dynasan® (e.g., trimyristin (Dynasan®114) or tristearin (Dynasan®118) or tripalmitin (Dynasan®116)).

The solid phase lipid can be, for example, a microcrystalline triglyceride, for example, one selected from trimyristin (Dynasan®114) or tristearin (Dynasan®118).

Preferably, the solid phase lipid of the oil core is solid at ambient temperature. When indoors, ambient temperature is typically between 15° C. and 25° C.

In any of the embodiments provided herein, the solid phase lipid can be a glycerolipid, for example, a microcrystalline triglyceride.

In any of the embodiments provided herein, the liquid phase lipid can be synthetic or naturally-occurring squalene.

B. Cationic Component

The NLCs described herein comprise a cationic component, typically a cationic lipid. The cationic component is useful for interacting with negatively charged bioactive agents on the surface on the NLC. Any cationic lipid capable of interacting with negatively charged bioactive agents that won't disturb the stability of the NLC and can be administered to a subject can be used. Generally, the cationic lipid contains a nitrogen atom that is positively charged under physiological conditions. Suitable cationic lipids include, benzalkonium chloride (BAK), benzethonium chloride, cetrimide (which contains tetradecyltrimethylammonium bromide and possibly small amounts of dodecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N', N'-polyoxyethylene (10)-N-tallow-1,3-diaminopropane, other quaternary amine salts, including but not limited to dodecyltrimethylammonium bromide, hexadecyltrimethylammonium bromide, mixed alkyl-trimethylammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride, N,N-dimethyl-N-[2 (2-methyl-4-(1,1,3,3tetramethylbutyl)-phenoxy]-ethoxy) ethyl]-benzenemetha-naminium chloride (DEBDA), dialkyldimethylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3(dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12Bu6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C12GluPhCnN+), ditetradecyl glutamate ester with pendant amino group (C14GluCnN+), cationic derivatives of cholesterol, including but not limited to cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio) propane (DOTAP), dimethyldioctadecylammonium (DDA), 1,2-Dimyristoyl-3-TrimethylAmmoniumPropane (DMTAP), dipalmitoyl(C16:0)trimethyl ammonium propane (DPTAP), distearoyltrimethylammonium propane (DSTAP), and combination thereof.

Other cationic lipids suitable for use in the invention include, e.g., the cationic lipids described in U.S. Patent Publications 2008/0085870 (published Apr. 10, 2008) and 2008/0057080 (published Mar. 6, 2008).

Other cationic lipids suitable for use in the invention include, e.g., Lipids E0001-E0118 or E0119-E0180 as disclosed in Table 6 (pages 112-139) of WO 2011/076807 (which also discloses methods of making, and method of using these cationic lipids). Additional suitable cationic lipids include N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3- dimethylammonium-propane (DODAP), 1,2-dilinoleyloxy-3-dimethylaminopropane (DLinDMA).

The NLCs may comprise one or any combination of two or more of the cationic lipids described herein.

In exemplary embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl(C16:0)trimethyl ammonium propane (DPTAP), distearoyltrimethylammonium propane (DSTAP), Lipids E0001-E0118 or E0119-E0180 as disclosed in Table 6 (pages 112-139) of WO 2011/076807, and combinations thereof.

In other exemplary embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl(C16:0)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), Lipids E0001-E0118 or E0119-E0180 as disclosed in Table 6 (pages 112-139) of WO 2011/076807, and combinations thereof.

Exemplary cationic lipids are selected from the following: 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl(C16:0)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), or a combination thereof. Additional suitable cationic lipids may be known by one of skill in the art.

In certain embodiments, the NLC-based composition or formulation comprises from about 0.5 mg/ml to about 50 mg/ml of the cationic component (e.g., the cationic lipid). In certain embodiments, the cationic lipid is DOTAP. The NLC may comprise, for example, from about 0.5 mg/ml to about 25 mg/ml or 30 mg/ml DOTAP or any other amount or range described herein for DOTAP.

In certain embodiments, the cationic lipid is DC Cholesterol. In certain aspects, the NLC may comprise DC Cholesterol at from about 0.1 mg/ml to about 5 mg/ml DC Cholesterol. In certain embodiments, the cationic lipid is DDA. The NLC may comprise, for example, from about 0.1 mg/ml to about 5 mg/ml DDA. In certain embodiments, the cationic lipid is DOTMA. The NLC may comprise, for example, from about 0.5 mg/ml to about 25 or 30 mg/ml DOTMA. In certain embodiments, the cationic lipid is DOEPC. The NLC may comprise, for example, from about 0.5 mg/ml to about 25 mg/ml DOEPC. In certain embodiments, the cationic lipid is DSTAP. The NLC may comprise, for example, from about 0.5 mg/ml to about 50 mg/ml DSTAP. In certain embodiments, the cationic lipid is DODAC. The NLC may comprise, for example, from about 0.5 mg/ml to about 50 mg/ml DODAC. In certain embodiments, the cationic lipid is DODAP. The NLC may comprise, for example, from about 0.5 mg/ml to about 50 mg/ml DODAP.

With respect to weight per volume, an exemplary NLC-based composition or formulation may comprise, for example, from about 0.05% to about 5% or to about 10% w/v cationic component (e.g., cationic lipid such as DOTAP), from about 0.2% to about 10% w/v cationic component (e.g., cationic lipid such as DOTAP), from about 0.2% to about 5% w/v cationic component (e.g., cationic lipid such as DOTAP), from about 0.2% to about 2% w/v cationic component (e.g., cationic lipid such as DOTAP), from about 2% to about 10% w/v cationic component (e.g., cationic lipid such as DOTAP), from about 2% to about 5% w/v cationic component (e.g., cationic lipid such as DOTAP), from about 1% to about 5% w/v cationic component (e.g., cationic lipid such as DOTAP), from about 3% to about 5% w/v cationic component (e.g., cationic lipid such as DOTAP), or from about 3% to about 4% w/v cationic component (e.g., cationic lipid such as DOTAP) or any other amount or range described herein for the cationic component. Higher or lower w/v percentages are contemplated herein, particular when considering diluted or concentrated formulations.

In some cases, it may be desirable to use a cationic lipid that is soluble in the oil core. For example, DOTAP DOEPC, DODAC, and DOTMA are soluble in squalene or squalane. In other cases, it may be desirable to use a cationic lipid that is not soluble in the oil core. For example, DDA and DSTAP are not soluble in squalene. It is within the knowledge in the art to determine whether a particular lipid is soluble or insoluble in the oil and choose an appropriate oil and lipid combination accordingly. For example, solubility can be predicted based on the structures of the lipid and oil (e.g., the solubility of a lipid may be determined by the structure of its tail). For example, lipids having one or two unsaturated fatty acid chains (e.g., oleoyl tails), such as DOTAP, DOEPC, DODAC, DOTMA, are soluble in squalene or squalane; whereas lipids having saturated fatty acid chains (e.g., stearoyl tails) are not soluble in squalene. Alternatively, solubility can be determined according to the quantity of the lipid that dissolves in a given quantity of the oil to form a saturated solution).

The NLC may comprise additional lipids (i.e., neutral and anionic lipids) in combination with the cationic lipid so long as the net surface charge of the NLC prior to mixing with the bioactive agent is positive. Methods of measuring surface charge of a NLC are known in the art and include for example, as measured by Dynamic Light Scattering (DLS), Photon Correlation Spectroscopy (PCS), or gel electrophoresis.

C. Sorbitan Monoester

The present inventors discovered that a sorbitan ester when added to the NLC can act to enhance the effectiveness of the NLC in delivering the bioactive agent to a cell and/or in eliciting antibodies to an antigen in a subject where the bioactive agent is an antigen or encodes antigen and the composition is administered to a subject. In particular, it was discovered that the immune response to encoded proteins in the bioactive nucleic acid can be modulated by selection of sorbitan ester used in the NLC. It was surprisingly discovered that use of a sorbitan monoester was particularly effective at enhancing the effectiveness of the NLC. In some aspects, the acyl chain of the sorbitan monoester is saturated. In addition, without being bound by theory, it was surprisingly discovered that the sorbitan ester, and in particular, sorbitan monoester, acts in combination with the solid lipid (e.g., microcrystalline triglycerides) to enhance the effectiveness of the adjuvant activity of the NLC (e.g., in eliciting antibodies to an antigen in a subject where the bioactive agent is an antigen or encodes antigen and the composition is administered to a subject).

Exemplary sorbitan monoesters are commercially available under the tradenames SPAN® or ARLACEL®. An exemplary sorbitan monoester for use herein can be represented as a compound of Formula I or a stereoisomer thereof (including, but not limited to, Formula Ia, Ib, Ic, or Id) wherein R is a saturated or unsaturated $C_1$-$C_{30}$ alkyl group, preferably a saturated or unsaturated $C_1$-$C_{20}$ alkyl group, more preferably a saturated or unsaturated $C_{10}$-$C_{20}$ alkyl group. In exemplary embodiments, the alkyl group is non-cyclic. Exemplary sorbitan monoesters also include positional isomers of Formulas I, Ia, Ib, Ic or Id (e.g., one of the hydroxy functional groups is replaced by an ester functional group (e.g., an alkyl ester wherein the alkyl is a saturated or unsaturated $C_1$-$C_{30}$ alkyl group, preferably a saturated or unsaturated $C_1$-$C_{20}$ alkyl group, more preferably a saturated or unsaturated $C_{10}$-$C_{20}$ alkyl group and R is OH). The skilled artisan will appreciate that exemplary sorbitan monoesters may be salt forms (e.g., pharmaceutically acceptable salts) of Formulas I, Ia, Ib, Ic, Id and stereoisomers or positional isomers thereof.

Formula I

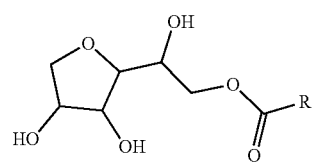

Formula Ia

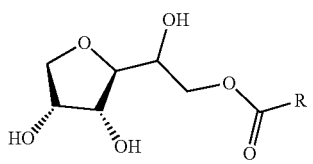

Formula Ib

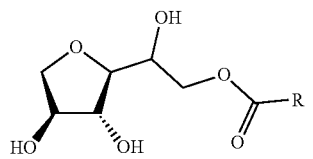

Formula Ic

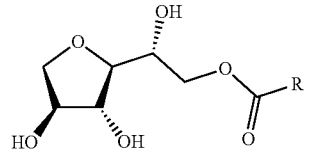

Formula Id

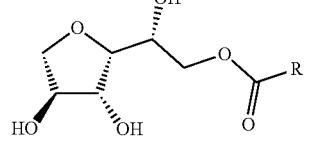

Particularly preferred sorbitan monoesters in this regard are sorbitan monostearate (also knowns as Span®60 and shown below) and sorbitan monooleate (also known as Span®80 and shown below), although other sorbitan monoesters can be used (including, but not limited to, sorbitan monolaurate (Span®20), sorbitan monopalmitate (Span®40)). Exemplary sorbitan monostearate is represented by Formula II or IIa or a salt form thereof and exemplary sorbitan monooleate is represented by Formula III or IIIa or a salt form thereof.

Formula II

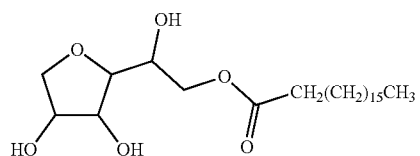

Formula IIa

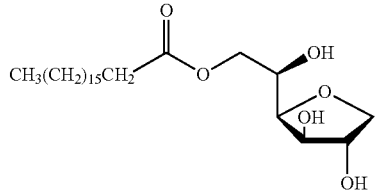

Formula III

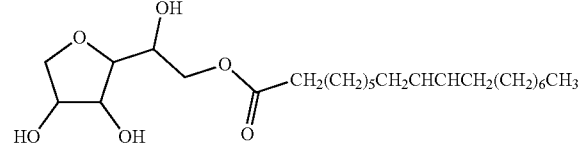

Formula IIIa

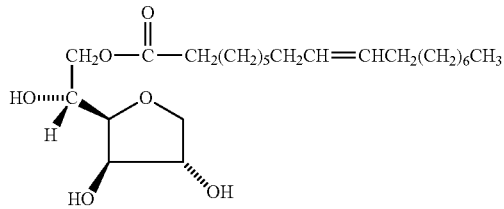

In addition to providing sorbitan monoesters as a component of a NLC, also contemplated is the substitution of the sorbitan monoester for an alternative hydrophobic surfactant, including alternative sorbitan-based non-ionic surfactants. Accordingly, also provided herein are NLC particles comprising an oil core comprising a liquid phase lipid and a solid phase lipid, a cationic component (preferably a cationic lipid or phospholipid), a hydrophobic surfactant (e.g., non-ionic surfactants including sorbitan-based non-ionic surfactants) and a hydrophilic surfactant. Sorbitan-based non-ionic surfactants include sorbitan esters other than sorbitan monoesters, for example sorbitan diesters and sorbitan triesters, such as for example, sorbitan trioleate (SPAN85™) and sorbitan tristearate (SPAN65™). Generally, the non-ionic surfactant (including sorbitan-based non-ionic surfactant) will have a hydrophilic-lipophilic balance (HLB) number between 1.8 to 8.6. All of the embodiments provided herein for the NLCs comprising a sorbitan monoester are applicable and contemplated for the NLCs comprising an alternative hydrophobic surfactant in place of the sorbitan monoester, e.g., NLCs comprising a sorbitan diester or triester in place of the sorbitan monoester. The sorbitan diester and triester or other hydrophobic surfactant can be present in the same concentrations as the sorbitan monoester. In some aspects, the acyl chains of the sorbitan diester or triester will be saturated.

Generally, the sorbitan esters (e.g., sorbitan monoesters) have a hydrophile-lipophile balance (HLB) value from 1 to 9. In some embodiments, the sorbitan esters (e.g., sorbitan monoesters) have an HLB value from 1 to 5. In some embodiments, the hydrophobic surfactant has a HLB value from about 4 to 5.

An exemplary sorbitan diester for use herein can be represented as a compound of Formula IV below or a stereoisomer thereof (e.g., wherein R is a saturated or unsaturated C1-C30 alkyl group, preferably a saturated or unsaturated C1-C20 alkyl group, more preferably a saturated or unsaturated C10-C20 alkyl group and at least one of R1 is H while the other is —C(=O)Y wherein Y is a saturated or unsaturated C1-C30 alkyl group, preferably a saturated or unsaturated C1-C20 alkyl group, more preferably a saturated or unsaturated C10-C20 alkyl group). In exemplary embodiments, the alkyl group is non-cyclic. Exemplary sorbitan diesters also include positional isomers of Formulas IV. The skilled artisan will appreciate that exemplary sorbitan diesters may be salt forms (e.g., pharmaceutically acceptable salts) of Formula IV and stereoisomers or positional isomers thereof.

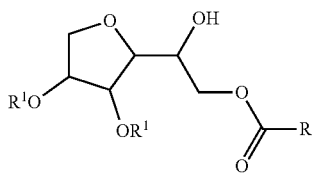

Formula IV

As exemplary sorbitan triester for use herein can be represented as a compound of Formula V below or a stereoisomer thereof (including, but not limited to, Formula Va, Vb, or Vc) wherein R is a saturated or unsaturated C1-C30 alkyl group, preferably a saturated or unsaturated C1-C20 alkyl group, more preferably a saturated or unsaturated C10-C20 alkyl group and R1 is-C(=O)Y wherein Y can be the same or different in each instance and is a saturated or unsaturated C1-C30 alkyl group, preferably a saturated or unsaturated C1-C20 alkyl group, more preferably a saturated or unsaturated C10-C20 alkyl group. In exemplary embodiments, the alkyl group is non-cyclic. Exemplary sorbitan triesters also include positional isomers of Formulas V, Va, Vb, or Vc (e.g., the hydroxy functional group is replaced by an ester functional group (e.g., an alkyl ester wherein the alkyl is a saturated or unsaturated C1-C30 alkyl group, preferably a saturated or unsaturated C1-C20 alkyl group, more preferably a saturated or unsaturated C10-C20 alkyl group) and one of the alkyl esters (e.g., a ring alkyl ester or non-ring alkyl ester) is replaced by a hydroxy functional group). The skilled artisan will appreciate that exemplary sorbitan triesters may be salt forms (e.g., pharmaceutically acceptable salts) of Formulas V, Va, Vb, or Vc and stereoisomers or positional isomers thereof.

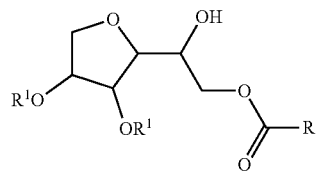

Formula V

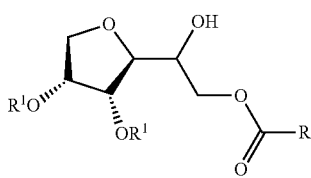

Formula Va

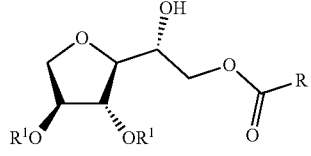

Formula Vb

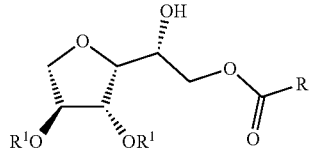

Formula Vc

With respect to stereoisomers, the skilled artisan will understand that the sorbitan esters may have chiral centers and may occur, for example, as racemates, racemic mixtures, and as individual enantiomers and diastereomers.

In embodiments wherein the sorbitan-based non-ionic surfactants is a sorbitan ester, typically, the NLC-based composition or formulation typically contains, for example, from about 0.1% to about 15% sorbitan ester (w/v), 0.1% to about 10% sorbitan ester (w/v), from 0.1% to about 5% sorbitan ester (w/v), about 0.1% to about 4% sorbitan ester (w/v), about 0.1% to about 4% sorbitan ester (w/v), about 0.1% to about 2.5% sorbitan ester (w/v), about 0.1% to about 2% sorbitan ester (w/v), 0.1% to about 1.5% sorbitan ester (w/v), 0.1% to about 1% sorbitan ester (w/v), 0.1% to about 0.5% sorbitan ester (w/v), 0.3% to about 2.5% sorbitan ester (w/v), about 0.3% to about 2% sorbitan ester (w/v), 0.3% to about 1.5% sorbitan ester (w/v), 0.3% to about 1% sorbitan ester (w/v), 0.3% to about 0.5% sorbitan ester (w/v) or any other amount or range described herein for a sorbitan ester, including from about 0.25% to about 15% sorbitan ester. In some aspects, the NLC-based compositions contain about 0.1%, about 0.2%, about 0.3%, about 0.4%, about 0.5%, about 0.6%, about 0.7%, about 0.8%, about 0.9%, about 1%, about 2%, about 3% or about 4% (w/v) sorbitan ester. Higher or lower w/v percentages are contemplated herein, particularly when considering diluted or concentrated formulations.

Accordingly, when the sorbitan ester is a sorbitan monoester (e.g., SPAN60™, SPAN80™), the NLC-based composition or formulation typically contains, for example, from about 0.1% to about 15% sorbitan monoester (w/v), 0.1% to about 10% sorbitan monoester (w/v), from 0.1% to about 5% sorbitan monoester (w/v), about 0.1% to about 4% sorbitan monoester (w/v), about 0.1% to about 4% sorbitan monoester (w/v), about 0.1% to about 2.5% sorbitan monoester (w/v), about 0.1% to about 2% sorbitan monoester (w/v), 0.1% to about 1.5% sorbitan monoester (w/v), 0.1% to about 1% sorbitan monoester (w/v), 0.1% to about 0.5% sorbitan monoester (w/v), 0.3% to about 2.5% sorbitan monoester (w/v), about 0.3% to about 2% sorbitan monoester (w/v), 0.3% to about 1.5% sorbitan monoester (w/v), 0.3% to about 1% sorbitan monoester (w/v), 0.3% to about 0.5% sorbitan monoester (w/v) or any other amount or range described herein for sorbitan monoester, including from about 0.25% to about 15% sorbitan monoester. In some aspects, the NLC-based composition or formulation contains about 0.1%, about 0.2%, about 0.3%, about 0.4%, about 0.5%, about 0.6%, about 0.7%, about 0.8%, about 0.9%, or about 1%, about 2%, about 3% or about 4% (w/v) sorbitan monoester. Higher or lower w/v percentages are contemplated herein, particularly when considering diluted or concentrated formulations.

Accordingly, when the sorbitan ester is a sorbitan diester, the NLC-based composition or formulation typically contain, for example, from about 0.1% to about 15% sorbitan diester (w/v), 0.1% to about 10% sorbitan diester (w/v), from 0.1% to about 5% sorbitan diester (w/v), about 0.1% to about 4% sorbitan diester (w/v), about 0.1% to about 4% sorbitan diester (w/v), about 0.1% to about 2.5% sorbitan diester (w/v), about 0.1% to about 2% sorbitan diester (w/v), 0.1% to about 1.5% sorbitan diester (w/v), 0.1% to about 1% sorbitan diester (w/v), 0.1% to about 0.5% sorbitan diester (w/v), 0.3% to about 2.5% sorbitan diester (w/v), about 0.3% to about 2% sorbitan diester (w/v), 0.3% to about 1.5% sorbitan diester (w/v), 0.3% to about 1% sorbitan diester (w/v), 0.3% to about 0.5% sorbitan diester (w/v) or any other amount or range described herein for sorbitan diester, including from about 0.25% to about 15% sorbitan diester. In some aspects, the NLC-based composition or formulation contains about 0.1%, about 0.2%, about 0.3%, about 0.4%, about 0.5%, about 0.6%, about 0.7%, about 0.8%, about 0.9%, or about 1%, about 2%, about 3% or about 4% (w/v) sorbitan diester. Higher or lower w/v percentages are contemplated herein, particularly when considering diluted or concentrated formulations.

Accordingly, when the sorbitan ester is a sorbitan triester (e.g., SPAN85™ or SPAN65™), the NLC-based composition or formulation typically contain, for example, from about 0.1% to about 15% sorbitan triester (w/v), 0.1% to about 10% sorbitan triester (w/v), from 0.1% to about 5% sorbitan triester (w/v), about 0.1% to about 4% sorbitan triester (w/v), about 0.1% to about 4% sorbitan triester (w/v), about 0.1% to about 2.5% sorbitan triester (w/v), about 0.1% to about 2% sorbitan triester (w/v), 0.1% to about 1.5% sorbitan triester (w/v), 0.1% to about 1% sorbitan triester (w/v), 0.1% to about 0.5% sorbitan triester (w/v), 0.3% to about 2.5% sorbitan triester (w/v), about 0.3% to about 2% sorbitan triester (w/v), 0.3% to about 1.5% sorbitan triester (w/v), 0.3% to about 1% sorbitan triester (w/v), 0.3% to about 0.5% sorbitan triester (w/v) or any other amount or range described herein for sorbitan triester, including from about 0.25% to about 15% sorbitan triester. In some aspects, the NLC-based composition or formulation contains about 0.1%, about 0.2%, about 0.3%, about 0.4%, about 0.5%, about 0.6%, about 0.7%, about 0.8%, about 0.9%, about 1%, about 2%, about 3% or about 4% (w/v) sorbitan triester. Higher or lower w/v percentages are contemplated herein, particularly when considering diluted or concentrated formulations.

In exemplary embodiments, the sorbitan ester (e.g., sorbitan monoester, diester or triester) is present in an amount sufficient to increase the ability of the composition to facilitate delivery and/or expression of the bioactive agent (e.g., RNA) as compared to a comparable composition lacking the sorbitan ester (e.g., sorbitan monoester, diester or triester respectively). In embodiments where the composition is administered to the subject in an effective amount, the composition may elicit antibody titers to the antigen equal to or greater than the antibody titers elicited when a comparable composition lacking the sorbitan ester is administered to the subject or when the bioactive agent is administered to the subject without the NLC. In some embodiments, the composition induces an immune response (e.g., neutralizing antibody titers) in the subject at a higher level than the immune response induced in the subject by a comparable composition lacking the sorbitan ester. Immune response may be, for example, innate, cellular or antibody responses. Neutralizing antibody titers may be determined by any assay known to one of skill in the art, including, without limitation, a plaque reduction neutralization titer analysis (Ratnam, S et al. *J. Clin. Microbiol* (2011), 33 (4): 811-815; Timiryazova, T et al. *Am J Trop Med Hyg* (2013), 88(5): 962-970).

D. Surfactants

The NLCs described herein comprise a surfactant, in addition to the sorbitan-based non-ionic surfactants (e.g., sorbitan ester). There are a number of surfactants specifically designed for and commonly used in biological applications. Such surfactants are divided into four basic types and can be used in the present invention: anionic, cationic, zwitterionic and nonionic. A particularly useful group of surfactants are the hydrophilic non-ionic surfactants and, in particular, polyoxyethylene sorbitan monoesters and polyoxyethylene sorbitan triesters. These materials are referred to as polysorbates and are commercially available under the mark TWEEN® and are useful for preparing the NLCs. TWEEN® surfactants generally have a HLB value falling between 9.6 to 16.7. TWEEN® surfactants are commercially available. Other non-ionic surfactants which can be used are, for example, polyoxyethylene fatty acid ethers derived from lauryl, acetyl, stearyl and oleyl alcohols, polyoxyethylene fatty acids made by the reaction of ethylene oxide with a long-chain fatty acid, polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene fatty acid, alcohol or ether derivatives of long-chain fatty acids of 12-22 carbon atoms.

In some embodiments, it is preferable to choose a non-ionic surfactant which has an HLB value in the range of about 7 to 16. This value may be obtained through the use of a single non-ionic surfactant such as a TWEEN® surfactant or may be achieved by the use of a blend of surfactants. In certain embodiments, the NLC comprises a single non-ionic surfactant, most particularly a TWEEN® surfactant, as the emulsion stabilizing non-ionic surfactant. In an exemplary embodiment, the emulsion comprises TWEEN® 80, otherwise known as polysorbate 80.

The NLC-based composition or formulation contains can contain, for example, from about 0.01% to about 15% surfactant (w/v), from about 0.01% to about 10% surfactant (w/v) from about 0.01% to about 5% surfactant (w/v), about 0.01% to about 2.5% surfactant, about 0.01% to about 2% surfactant, 0.01% to about 1.5% surfactant, 0.01% to about 1% surfactant, 0.01% to about 0.5% surfactant, 0.05% to about 0.5% surfactant, 0.08% to about 0.5% surfactant, about 0.08% surfactant, about 0.5% surfactant, about 0.6% surfactant, about 0.7% surfactant, about 0.8% surfactant, about 0.9% surfactant, or about 1% surfactant, or about 2%, about 3%, about 4% surfactant or any other amount or range described herein for surfactant. Higher or lower w/v percentages are contemplated herein, particularly when considering diluted or concentrated formulations.

Additional components can be included in the NLCs of the present invention including, for examples, components that promote NLC formation, improve the complex formation between the negatively charged molecules and the cationic particles, facilitate appropriate release of the negatively charged molecules (such as an RNA molecule), and/or increase the stability of the negatively charged molecule (e.g., to prevent degradation of an RNA molecule).

The aqueous phase (continuous phase) of the NLCs is typically a buffered salt solution (e.g., saline) or water. The buffered salt solution is typically an aqueous solution that comprises a salt (e.g., NaCl), a buffer (e.g., a citrate buffer), and can further comprise, for example, an osmolality adjusting agent (e.g., a saccharide), a polymer, a surfactant, or a combination thereof. If the emulsions are formulated for parenteral administration, it is preferable to make up final buffered solutions so that the tonicity, i.e., osmolality is essentially the same as normal physiological fluids in order to prevent undesired post-administration consequences, such as post-administration swelling or rapid absorption of the composition. It is also preferable to buffer the aqueous phase in order to maintain a pH compatible with normal physiological conditions. Also, in certain instances, it may be desirable to maintain the pH at a particular level in order to ensure the stability of certain components of the NLC. For example, it may be desirable to prepare a NLC that is isotonic (i.e., the same permeable solute (e.g., salt) concentration as the normal cells of the body and the blood) and isosmotic. To control tonicity, the NLC may comprise a physiological salt, such as a sodium salt. In some aspects, sodium chloride (NaCl), for example, may be used at about 0.9% (w/v) (physiological saline). Other salts that may be present include, for example, potassium chloride, potassium dihydrogen phosphate, disodium phosphate, magnesium chloride, calcium chloride, and the like. Non-ionic tonicifying agents can also be used to control tonicity. Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents that can be useful in the present invention. Non-ionic tonicity modifying agents can be present, for example, at a concentration of from about 0.1% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 4.0-8.0 or from about 4.5 to about 6.8. In another exemplary embodiment, the aqueous phase is, or the buffer prepared using, RNase-free water or DEPC treated water. In some cases, high salt in the buffer might interfere with complexation of negatively charged molecule to the emulsion particle therefore is avoided. In other cases, certain amount of salt in the buffer may be included.

In an exemplary embodiment, the buffer is 10 mM citrate buffer e.g., (sodium citrate) with a pH between about 5.0 and 8.0. In another exemplary embodiment, the aqueous phase is, or the buffer is prepared using, RNase-free water or DEPC treated water. In other exemplary embodiments, the compositions of the present invention do not comprise a citrate buffer.

The aqueous phase may also comprise additional components such as molecules that change the osmolarity of the aqueous phase or molecules that stabilize the negatively charged molecule after complexation. Preferably, the osmolarity of the aqueous phase is adjusting using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.), or combinations thereof. If desired, a nonionic polymer (e.g., a poly(alkyl glycol) such as polyethylene glycol, polypropylene glycol, or polybutlyene glycol) or nonionic surfactant can be used.

E. Oil:Surfactant Ratios

Exemplary NLCs are composed of a hydrophobic core containing the liquid oil and solid lipid, and surfactants (also known as emulsifiers or emulsifying agents) that make up the interface separating the hydrophobic phase—liquid oil and solid lipid, collectively referred to here as oil—from the aqueous phase. Since surfactants typically reside on the surface of NLC nanoparticles, their amount dictates the total available surface area. On the other hand, the oil resides in the core and primarily contributes to the total available volume. Increasing the surfactant to oil ratio consequently increases the surface area (SA) to volume ratio (V); thus, for a fixed volume of material, increasing the SAN ratio translates to reducing NLC particle diameter. Instead of, or, in addition, to describing exemplary NLC compositions in terms of the w/v percentages of various components, they can be described by the molar ratios of various components. In some aspects, exemplary NLCs of the present invention, have an oil to surfactant molar ratio of from about 0.05 to about 12 or from about 0.05 to about 9 or from about 0.05 to about 8 or from about 0.05 to about 1 or from about 0.1 to about 1. The present inventors have demonstrated that by reducing the oil to surfactant molar ratio, smaller NLCs can be synthesized. In addition, by reducing the amount of oil in the NLCs, potential toxicity of the formulations can be reduced. In other aspects, exemplary NLCs of the present invention, have an oil to surfactant molar ratio of from about 0.5 to about 12, from about 0.5 to about 9, from 1 to about 9, from about 2 to about 9, from about 3 to about 9, from about 4 to about 9, from about 4.5 to about 9, or from about 4.5 or about 5 to about 7. Exemplary formulations have an oil to surfactant molar ratio of about 0.5, about 1, about 1.5, about 2, about 2.5, about 3, about 3.5, about 4, about 4.5, about 5, about 5.5, about 6, about 7, about 8, about 9, about 10, about 11, or about 12. As used herein, the oil to surfactant molar ratio is determined by (i) adding the moles of lipid that make up the oil core (solid phase lipid and liquid phase lipid) to arrive at a value for moles of oil core lipid (ii) adding the moles of the cationic component (e.g., DOTAP), hydrophobic surfactant (e.g., sorbitan ester) and hydrophilic surfactant (tween 80) to arrive at a value for moles surfactant, and (iii) dividing moles of oil core lipid by moles of surfactant.

F. Hydrophilic Surfactant:Cationic Component Ratios

The present inventors have discovered that the ratio of hydrophilic surfactant to cationic component can impact the ability of the NLC to have a protective effect from RNAase degradation and can impact the immunogenicity of the formulations. In particular, the inventors have found that Tween:DOTAP ratios at about 0.6 are optimal for obtaining consistent results for delivery and expression of RNA bioactive agents whereas Tween:DOTAP ratios at about 2.0 and higher are not as optimal for obtaining such consistency. Accordingly, exemplary NLCs of the present invention have a hydrophilic Surfactant:Cationic component (e.g., cationic lipid) ratio of from about 0.2 to about 1.5, from about 0.2 to about 1 or from about 0.5 to about 1. When Tween and DOTAP are in the composition, exemplary NLCs of the present invention have a tween:DOTAP ratio of from about 0.2 to about 1.5, from about 0.2 to about 1 or from about 0.5 to about 1. As used herein, the hydrophilic surfactant: cationic component ratio is determined by (i) adding the moles of hydrophilic surfactant to arrive at a value for moles of hydrophilic surfactant (ii) adding the moles of the cationic component to arrive at a value for moles of cationic component, and (iii) dividing moles of hydrophilic surfactant by moles of cationic component.

G. Loading Capacities

The present inventors have discovered the loading capacity of the NLC formulations can be manipulated by modulating the ratio of hydrophilic surfactant to cationic component and the amount of oil present in the formulations thereby reducing the average NLC particle size. Exemplary NLC formulations have loading capacity for RNA of at least about 10 μg/ml RNA, at least about 20 μg/ml RNA, at least about 50 μg/ml RNA, at least about 100 μg/ml RNA, at least about 200 μg/ml RNA, at least about 300 μg/ml, or at least about 400 μg/ml RNA. NLC formulations having an average particle size of from 20 nm to about 110 nm, from about 20 nm to about 80 nm, from about 20 nm to about 70 nm, from about 20 nm to about 60 nm typically have increased loading capacity.

H. Exemplary Nanostructured Carriers and their w/v Percentages

In select exemplary embodiments, the NLC composition comprises from about 0.2% to about 40% w/v liquid phase lipid, from about 0.02% to about 10% w/v solid phase lipid, from about 0.2% to about 10% w/v cationic lipid, from about 0.25% to about 5% w/v hydrophobic surfactant (e.g., sorbitan ester), and from about 0.2% to about 10% w/v, from about 0.2% to about 5% w/v, from about 0.5% to about 5% w/v or from about 0.5% to about 10% w/v hydrophilic surfactant. This NLC composition is referred to herein as formulation A. In any aspect of formulation A, the hydrophilic surfactant can be present at 0.2% to about 10% w/v, 0.2% to about 5% w/v, 0.5% to about 5% w/v or from about 0.5% to about 10% w/v.

In select exemplary embodiments, the NLC composition comprises from about 0.2% to about 40% w/v liquid phase lipid, from about 0.1% to about 10% w/v solid phase lipid, from about 0.2% to about 10% w/v cationic lipid, from about 0.25% to about 5% w/v hydrophobic surfactant (e.g., sorbitan ester), and from about 0.2% to about 10% w/v, from about 0.2% to about 5% w/v, from about 0.5% to about 5% w/v or from about 0.5% to about 10% w/v hydrophilic surfactant. This NLC composition is referred to herein as formulation B. In any aspect of formulation B, the hydrophilic surfactant can be present at 0.2% to about 10% w/v, 0.2% to about 5% w/v, 0.5% to about 5% w/v or from about 0.5% to about 10% w/v.

In select exemplary embodiments, the NLC composition comprises from about 0.2% to about 1% w/v liquid phase lipid, from about 0.02% to about 1% w/v solid phase lipid, from about 2% to about 10% w/v cationic lipid, from about 2% to about 5% w/v sorbitan ester, and from about 2% to about 5% w/v hydrophilic surfactant. This NLC composition is referred to herein as formulation C.

In select exemplary embodiments, the NLC composition comprises from about 2% to about 40% w/v liquid phase lipid, from about 0.1% to about 10% w/v solid phase lipid, from about 0.2% to about 10% w/v cationic lipid, from about 0.25% to about 5% w/v hydrophobic surfactant (e.g., sorbitan ester), and from about 0.2% to about 10% w/v, from about 0.2% to about 5% w/v, from about 0.5% to about 5% w/v or from about 0.5% to about 10% w/v hydrophilic surfactant. This NLC composition is referred to herein as formulation D. In any aspect of formulation D the hydrophilic surfactant can be present at 0.2% to about 10% w/v, 0.2% to about 5% w/v, about 0.5% to about 5% w/v or from about 0.5% to about 10% w/v hydrophilic surfactant In select exemplary embodiments, the NLC composition comprises from about 2% to about 10% w/v liquid phase lipid, from about 0.1% to about 10% w/v solid phase lipid, from about 0.2% to about 10% w/v cationic lipid, from about 0.25% to about 5% w/v sorbitan ester, and from about 0.2% to about 10% or from about 0.2% to about 5% w/v hydrophilic surfactant. This NLC composition is referred to herein as formulation E. In any aspect of formulation E, the hydrophilic surfactant can be present at 0.2% to about 10% or from about 0.2% to about 5% w/v.

In select exemplary embodiments, the NLC composition comprises from about 2% to about 10% w/v liquid phase lipid, from about 0.1% to about 3% w/v solid phase lipid, from about 1% to about 5% w/v cationic lipid, from about 1% to about 5% w/v sorbitan ester, and from about 1% to about 5% w/v hydrophilic surfactant. This NLC composition is referred to herein as formulation F.

In select exemplary embodiments, the NLC composition comprises from about 2% to about 5% w/v liquid phase lipid, from about 0.1% to about 2% w/v solid phase lipid, from about 2% to about 5% w/v cationic lipid, from about 2% to about 5% w/v sorbitan ester, and from about 2% to about 5% w/v hydrophilic surfactant. This NLC composition is referred to herein as formulation G.

In select exemplary embodiments, the NLC composition comprises from about 2% to about 10% w/v liquid phase lipid, from about 0.1% to about 3% w/v solid phase lipid, from about 0.2% to about 2% w/v cationic lipid, from about 0.25% to about 2% w/v sorbitan ester, and from about 0.2% to about 5% w/v or from about 0.5% to about 5% w/v hydrophilic surfactant. This NLC composition is referred to herein as formulation H. In any aspect of formulation H, the hydrophilic surfactant can be present at about 0.2% to about 5% w/v or from about 0.5% to about 5% w/v.

In select exemplary embodiments, the NLC composition comprises from about 2% to about 6% w/v liquid phase lipid, from about 0.1% to about 1% w/v solid phase lipid, from about 0.2% to about 1% w/v cationic lipid, from about 0.25% to about 1% w/v sorbitan ester, and from about 0.2% to about 5% w/v or from about 0.5% to about 5% w/v hydrophilic surfactant. This NLC composition is referred to herein as formulation I. In any aspect of formulation I, the hydrophilic surfactant can be present at about 0.2% to about 5% w/v or from about 0.5% to about 5% w/v.

In select exemplary embodiments, the NLC composition comprises from about 2% to about 6% w/v liquid phase lipid, from about 0.1% to about 1% w/v solid phase lipid, from about 0.2% to about 1% w/v cationic lipid, from about 0.25% to about 1% w/v sorbitan ester, and from about 0.2% to about 2% w/v or from about 0.2% to about 1% hydrophilic surfactant. This NLC composition is referred to herein as formulation J.

In select exemplary embodiments, the NLC composition comprises from about 2% to about 6% w/v liquid phase lipid, from about 0.1% to about 1% w/v solid phase lipid, from about 0.2% to about 1% w/v cationic lipid, from about 0.25% to about 1% w/v sorbitan ester, and from about 0.2% to about 0.5% or from 0.2% to about 1% w/v hydrophilic surfactant. This NLC composition is referred to herein as formulation K. In any aspect of formulation K, the hydrophilic surfactant can be present at about 0.2% to about 0.5% or from 0.2% to about 1% w/v.

In select exemplary embodiments, the NLC composition comprises from about 10% to about 40% w/v liquid phase lipid, from about 1% to about 2% solid phase lipid, from about 2% to about 5% cationic lipid, from about 3 to about 5% w/v sorbitan ester, and from about 3% to about 5% w/v hydrophilic surfactant. This NLC composition is referred to herein as formulation L.

In select exemplary embodiments, the NLC composition comprises from about 10% to about 20% w/v liquid phase lipid, from about 0.5 to about 1.5% solid phase lipid, from about 3% to about 4% cationic lipid, from about 3 to about 4% w/v sorbitan ester, and from about 3% to about 5% w/v hydrophilic surfactant. This NLC composition is referred to herein as formulation M.

In select exemplary embodiments, the NLC composition comprises about 15% w/v liquid phase lipid, about 1% solid phase lipid, about 3% cationic lipid, about 3.7% w/v sorbitan ester, and about 3.7% w/v hydrophilic surfactant. This NLC composition is referred to herein as formulation N.

In select exemplary embodiments, the NLC composition comprises about 30% w/v liquid phase lipid, about 1.8% solid phase lipid, about 3% cationic lipid, about 3.7% w/v sorbitan ester, and about 3.7% w/v hydrophilic surfactant. This NLC composition is referred to herein as formulation O.

In select exemplary embodiments, the NLC composition comprises between about 3 to about 4% w/v liquid phase lipid, between about 0.2% to about 1% solid phase lipid, between about 3% to about 5% cationic lipid, between about 3% to about 5% sorbitan ester, and between about 3 to about 5% hydrophilic surfactant. This NLC composition is referred to herein as formulation P.

In select exemplary embodiments, the NLC composition comprises from about 0.2% to about 40% w/v liquid phase lipid, from about 0.1% to about 10% w/v solid phase lipid, from about 0.2% to about 10% w/v cationic lipid, from about 0.25% to about 15% w/v sorbitan monoester, and from about 0.5% to about 15% w/v hydrophilic surfactant. This NLC composition is referred to herein as formulation Q.

In select exemplary embodiments, the NLC composition comprises about 4% w/v liquid phase lipid, about 0.25% w/v solid phase lipid, about 0.4% w/v cationic lipid, about 0.5% w/v sorbitan ester, and about 2% w/v hydrophilic surfactant. This NLC composition is referred to herein as formulation R.

In select exemplary embodiments, the NLC composition comprises about 4% w/v liquid phase lipid, about 0.25% w/v solid phase lipid, about 0.4% w/v cationic lipid, about 0.5% w/v sorbitan ester, and about 0.5% w/v hydrophilic surfactant. This NLC composition is referred to herein as formulation S.

In select exemplary embodiments, the NLC composition comprises about 3.75% w/v liquid phase lipid, about 0.25% w/v solid phase lipid, about 3% w/v cationic lipid, about 3.7% w/v sorbitan ester, and about 3.7% w/v hydrophilic surfactant. This NLC composition is referred to herein as formulation T.

In select exemplary embodiments, the NLC composition comprises about 3.75% w/v liquid phase lipid, about 0.25% w/v solid phase lipid, about 1.5% w/v cationic lipid, about 3.7% w/v sorbitan ester, and about 1.5% w/v hydrophilic surfactant. This NLC composition is referred to herein as formulation U.

In select exemplary embodiments, the NLC composition comprises about 4.75% w/v liquid phase lipid, about 0.25% w/v solid phase lipid, about 0.5% w/v cationic lipid, about 0.5% w/v sorbitan ester, and about 0.4% w/v hydrophilic surfactant. This NLC composition is referred to herein as formulation V.

In select exemplary embodiments, the NLC composition comprises from about 0.2% to about 40% w/v liquid phase lipid, from about 0.2% to about 10% w/v cationic lipid, from about 0.25% to about 5% w/v hydrophobic surfactant (e.g., sorbitan ester), and from about 0.2% to about 10% w/v, from about 0.2% to about 5% w/v, from about 0.5% to about 5% w/v or from about 0.5% to about 10% w/v hydrophilic surfactant. This NLC composition is referred to herein as formulation W. In any aspect of formulation W, the hydrophilic surfactant can be present at 0.2% to about 10% w/v, 0.2% to about 5% w/v, 0.5% to about 5% w/v or from about 0.5% to about 10% w/v.

The skilled artisan will understand that any of the NLC compositions/formulations described herein, including formulations A through W can be diluted or concentrated for use in the present invention. For example, when mixed with a bioactive agent for delivery, the formulation may be diluted in the mixing process. The NLC compositions/formulations can be diluted for example, 1:2. All of the NLC compositions/formulations described herein can be diluted, for example, from about 2 to about 500 fold, preferably from about 2 to about 100 fold. Typically, but not always, dilution occurs when mixing the formulation with a bioactive agent (e.g., RNA or DNA) for delivery. They may be diluted, for example, about 2 fold, about 3 fold, about 4 fold, about 5 fold, about 6 fold, about 7 fold, about 8 fold, about 9 fold, about 10 fold, about 15 fold, about 20 fold, about 25 fold, about 30 fold, about 100 fold, or about 500 fold. As will be understood by the skilled practitioner, a diluted formulation of the present invention will have a decreased concentration of the liquid phase lipid, solid phase lipid, cationic component, hydrophobic surfactant (e.g., sorbitan ester), and surfactant (e.g., hydrophilic surfactant), however, the ratio of liquid phase lipid to solid phase lipid to cationic component to hydrophobic surfactant (e.g., sorbitan ester) to surfactant will remain the same. The present invention provides not only formulations A through W but diluted versions of the formulations A through W. In some cases, it is the diluted formulations that are associated with (e.g., complexed to) the bioactive agent. For example, a particularly preferred formulation is formulation S or formulation T diluted 2 fold. Such diluted formulation S comprises about 2% w/v liquid phase lipid, about 0.13% w/v solid phase lipid, about 0.2% w/v cationic lipid, about 0.25% w/v sorbitan ester, and about 0.25% w/v hydrophilic surfactant. Such diluted formulation T comprises about 1.88% w/v liquid phase lipid, about 0.13% w/v solid phase lipid, about 1.5% w/v cationic lipid, about 1.85% w/v sorbitan ester, and about 1.85% w/v hydrophilic surfactant.

Alternatively, the compositions/formulations, may be concentrated, for example from about 2 to about 30 fold, preferably from about 2 to about 20 fold. They may be concentrated, for example, about 2 fold, about 3 fold, about 4 fold, about 5 fold, about 6 fold, about 7 fold, about 8 fold, about 9 fold, about 10 fold, about 15 old, about 20 fold, about 25 fold or about 30 fold. Accordingly, the present invention provides not only formulations A through W but concentrated versions of the formulations A through U.

For any of NLC formulations of the present invention including formulations A through V, and included diluted and concentrated formulations of formulations A through V, the following and any combination of the following can apply: (i) the sorbitan ester is a sorbitan monoester, diester, or triester; (ii) the sorbitan ester is a sorbitan monoester selected from sorbitan monostearate or sorbitan monooleate or sorbitan monolaurate or a sorbitan triester selected from sorbitan trioleate or sorbitan tristearate; (iii) the liquid phase lipid is squalene; (iv) the solid phase lipid is a glycerolipid; (v) the solid phase lipid is microcrystalline triglyceride; (vi) The solid phase lipid is trimyristin; (vii) The cationic lipid is DOTAP; (viii) the hydrophilic surfactant is polysorbate 80 (also referred to as Tween 80); (ix) the sorbitan ester is a monoester, the liquid phase lipid is squalene; and the solid phase lipid is a glycerolipid; (x) the sorbitan ester is a monoester, the liquid phase lipid is squalene; the solid phase lipid is a glycerolipid; the cationic lipid is DOTAP and the hydrophilic surfactant is polysorbate 80; (xi) the sorbitan ester is sorbitan monostearate or sorbitan monooleate or sorbitan monolaurate, the liquid phase lipid is squalene; the solid phase lipid is trimyristin; the cationic lipid is DOTAP and the hydrophilic surfactant is polysorbate 80; (xii) the sorbitan ester is a triester, the liquid phase lipid is squalene; and the solid phase lipid is a glycerolipid; (xiii) the sorbitan ester is a triester, the liquid phase lipid is squalene; the solid phase lipid is a glycerolipid; the cationic lipid is DOTAP and the hydrophilic surfactant is polysorbate 80; (xiv) the sorbitan ester is sorbitan trioleate or sorbitan tristearate, the liquid phase lipid is squalene; the solid phase lipid is trimyristin; the cationic lipid is DOTAP and the hydrophilic surfactant is polysorbate 80.

The present invention also provides formulations A through Q, including those indicated above, wherein the oil to surfactant ratio is from about 0.05 to about 12 or from about 0.05 to about 9 or from about 0.05 to about 8 or from about 0.05 to about 1 or from about 0.1 to about 1. Also provided are formulations A through Q, including those indicated above, wherein the oil to surfactant molar ratio of from about 0.5 to about 12, from about 1 to about 9, from about 2 to about 9, from about 3 to about 9, from about 4 to about 9, from about 4.5 to about 9, or from about 4.5 or about 5 to about 7.

The present invention provides formulations A through Q, including those indicated above, wherein the hydrophilic Surfactant:Cationic component (e.g., cationic lipid) ratio is from about 0.2 to about 1 or from about 0.5 to about 1.

Accordingly, some exemplary NLC compositions are formulations A, B, or Q diluted or concentrated, with an oil to surfactant molar ratio of about 0.5 to about 12, from about 1 to about 9, from about 2 to about 9, from about 3 to about 9, from about 4 to about 9, from about 4.5 to about 9, or from about 4.5 or about 5 to about 7 and a hydrophilic Surfactant:Cationic component (e.g., cationic lipid) ratio from about 0.2 to about 1.5.

Accordingly, some exemplary NLC compositions are formulations A, B, or Q, diluted or concentrated, with an oil to surfactant molar ratio of about 0.5 to about 12, from about 1 to about 9, from about 2 to about 9, from about 3 to about 9, from about 4 to about 9, from about 4.5 to about 9, or from about 4.5 or about 5 to about 7 and a hydrophilic Surfactant:Cationic component (e.g., cationic lipid) ratio from about 0.2 to about 1.

Some exemplary NLC compositions are formulations A, B, or Q, diluted or concentrated, with an oil to surfactant molar ratio of about 0.5 to about 12, from about 1 to about 9, from about 2 to about 9, from about 3 to about 9, from about 4 to about 9, from about 4.5 to about 9, or from about 4.5 or about 5 to about 7 and a hydrophilic Surfactant:Cationic component (e.g., cationic lipid) ratio from about 0.5 to about 1.

Some exemplary NLC compositions are formulations A, B, or Q, diluted or concentrated, with an oil to surfactant molar ratio of 0.05 to about 12 or from about 0.05 to about 9 or from about 0.05 to about 8 or from about 0.05 to about 1 or from about 0.1 to about 1 and a hydrophilic Surfactant:Cationic component (e.g., cationic lipid) ratio from about 0.5 to about 1.5.

Some exemplary NLC compositions are formulations A, B, or Q, diluted or concentrated, with an oil to surfactant molar ratio of 0.05 to about 12 or from about 0.05 to about 9 or from about 0.05 to about 8 or from about 0.05 to about 1 or from about 0.1 to about 1 and a hydrophilic Surfactant:Cationic component (e.g., cationic lipid) ratio from about 0.5 to about 1.

The present invention provides formulations A through W including all of the formulations describe in section H. Exemplary Nanostructured Carriers and their w/v percentages, wherein the average diameter of the NLC particles is from about 40 nm or 50 nm to about 80 nm, from about 40 nm or 50 nm to about 70 nm, from about 40 nm or 50 nm to about 60 nm.

III. PHYSIOCHEMICAL CHARACTERISTICS OF THE NANOSTRUCTURED LIPID CARRIERS

A. Size

The size of the NLC can be assessed by known techniques in the art, including but not limited to, x-ray and laser diffraction, dynamic light scattering (DLS), CryoEM, or Malvern Zetasize. In some embodiments, the size of the NLC refers to the Z-average diameter.

The NLCs have an average diameter (i.e., the number average diameter) of 1 micrometer or less. It is particularly desirable that the average particle size (i.e., the number average diameter) of the NLC is about 900 nm or less, about 800 nm or less, about 700 nm or less, about 600 nm or less, about 500 nm or less, about 400 nm or less, 300 nm or less, 200 nm or less, 100 nm or less or 80 nm or less, for example, from about 50 nm to about 900 nm, from about 50 nm to about 800 nm, from about 50 nm to about 700 nm, from about 50 nm to about 600 nm, from about 50 nm to about 500 nm, from about 50 nm to about 400 nm, from about 50 nm to about 300 nm, from about 50 nm to about 200 nm, from about 50 nm to about 175 nm, from about 50 nm to about 150 nm, from about 50 nm to about 125 nm, from about 50 nm to about 100 nm, from about 50 nm to about 80 nm, from about 40 nm to about 80 nm, from about 20 nm to about 80 nm, from about 40 nm to about 80 nm, or from about 40 nm to about 60 nm. It will be understood by the skilled practitioner that a NLC is made up of NLC particles. The average particle size refers to the average diameter of the particles that make up the NLC. The average diameter of the NLC particles is typically about 40 nm, is about 60 nm, is about 80 nm, is about 85 nm, is about 90 nm, is about 95 nm, is about 100 nm, is about 105 nm, is about 110 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, or is about 200 nm.

In some aspects, the average diameter of the NLC particles is from about 20 nm to about 200 nm, from about 20 nm to about 150 nm, from about 20 nm to about 110 nm, from about 20 nm to about 80 nm, from about 20 nm to about 70 nm, from about 20 nm to about 60 nm.

In some aspects, the average diameter of the NLC particles is from about 50 nm to about 200 nm, from about 50 nm to about 150 nm, from about 50 nm to about 110 nm, from about 50 nm to about 80 nm, from about 50 nm to about 70 nm, from about 50 nm to about 60 nm.

In some aspects, the average diameter of the NLC particles is from about 40 nm to about 80 or from about 40 nm to about 60 nm.

An exemplary NLC of the present invention is capable of being filtered through at least a 0.45 micron filter. In an exemplary embodiment, the NLC is capable of being filtered through a 0.20 or 0.22 micron filter.

B. Stability

Exemplary NLCs provided herein are stable, allowing for ease of use, manufacturability, transportability, and storage. The physiochemical characteristics of the NLC, including, but not limited to its size, is maintained over time, at various temperatures, and under various conditions.

The evolution of particle size over a function of time provides colloidal stability information. An exemplary stable NLC composition is one whose particles retain substantially the same z-average diameter size over a time period (e.g., a 30 day or 7 day time period) at different temperatures typically but not limited to 37, 25 or 5 degrees Celsius. By retaining substantially the same z-average diameter size, it is meant that a particle remains within 20%, 15%, 10%, 5%, of its original size over a 30 day time period. A particularly stable NLC composition is one whose particles retain substantially the same z-average diameter size over a 30 day period at 4 degrees Celsius, 25 degrees Celsius or even 37 degrees Celsius.

The stability of the NLC can be measured by techniques familiar to those of skill in the art. In some embodiments, the stability is observed visually. Visual inspection can include inspection for particulates, flocculence, or aggregates. Typically, colloidal stability is determined by the particle size of the NLC, such as by measuring the z-average diameter and optionally expressed as change in size over time, or at various temperatures, or under certain conditions. In some embodiments, the stability is determined by assessing the increase in particle size. In some embodiments, stability is determined by measurement of the polydispersity index (PDI), for example with the use of the dynamic light scattering (DLS) technique. In other embodiments, stability is determined by measurement of the zeta potential with the use of the DLS technique.

In some embodiments, the Z-average diameter of the NLC increases less than 50%, less than 40%, less than 30%, less than 25%, less than 20%, less than 15%, less than 12%, less than 10%, less than 7%, less than 5%, less than 3%, less than 1% over the time period assayed.

In some embodiments the polydispersity index of the NLC is maintained at about 0.5, at about 0.4, at about 0.3, at about 0.2, at about 0.1 or at from about 0.1 to about 0.5, at from about 0.1 to about 0.4, at from about 0.1 to about 0.3, at from about 0.1 to about 0.2, at from about 0.2 to about 0.4, or at from about 0.2 to about 0.3. In some preferred aspects, the polydispersity index is greater than 0.1, greater than 0.15, or greater than 0.2.

Exemplary NLC-based compositions of the present invention are stable for greater than 6 months at 25 degrees Celsius (e.g., retain substantially the same z-average diameter size).

IV. BIOACTIVE AGENTS

In some exemplary embodiments, in order to deliver a bioactive agent, the formulations of the present invention are mixed or otherwise formulated with one or more bioactive agents. The term "bioactive agent" as used herein refers to any material to be delivered by the formulations of the present disclosure and can include without limitation macromolecules, peptides, proteins, peptidomimetics, nucleic acids, oligonucleotides, deoxyribonucleotides, plasmid DNA, circular DNA, linear DNA, single-stranded DNA, modified DNA, antisense DNA, ribonucleotides, mRNA, chemically modified RNA, non-coding RNA, miRNA, siRNA, tRNA, ribosomal RNA, RNA ribozymes, replicon RNA, RNA aptamers, DNA aptamers, double-stranded RNA, base-substituted RNA, inosine-containing RNA, adjuvants including TLR agonists (for example TLR2, TLR3, TLR4, TLR 7, TLR8, and TLR9 agonists), Rig-I agonists, saponins, carbohydrates, carbohydrate polymers, conjugated carbohydrates, whole viral particles, virus-like particles, viral fragments, and cellular fragments. Nonlimiting exemplary adjuvants include double-stranded RNA, RIBOXXOL, poly(I:C), and Hiltonol® (poly-ICLC). Hiltonol® (poly-ICLC) is a synthetic complex of carboxymethylcellulose, polyinosinic-polycytidylic acid double-stranded RNA, and poly-L-lysine. RIBOXXOL is an annealed 50 bp RNA duplex (Riboxx GmbH). Any bioactive agent that can be delivered safely to a cell can be mixed with a NLC of the present invention. When negatively charged molecules are to be delivered, in some embodiments, the cationic NLC surface can interact with negatively charged bioactive agents thereby anchoring the molecules to the NLC.

Exemplary negatively charged molecules to be used as bioactive agents include, for example, peptide-containing antigens, nucleic acid molecules (e.g., RNA or DNA) that encode one or more peptide-containing antigens, negatively charged polysaccharides, negatively charged small molecules, and negatively charged immunological adjuvants. Negatively charged immunological adjuvants include, for example, immunostimulatory oligonucleotides (e.g., CpG oligonucleotides), single-stranded RNAs, small molecule immune potentiators (SMIPs), and the like. Negatively charged small molecules include, for example, phosphonate, fluorophosphonate, and the like.

Current adjuvants are largely Th2 biased, such as alum. In some embodiments, for vaccines against cancer and infectious disease targets (e.g. tuberculosis, several viral diseases, etc.) as well as allergy, adjuvants that promote a Th1 bias are an unmet need. In this regard, as described herein, the present inventors have demonstrated formulations promoting a Th1 bias for TLR3 agonists, for example. Such formulations promote IFN gamma production and down-regulate IL-5- and are suitable for various uses in which a Th1 bias is desired.

One or more bioactive agents may be associated with the formulations of the present invention. One of skill in the art would understand that various combinations of bioactive agents may be associated with the formulations such as, but not limited to, multiple RNAs, multiple DNAs, one or more RNAs of a defined sequence and one or more proteins, one or more DNAs and one or more proteins, and one or more RNAs and one or more DNAs. In some aspects, one bioactive agent can be present in the oil core of an NLC while the other is associated with its surface of the NLC. For example, a nucleic acid may be associated with the NLC surface whereas a biologically active small molecule may be present within the oil core of the NLC.

In an exemplary embodiment, the negatively charged bioactive agent is complexed with an NLC by association with cationic surface. The association of the negatively charged bioactive agent with the NLC surface may be a non-covalent or a reversible covalent interaction.

In another embodiment, a hydrophobic bioactive agent such as a Toll-like receptor ligand (e.g., TLR4 ligand) can be incorporated in the oily core or at the interface of the NLC particle.

A. RNA Molecules

In embodiments where the bioactive agent is a RNA molecule, the RNA molecule may encode proteins of various types, including, without limitation, antigens, antibodies, toxins, growth factors, cytokines, and hormones. RNA molecules used herein may also represent non-coding RNAs, including, without limitation, siRNA, miRNA, CRISPR guide RNA, ribozyme RNA, hairpins, RNA aptamers, RNA agonists, and immunomodulatory RNAs.

In an exemplary embodiment, the negatively charged RNA molecule is complexed with the NLC by association with the cationic surface. The association of the RNA molecule with the NLC surface may be a non-covalent or reversible covalent interaction.

In exemplary embodiments, the bioactive agent is a self-replicating RNA molecule. Self-replicating RNA molecules are well known in the art and can be produced by using replication elements derived from viruses (e.g., alphavirus, flavivirus, picornavirus), and substituting the structural viral proteins with a nucleotide sequence encoding a protein of interest. A self-replicating RNA molecule is typically a (+)-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as co-linear subgenomic transcripts, may be translated themselves to provide in situ expression of an encoded antigen, or may be transcribed to provide further transcripts with the same sense as the delivered RNA which are translated to provide in situ expression of the antigen. The overall results of this sequence of transcriptions is an amplification in the number of the introduced replicon RNAs and thereby the encoded antigen becomes a major polypeptide product of the cells.

Advantageously, the cell's translational machinery is used by self-replicating RNA molecules to generate a significant increase of encoded gene products, such as proteins or antigens, which can accumulate in the cells or be secreted from the cells. Self-replicating RNA molecules may, for example, stimulate toll-like receptors (TLR) 3, 7 and 8 and non TLR pathways (e.g., RIG-I, MD-5) by the products of RNA replication and amplification, and translation which may induce apoptosis of the transfected cell.

The self-replicating RNA can, for example, contain at least one or more genes selected from the group consisting of viral replicases, viral proteases, viral helicases and other nonstructural viral proteins, and also comprise 5'- and 3'-end cis-active replication sequences, and if desired, heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions, with or without a ribosomal skipping peptide sequence in the self-replicating RNA and/or may be under the control of an internal ribosome entry site (IRES)

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding viral structural proteins, such as capsid (C) and/or envelope (E) glycoproteins, can be omitted.

If desired, self-replicating RNA molecules of the invention can also be designed to induce production of infectious viral particles that are attenuated or virulent, or to produce viral particles that are capable of a single round of subsequent infection.

One suitable system for achieving self-replication in this manner is to use an alphavirus-based replicon. Alphaviruses comprise a set of genetically, structurally, and serologically related arthropod-borne viruses of the Togaviridae family. Thirty-one species have been classified within the alphavirus genus, including, Sindbis virus, Semliki Forest virus, Ross River virus, chikungunya virus, and Venezuelan equine encephalitis virus. As such, the self-replicating RNA of the invention may incorporate an RNA replicase derived from semliki forest virus (SFV), sindbis virus (SIN), Venezuelan equine encephalitis virus (VEE), Ross-River virus (RRV), eastern equine encephalitis virus, chikungunya virus, or other viruses belonging to the alphavirus genus.

An alphavirus-based "replicon" expression vector can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., interferon sensitivity, and disease profile) that is unique. Therefore, chimeric alphavirus replicons made from divergent virus families may also be useful.

Alphavirus-based RNA replicons are typically (+)-stranded RNAs which lead to translation of a replicase (or replicase-transcriptase) after delivery to a cell. The replicase is translated as a polyprotein which auto-cleaves to provide a replication complex which creates genomic (−)-strand copies of the (+)-strand delivered RNA. These (−)-strand transcripts can themselves be transcribed to give further copies of the (+)-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc.

An RNA replicon can comprise, for example, an RNA genome from a picornavirus, togavirus (e.g., alphaviruses such as, for example, Sindbis virus, Semliki Forest virus, Venezuelan equine encephalitis virus, or Ross River virus), flavivirus (e.g., yellow fever virus), coronavirus, paramyxovirus, which has been modified by the replacement of one or more structural protein genes with a selected heterologous nucleic acid sequence encoding a product of interest.

In some aspects, a replicon will encode (i) a RNA-dependent RNA polymerase which can transcribe RNA from the replicon and (ii) an antigen. The polymerase can be, for example, an alphavirus replicase e.g. comprising one or more of alphavirus proteins nsP1, nsP2, nsP3 and nsP4. Whereas natural alphavirus genomes encode structural virion proteins in addition to the non-structural replicase polyprotein, it is preferred that the replicon does not encode alphavirus structural proteins. Thus, a replicon can lead to the production of genomic RNA copies of itself in a cell, but not to the production of RNA-containing virions. The inability to produce these virions means that, unlike a wild-type alphavirus, the preferred replicon cannot perpetuate itself in infectious form. The alphavirus structural proteins which are necessary for perpetuation in wild-type viruses are absent from the preferred replicon and their place is taken by gene(s) encoding the antigen of interest, such that the subgenomic transcript encodes the antigen rather than the structural alphavirus virion proteins.

A replicon useful with the invention can, for example, have two open reading frames. In one example, the first (5') open reading frame encodes a replicase; the second (3') open reading frame encodes an antigen. In some embodiments the RNA may have additional (e.g. downstream) open reading frames e.g. to encode additional antigens or to encode accessory polypeptides.

A replicon can, for example, have a 5' cap (e.g. a 7-methylguanosine), which often can enhance in vivo translation of the RNA. In some embodiments the 5' sequence of the replicon may need to be selected to ensure compatibility with the encoded replicase.

A replicon may have a 3' poly-A tail. It may also include a poly-A polymerase recognition sequence (e.g. AAUAAA) near its 3' end.

Replicons can have various lengths, but they are typically 5000-25000 nucleotides long e.g. 8000-15000 nucleotides, or 9000-12000 nucleotides.

The replicon can conveniently be prepared by in vitro transcription (IVT). IVT can use a (cDNA) template created and propagated in plasmid form in bacteria or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the replicon from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such replicons, in general, is described in U.S. Pat. Nos. 5,814,482 and 6,015,686.

In other aspects, the self-replicating RNA molecule is derived from or based on a virus other than an alphavirus, preferably, a positive-stranded RNA virus, a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

In other aspects, the self-replicating RNA molecule is derived from or based on a replication competent virus (e.g., an oncolytic virus). An oncolytic virus preferentially infects and lyses (breaks down) cancer cells. As the infected cancer cells are destroyed, new infectious virus particles or virions are released, which can infect and destroy further cancer cells. Thus, oncolytic viruses not only cause direct destruction of cancer cells, but also stimulate host anti-cancer immune responses. In some embodiments, the oncolytic virus may encode a tumor- or viral-associated antigen, neoantigen, and/or peptides. Suitable oncolytic viruses are known in the art and are available from sequence depositories, such as the American Type Culture Collection, Rockville, Md. Representative examples of suitable oncolytic viruses include, but are not limited to, poxvirus, adenovirus, adeno-associated virus, reovirus, retrovirus, senecavirus, measles, herpes simplex virus, Newcastle disease virus (NDV), vesicular stomatitis virus (VSV), mumps, influenza, Parvovirus, human hanta virus, myxoma virus, cytomegalovirus (CMV), lentivirus, coxsackievirus, echoviruses, Seneca Valley virus, Sindbis virus, JX-594, p53 expressing viruses, ONYX-15, Delta24, Telemelysin, Telomelysin-GFP, and vaccinia, and the like, and recombinant variants thereof. In some embodiments, the oncolytic virus is genetically engineered for tumour selectivity. In other embodiments, the oncolytic virus is naturally occurring. Naturally occurring oncolytic viruses include, but are not limited to, reovirus and senecavirus.

The self-replicating RNA molecules of the invention are typically larger than other types of RNA (e.g. mRNA) that have been prepared using modified nucleotides. Typically, the self-replicating RNA molecules of the invention contain at least about 3 kb. For example, the self-replicating RNA can contain at least about 4 kb, at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more types of modified nucleotides (e.g., pseudouridine, N6-methyladenosine, 5-methylcytidine, 5-methyluridine).

The self-replicating RNA molecule may encode a single heterologous polypeptide antigen or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA of the invention may encode one or more polypeptides. These polypeptides may consist of binding proteins, enzymes, cytokines, chemokines, hormones or other functional proteins. Alternatively, these polypeptides may consist of antigens that contain a range of epitopes, preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antibody sequences or two or more antigens together with cytokines or other immunomodulators, which can enhance the generation of an immune response. Such a self-replicating RNA molecule might be particularly useful, for example, in the production of various gene products (e.g., proteins) at the same time, for example, as a two different single chain antibody sequences, heavy and light chain antibody sequences or multiple antigens to create a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM, the β-cyanoethyl phosphoramidite method; and the nucleoside H-phosphonate method. These chemistries can be performed or adapted for use with automated nucleic acid synthesizers that are commercially available. Additional suitable synthetic methods are disclosed in Uhlmann et al. (1990) Chem Rev 90:544-84, and Goodchild J (1990) Bioconjugate Chem 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art.

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC.

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry after antigen stimulation.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

B. DNA Molecules

In embodiments where the bioactive agent is a DNA molecule, the DNA molecule may encode proteins of various types, including, without limitation, antigens, antibodies, toxins, growth factors, cytokines, and hormones. The DNA can include, without limitation, plasmid DNA, circular DNA, linear DNA, single-stranded DNA, modified DNA, antisense DNA, and aptamer DNA.

C. Antigens

The bioactive agent described herein can be a nucleic acid molecule (e.g., DNA or RNA) that encodes an antigen. Suitable antigens include, but are not limited to, a bacterial antigen, a viral antigen, a fungal antigen, a protozoan antigen, a plant antigen, a cancer antigen, or a combination thereto. The antigen can be involved in, or derived from, for example, an allergy, cancer, infectious disease, or autoimmune disease.

An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. In certain embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Certain embodiments contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Escherichia, Salmonella, Neisseria, Borrelia, Chlamydia, Clostridium* or *Bordetella*; a virus such as a herpes simplex virus, a human immunodeficiency virus (HIV such as HIV-1 or HIV-2), an influenza virus, a parainfluenza virus, a measles virus, a mumps virus, a rubella virus, a coronavirus (such as SARS or MERS), a rotavirus, a norovirus, a picorna virus (such as a poliovirus, an enterovirus, or a coxsacchie virus), a veterinary pathogen, for example, a feline immunodeficiency virus (FIV), cytomegalovirus, Varicella Zoster Virus, hepatitis virus, Epstein Barr Virus (EBV), a flavivirus virus (such as dengue virus, Japanese encephalitis virus, yellow fever virus, Zika virus, Powassan virus or tick-borne encephalitis virus), a henipah virus (such as hendra or nipah virus), a bunyavirus (such as Hantavirus or Rift Valley Fever virus), an arenavirus (such as lassa virus, junin virus, machupo virus, or guanarito virus), a filovirus (such as Ebola virus or Marburg virus), a lyssavirus (such as Rabies virus), respiratory syncytial virus, human papilloma virus (HPV) and a cytomegalovirus; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia, Toxoplasma gondii*, and *Leishmania*. In specific embodiments, the antigen may be from, or related to antigens involved in tuberculosis, influenza, amebiasis, HIV, hepatitis, or Leishmaniasis.

In some embodiments, the antigen is an influenza-related antigen. In some embodiments, the antigen is an influenza-causing antigen. In some embodiments, the antigen is from an influenza causing virus. In one embodiment, the antigen comprises hemagglutinin (HA) from H5N1. In one embodiment, the antigen comprises neuraminidase from H5N1.

For example, in certain embodiments, antigens are derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

In certain embodiments the antigen is derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., dengue virus, Japanese encephalitis virus, yellow fever virus, Zika virus, Poswanan virus, tick-borne encephalitis virus) or Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, PB1, PB2, PA, NS1 or M proteins, or combinations thereof).

In certain other embodiments, the antigen is derived from one or more bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexneri; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci*; Leptospira spp., including *L. interrogans; Treponema* spp., including *T. pallidum* (for example the rare outer membrane proteins), *T. denticola, T. hyodysenteriae*; or other bacterial pathogens.

In certain other embodiments, the antigen is derived from one or more parasites (See, e.g., John, D. T. and Petri, W. A., Markell and Voge's Medical Parasitology-9th Ed., 2006, WB Saunders, Philadelphia; Bowman, D. D., Georgis' Parasitology for Veterinarians-8th Ed., 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leishmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis*, and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). In certain embodiments, the antigen is derived from *Schisostoma* spp., *Schistosoma mansonii, Schistosoma haematobium*, and/or *Schistosoma japonicum*, or derived from yeast such as *Candida* spp., including *C. albicans; Cryptococcus* spp., including *C. neoformans*.

Other specific antigens are derived from *M. tuberculosis*, for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, three, or four or more, polypeptides of *M. tuberculosis* are fused into a larger protein. Certain fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647. In one exemplary embodiment, the fusion protein is ID93. In one exemplary embodiment, the fusion protein is ID91 (SEQ ID NO: 1).

Figure 29:
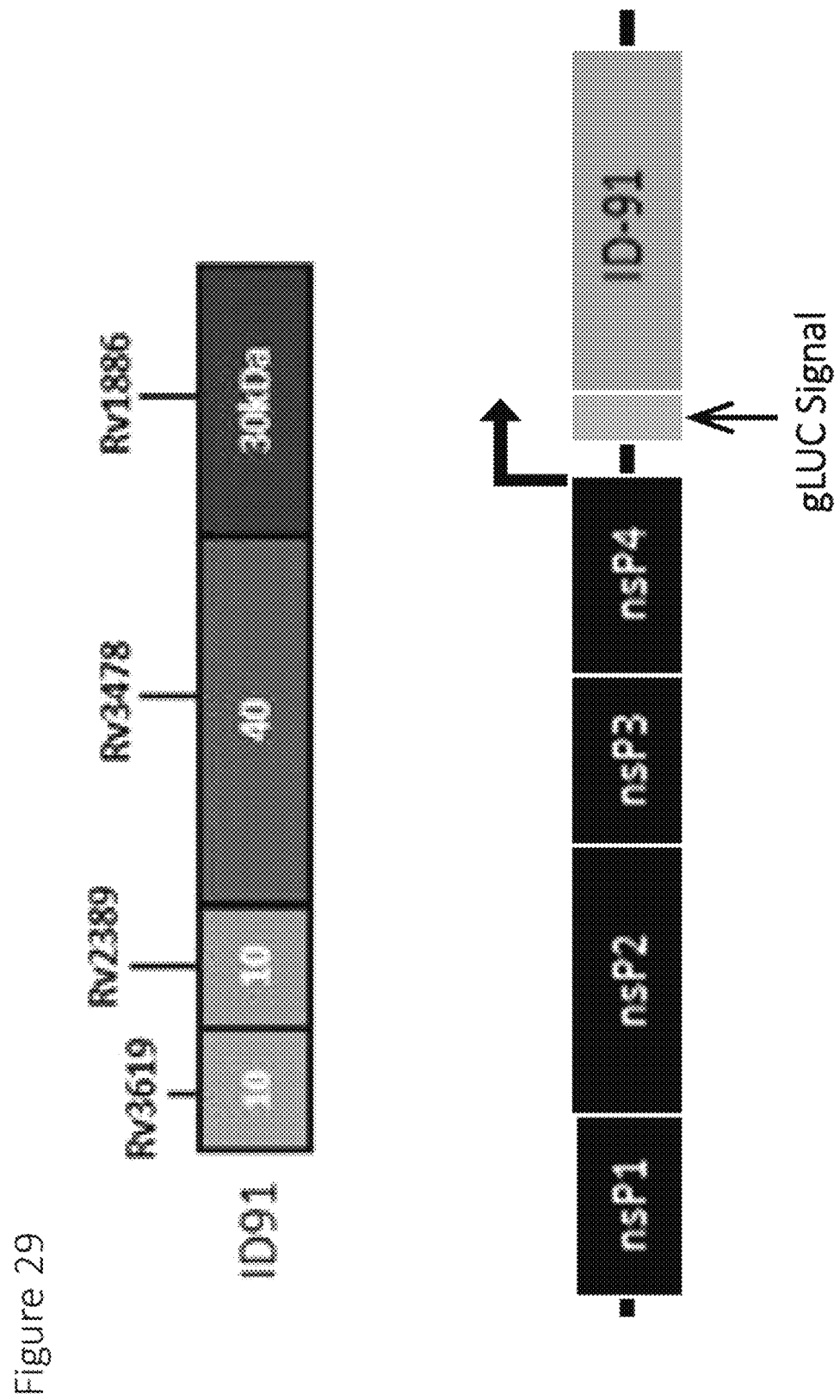
Figure 30A:
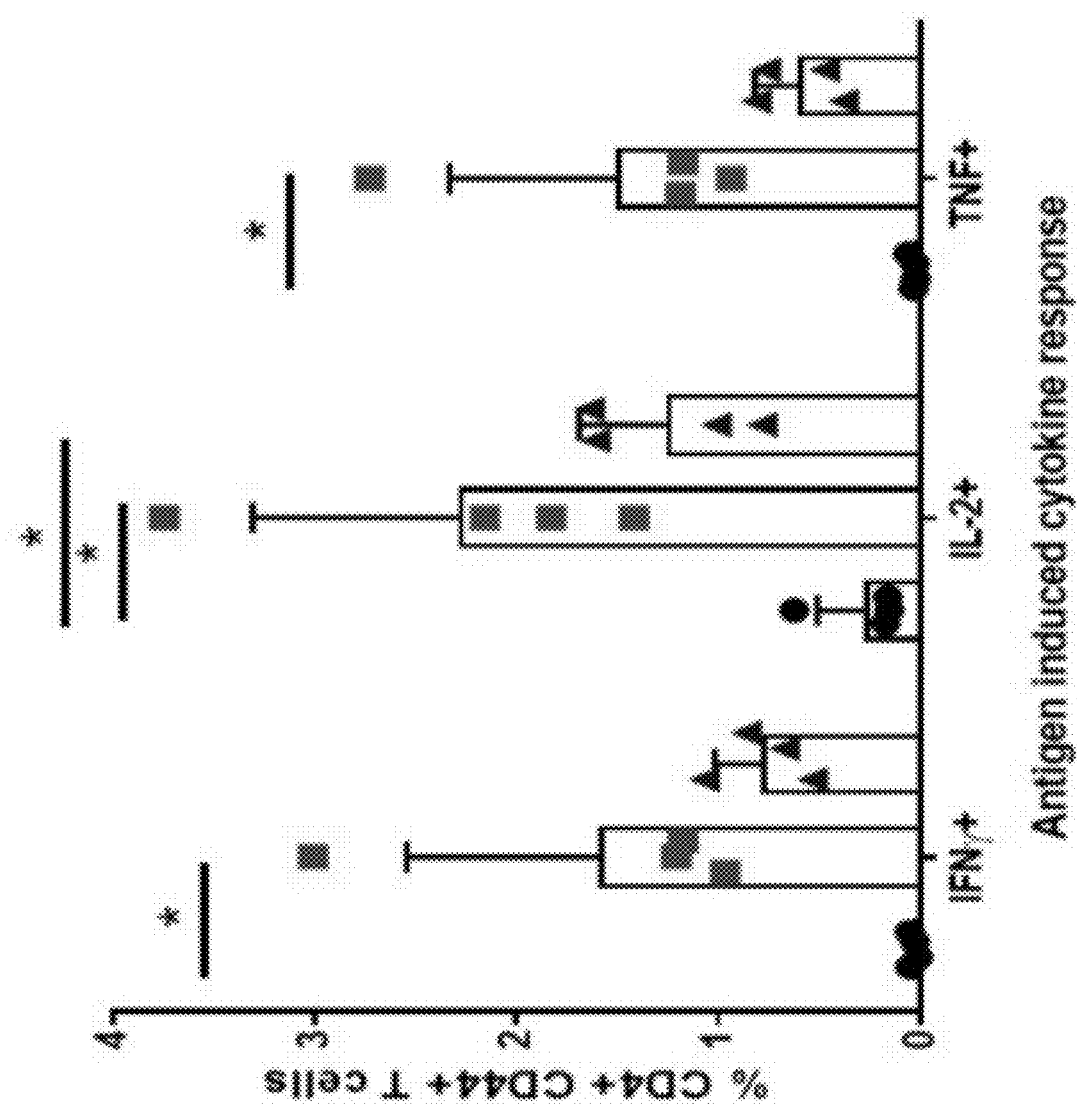
Figure 30B:
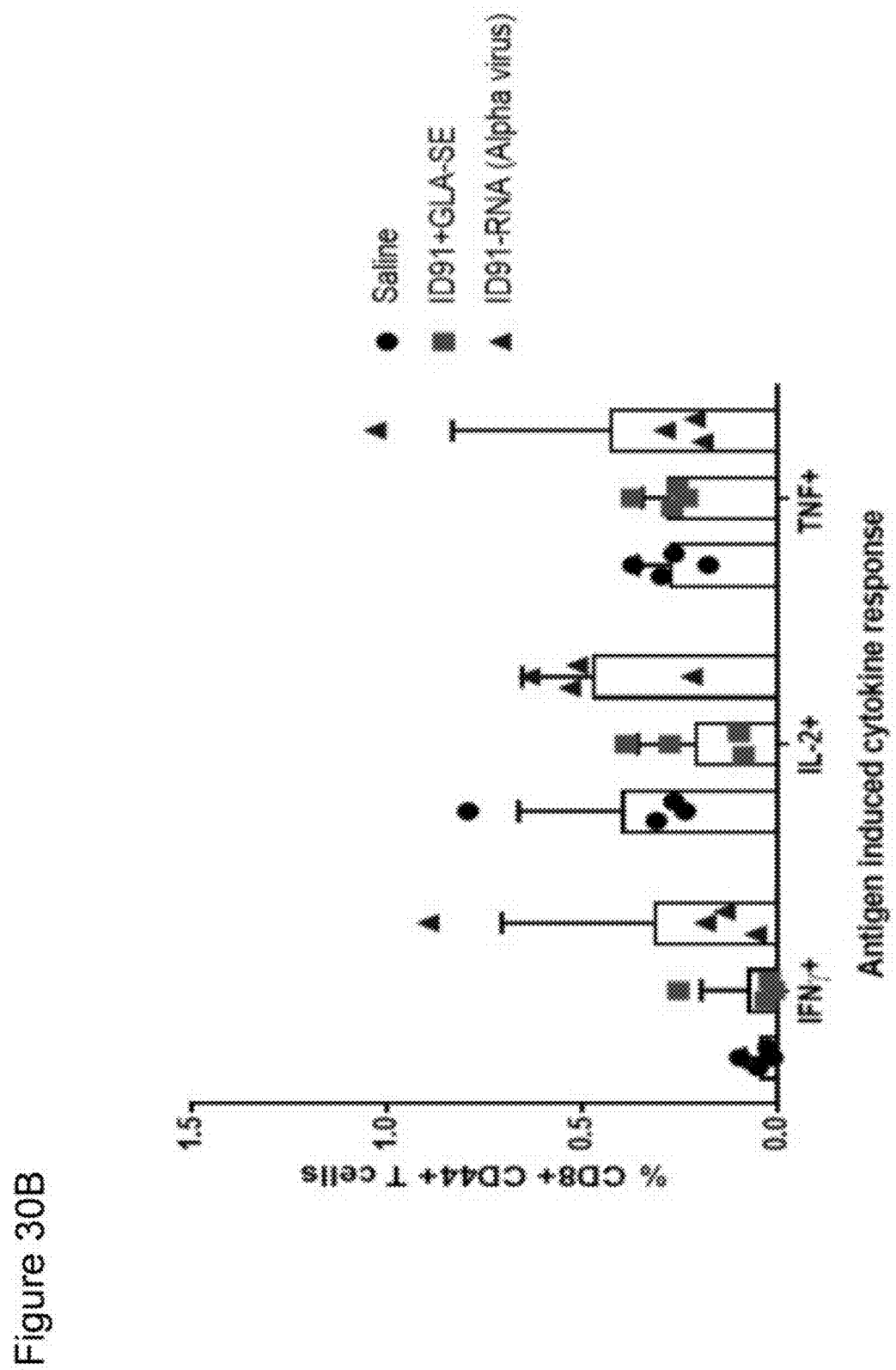
Figure 31A:
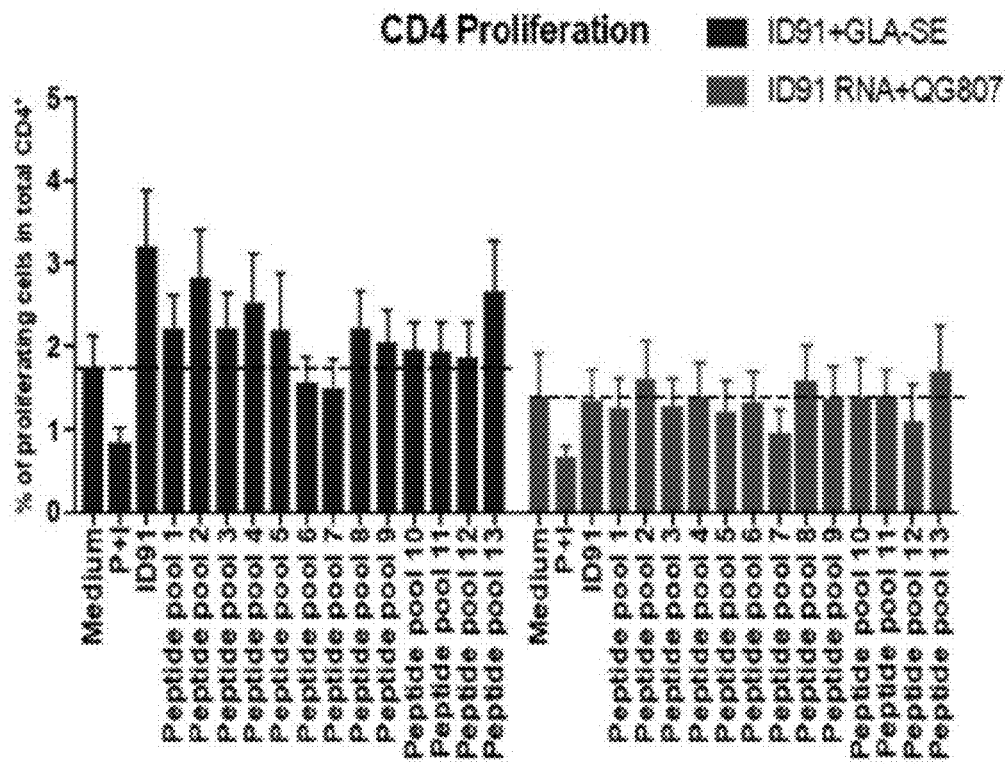
Figure 31B:
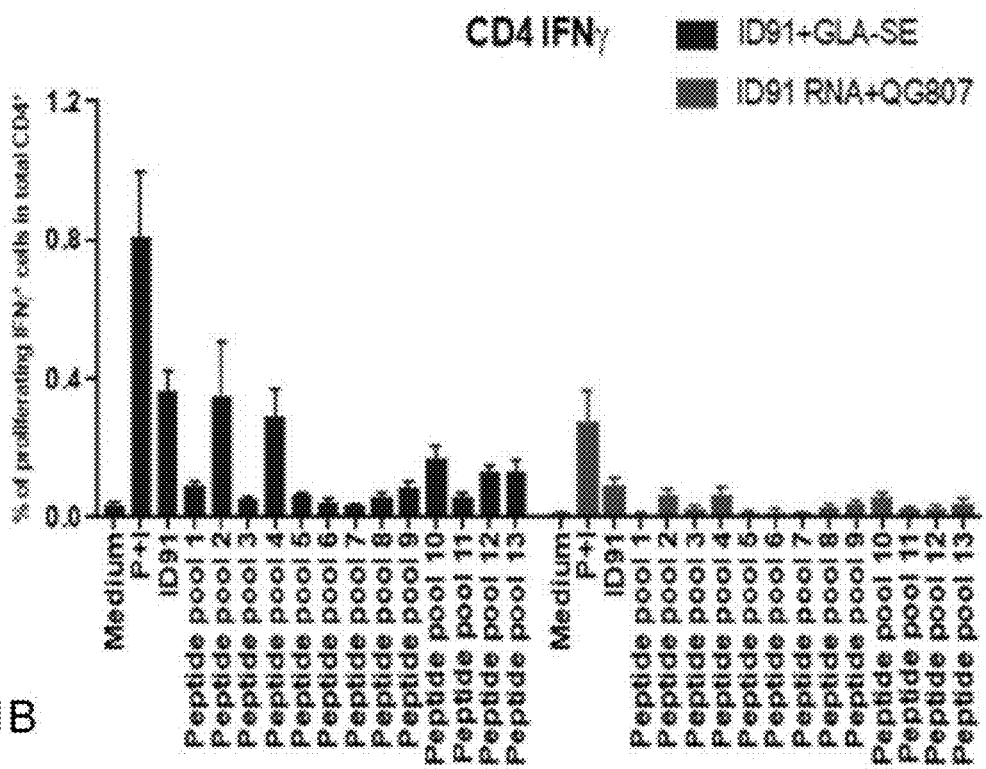
Figures 32A, 32B:
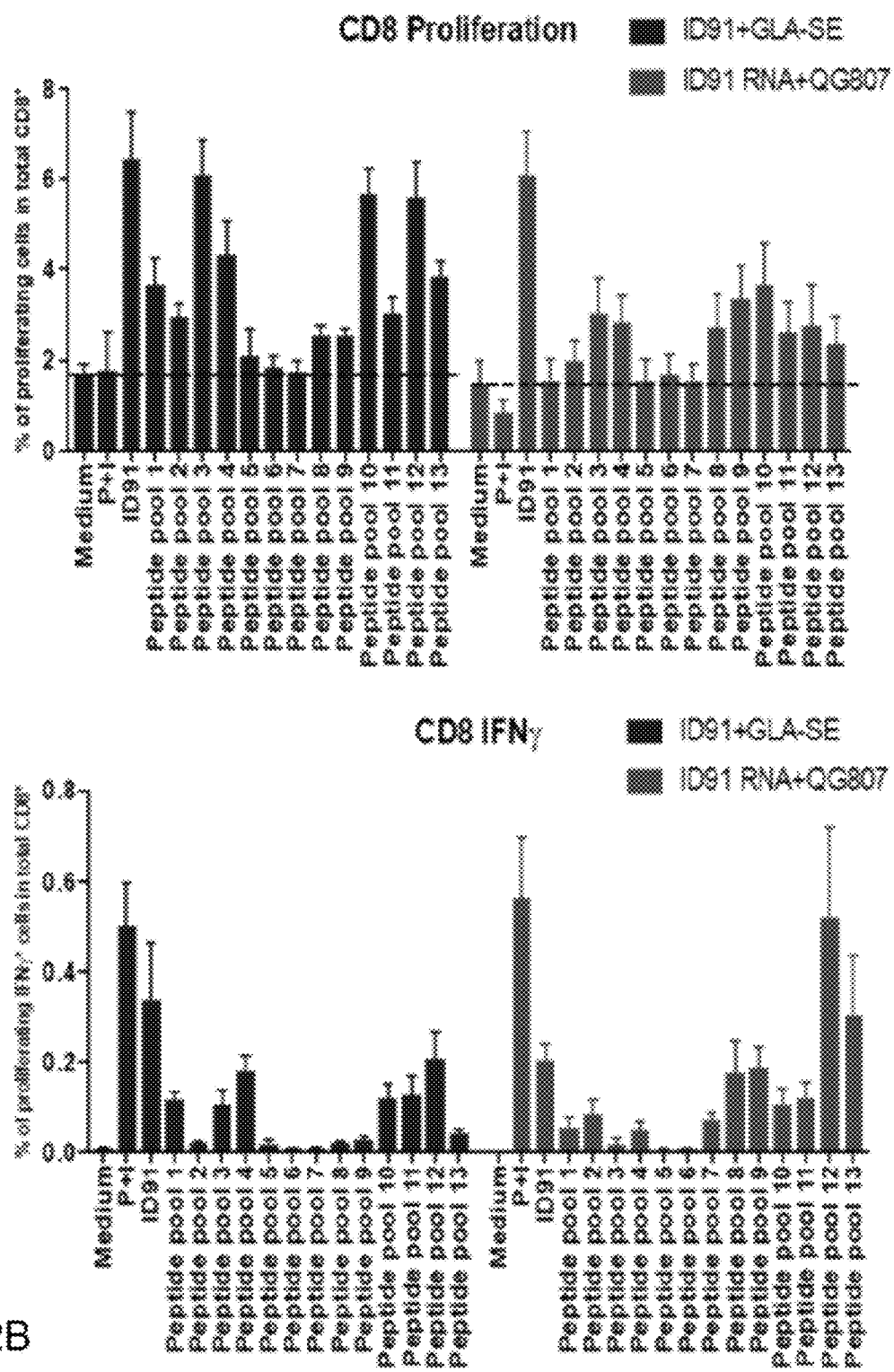

The fusion protein ID91 includes a fusion of four Mtb proteins: Rv3619 (a virulence factor, EsX family, SEQ ID NO: 2), Rv2389 (produced under hypoxic conditions, resuscitation factor D SEQ ID NO: 3), Rv3478 (a member of the PE/PPE family, SEQ ID NO: 4) and Rv1886 (Ag85A, secreted/membrane protein; mycolyltransferase, SEQ ID NO: 5) (FIG. 29). Mtb antigens included in ID91 were prioritized based on lack of human sequence homology and human PBMC IFN-g secretion from PPD+ donors (and not PPD− donors) after stimulation with antigen to ensure immunogenicity in the human population (Bertholet et al., J Immunol. 181(11):7948-57 (2008)). ID91 protein combined with synthetic Toll-like receptor 4 (TLR4) agonist glucopyranosyl lipid adjuvant in a stable emulsion (GLA-SE) demonstrates protection against Mtb H37Rv four weeks after one immunization in a preclinical mouse model (Orr et al., J Immunol. 193(6):2911-18 (2014)). With this subunit vaccine a robust TH1 response (IFN-g, TNF, and IL-2) to ID91 was observed. Id.

In some embodiments, ID91 may be include restriction enzymes well known to those of skill in the art. Exemplary restriction enzymes, include but are not limited to, NdeI, KpnI, BamHI, EcoRI, and/or HindIII. See, for example, vector pET29 in FIG. 38A and SEQ ID NOs: 6 and 12, and vector pET28 in FIG. 38B.

Other specific antigens are derived from *Chlamydia* and include for example the High Molecular Weight Protein (HWMP) (WO 99/17741), ORF3 (EP 366 412), and putative membrane proteins (Pmps). Other *Chlamydia* antigens can be selected from the group described in WO 99128475. Certain antigens may be derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial vaccines comprise antigens derived from *Haemophilus* spp., including *H. influenzae* type B (for example PRP and conjugates thereof), non-typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Other specific antigens are derived from Hepatitis B. Derivatives of Hepatitis B Surface antigen are well known in the art and include, inter alia, those PreS1, PreS2, S antigens set forth described in European Patent applications EP-A414 374; EP-A-0304 578, and EP 198474.

In other embodiments, the antigen is derived from the Human Papilloma Virus (HPV) considered to be responsible for genital warts (HPV 6 or HPV 11 and others), and the HPV viruses responsible for cervical cancer (HPV16, HPV18 and others). Particular antigens include L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and protein D(1/3)-E7 disclosed in GB 9717953.5 (PCT/EP98/05285). Additional possible antigens include HPV 16, 18, 33, 58 antigens. For example, L1 or L2 antigen monomers, or L1 or L2 antigens presented together as a virus like particle (VLP) or the L1 alone protein presented alone in a VLP or capsomer structure. Such antigens, virus like particles and capsomer are per se known. See for example WO94/00152, WO94/20137, WO94/05792, and WO93/02184.

In other embodiments, the antigen is a fusion protein. Fusion proteins may be included alone or as fusion proteins such as E7, E2 or F5 for example; particular embodiments include a VLP comprising L1E7 fusion proteins (WO 96/11272). Particular HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively, the HPV 16 or 18 early proteins E6 and E7, may be presented in a single molecule, for example a Protein D-E6/E7 fusion. Compositions may optionally contain either or both E6 and E7 proteins front HPV 18, for example in the form of a Protein D-E6 or Protein D-E7 fusion protein or Protein D E6/E7 fusion protein. Compositions may additionally comprise antigens from other HPV strains, for example from strains HPV 31 or 33.

Antigens may also be derived from parasites that cause Malaria. For example, antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

In one embodiment, the antigen is derived from a cancer cell, as may be useful for the immunotherapeutic treatment of cancers. For example, the antigen may be a tumor rejection antigen such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 Current Opinions in Immunology 8, pp. 628-636; Van den Eynde et al., International Journal of Clinical & Laboratory Research (1997 & 1998); Correale et al. (1997), Journal of the National Cancer Institute 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens include, but are not restricted to, tumor-specific or tumor-associated gangliosides such as GM2, and GM3 or conjugates thereof to carrier proteins; or a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., Proc. Nat. Acad. Sci. USA 95(4) 1735-1740 1998), PSMA or, in one embodiment an antigen known as Prostase. (e.g., Nelson, et al., Proc. Natl. Acad. Sci. USA (1999) 96: 3114-3119; Ferguson, et al. Proc. Natl. Acad. Sci. USA 1999. 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present invention include: Plu-1 (J Biol. Chem 274 (22) 15633-15645, 1999), HASH-1, HasH-2, Cripto (Salomon et al Bioessays 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

In other embodiments, the agents used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g. pneumococcal) infection (Clin Microbiol Rev. 2001 April; 14(2):336-63).

D. Antibody-Encoding Nucleic Acid

The bioactive agents described herein (e.g., RNA) may encode an antibody and/or antigen-binding fragment of an antibody, optionally operably linked to one or more expression control elements, such that delivery to a subject results in the production of said antibody or antigen-binding fragment in the subject. In some embodiments, the bioactive agent may contain the coding sequence of the heavy chain and light chain in a single open reading frame. In other embodiments, an NLC of the present invention may comprise two bioactive agents wherein one of the bioactive agents encodes a heavy chain whereas the other encodes a light chain. In other embodiments, the bioactive agent may contain the coding sequence of the variable regions of the heavy and light chains linked by a short flexible polypeptide sequence such that the expressed biomolecule binds the antigen of interest. In some particular embodiments, the produced antibody is capable of eliciting an immune response in an individual.

E. RNA Interference

In some embodiments the bioactive polynucleotide associated with the NLC is a non-coding RNA such as an RNA interference (RNAi) polynucleotide. RNAi is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure.

MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target-plays a key role in miRNA specificity. Binding of the RISC/miRNA complex to the mRNA can lead to either the repression of protein translation or cleavage and degradation of the mRNA.

F. CRISPR RNAs

In some embodiments the NLC formulation comprises a synthetic short guide RNA (sgRNA) of the CRISPR/Cas9 genome editing thereby targeting a gene of interest. CRISPRs (Clustered Regularly Interspaced Short Palindromic Repeats) are loci containing multiple short direct repeats that are found in the genomes of approximately 40% of sequenced bacteria and 90% of sequenced archaea. CRISPR functions as a prokaryotic immune system, in that it confers resistance to exogenous genetic elements such as plasmids and phages. The CRISPR system provides a form of acquired immunity. Short segments of foreign DNA, called spacers, are incorporated into the genome between CRISPR repeats, and serve as a memory of past exposures. CRISPR spacers are then used to recognize and silence exogenous genetic elements in a manner analogous to RNAi in eukaryotic organisms. Cas9, an essential protein component in the Type II CRISPR/Cas9 system, forms an active endonuclease when complexed with two RNAs termed CRISPR RNA (crRNA) and trans-activating crRNA (tracrRNA), thereby slicing foreign genetic elements in invading phages or plasmids to protect the host cells.

The RNA-guided endonuclease based on CRISPR/Cas9 system been employed for eukaryotic genome editing. In certain embodiments of the present invention, the bioactive agent is RNA that encodes sgRNAs and/or Cas9 endonucleases. In some embodiments, the RNA comprises one or more polynucleotides encoding Cas9 and two guide RNAs, the first guide RNA comprising a spacer sequence that is complementary to a segment of the 5' double-stranded break (DSB) locus, and the second guide RNA comprising a spacer sequence that is complementary to a segment of the 3' DSB locus. Both guide RNAs may be provided as single-molecule guide RNAs (comprising tracrRNA and crRNA), or either or both may be provided as double-molecule guide RNAs comprising a crRNA and a tracrRNA that are not joined to each other but rather are separate molecules.

G. Polypeptides

In some embodiments the one or more bioactive agents is a polypeptide. The polypeptide can be a full-length protein or a fragment thereof. In some embodiments the polypeptide is a peptide. In some embodiments, the polypeptide is a fusion protein. In some particular embodiments, the fusion protein is capable of eliciting an immune response upon administration to an individual. In some embodiments, the polypeptide is an antigen, as further described above. Polypeptides may be made by any suitable method known to one of skill in the art, including, for example, recombinant expression.

H. Small Molecules

In certain embodiments, the present disclosure generally relates to a NLC composition where the one or more bioactive agents is a small molecule or therapeutic agent for drug delivery. A close association of drug molecule and the NLC may be influenced by drug physicochemical properties, surfactant type and concentration, lipid type, and production method. In certain embodiments, the small molecule drug is encapsulated by the NLC, which is enabled by the liquid lipid phase component of the oil core that provides high drug solubility (Beloqui, A., et al. Nanomedicine 2016; 12(1): 143-161).

The NLC compositions provided herein may be suitable for drug delivery through various routes of administration, including, without limitation, dermal, transdermal, oral, intranasal, pulmonary, or ophthalmological routes of administration.

I. Hormones

In some embodiments the one or more bioactive agents associated with the NLC is a polynucleotide or polypeptide that encodes a hormone or analog of a hormone. In some embodiments, the NLC comprises a lipid that is conjugated to a hormone. The hormone may be selected from the group comprising human growth hormone, adrenocorticotropin, gonadotropin releasing hormone, oxytocin, leutinizing-hormone-releasing-hormone, follicle stimulating hormone, insulin, insulin-like growth factor, leptin, parathyroid hormone, thyroid stimulating hormone, or some combination thereof. In certain embodiments the NLC formulation comprises a hormone or analog of a hormone in combination with a small molecule therapeutic compound as described above.

J. Adjuvants

In some embodiments, the NLC is for vaccine delivery and one or more of the bioactive agents is an adjuvant or alternatively, the NLC compositions provided herein may be co-administered with an adjuvant. As used herein, the term adjuvant refers to a substance that enhances or potentiates an immune response. The immune response can be, for example, an antigen-specific immune response e.g., to an exogenous antigen.

Many adjuvants contain a substance designed to protect the antigen from rapid catabolism, such as aluminum hydroxide or mineral oil, and a stimulator of immune responses, such as lipid A (natural or synthetic). Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Certain exemplary compositions employ adjuvant systems designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a compositions as provided herein, a patient may support an immune response that includes Th1- and Th2-type responses. Within an exemplary embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, Ann. Rev. Immunol. 7:145-173 (1989).

Certain adjuvants for use in eliciting a predominantly Th1-type response include, for example, a combination of monophosphoryl lipid A, for example 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other illustrative formulations include more than one saponin in the adjuvant combinations of the present disclosure, for example combinations of at least two of the following group comprising QS21, QS7, Quil A, 0-escin, or digitonin.

Other illustrative adjuvants useful in the context of the disclosure include Toll-like receptor agonists, such as TLR1, TLR2, TLR3, TLR4, TLR5, TLR6, TLR7, TLR8, TLR7/8, TLR9 agonists, and the like. Still other illustrative adjuvants include imiquimod, gardiquimod, resiquimod, and related compounds.

In other embodiments, the adjuvant is a glucopyranosyl lipid A (GLA) adjuvant, as described in U.S. Pat. No. 8,609,114 or 8,722,064, the disclosure of which is incorporated herein by reference in its entirety.

For example, in certain embodiments, the TLR4 agonist is a synthetic GLA adjuvant having the following structure of Formula (VII):

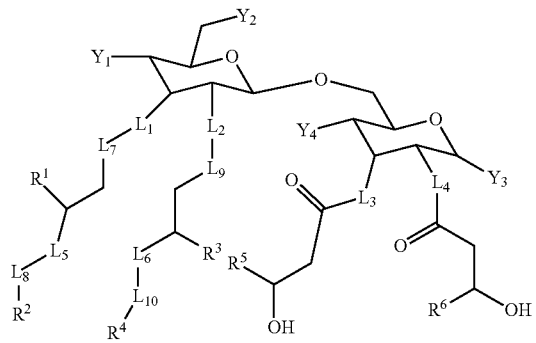

(VII)

or a pharmaceutically acceptable salt thereof, wherein:

$L_1$, $L_2$, $L_3$, $L_4$, $L_5$ and $L_6$ are the same or different and independently —O—, —NH— or —(CH$_2$)—;

$L_7$, $L_8$, $L_9$, and $L_{10}$ are the same or different and independently absent or —C(=O)—;

$Y_1$ is an acid functional group;

$Y_2$ and $Y_3$ are the same or different and independently —OH, —SH, or an acid functional group;

$Y_4$ is —OH or —SH;

$R_1$, $R_3$, $R_5$ and $R_6$ are the same or different and independently $C_{8-13}$ alkyl; and $R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl. In certain embodiments, $R^1$, $R^3$, $R^5$ and $R^6$ are $C_{11}$ alkyl; and $R^2$ and $R^4$ are $C_9$ alkyl.

For example, in certain embodiments, the TLR4 agonist is a synthetic GLA adjuvant having the following structure of Formula (VIII) or a pharmaceutically acceptable salt thereof:

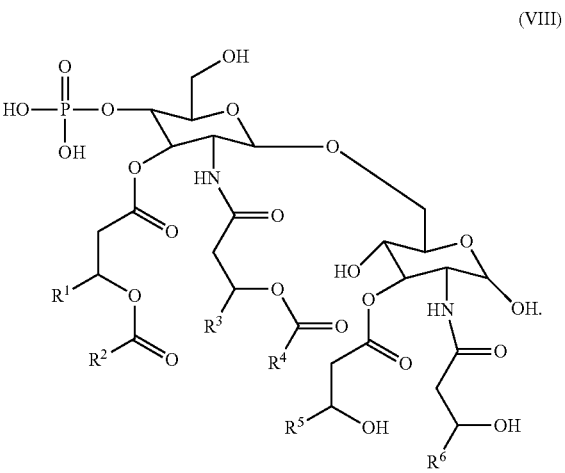

(VIII)

In certain embodiments of the above GLA structure, $R^1$, $R^3$, $R^5$ and $R^6$ are $C_{11}$-$C_{20}$ alkyl; and $R^2$ and $R^4$ are $C_{12}$-$C_{20}$ alkyl. In another specific embodiment, the GLA has the formula set forth above wherein $R^1$, $R^3$, $R^5$ and $R^6$ are $C_{11}$ alkyl; and $R^2$ and $R^4$ are $C_{13}$ alkyl. In another specific embodiment, the GLA has the formula set forth above wherein $R^1$, $R^3$, $R^5$ and $R^6$ are $C_{10}$ alkyl; and $R^2$ and $R^4$ are $C_8$ alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (IX) or a pharmaceutically acceptable salt thereof:

(IX)

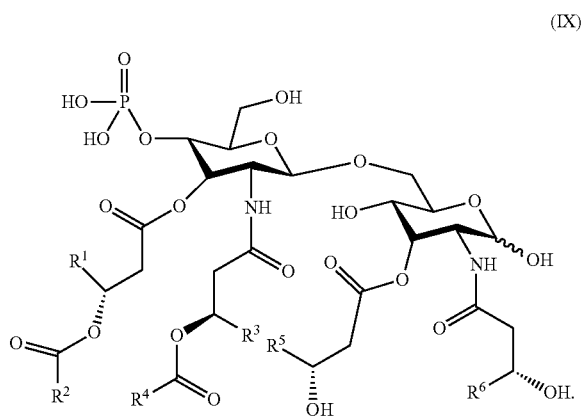

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure of Formula (X):

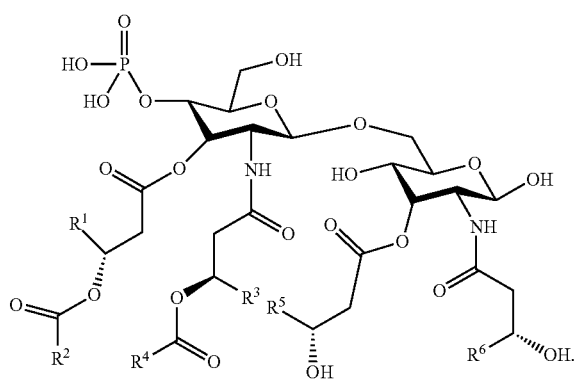

(X)

In certain embodiments of the above GLA structure, R1, R3, R5 and R6 are C11-C20 alkyl; and R2 and R4 are C9-C20 alkyl. In certain embodiments, R1, R3, R5 and R6 are C11 alkyl; and R2 and R4 are C9 alkyl.

In certain embodiments, the TLR4 agonist is a synthetic GLA adjuvant having the following structure of Formula (XI) or a pharmaceutically acceptable salt thereof:

(XI)

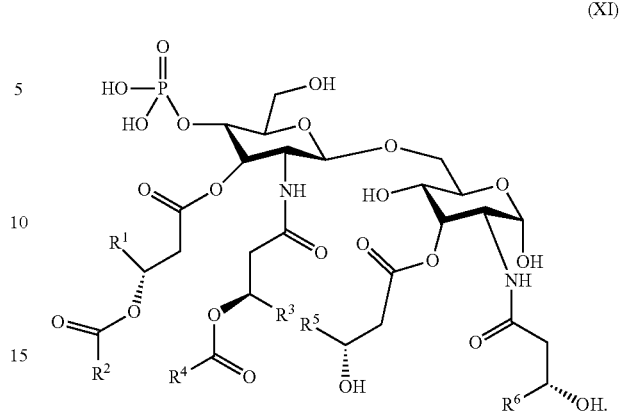

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure or a pharmaceutically acceptable salt thereof:

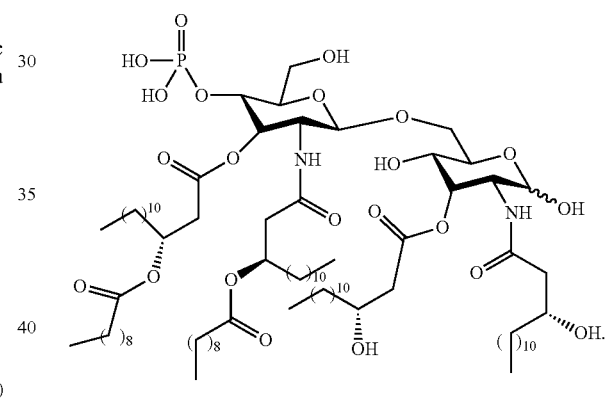

In certain embodiments, the TLR4 agonist is a synthetic GLA adjuvant having the following structure or a pharmaceutically acceptable salt thereof:

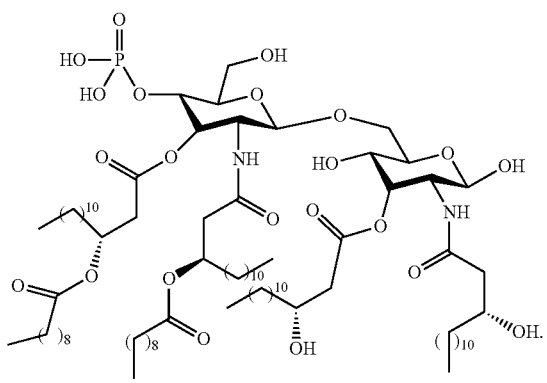

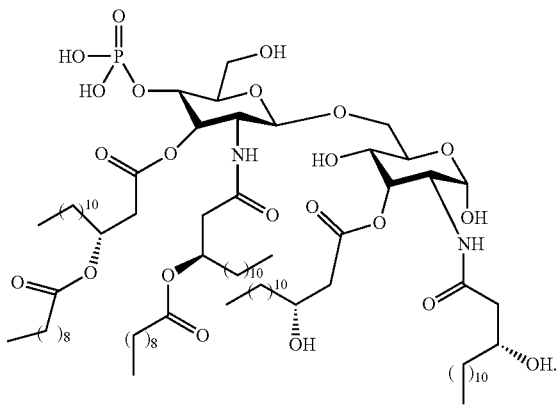

In another embodiment, an attenuated lipid A derivative (ALD) is incorporated into the compositions described herein. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay (CELD50). ALDs useful according to the present disclosure include monophosphoryl lipid A (MLA or MPL) and 3-deacylated monophosphoryl lipid A (3D-MLA or 3D-MPL). MLA (MPL) and 3D-MLA (3D-MPL) are known and need not be described in detail herein.

In the TLR4 agonist compounds above, the overall charge can be determined according to the functional groups in the molecule. For example, a phosphate group can be negatively charged or neutral, depending on the ionization state of the phosphate group.

V. METHODS OF MAKING EXEMPLARY COMPOSITIONS COMPRISING BIOACTIVE AGENTS AND NANOSTRUCTURED LIPID CARRIERS

As provided herein, one method of making the NLCs described herein comprises (a) mixing the solid phase lipid, the liquid phase lipid, the cationic lipid, and the hydrophobic surfactant (e.g., sorbitan ester) to form an oil phase mixture; (b) mixing the hydrophilic surfactant and water to form an aqueous phase; and (c) mixing the oil phase mixture with the aqueous phase mixture to form the NLC. In some embodiments, a further step comprises combining the bioactive agent with the NLC such that the bioactive agent associates with the surface of the NLC by non-covalent interactions or by reversible covalent interactions. Such embodiments are preferred where the bioactive agent is negatively charged, such as an RNA molecule or a DNA molecule. The negative charges on the bioactive agent interact with the cationic lipid in the NLC, thereby associating the negatively charged bioactive agent with the NLC. In other embodiments, where the bioactive agent is hydrophobic, it is combined with the components in step (a) to form part of the oil phase mixture. In some embodiments, the bioactive agent may be attached to a component of the surface of the NLC via covalent interactions.

Mixing the solid phase lipid, the liquid phase lipid, the cationic lipid, and the hydrophobic surfactant (e.g., sorbitan ester) to form an oil phase mixture may be achieved, for example, by heating and sonication. Mixing the oil phase mixture with the aqueous phase mixture may be achieved, for example, by various emulsification methods, including, without limitation, high shear emulsification and microfluidization.

VI. COMPOSITIONS COMPRISING THE NANOSTRUCTURED LIPID CARRIERS

Provided herein are formulations, compositions, and pharmaceutical compositions comprising the NLC compositions described herein.

The compositions comprising the NLC and bioactive agent can optionally further comprise a pharmaceutically acceptable carrier, excipient or diluent.

The compositions described herein can be administered to a subject for any vaccination, therapeutic or diagnostic purposes.

Provided here are pharmaceutical compositions comprising the presently disclosed compositions further in combination with a pharmaceutically acceptable carrier, excipient or diluent.

In particularly preferred embodiments provided herein, the NLC and pharmaceutical compositions provided herein capable of being filtered through a 0.45 micron filter. In some embodiments, the pharmaceutical composition is capable of being filtered through a 0.20 micron filter. In some embodiments, the pharmaceutical composition is capable of being filtered through a 0.22 micron filter.

In one embodiment, the present invention is drawn to a pharmaceutical composition comprising a composition comprising an NLC and an associated bioactive agent. Such a composition may be administered to a subject in order to stimulate an immune response, e.g., a non-specific immune response or an antigen-specific immune response, for the purpose of diagnosis, treating or preventing a disease or other condition, such as an infection by an organism.

In some other embodiments, the pharmaceutical composition is a vaccine composition that comprises the compositions described herein in combination with a pharmaceutically acceptable carrier, excipient or diluent. Illustrative carriers are usually nontoxic to recipients at the dosages and concentrations employed.

In some aspects, the pharmaceutical compositions provided herein are administered to a subject to generate a response in the subject, for example, for generating an immune response in the subject. Typically, a therapeutically effective amount is administered to the subject.

The term "effective amount" or "therapeutically effective amount" refers to an amount that is sufficient to achieve or at least partially achieve the desired effect, e.g., sufficient to generate the desired immune response. An effective amount of a NLC or pharmaceutical composition is administered in an "effective regime". The term "effective regime" refers to a combination of amount of the composition being administered and dosage frequency adequate to accomplish the desired effect.

Actual dosage levels may be varied so as to obtain an amount that is effective to achieve a desired response for a particular patient, composition, and mode of administration, without being toxic to the patient. The selected dosage level will depend upon a variety of pharmacokinetic factors in combination with the particular compositions employed, the age, sex, weight, condition, general health and prior medical history of the subject being treated, and like factors well-known in the medical arts.

In exemplary therapeutic embodiments provided herein, a dosage of about 1 µg/kg to about 10 mg/kg of a therapeutic pharmaceutical composition is administered. It will be evident to those skilled in the art that the number and frequency of administrations will be dependent upon the response of the subject.

In exemplary vaccine-based embodiments provided herein, about 1 µg-100 µg of the antigen or 0.1 µg-10 mg of the nucleic acid encoding the antigen will be administered per administration. Exemplary formulations of the present permit a human dose of from about 0.1 ug, about 1 ug, about 5 µg or about 10 ug to about 500 µg of replicon RNA. Exemplary formulations of the present permit a human dose of about 5 µg to about 20 ug replicon RNA.

It will be evident to those skilled in the art that the number and frequency of administrations will be dependent upon the response of the subject. Exemplary formulations allow for therapeutic efficacy after as little as one immunization.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions may be in any form which allows for the composition to be administered to a patient. For example, the composition may be in the form of a solid, liquid or gas (aerosol). Typical routes of administration include, without limitation, oral, topical, parenteral, sublingual, buccal, rectal, vaginal, intravenous, intradermal, transdermal, intranasal, intramucosal, pulmonary or subcutaneous. The term parenteral as used herein includes iontophoretic, sonophoretic, thermal, transdermal administration and also subcutaneous injections, intravenous, intramuscular, intrasternal, intracavernous, intrathecal, intrameatal, intraurethral injection or infusion techniques. In some embodiments, a composition as described herein (including vaccine and pharmaceutical compositions) is administered intradermally by a technique selected from iontophoresis, microcavitation, sonophoresis, jet injection, or microneedles. In one preferred embodiment, a composition as described herein is administered intradermally using the microneedle device manufactured by NanoPass Technologies Ltd., Nes Ziona, Israel, e.g., MicronJet600 (see, e.g., U.S. Pat. Nos. 6,533,949 and 7,998,119 and Yotam, et al., Human vaccines & immunotherapeutics 11(4): 991-997 (2015), each of which is incorporated herein by reference in its entirety.

The pharmaceutical composition can be formulated so as to allow the active ingredients contained therein to be bioavailable upon administration of the composition to a subject. Compositions that will be administered to a subject take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, compositions can contain one or more of a sweetening agent, preservatives, dye/colorant and flavor enhancer. In a composition intended to be administered by injection by needle and syringe or needle freejet injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In another embodiment, a composition of the present disclosure is formulated in a manner which can be aerosolized.

It may also be desirable to include other components in a pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of the present disclosure, the type of carrier will vary depending on the mode of administration and whether a sustained release is desired. For parenteral administration, such as subcutaneous injection, the carrier can comprise water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, polypeptides, proteins, amino acids, carbohydrates including glucose, sucrose or dextrins, chelating agents such as EDTA, glutathione and other stabilizers and excipients. Neutral buffered saline or saline mixed with nonspecific serum albumiskilln are exemplary appropriate diluents. For example, a product may be formulated as a lyophilizate using appropriate excipient solutions (e.g., sucrose) as diluents.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, Ala.; e.g., product number 699800) of from about 0.1 to about 10% w/v (weight per unit volume).

The composition may be intended for rectal administration, in the form, e.g., of a suppository which can melt in the rectum and release the drug. The composition for rectal administration may contain an oleaginous base as a suitable nonirritating excipient. Such bases include, without limitation, lanolin, cocoa butter and polyethylene glycol. In the methods of the invention, the pharmaceutical compositions/adjuvants may be administered through use of insert(s), bead(s), timed-release formulation(s), patch(es) or fast-release formulation(s).

Optionally, to control tonicity, the NLC may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate, magnesium chloride, calcium chloride, etc. Non-ionic tonicifying agents can also be used to control tonicity. Monosaccharides classified as aldoses such as glucose, mannose, arabinose, and ribose, as well as those classified as ketoses such as fructose, sorbose, and xylulose can be used as non-ionic tonicifying agents in the presently disclosed compositions. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents useful in the presently disclosed compositions. Non-ionic tonicity modifying agents can be present at a concentration of from about 0.1% to about 10% or about 1% to about 10%, depending upon the agent that is used. If NLCs are formulated for parenteral administration, it is preferable to make the osmolarity of the NLC composition the same as normal physiological fluids, preventing post-administration consequences, such as post-administration swelling or rapid absorption of the composition.

Optionally, NLCs may be formulated with cryoprotectants comprising trehalose, sucrose, mannitol, sorbitol, Avicel PH102 (microcrystalline cellulose), Avicel RC591 (mixture of microcrystalline cellulose and sodium carboxymethyl cellulose), Mircrocelac® (mixture of lactose and Avicel), or a combination thereof. Optionally, NLCs may be formulated with a preservative agent such as, for example, Hydrolite 5.

VII. STABLE EMULSIONS

In some embodiments, stable emulsions are provided, wherein the stable emulsions comprise at least one adjuvant. Nonlimiting exemplary adjuvants that may be formulated with a stable emulsion include TLR3 agonists and Rig-I agonists. Nonlimiting exemplary such adjuvants include double-stranded RNA, RIBOXXOL, poly(I:C), and Hiltonol®.

In some embodiments, a stable emulsion (SE) is an oil in water emulsion. In some such embodiments, the oil-in-water emulsion is a squalene in water emulsion. In some embodiments, an emulsion comprises an antioxidant, such as alpha-tocopherol (vitamin E, see, e.g., EP 0 382 271 B1). WO 95/17210 and WO 99/11241 discuss emulsions based on squalene, alpha-tocopherol, and TWEEN® 80. WO 99/12565 discusses an improvement to these squalene emulsions with the addition of a sterol into the oil phase.

WO08/153541 discusses oil-in-water emulsions as conventionally having amounts of the components present in the range of from 2 to 10% oil, such as squalene; and when present, from 0.01 to 0.1% alpha tocopherol; and from 0.3 to 3% of a surfactant, such as polyoxyethylene sorbitan monooleate or Poloxamer 188 (copolymer of polyoxyethylene and polyoxypropylene). The ratio of oil:surfactant may be equal or less than 1 to improve stability of the emulsion. Span 85 may also be present at a level of about 1%. In some cases it may be advantageous that the vaccines further contain a stabiliser. In one embodiment, the stabilizer may be a triglyceride, such as tricaprylin (C 27 H 5O O 6) (see, e.g., WO 98/56414). In some embodiments, an oil-in-water emulsion comprises 0.5% to 5%, or 0.5% to 5%, or 0.5% to 3%, or 1% to 3% glycerol. In some embodiments, an oil-in-water emulsion comprises 0.5% to 5%, or 0.5% to 5%, or 0.5% to 3%, or 1% to 3% 1,2-dimyristoyl-sn-glycero-3-phosphocholine (DMPC). A nonlimiting exemplary oil-in-water emulsion is discussed in the examples herein.

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges The amounts of the components present in the oil emulsions of the present invention are conventionally in the range of from 2 to 10% oil, such as squalene; and when present, from 2 to 10% alpha tocopherol; and from 0.3 to 3% surfactant, such as polyoxyethylene sorbitan monooleate. Preferably the ratio of oil:alpha tocopherol is greater than 1 as this provides a more stable emulsion. Span 85 may also be present at a level of about 1%. In some cases it may be advantageous that the vaccines of the present invention will further contain a stabiliser.

Methods of producing oil in water emulsions are well known to the person skilled in the art. Commonly, the method comprises the mixing the oil phase with a surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

VIII. METHODS OF USING THE COMPOSITIONS OF THE PRESENT DISCLOSURE

A. Therapeutics

In some embodiments the agent is useful for therapeutic purposes. Thus, in some embodiments, the compositions described comprise the NLCs provided herein, and further comprise a bioactive agent for the treatment of a disease, condition, or disorder.

In some embodiments the agent is useful for the treatment or prevention of allergy, cancer, infectious disease, autoimmunity, or addiction. In some embodiments the agent is useful for the stimulating, enhancing and/or modulating an immune response.

In some aspects of the disclosed embodiments, the compositions comprise cancer antigens or nucleic acids encoding a cancer antigen. In some embodiments, a vaccine composition comprises a cancer antigen will be useful against any cancer characterized by tumor associated antigen expression, such as HER-2/neu expression or other cancer-specific or cancer-associated antigens.

Compositions and methods according to certain embodiments of the present disclosure may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells; pemphigus is cadherin-like pemphigus antigens such as desmoglein 3 and other adhesion molecules; and thrombic thrombocytopenic purpura is antigens of platelets.

The compositions provided herein may be used for inducing protective immunity, for example against tuberculosis include the use of polypeptides that contain at least one immunogenic portion of one or more *Mycobacterium* proteins and DNA and RNA molecules encoding such polypeptides. In addition, such compounds may be formulated into vaccines and/or pharmaceutical compositions for immunization against *Mycobacterium* infection.

In other embodiments, the compositions of the present disclosure include antigens associated with respiratory diseases, such as those caused or exacerbated by bacterial infection (e.g. pneumococcal), for the prophylaxis and therapy of conditions such as chronic obstructive pulmonary disease (COPD).

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

In some embodiments, the compositions of the present disclosure are used to boost or enhance an immune response in a subject. In some such embodiments, the bioactive agent is an adjuvant. Nonlimiting exemplary adjuvants include TLR agonists (including TLR2, TLR3, TLR4, TLR7, TLR8, and TLR9 agonists), Rig-I agonists, saponins, carbohydrates, carbohydrate polymers, conjugated carbohydrates, whole viral particles, virus-like particles, viral fragments, and cellular fragments. Examples of such adjuvants include, but are not limited to, double-stranded RNA, RIBOXXOL, poly(I:C), and Hiltonol®. In some embodiments, the composition comprises a stable emulsion and/or a nanostructured lipid carrier. In some embodiments, the composition comprises a stable emulsion and/or a nanostructured lipid carrier that comprises squalene. The present inventors have found that squalene-based formulations unexpectedly potentiate, for example, TLR3 agonists.

In some preferred aspects, the compositions of the present disclosure are useful for enhancing or eliciting, in a host, a patient or in cell culture, an immune response. As used herein, the term "subject" refers to any mammal. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer- and may be reintroduced into a patient after treatment.

B. Vaccine

The present disclosure thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Determination of the induction of an immune response by the compositions of the present disclosure may be established by any of a number of well-known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca2+ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present disclosure using in vitro methodologies such as radioimmunoassay (RIA), enzyme linked immunosorbent assays (ELISA), equilibrium dialysis or solid phase immunoblotting including Western blotting. In embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), Manual of Clinical Laboratory Immunolog, 5th Ed., 1997 American Society of Microbiology, Washington, D.C.

Accordingly, it is contemplated that the compositions provided herein will be capable of eliciting or enhancing in a host at least one immune response that is selected from a Th1-type T lymphocyte response, a TH2-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, CCL2, CCL4, CCL5, CXCL1, and CXCL5, and a lymphocyte response that is selected from a memory T cell response, a memory B cell response, an effector T cell response, a cytotoxic T cell response and an effector B cell response.

C. Diagnostic Agents

In some embodiments the bioactive agent is a diagnostic agent. Thus, in these embodiments, the compositions described comprise the NLC provided herein, and further comprise a diagnostic agent and are useful for the diagnosis of any disease, condition, or disorder.

In some embodiments, the diagnostic agents are useful for the detection cancer. Compositions and methods are known in the art for identifying subjects having or suspected of being at risk for developing cancer are described herein. Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistocytochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar.

In some embodiments, the diagnostic agents are useful for the detection of an autoimmune disease. Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests.

In one embodiment, the diagnostic agents are useful for the detection of infectious diseases. Compositions and methods are known in the art for identifying subjects having, or suspected of being at risk for having, an infection with an infectious pathogen as described herein.

For example, the bacterium *Mycobacterium tuberculosis* causes tuberculosis (TB). Thus, in some embodiments, the compositions comprising any of the NLCs described herein further comprise an agent for diagnosing tuberculosis.

In some embodiments, the compositions comprising any of the NLCs described herein further comprise an agent for diagnosing malaria.

Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection.

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. Similarly known are the expression and purification of a recombinant *Plasmodium falciparum* (3D7) MSP-142, which retains folding and disulfide bridging of the native molecule. The recombinant MSP-142 is useful as a diagnostic reagent, for use in antibody production, and as a vaccine In some embodiments, the compositions comprising any of the NLCs described herein further comprise an agent useful for diagnosing Leishmaniasis.

In some embodiments, the compositions comprising any of the NLCs described herein further comprise an agent useful for diagnosing HIV.

IX. METHODS OF GENERATING AN IMMUNE RESPONSE

Provided herein are methods of generating an immune response in a subject, including the step of administering to a subject in need thereof a therapeutically effective amount of a composition described herein, where the bioactive agent is a protein antigen or a nucleic acid molecule encoding a protein antigen. In exemplary embodiments, the bioactive agent is a RNA (e.g., mRNA) or a DNA molecule encoding a protein antigen. In some embodiments, methods of boosting or enhancing an immune response are provided, wherein the bioactive agent is an adjuvant.

Typical routes of administration of the therapeutically effective amount of the composition include, without limitation, oral, topical, parenteral, sublingual, buccal, rectal, vaginal, intravenous, intradermal, transdermal, intranasal, intramucosal, or subcutaneous. In some exemplary embodiments, administration of the composition is intramuscular, ocular, parenteral, or pulmonary.

In exemplary embodiments, the compositions disclosed herein are vaccine compositions and are used as vaccines. The compositions described herein can be used for generating an immune response in the subject (including a non-specific response and an antigen-specific response). In some embodiments, the immune response comprises a systemic immune response. In some embodiments, the immune response comprises a mucosal immune response. Generation of an immune response includes stimulating an immune response, boosting an immune response, or enhancing an immune response.

The compositions described herein may be used to enhance protective immunity against a virus. Such viruses and viral antigens include, for example, HIV-1, (such as tat, nef, gp120 or gp160), human herpes viruses (such as gD or derivatives thereof or Immediate Early protein such as ICP27 from HSV1 or HSV2), cytomegalovirus ((esp. Human, such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., dengue virus, Japanese encephalitis virus, yellow fever virus, Zika virus, Poswanan virus, tick-borne encephalitis virus) or Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

The compositions described herein may be used to enhance protective immunity against one or more bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, —B or —C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexneri; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli;*

*Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including E. equi and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci*; Leptospira spp., including *L. interrogans; Treponema* spp., including *T. pallidum* (for example the rare outer membrane proteins), *T. denticola, T. hyodysenteriae*; or other bacterial pathogens.

The compositions described herein may be used to enhance protective immunity against one or more parasites (See, e.g., John, D. T. and Petri, W. A., Markell and Voge's Medical Parasitology-9th Ed., 2006, WB Saunders, Philadelphia; Bowman, D. D., Georgis' Parasitology for Veterinarians-8th Ed., 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leishmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis*, and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). In certain embodiments, the antigen is derived from *Schisostoma* spp., *Schistosoma mansonii, Schistosoma haematobium*, and/or *Schistosoma japonicum*, or derived from yeast such as *Candida* spp., including *C. albicans; Cryptococcus* spp., including *C. neoformans*. infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), Zika virus (ZIKV) respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia*, and *Leishmania*.

Methods for determining whether a composition of the present inventions is capable of effectively delivering the bioactive agent and/or having the desired effect in a subject are known in the art and not described herein in detail. In one aspect, immune responses against an antigen can be determined by monitoring the level antigen-specific antibody before and after administration (e.g., systemic IgM, IgG (IgG1, IgG2a, et al.) or IgA) in blood samples or from mucosal sites. Cellular immune responses also can be monitored after administration by assessing T and B cell function after antigen stimulation.

Another way of assessing the immunogenicity of the compositions or vaccines disclosed herein where the nucleic acid molecule (e.g., the RNA) encodes a protein antigen is to express the recombinant protein antigen for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

In the embodiments provided herein, the subject is a mammal (e.g., an animal including farm animals (cows, pigs, goats, horses, etc.), pets (cats, dogs, etc.), and rodents (rats, mice, etc.), or a human). In one embodiment, the subject is a human. In another embodiment, the subject is a non-human mammal. In another embodiment, the non-human mammal is a dog, cow, or horse.

X. METHODS OF DELIVERING A BIOACTIVE AGENT TO A CELL

Provided herein are methods of delivering a bioactive agent to a cell, including the step of contacting the cell with a composition described herein. In some embodiments, the bioactive agent is a nucleic acid. In some embodiments, contacting the cell with the composition includes a step of administering the composition to a subject where the cell is in the subject. Such methods are useful in the delivery of antigen or antigen-encoding nucleic acids for generation of an immune response. Such methods are also useful for the delivery of antibody-encoding nucleic acids, protein or small molecule drugs, hormones, non-coding RNA molecules, and other bioactive agents for treatment of disease and health conditions.

The methods described herein for delivering a bioactive agent to a cell may find use in the treatment of diseases and health conditions including, without limitation, cancer, such as meningiomas, hepatic cell carcinoma, pancreatic tumors; allergy; infectious diseases including fungal, bacterial, or parasitic diseases; inflammatory diseases including psoriasis and arthritis and atrial-ventricular malformations; autoimmune diseases; and neurological diseases.

In embodiments of methods of delivering a composition to a cell including the step of administering the composition to a subject where the cell is in the subject, typical routes of administration of the therapeutically effective amount of the composition include, without limitation, oral, topical, parenteral, sublingual, buccal, rectal, vaginal, intravenous, intradermal, transdermal, intranasal, intramucosal, or subcutaneous. In preferred embodiments, administration of the composition is intramuscular, parenteral, or intradermal. In such embodiments, the subject is a mammal (e.g., an animal including farm animals (cows, pigs, goats, horses, etc.), pets (cats, dogs, etc.), and rodents (rats, mice, etc.), or a human). In one embodiment, the subject is a human. In another embodiment, the subject is a non-human mammal. In another embodiment, the non-human mammal is a dog, cow, or horse.

In some embodiments, multiple modes of delivery may be used to obtain greater immune response. For example, the composition can be administered 1, 2, 3, or 4 times. In some embodiment, the one or more administrations may occur as part of a so-called "prime-boost" protocol. In some embodiments the "prime-boost" approach comprises administration in in several stages that present the same antigen through different vectors or multiple doses. In some embodiments, administration may occur more than twice, e.g., three times, four times, etc., so that the first priming administration is followed by more than one boosting administration. When multiple vectors or doses are administered, they can be separated from one another by, for example, one week, two weeks, three weeks, one month, six weeks, two months, three months, six months, one year, or longer. In some embodiments, a prime-boost approach comprises a RNA stage and a protein stage. The RNA stage may include, for example, administration of RNA carrying a gene coding for the antigenic protein, translation of the RNA into the antigen, and production of the corresponding antibodies in the subject. The protein stage may include, for example, administration of the antigen directly in the form of a protein. In some embodiments, the subject is administered (e.g., primed with) an oncolytic virus (which may be formulated with an NLC or without an NLC) that encodes a neoantigen, and then subsequently administered (e.g., boosted with) an NLC comprising an RNA construct that encodes the neoantigen.

XI. INTRADERMAL DELIVERY OF RNA (OPTIONALLY VIA MICRONJET600™)

The MicronJet600® is a small plastic device equipped with 3 microneedles, each 600 micrometers (0.6 mm) in length. This device can be mounted on any standard syringe instead of a standard needle. The microneedles themselves are made of silicon crystal and are integrated (bonded) after cutting into rows to their polycarbonate base using biocompatible UV cured glue.

The intradermal delivery can be conducted by the use of microneedles, with height of less than 1 mm or 1000 micron; and more preferably with height of 500-750 micron.

The microneedle injection device preferably has multiple needles, typically 3 microneedles The microneedle injection device is facing "downward" (bevel down) i.e., the injection aperture is facing deeper into the skin, and not bevel up. This enables reliable injection without leakage. The injection orientation is preferably defined by visible or mechanical features of the base/adapter.

The microneedle injection is done into the shallow dermis, and the epidermis. This allows for effective expression and immunization.

The injection depth with a microneedle is typically about 100-750 micron, and more preferably about 300-400 micron; This is in contrast with regular needles, or other mini or microneedles which typically deliver to a deeper layer of the skin or below the skin The injection angle is preferably about 45 degrees (typically ±20°, and more preferably ±10°), allowing shallow injection point, relative to standard needles, and other perpendicular microneedles.

Provided herein is a system and method of delivering RNA including rvRNA (replicon RNA) into an animal or a human patient (e.g., a subject), comprising administering the RNA (e.g., rvRNA) to the epidermis or the dermis of the skin at a depth of between about 100 and about 700 microns from the surface of the skin. An effective amount of RNA will be delivered to allow for expression of a protein encoded by the RNA. The protein can be an antigen as described herein and can be, for example, a vaccine component.

The RNA can be administered with an intradermal delivery device comprising one or more microneedles; wherein the intradermal delivery device is designed for shallow intradermal delivery.

The RNA can be administered with an intradermal delivery device according to the teachings of U.S. Pat. No. 6,533,949 and/or 7,998,119, incorporated herein by reference in their entirety.

Any of the RNA containing formulations and/or compositions described herein can be administered intradermally via a microneedle device as described herein. Other intradermal devices for delivery RNA can be used as well, including, for example, intradermal electroporation delivery devices. In some preferred embodiments, delivery of the RNA will generate an immune response in a subject.

XII. METHODS FOR OPTIMIZING DELIVERY OF RNA TO A CELL

Provided herein are methods for optimizing delivery of RNA to a cell comprising a step of selecting a molar ratio of nitrogen (N) to phosphate (P) that optimizes antibody titers produced in a subject comprising the cell. In an exemplary embodiment, actual N to P ratio is used to provide an interpretation of the RNA-NLC binding and corresponding in vitro expression of the RNA-encoded protein. Exemplary molar ratio of N to P may be from 1 to 200, from 1 to 100, preferably from 1 to 50, more preferably from about 5 to about 50 or from about 5 to about 40. In some exemplary embodiments, the molar ratio of N to P may be from 1 to 15 or from 1 to 7.

XIII. KITS AND ARTICLES OF MANUFACTURE

Also contemplated in certain embodiments are kits comprising the herein described nanostructured lipid carriers (NLCs) and compositions, which may be provided in one or more containers. In one embodiment all components of the compositions are present together in a single container. In other embodiments, components of the compositions may be in two or more containers. In a preferred embodiment, the NLC is provided in one container, and the bioactive agent is provided in another container.

In some embodiments, one vial of the kit comprises an NLC provided herein, and a second vial of the kit contains an RNA molecule. In some embodiments, the kit comprises a third vial containing an optional component.

The kits of the invention may further comprise instructions for use as herein described or instructions for mixing the materials contained in the vials. In some embodiments, the material in the vial is dry or lyophilized. In some embodiments, the material in the vial is liquid.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically, such a container may be made of a material that is compatible with the intended use and from which recovery of the contained contents can be readily achieved. Non-limiting examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizeable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

XIV. EXEMPLARY EMBODIMENTS

Embodiment 1. A composition comprising nanostructured lipid carrier (NLC) particles for delivery of a bioactive agent to a cell, wherein the NLC particles comprise:
  (a) an oil core comprising a mixture of a liquid phase lipid and a solid phase lipid,
  (b) a cationic component, preferably a cationic lipid,
  (c) a hydrophobic surfactant, preferably a sorbitan ester, and
  (d) a surfactant, preferably a hydrophilic surfactant.

Embodiment 2. The composition of embodiment 1 wherein the bioactive agent is associated with the NLC particles.

Embodiment 3. The composition of embodiment 1 or embodiment 2, wherein the composition delivers the bioactive agent to the cell.

Embodiment 4. The composition of any one of embodiment 1 to 3, wherein the hydrophobic surfactant is a sorbitan ester and it is present in an amount sufficient to increase the ability of the composition to deliver the bioactive agent to the cell as compared to a comparable composition without the sorbitan ester.

Embodiment 5. The composition of any one of embodiments 1 to 4, wherein the bioactive agent is a protein or the bioactive agent encodes a protein.

Embodiment 6. The composition of any one of embodiments 1 to 4, wherein the bioactive agent is a protein antigen or the bioactive agent encodes a protein antigen.

Embodiment 7. The composition of embodiment 6, wherein the cell is in a subject and wherein the composition elicits an immune response in the subject against the antigen.

Embodiment 8. The composition of embodiment 6 or 7 wherein the antigen is derived from, or immunologically cross-reactive with, an infectious pathogen and/or an epitope, biomolecule, cell or tissue that is associated with infection, cancer, or autoimmune disease.

Embodiment 9. The composition of any one of embodiments 6 to 8, wherein the hydrophobic surfactant is a sorbitan ester and the sorbitan ester is present in an amount sufficient to increase the ability of the composition to elicit an immune response to the antigen as compared to a comparable composition without the sorbitan ester.

Embodiment 10. The composition of any one of embodiments 6 to 9, wherein when administered in an effective amount to the subject, the composition elicits an immune response to the antigen equal to or greater than the immune response elicited when the bioactive agent is administered to the subject without the NLC.

Embodiment 11. The composition of any one of embodiments 6 to 10, wherein the hydrophobic surfactant is a sorbitan ester and when administered in an effective amount to the subject, the composition elicits antibody titers to the antigen at a higher level than the antibody titers elicited when a comparable composition lacking the sorbitan ester is administered to the subject.

Embodiment 12. The composition of any one of embodiments 6 to 11 wherein the hydrophobic surfactant is a sorbitan ester and the composition induces neutralizing antibody titers in the subject at a higher level than the neutralizing antibody titers induced in the subject by a comparable composition lacking the sorbitan ester.

Embodiment 13. The composition of any one of embodiments 1 to 12, wherein the bioactive agent is RNA or DNA.

Embodiment 14. The composition of any one of embodiments 1 to 12, wherein the bioactive agent is mRNA.

Embodiment 15. The composition of any one of embodiments 1 to 12, wherein the bioactive agent is oncolytic viral RNA.

Embodiment 16. The composition of embodiment 13 or 14, wherein the RNA is a replicon.

Embodiment 17. The composition of any one of embodiments 13 to 16, wherein the RNA encodes an antigen.

Embodiment 18. The composition of any one of embodiments 13 to 16, wherein the RNA encodes an antibody.

Embodiment 19. The composition of any one of embodiments 13 to 16, wherein the RNA is a non-coding RNA.

Embodiment 20. The composition of any one of embodiments 1 to 19, wherein the liquid phase lipid is metabolizable.

Embodiment 21. The composition of any one of embodiments 1 to 20, wherein the liquid phase lipid is a vegetable oil, animal oil or synthetically prepared oil.

Embodiment 22. The composition of any one of embodiments 1 to 21, wherein the liquid phase lipid is a fish oil.

Embodiment 23. The composition of any one of embodiments 1 to 20 wherein the liquid phase lipid is capric/caprylic triglyceride, vitamin E, lauroyl polyoxylglyceride, monoacylglycerol, soy lecithin, squalene, or squalane or a combination thereof.

Embodiment 24. The composition of any one of embodiments 1 to 21, wherein the liquid phase lipid is squalene, sunflower oil, soybean oil, olive oil, grapeseed oil, squalane, capric/caprylic triglyceride, or a combination thereof.

Embodiment 25. The composition of any one of embodiments 1 to 21, wherein the liquid phase lipid is a naturally occurring or synthetic terpenoid.

Embodiment 26. The composition of any one of embodiments 1 to 21, wherein the liquid phase lipid is squalene.

Embodiment 27. The composition of any one of embodiments 1 to 26, wherein the solid phase lipid is a glycerolipid.

Embodiment 28. The composition of any one of embodiments 1 to 26, wherein the solid phase lipid is a microcrystalline triglyceride.

Embodiment 29. The composition of embodiment 28, wherein the microcrystalline triglyceride is trimyristin.

Embodiment 30. The composition of any one of embodiments 1 to 29, wherein the cationic component is a cationic lipid selected from: 1,2-dioleoyloxy-3-(trimethylammonio) propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl(C16:0)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA), and combinations thereof.

Embodiment 31. The composition of embodiment 30, wherein the cationic lipid is 1,2-dioleoyloxy-3-(trimethylammonio)propane (DOTAP).

Embodiment 32. The composition of any one of embodiments 1 to 31, wherein the hydrophilic surfactant is a polyethylene glycol.

Embodiment 33. The composition of embodiment 32, wherein the hydrophilic surfactant is a polyoxyethylene sorbitan ester.

Embodiment 34. The composition of any one of embodiments 1 to 33, wherein the average polydispersity index of the NLC particles is from 0.1 to about 0.5 Embodiment 35. The composition of any one of embodiments 1 to 33, wherein the average polydispersity index of the NLC particles is from about 0.2 to about 0.5.

Embodiment 36. The composition of any one of embodiments 1 to 33, wherein the average polydispersity index of the NLC particles is from about 0.2 to about 0.4 or from about 0.1 to about 0.4.

Embodiment 37. The composition of any one of embodiments 1 to 33, wherein the average polydispersity index of the NLC particles is from about 0.2 to about 0.3, or from about 0.1 to about 0.3.

Embodiment 38. The composition of any one of embodiments 1 to 37, wherein the z-average diameter of the NLC particles is from about 40 nm to about 60 nm.

Embodiment 39. The composition of any one of embodiments 1 to 37, wherein the z-average diameter of the NLC particles is from about 20 nm to about 200 nm, from about 20 nm to about 150 from about 20 nm to about 100 nm, from about 20 nm to about 80 nm, or from about 20 nm to about 60 nm or from about 40 nm to about 200 nm, from about 40 nm to about 150 from about 40 nm to about 100 nm, from about 40 nm to about 80 nm, or from about 40 nm to about 60 nm.

Embodiment 40. The composition of any one of embodiments 1 to 39, wherein the hydrophobic surfactant is a sorbitan ester having a hydrophilic-lipophilic balance (HLB) value from 1 to 5.

Embodiment 41. The composition of embodiment 40, wherein the hydrophobic surfactant is a sorbitan ester having a HLB value from 4 to 5.

Embodiment 42. The composition of any one of embodiments 1 to 40, wherein the hydrophobic surfactant is a sorbitan ester and the sorbitan ester is a sorbitan monoester.

Embodiment 43. The composition of any one of embodiments 1 to 40, wherein the hydrophobic surfactant is a sorbitan ester and the sorbitan ester is sorbitan monostearate.

Embodiment 44. The composition of any one of embodiments 1 to 40, wherein the hydrophobic surfactant is a sorbitan ester and the sorbitan ester is sorbitan monooleate.

Embodiment 45. The composition of any one of embodiments 1 to 44, wherein the z-average diameter of the NLC particles is from about 40 nm to about 80 nm.

Embodiment 46. The composition of any one of embodiments 1 to 44, wherein the z-average diameter of the NLC particles is from about 40 nm to about 60 nm.

Embodiment 47. The composition of any one of embodiments 1 to 46, having an oil to surfactant molar ratio of about 0.5 to about 12, more preferably from about 0.5 to about 9.

Embodiment 48. The composition of any one of embodiments 1 to 46, having an oil to surfactant molar ratio of about 0.5 to about 1.

Embodiment 49. The composition of any one of embodiments 1 to 48, having a hydrophilic surfactant to cationic component ratio of about 0.2 to about 1.5.

Embodiment 50. The composition of any one of embodiments 1 to 48, having a hydrophilic surfactant to cationic component ratio of about 0.2 to about 1.

Embodiment 51. The composition of any one of embodiments 1 to 50, having a loading capacity for RNA of at least at least about 100 µg/ml RNA.

Embodiment 52. The composition of any one of embodiments 1 to 51, wherein the hydrophobic surfactant is a sorbitan ester and the sorbitan ester a sorbitan triester.

Embodiment 53. The composition of any one of embodiments 1 to 51, wherein the hydrophobic surfactant is a sorbitan ester and the sorbitan ester is sorbitan trioleate.

Embodiment 54. The composition of any one of embodiments 1 to 51, comprising from about 0.2% to about 40% w/v liquid phase lipid, from about 0.1% to about 10% w/v solid phase lipid, from about 0.2% to about 10% w/v cationic lipid, from about 0.25% to about 5% w/v sorbitan monoester, and from about 0.5% to about 10% w/v hydrophilic surfactant.

Embodiment 55. The composition of any one of embodiments 1 to 51, comprising from about 2% to about 40% w/v liquid phase lipid, from about 0.1% to about 10% w/v solid phase lipid, from about 0.2% to about 10% w/v cationic lipid, from about 0.25% to about 5% w/v sorbitan monoester, and from about 0.5% to about 10% w/v hydrophilic surfactant.

Embodiment 56. The composition of any one of embodiments 1 to 53, comprising from about 10% to about 40% w/v liquid phase lipid, from about 1% to about 2% solid phase lipid, from about 2% to about 5% cationic lipid, from about 3 to about 5% w/v sorbitan ester, and from about 3% to about 5% w/v hydrophilic surfactant.

Embodiment 57. The composition of any one of embodiments 1 to 53, comprising about 15% w/v liquid phase lipid and about 1% solid phase lipid, or about 30% w/v liquid phase lipid and about 1.8% solid phase lipid, and about 3% cationic lipid, about 3.7% w/v sorbitan ester, and about 3.7% w/v hydrophilic surfactant Embodiment 58. The composition of any one of embodiments 1 to 53, comprising from about 2% to about 6% w/v liquid phase lipid, from about 0.1% to about 1% w/v solid phase lipid, from about 0.2% to about 1% w/v cationic lipid, from about 0.25% to about 1% w/v sorbitan monoester, and from about 0.5% to about 5% w/v hydrophilic surfactant.

Embodiment 59. The composition of any one of embodiments 1 to 53, comprising about 3.75% w/v liquid phase lipid, about 0.25% w/v solid phase lipid, about 3% w/v cationic lipid, about 3.7% w/v sorbitan ester, and about 3.7% w/v hydrophilic surfactant.

Embodiment 60. The composition of any one of embodiments 1 to 53, comprising from about 0.2% to about 40% w/v liquid phase lipid, from about 0.1% to about 10% w/v solid phase lipid, from about 0.2% to about 10% w/v cationic lipid, from about 0.25% to about 5% w/v sorbitan ester, and from about 0.2% to about 10% w/v hydrophilic surfactant.

Embodiment 61. The composition of any one of embodiments 1 to 53, comprising from about 0.2% to about 40% w/v liquid phase lipid, from about 0.1% to about 10% w/v solid phase lipid, from about 0.2% to about 10% w/v cationic lipid, from about 0.25% to about 15% w/v sorbitan ester, and from about 0.2% or about 0.5% to about 15% w/v hydrophilic surfactant.

Embodiment 62. The composition of any one of embodiments 1 to 53, comprising from about 2% to about 40% w/v liquid phase lipid, from about 0.1% to about 10% w/v solid phase lipid, from about 0.2% to about 10% w/v cationic lipid, from about 0.25% to about 5% w/v sorbitan ester, and from about 0.2% to about 10% w/v hydrophilic surfactant.

Embodiment 63. The composition of any one of embodiments 1 to 53, comprising from about 2% to about 6% w/v liquid phase lipid, from about 0.1% to about 1% w/v solid phase lipid, from about 0.2% to about 1% w/v cationic lipid, from about 0.25% to about 1% w/v sorbitan monoester, and from about 0.2% to about 5% w/v hydrophilic surfactant.

Embodiment 64. The composition of any one of embodiments 1 to 53, comprising about 4% w/v liquid phase lipid, about 0.25% w/v solid phase lipid, about 0.4% w/v cationic lipid, about 0.5% w/v sorbitan ester, and about 0.5% w/v hydrophilic surfactant.

Embodiment 65. A composition comprising a diluted or concentrated form of the composition of any one of embodiments 54 to 64.

Embodiment 66. The composition of embodiment 65 wherein the composition of any one of embodiments 54 to 64 is diluted 2 to 30 fold.

Embodiment 67. The composition of embodiment 65 wherein the composition of any one of embodiments 54 to 64 is diluted 2 to 20 fold.

Embodiment 68. The composition of embodiment 65 wherein the composition of any one of embodiments 54 to 64 is diluted 2 fold.

Embodiment 69. The composition of embodiment 65 wherein the composition of any one of embodiments 54 to 64 is concentrated 2 to 30 fold.

Embodiment 70. The composition of embodiment 65 wherein the composition of any one of embodiments 54 to 64 is concentrated 2 to 10 fold.

Embodiment 71. The composition of any one of embodiments 54 to 70 wherein the liquid phase lipid is naturally occurring or synthetic terpenoid.

Embodiment 72. The composition of any one of embodiments 54 to 70 wherein the liquid phase lipid is naturally occurring or synthetic squalene.

Embodiment 73. The composition of any one of embodiments 54 to 72, wherein the solid phase lipid is a glycerolipid.

Embodiment 74. The composition of any one of embodiments 54 to 72, wherein the solid phase lipid is a microcrystalline triglyceride.

Embodiment 75. The composition of any one of embodiments 54 to 72, wherein the solid phase lipid is trimyristin.

Embodiment 76. The composition of any one of embodiments 54 to 75, wherein the cationic lipid is DOTAP.

Embodiment 77. The composition of any one of embodiments 54 to 76, wherein the sorbitan ester is sorbitan monostearate.

Embodiment 78. The composition of any one of embodiments 54 to 76, wherein the sorbitan ester is sorbitan monooleate.

Embodiment 79. The composition of any one of embodiments 54 to 76, wherein the sorbitan ester is sorbitan trioleate.

Embodiment 80. The composition of any one of embodiments 54 to 77, wherein the hydrophilic surfactant is a polysorbate.

Embodiment 81. The composition of any one of embodiments 54 to 77, wherein the hydrophilic surfactant is polysorbate 80.

Embodiment 82. The composition of any one of embodiments 1 to 20, 34 to 41, 45 to 51, and 54 to 70, wherein the oil core comprises naturally occurring or synthetic squalene and a glycerolipid, wherein the cationic lipid is DOTAP, wherein the sorbitan ester is sorbitan monostearate or sorbitan monooleate, and wherein the hydrophilic surfactant is a polysorbate.

Embodiment 83. The composition of any one of embodiments 1 to 20, 34 to 41, 45 to 51, and 54 to 70, wherein the oil core comprises squalene and trimyristin, wherein the cationic lipid is DOTAP, wherein the sorbitan ester is sorbitan monostearate, and wherein the hydrophilic surfactant is polysorbate 80.

Embodiment 84. The composition of embodiment 83, wherein the NLC comprises from about 2% to about 40% w/v squalene, from about 0.1% to about 10% w/v trimyristin, from about 0.2% to about 10% w/v DOTAP, from about 0.25% to about 5% w/v sorbitan monostearate, and from about 0.5% to about 10% w/v polysorbate 80.

Embodiment 85. The composition of embodiment 83, wherein the NLC comprises from about 2% to about 6% w/v squalene, from about 0.1% to about 1% w/v trimyristin, from about 0.2% to about 1% w/v DOTAP, from about 0.25% to about 1% w/v sorbitan monostearate, and from about 0.5% to about 5% w/v polysorbate 80.

Embodiment 86. The composition of embodiment 85, wherein the NLC comprises about 3.75% w/v squalene, about 0.25% w/v trimyristin, about w/v 3% DOTAP, about 3.7% w/v sorbitan monostearate, and about 3.7% w/v polysorbate 80.

Embodiment 87. The composition of any one of embodiments 1 to 20, 34 to 41, 45 to 51, and 54 to 70, wherein the oil core comprises naturally occurring or synthetic squalene and a glycerolipid, wherein the cationic lipid is DOTAP, wherein the sorbitan ester is sorbitan monostearate or sorbitan monooleate or sorbitan trioleate, and wherein the hydrophilic surfactant is a polysorbate.

Embodiment 88. The composition of any one of embodiments 1 to 20, 34 to 41, 45 to 51, and 54 to 70, wherein the oil core comprises squalene and trimyristin, wherein the cationic lipid is DOTAP, wherein the sorbitan ester is sorbitan monostearate or sorbitan monooleate or sorbitan trioleate, and wherein the hydrophilic surfactant is polysorbate 80.

Embodiment 89. The composition of embodiment 87 or embodiment 88, wherein the NLC comprises from about 2% to about 40% w/v squalene, from about 0.1% to about 10% w/v trimyristin, from about 0.2% to about 10% w/v DOTAP, from about 0.25% to about 5% w/v sorbitan monostearate or sorbitan monooleate or sorbitan trioleate, and from about 0.2% to about 10% w/v polysorbate 80.

Embodiment 90. The composition of embodiment 87 or embodiment 88, wherein the NLC comprises from about 2% to about 6% w/v squalene, from about 0.1% to about 1% w/v trimyristin, from about 0.2% to about 1% w/v DOTAP, from about 0.25% to about 1% w/v sorbitan monostearate or sorbitan monooleate or sorbitan trioleate, and from about 0.2% to about 5% w/v polysorbate 80.

Embodiment 91. The composition of embodiment 87 or embodiment 88, wherein the NLC comprises about 4% w/v squalene, about 0.25% w/v trimyristin, about w/v 0.4% DOTAP, about 0.5% w/v sorbitan monostearate or sorbitan monooleate or sorbitan trioleate, and about 0.5% w/v polysorbate 80.

Embodiment 92. A method of generating an immune response in a subject, comprising administering to a subject in need thereof a therapeutically effective amount of the composition of any one of embodiments 1 to 91, wherein the bioactive agent is a protein antigen or a nucleic acid molecule encoding a protein antigen.

Embodiment 93. The method of embodiment 92 wherein the bioactive agent is RNA.

Embodiment 94. The method of embodiment 92 or 93, wherein administration of the composition is intramuscular, parenteral or intradermal.

Embodiment 95. A method of generating an immune response in a subject, comprising (a) administering to a subject in need thereof a therapeutically effective amount of an oncolytic virus encoding a protein antigen, and (b) administering to the subject a therapeutically effective amount of the composition of any one of embodiment 1 to 91, wherein the bioactive agent is the protein antigen or a nucleic acid molecule encoding the protein antigen.

Embodiment 96. The method of embodiment 95, wherein the administration of (a) and the administration of (b) occur at least 1 week, at least 2 weeks, at least 3 weeks, at least 1 month, at least 6 weeks, at least two months, at least three months, at least 6 months, or at least 1 year apart.

Embodiment 97. A method of delivering a bioactive agent to a cell, comprising contacting the cell with the composition of any one of embodiments 1 to 91.

Embodiment 98. The method of embodiment 97 wherein the bioactive agent is a nucleic acid.

Embodiment 99. The method of embodiment 97 or embodiment 98, wherein contacting the cell with the composition comprises administering the composition to a subject wherein the cell is in the subject.

Embodiment 100. A method for optimizing delivery of a bioactive agent to a cell comprising selecting a molar ratio of bioactive agent to NLC that optimizes antibody titers produced in a subject comprising the cell.

Embodiment 101. The method of embodiment 100, wherein the NLC is an NLC particle of any one of embodiments 1 to 91.

Embodiment 102. A method of making the composition of any one of embodiments 1 to 91, comprising:
  (e) mixing the solid phase lipid, the liquid phase lipid, the cationic lipid, and the hydrophobic surfactant to form an oil phase mixture;
  (f) mixing the hydrophilic surfactant and water to form an aqueous phase mixture;
  (g) mixing the oil phase mixture with the aqueous phase mixture to form the NLC particles; and
  (h) optionally combining the bioactive agent with the NLC particles such that the bioactive agent associates with the surface of the NLC particles by non-covalent interactions or by reversible covalent interactions.

Embodiment 103. The composition of any one of embodiments 1 to 91, wherein the bioactive agent is RNA, and wherein the RNA encodes one or more TB antigens.

Embodiment 104. The composition of embodiment 103, wherein the RNA encodes one or more TB antigens selected from Rv3619, Rv2389, Rv3478, and Rv1886.

Embodiment 105. The composition of embodiment 104, wherein the RNA encodes TB antigens Rv3619, Rv 2389, Rv3478, and Rv1886.

Embodiment 106. The method of any one of embodiments 92 to 99, wherein the bioactive agent is RNA, and wherein the RNA encodes one or more TB antigens.

Embodiment 107. The method of embodiment 106, wherein the RNA encodes one or more TB antigens selected from Rv3619, Rv 2389, Rv3478, and Rv1886.

Embodiment 108. The method of embodiment 107, wherein the RNA encodes TB antigens Rv3619, Rv 2389, Rv3478, and Rv1886.

Embodiment 109. The composition of any one of embodiments 1 to 91, wherein the bioactive agent is an adjuvant.

Embodiment 110. The composition of embodiment 109, wherein the adjuvant is selected from a TLR agonist, a Rig-I agonist, a saponin, a carbohydrate, a carbohydrate polymer, a conjugated carbohydrate, a whole viral particle, a virus-like particle, viral fragments, and cellular fragments.

Embodiment 111. The composition of embodiment 110, wherein the adjuvant is selected from a TLR agonist and a Rig-I agonist.

Embodiment 112. The composition of embodiment 111, wherein the TLR agonist is a TLR2, TLR3, TLR4, TLR7, TLR8, or TLR9 agonist.

Embodiment 113. The composition of embodiment 111, wherein the TLR agonist is a TLR3 agonist.

Embodiment 114. The composition of any one of embodiments 109 to 112, wherein the bioactive agent is selected from double-stranded RNA, RIBOXXOL, poly(I:C), and Hiltonol®.

Embodiment 115. A composition comprising an adjuvant in a stable emulsion, wherein the adjuvant is selected from a TLR3 agonist and a Rig-I agonist, and wherein the stable emulsion is an oil-in-water emulsion.

Embodiment 116. The composition of embodiment 115, wherein the emulsion comprises 2 to 10% oil.

Embodiment 117. The composition of embodiment 115 or 116, wherein the oil is squalene.

Embodiment 118. The composition of any one of embodiments 115 to 117, wherein the oil-in-water emulsion comprises 0.01% to 0.1% alpha tocopherol.

Embodiment 119. The composition of embodiment 118, wherein the ratio of oil to alpha tocopherol is greater than 1.

Embodiment 120. The composition of any one of embodiments 115 to 118, wherein the oil-in-water emulsion comprises 0.3 to 3% surfactant.

Embodiment 121. The composition of embodiment 120, wherein the surfactant is polyoxyethylene sorbitan monooleate or Poloxamer 188 (copolymer of polyoxyethylene and polyoxypropylene).

Embodiment 122. The composition of any one of embodiments 115 to 121, wherein the oil-in-water emulsion comprises about 1% Span 85.

Embodiment 123. The composition of any one of embodiments 115 to 121, wherein the oil-in-water emulsion comprises 0.5% to 5%, or 0.5% to 5%, or 0.5% to 3%, or 1% to 3% 1,2-dimyristoyl-sn-glycero-3-phosphocholine (DMPC).
Embodiment 124. The composition of any one of embodiments 115 to 123, wherein the oil-in-water emulsion comprises 0.5% to 5%, or 0.5% to 5%, or 0.5% to 3%, or 1% to 3% glycerol.
Embodiment 125. A method of generating or enhancing an immune response comprising administering to a subject in need thereof a therapeutically effective amount of the composition of any one of embodiments 109 to 124.
Embodiment 126. The method of embodiment 125, wherein the immune response is greater than the immune response when the subject is administered adjuvant alone.
Embodiment 127. The method of embodiment 125 or embodiment 126, wherein administration of the composition is intramuscular, parenteral or intradermal.
Embodiment 128. A composition comprising (a) an adjuvant and (b) an oil-in-water emulsion or nanoparticle lipid carrier (NLC) particles, wherein the oil-in-water emulsion or NLC particles comprises squalene.
Embodiment 129. The composition of embodiment 128, wherein the adjuvant is selected from a TLR agonist, a Rig-I agonist, a saponin, a carbohydrate, a carbohydrate polymer, a conjugated carbohydrate, a whole viral particle, a virus-like particle, viral fragments, and cellular fragments.
Embodiment 130. The composition of embodiment 129, wherein the adjuvant is selected from a TLR agonist and a Rig-I agonist.
Embodiment 131. The composition of embodiment 130, wherein the TLR agonist is a TLR2, TLR3, TLR4, TLR7, TLR8, or TLR9 agonist.
Embodiment 132. The composition of embodiment 131, wherein the TLR agonist is a TLR3 agonist.
Embodiment 133. The composition of any one of embodiments 128 to 132, wherein the bioactive agent is selected from double-stranded RNA, RIBOXXOL, poly(I:C), and Hiltonol®.
Embodiment 134. A method of generating or enhancing an immune response comprising administering to a subject in need thereof a therapeutically effective amount of the composition of any one of embodiments 128 to 133.
Embodiment 135. The method of embodiment 134, wherein the immune response is greater than the immune response when the subject is administered adjuvant alone.
Embodiment 136. The method of embodiment 134 or embodiment 135, wherein administration of the composition is intramuscular, parenteral or intradermal.

The following Examples are offered by way of illustration and not by way of limitation.

EXAMPLES

Example 1: Development of NLC Formulations

Nanostructured Lipid Carrier (NLC) compositions were prepared using a combination of emulsifying agents, and the stability of resulting compositions was evaluated using particle size measurements under storage conditions (5° C.). The oil phase was composed of squalene—the liquid-phase of the oil core—a non-ionic sorbitan ester surfactant, either sorbitan trioleate (Span® 85) or sorbitan monostearate (Span® 60), the cationic lipid DOTAP (N-[1-(2,3-Dioleoyloxy)propyl]-N,N,N-trimethylammonium chloride), and in the case of NLC formulations, the solid lipid (glyceryl trimyristate—Dynasan® 114). The aqueous phase was a 10 mM sodium citrate trihydrate buffer containing the non-ionic PEGylated surfactant Tween® 80.

The make-up of the formulations depicted in the examples are shown in Table 2 below:

TABLE 2

Compositions of representative formulations

| ID | Liquid Oil % (W/V) | Solid Oil % (W/V) | Hydrophilic surfactant % (W/V) | Sorbitan ester | Cationic lipid % (W/V) | Oil to Surfactant molar ratio | Tween 80:DOTAP molar ratio |
|---|---|---|---|---|---|---|---|
| QG386 (CNE) | 4.3% squalene | — | 0.5% Tween 80 | 0.5% Span 85 | 0.4% DOTAP | 6.9 | |
| QG711 | 4.08% Squalene | 0.25% Dynasan 114 | 2% Tween 80 | — | 0.4% DOTAP | 4.8 | |
| QG752 | 4.08% Squalene | 0.25% Dynasan 114 | 2% Tween 80 | 0.5% Span 85 | 0.4% DOTAP | 3.9 | |
| QG762 | 4.08% Squalene | 0.25% Dynasan 114 | 2% Tween 80 | 0.25% Span 85 | 0.4% DOTAP | 4.3 | |
| QG766 | 5% Squalene | — | 2% Tween 80 | 0.5% Span 85 | 0.4% DOTAP | 4.6 | 2.53 |
| QG868 | 5% Squalene | — | 2% Tween 80 | 0.5% Span 60 | 0.4% DOTAP | 3.7 | 2.53 |
| QG767 | 4.08% Squalene | 0.25% Dynasan 114 | 2% Tween 80 | 0.5% Span 80 | 0.4% DOTAP | 3.1 | |
| QG768 or QG863 | 4.08% Squalene | 0.25% Dynasan 114 | 2% Tween 80 | 0.5% Span60 | 0.4% DOTAP | 3.1 | 2.53 |
| QG769 | 4.37% grapeseed oil | 0.25% Dynasan 114 | 2% Tween 80 | 0.5% Span 85 | 0.4% DOTAP | | |

TABLE 2-continued

Compositions of representative formulations

| ID | Liquid Oil % (W/V) | Solid Oil % (W/V) | Hydrophilic surfactant % (W/V) | Sorbitan ester | Cationic lipid % (W/V) | Oil to Surfactant molar ratio | Tween 80:DOTAP molar ratio |
|---|---|---|---|---|---|---|---|
| QG866 | 4.37% grapeseed oil | 0.25% Dynasan 114 | 2% Tween 80 | 0.5% Span 60 | 0.4% DOTAP | | |
| QG770 | 4.49% Myglyol 810 | 0.25% Dynasan 114 | 2% Tween 80 | 0.5% Span 85 | 0.4% DOTAP | | |
| QG865 | 4.49% Myglyol 810 | 0.25% Dynasan 114 | 2% Tween 80 | 0.5% Span 60 | 0.4% DOTAP | | |
| QG807 | 4.08% Squalene | 0.25% Dynasan 114 | 0.5% Tween 80 | 0.5% Span60 | 0.4% DOTAP | 5.5 | 0.63 |
| QG808 | 4.08% Squalene | 0.25% Dynasan 114 | 0.5% Tween 80 | 0.5% Span 85 | 0.4% DOTAP | 6.8 | |
| QG906 | 4.08% Squalene | 0.25% Dynasan 114 | 0.5% Tween 80 | 0.5% Span 80 | 0.4% DOTAP | 4.7 | |
| QG925 | 15% Squalene | 0.9% Dynasan 114 | 3.7% Tween 80 | 3.7% Span60 | 3% DOTAP | 2.4 | 0.63 |
| QG912 | 2.03% Squalene | 0.125% Dynasan 114 | 0.5% Tween 80 | 0.5% Span60 | 0.4% DOTAP | 2.4 | |
| QG924 | 30% Squalene | 1.85% Dynasan 114 | 3.7% Tween 80 | 3.7% Span 60 | 3% DOTAP | 4.8 | 0.63 |
| QG911 | 4.05% Squalene | 0.25 % Dyanasan 114 | 0.5% Tween 80 | 0.5% Span 60 | 0.4% DOTAP | 4.8 | |
| QG941 | 7.50% Squalene | 0.24% Dynasan 114 | 3.7% Tween 80 | 3.7% Span 60 | 3% DOTAP | 1.2 | 0.63 |
| QG942 (NCLv2) | 3.75% Squalene | 0.24% Dynasan 114 | 3.7% Tween 80 | 3.7% Span 60 | 3% DOTAP | 0.6 | 0.63 |
| QG963 | 3.75% Squalene | 0.24% Dynasan 114 | 1.5% Tween 80 | 3.7% Span 60 | 1.5% DOTAP | 0.8 | |
| $NCL_{v1}$ | 4.75% Squalene | 0.25% Dynasan 114 | 0.5% Tween 80 | 0.5% Span 60 | 0.4% DOTAP | | |

*QG386 is a prior art cationic nanoemulsion (also referred to herein as CNE); the formulations were optionally buffered with 10 mM citrate.

In order to synthesize NLC formulations, the oil phase was first prepared by mixing the liquid phase lipid, solid phase lipid, positively charged lipid, and hydrophobic surfactant in a Blend Vessel, which was placed in a sonicating water bath (70±5° C.) to facilitate solubilization. Preparation of the aqueous phase involved dilution of a hydrophilic surfactant, preferably Tween 80, in ultrapure water for injection (WFI) or an aqueous buffer, such as 10 mM sodium citrate trihydrate, followed by stirring for complete dissolution. The aqueous composition was heated to 60-70° C. in, for example, a bath sonicator, before blending with the oil phase. In some instances, the two phases were both heated separately to 60° C. in a bath sonicator. A high shear mixer was used to combine the oil and aqueous phases by high shearing of the composite mixture. The blending speed was gradually increased to 5,000 RPM, or a maximum of 10,000 RPM, in a high-speed laboratory emulsifier (Silverson Machines, Inc.), and mixing then occurred for a period of ten minutes to one hour to produce a crude mixture containing micron-sized oil droplets. The positioning of the Silverson mixing probe was adjusted as necessary for uniform dispersal of oil and complete emulsification. Further particle size reduction was achieved by high-shear homogenization in a M-110P microfluidizer (Microfluidics, Corp.). NLC particles were obtained from the crude emulsion using a M-110P Microfluidizer Materials Processor (Microfluidics, Corp.). Each emulsion was processed for approximately 5 passes on the microfluidizer at 45° C. at 30,000 psi. The final pH was between 6.5-6.8. The resulting NLC particle suspension was strained using a 0.2 μm sterile filter (e.g., 0.2 μm polyethersulfone membrane syringe filter) in order to collect the final NLC formulation and store at 2-8° C., which was subsequently assessed for particle size.

To assess stability of the NLCs (uncomplexed NLCs), the average hydrodynamic diameter (Z-average) and polydispersity index (PDI) for each formulation was measured using Dynamic Light Scattering (DLS) after varying times of storage at 5° C. (Table 3).

TABLE 3

Particle size and polydispersity index measurements of representative formulations

| ID | Stability temperature and time for columns (b), (c) and (d) | (b) Z-average [nm] | (c) Poly-dispersity Index (PDI) | (d) Zeta potential (mV) | Stability temperature and time for columns (e) and (f) | (e) Z-average [nm] | (f) Poly-dispersity Index (PDI) |
|---|---|---|---|---|---|---|---|
| QG770 | @synthesis | 92.1 | 0.241 | | 5° C. at t = 2 weeks | 100.3 | 0.224 |
| QG769 | @synthesis | 105.8 | 0.223 | | | Not tested | Not tested |
| QG768 | @synthesis | 105.4 | 0.27 | | 5° C. at t = 1 month | 105.4 | 0.271 |
| QG767 | @synthesis | 106.9 | 0.261 | | 5° C. at t = 1 month | 108.3 | 0.264 |
| QG762 | @synthesis | 110.7 | 0.258 | | | Not tested | Not tested |
| QG752 | @synthesis | 79.4 | 0.284 | | 5° C. at t = 1 month | 75.7 | 0.27 |
| QG808 | @synthesis | 111.5 | 0.228 | | 5° C. at t = 1 month | 108.5 | 0.218 |
| QG807 | @synthesis | 107.0 | 0.248 | | 5° C. at t = 1 month | 106.9 | 0.234 |
| QG906 | @synthesis | 105.0 | 0.068 | | 5° C. at t = 1 month | 105.0 | 0.067 |
| QG386 (CNE) | @synthesis | 97.23 | 0.056 | 13.1 ± 3.25 | 5° C. at t = 1 month | 103.1 | 0.095 |
| QG912 | @synthesis | 63.06 | 0.117 | | 5° C. at t = 1 month | | |
| QG925 | @synthesis | 58.57 | 0.149 | | 5° C. at t = 1 month | 48.53 | 0.221 |
| QG942 (NLC$_{v2}$) | @synthesis | 40.6 | 0.198 | 28.4 ± 1.27 | | | |
| NLC$_{v1}$ | @synthesis | 91.90 | 0.17 | 15.6 ± 0.12 | | | |

FIGS. 1A-1E compare the z-average diameter, measured using Dynamic Light Scattering (Zetasizer Nano ZS, Malvern Instruments, Ltd.), of formulations incubated at different temperatures. Formulations were diluted 1:100 with water in triplicate preparations and measured in a disposable polystyrene cuvette (SOP parameters: material RI=1.59, dispersant RI (water)=1.33, T=25° C., viscosity (water)=0.887 cP, measurement angle=173° backscatter, measurement position=4.65 mm, automatic attenuation). For zeta potential measurement, formulations were diluted 1:100 in triplicates and loaded in a disposable DTS1070 (Malvern instruments, Ltd.) folded capillary cell. The following SOP parameters were used: material RI=1.59, dispersant RI (water)=1.33, viscosity (water)=0.887 cP, T=25° C., automatic attenuation and voltage selection. The intensity-weighted Z-average diameter, PDI and zeta potential values for each formulation, averaged from three measurements/replicate (9 total measurements), are reported in Table 3. Particle size of formulated RNA (NLC+RNA or CNE+RNA complex) at different N:P values was measured in triplicate using the Zetasizer Auto Plate Sampler (APS, Malvern Instruments, Ltd.) in a 384-well plate configuration. Zeta potential of formulated RNA at different N:P values was measured in triplicate following the same method described above for formulation alone. NLC binding capacity was determined using a gel retardation assay. Briefly, NLC and rvRNA complexes were prepared at various N:P values and electrophoresed as is in 1% agarose gel. Standard concentrations were used to quantify unbound or excess rvRNA migrating in the gel.

Figure 16B:
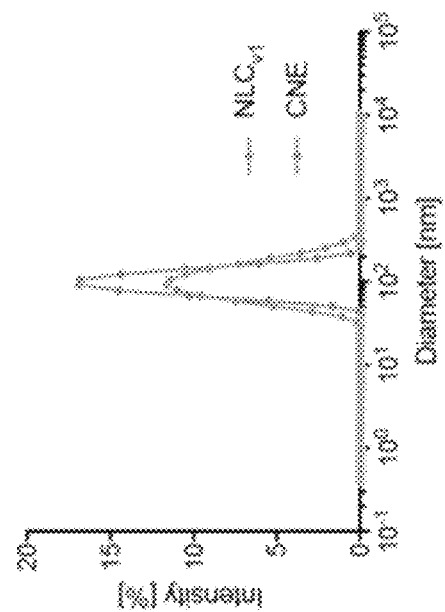
FIGS. 16A-D.
Figure 16A:
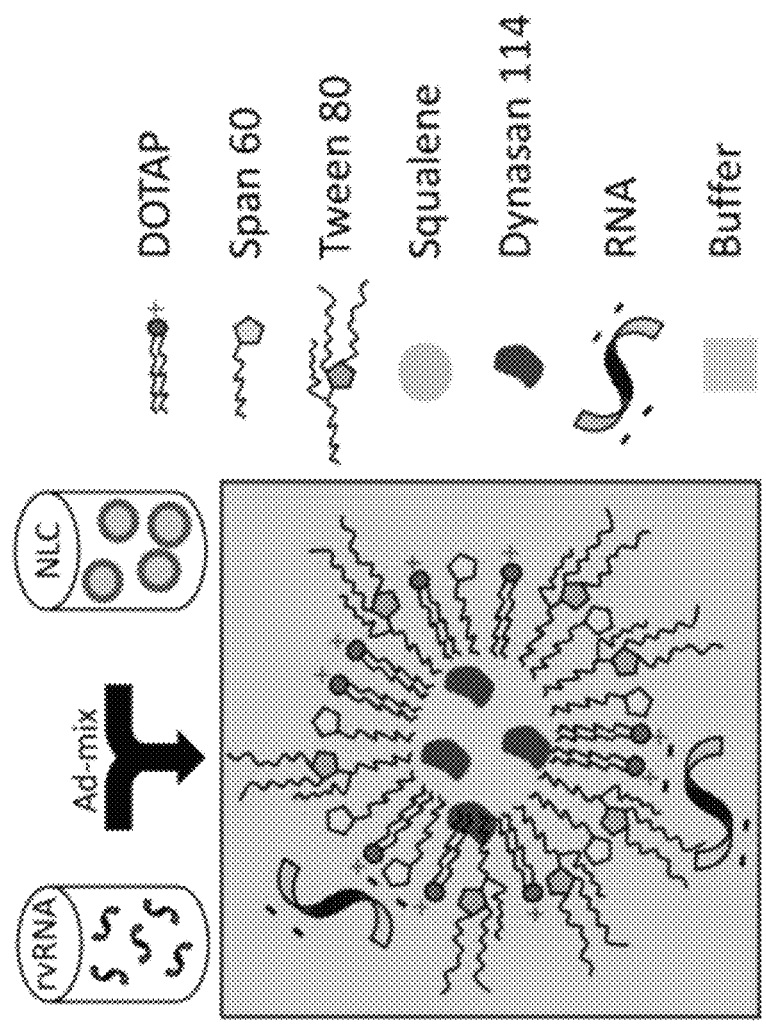
Figure 16D:
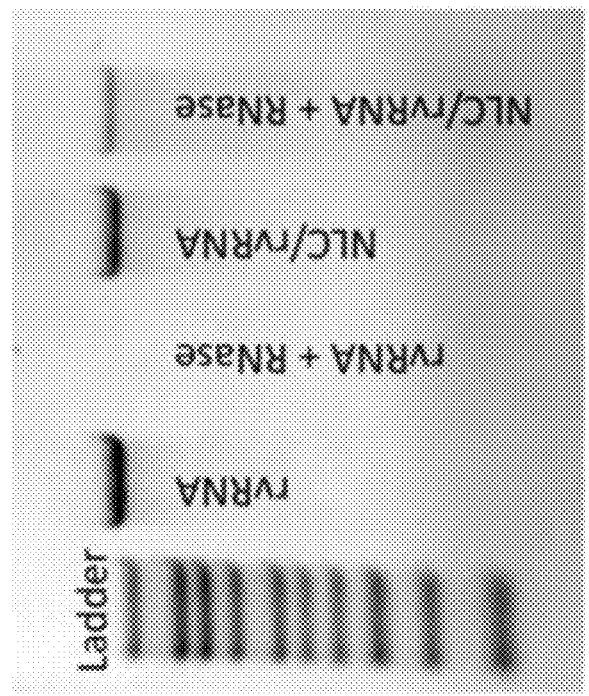
Figure 16C:
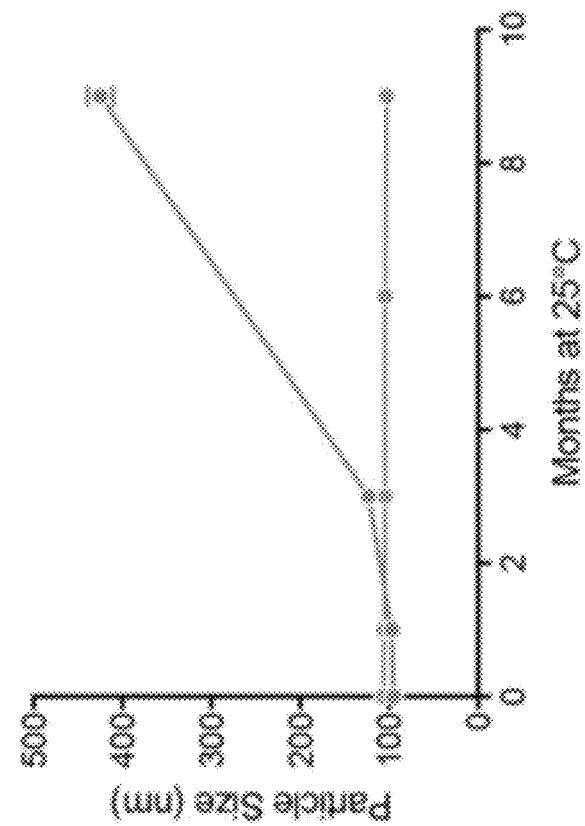
Figure 17:
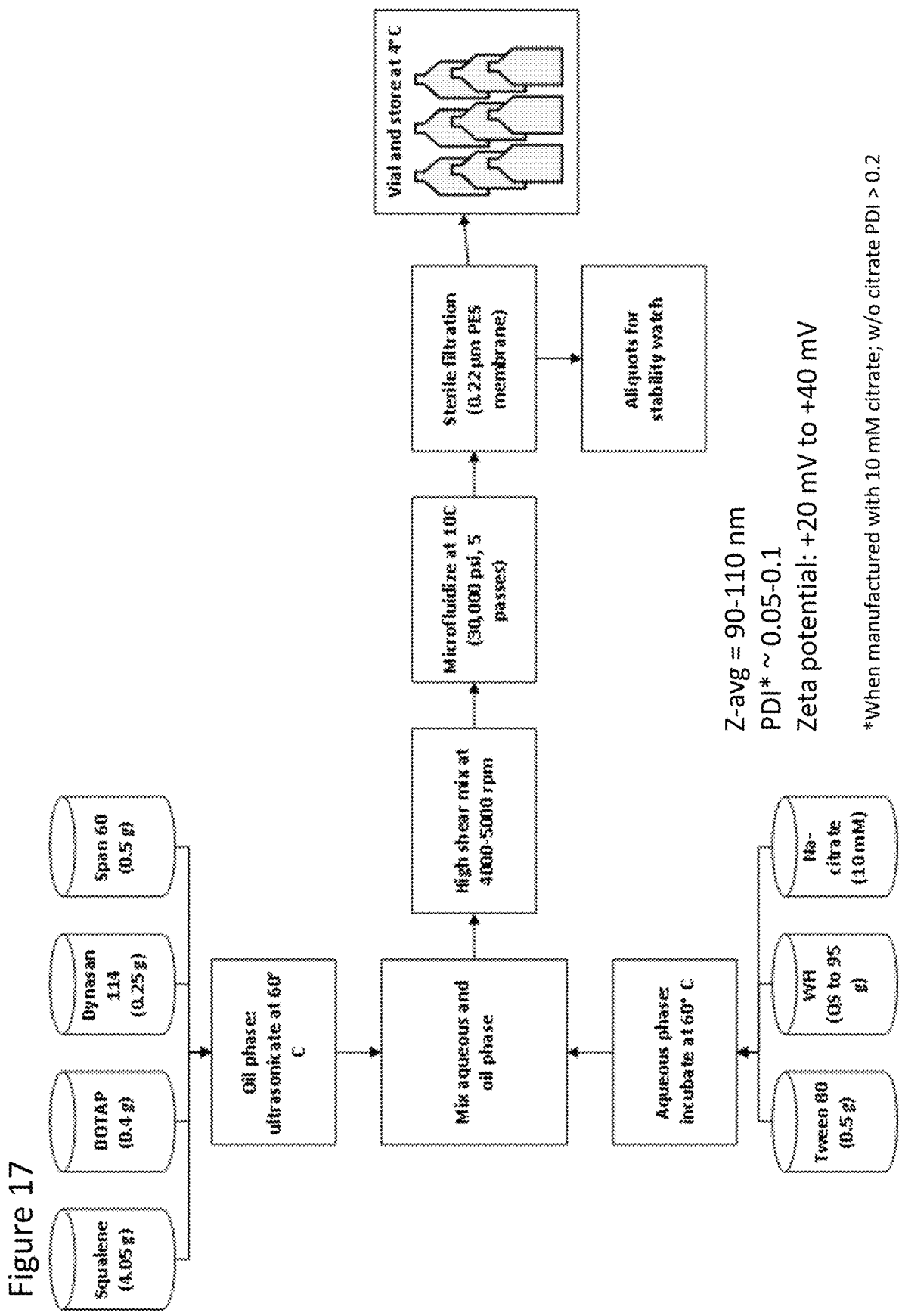
FIG. 17 depicts an exemplary NLC manufacturing process.
Figure 35:
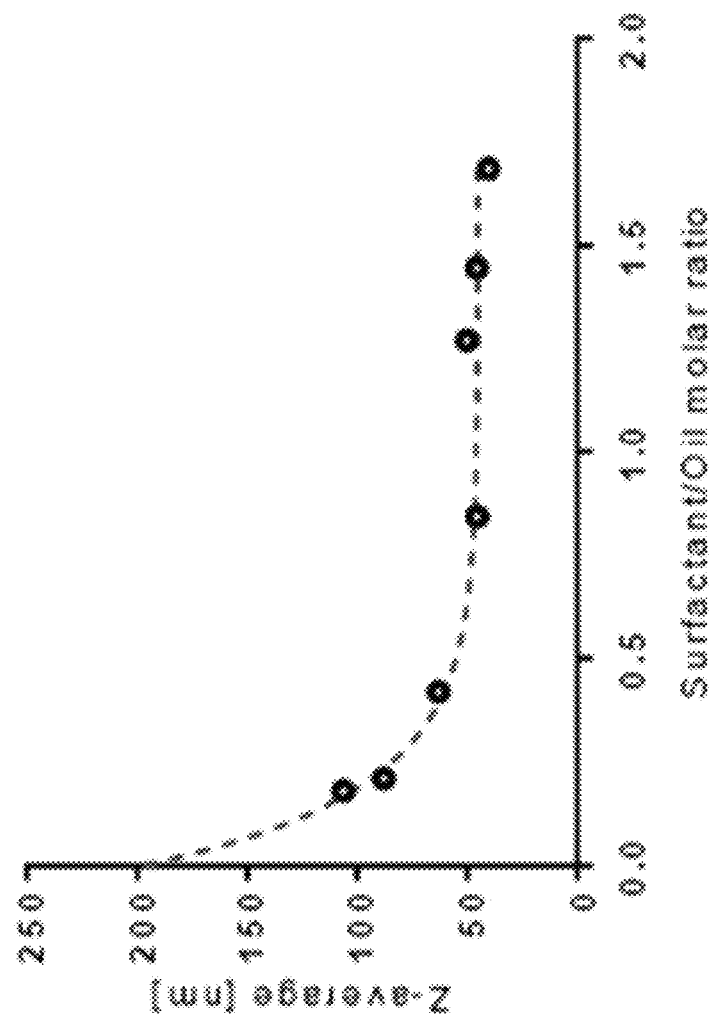

FIG. 16B compares the particle size distribution, measured using dynamic light scattering (DLS), between an NLC and CNE formulation at the time of manufacturing. Since long-term colloidal stability was a prerequisite to develop formulations that were suitable for stockpiling in a rapid response scenario, average particle diameter of formulations stored at 25° C. were monitored. Particle diameter of NLCs was nearly unchanged (<3% change) for at least nine months compared to CNE, which increased 30% after three months and 350% after nine months of storage (FIG. 16C). The nonionic surfactants, which include the hydrophobic sorbitan ester (Span), the hydrophilic ethoxylated sorbitan ester (Tween), and the cationic lipid DOTAP, are critical to preserving colloidal stability, and due to their interfacial presence play a key role in governing biophysical interactions. As a result, this work empirically elucidates the role of surfactants in mediating rvRNA protection, protein expression, and immunogenicity. NLCs of varying physicochemical properties were synthesized using a high pressure microfluidization process (see methods). Compositions of exemplary NLC formulations and a CNE formulation, manufactured in-house according to a previously published method, see Brito et al. Mol. Ther. 22(12):2118-29 (2014), are summarized in Table 2. Increasing the surfactant-to-oil (S:O) molar ratio reduced particle size (FIG. 35), which allowed us to generate unimodal NLCs with Z-average diameter ranging from 40 nm to 100 nm as measured by DLS. Zeta potential correlated with the amount of DOTAP, increasing from approximately +15 mV with 0.4% w/v DOTAP to +28 mV with 3.0% w/v DOTAP.

Figures 1A, 1B:
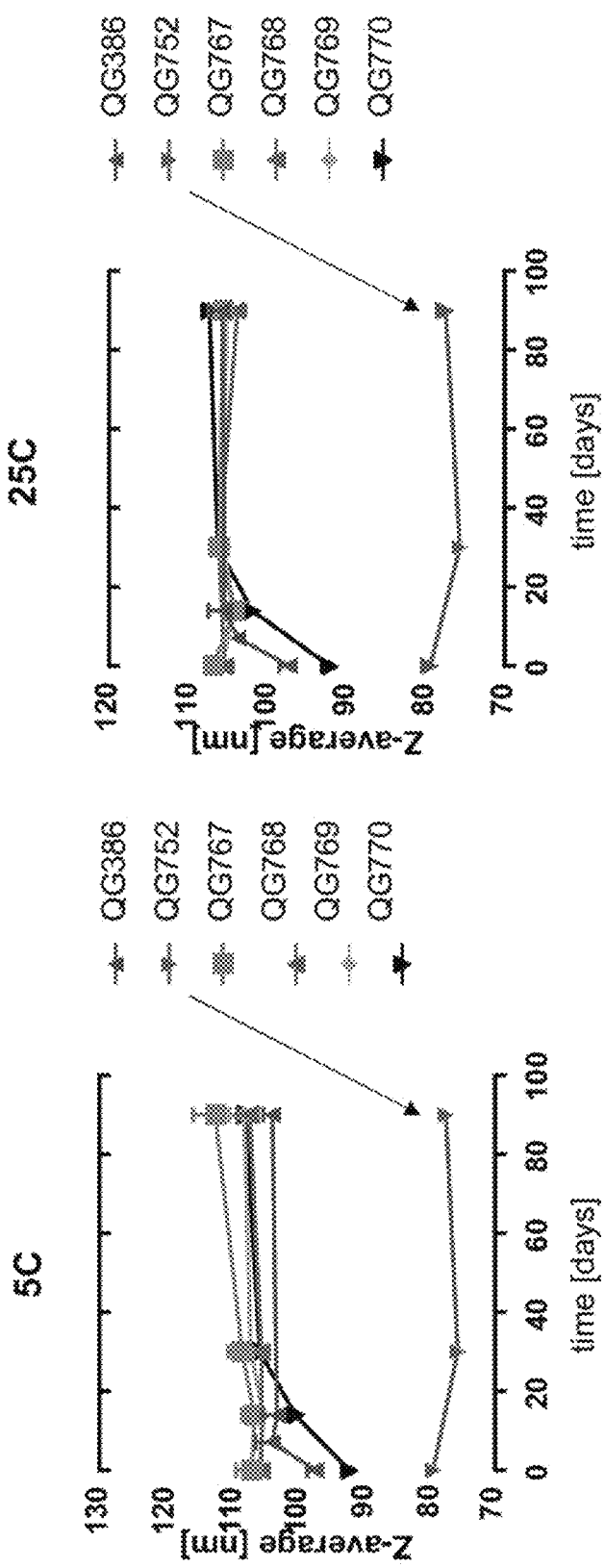
FIG. 1A-E depict stability comparisons between CNE and NLC formulations. Dynamic light scattering (DLS) particle size (Malvern Zetasizer Z/ZS) comparison between CNE (QG386) and QG752, a NLC formulation, stored at 5° C.
Figure 1C:
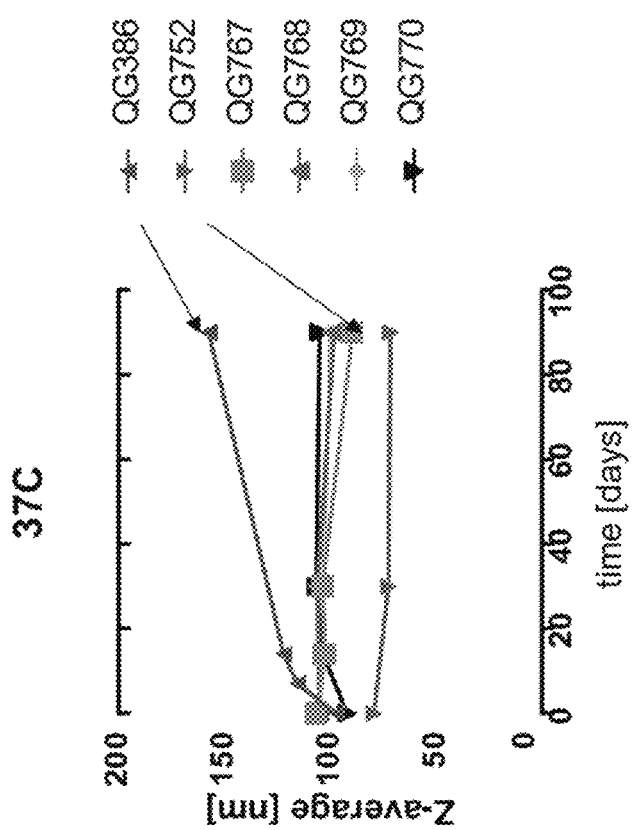
Figures 1D, 1E:
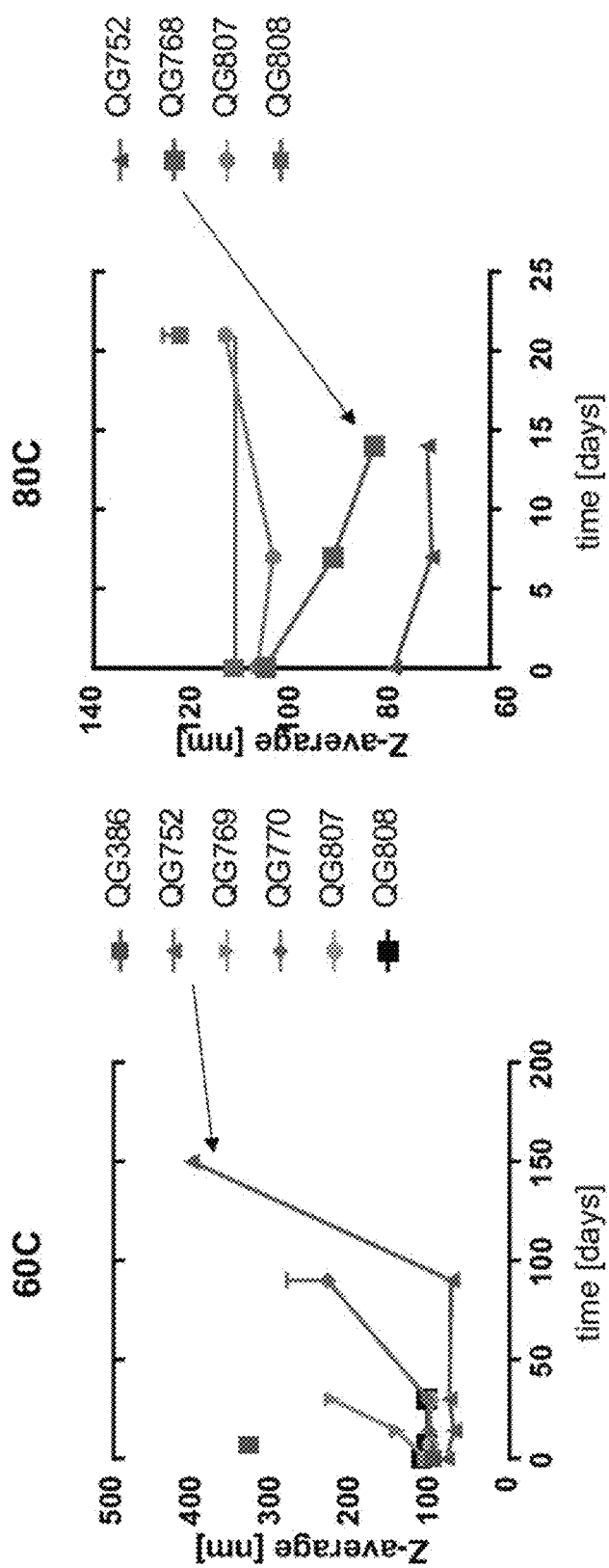

The evolution of particle size as a function of time provides colloidal stability information. Incubation at 5° C. and 25° C. simulates typical storage conditions (FIGS. 1A and 1B), 37° C. simulates physiological temperature (FIG. 1C), 60° C. and 80° C. exposes formulations to high thermal stress in order to accelerate colloidal stability and help differentiate between formulations (FIGS. 1D and 1E). NLC formulations QG807 is stable for at least a month at 60° C., based on most recent data available at the time. On the other hand, particle size of the cationic nanoemulsion (CNE) QG386 increased over 3-fold after only 7 days of incubation at 60° C. Particle size data at 60° C. suggests NLCs have significantly improved colloidal stability compared to CNE. See FIG. 1D.

Example 2: Evaluation of NLC Particle Size and the Oil:Surfactant Ratio

Figure 2B:
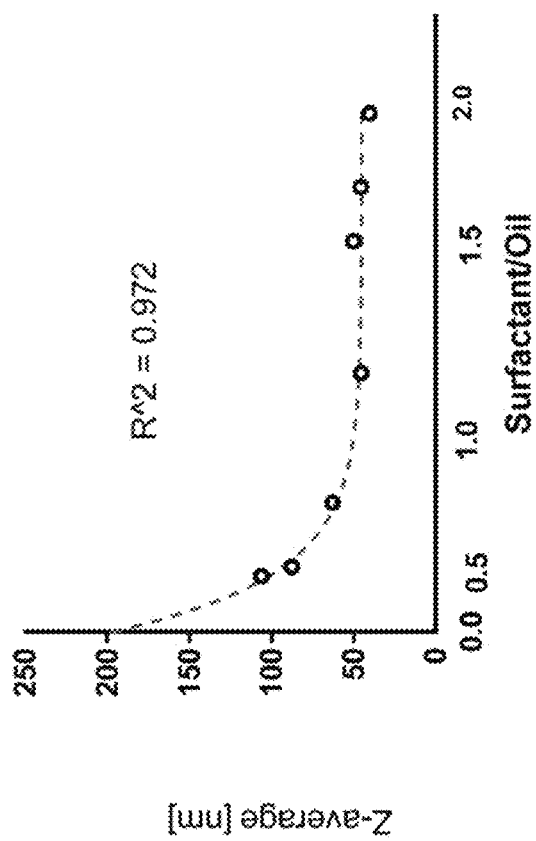
FIGS. 2A-B depict the z-average diameter of NLCs as a function of oil/surfactant or surfactant/oil ratio measured using dynamic light scattering (DLS).

NLCs are composed of a hydrophobic core containing the liquid oil and solid lipid, and surfactants (also known as emulsifiers or emulsifying agents) that make up the interface separating the hydrophobic phase—liquid oil and solid lipid, collectively referred to here as oil—from the aqueous phase. Since surfactants reside on the surface of NLC nanoparticles, their amount dictates the total available surface area. On the other hand, the oil resides in the core and primarily contributes to the total available volume. Increasing the surfactant to oil ratio consequently increases the surface area (SA) to volume ratio (V); thus, for a fixed volume of material, increasing the SAN ratio translates to reducing NLC particle diameter. The latter is demonstrated empirically in FIG. 2A-2B—NLCs manufactured under identical processing conditions, but different oil/surfactant ratio, resulted in an increasing particle size with increasing oil/surfactant. Particle size is linearly related to oil/surfactant (R2=0.97); alternatively, particle size is inversely related to the surfactant/oil ratio (R2=0.97).

Example 3: Determining the N/P Ratio

The Nitrogen to Phosphate (N/P) ratio is a theoretical representation of the molar stoichiometry of cationic nitrogens (positive charge) and anionic phosphate groups (negative charge) available to form the RNA-NLC complex. The cationic lipid DOTAP chloride (N-[1-(2,3-Dioleoyloxy)propyl]-N,N,N-trimethylammonium chloride) used in NLCs contains a quaternary trimethylammonium head group and carries a positive charge that is independent of pH. Since each DOTAP molecule contains one trimethylammonium head group, nitrogen concentration (or the amount of positive charge) is essentially equal to DOTAP concentration. On the other hand, each ribonucleotide monophosphate in a RNA copy consists of a single 1 approximately proportional to the RNA concentration normalized to the average molecular weight of ribonucleotide monophosphates (339.5 g/mol). Thus, $$N/P = \frac{[DOTAP]}{[RNA]/339.5},$$

where [DOTAP] and [RNA] are molar concentrations of DOTAP and RNA, respectively.

Figure 3A:
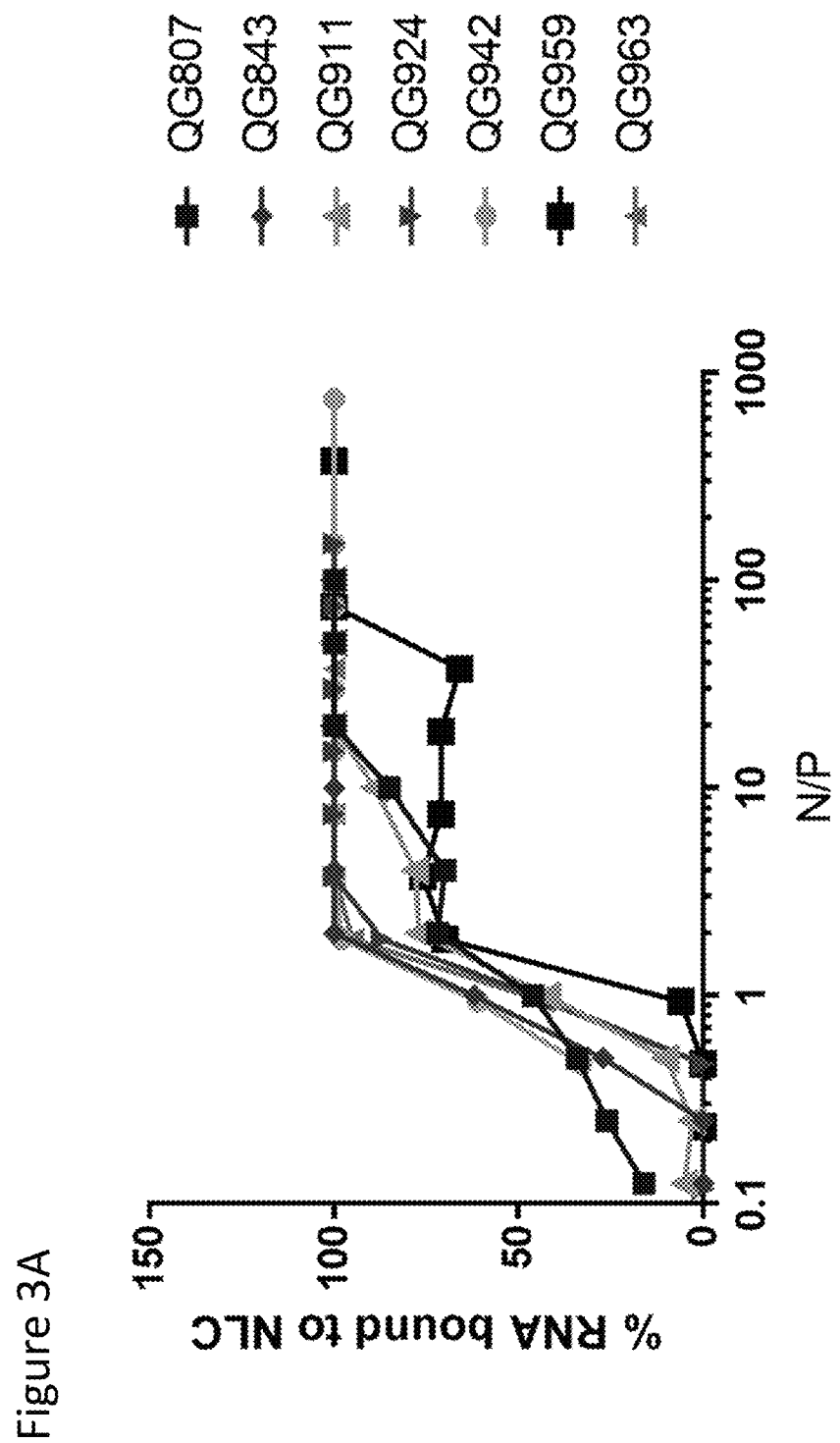
FIGS. 3A-E depict the optical densitometry analysis of gel-retardation assay (GRA) to determine the amount of RNA bound to NLCs as a function of the nitrogen/phosphate (N/P) ratio (FIG. 3A).
Figure 3C:
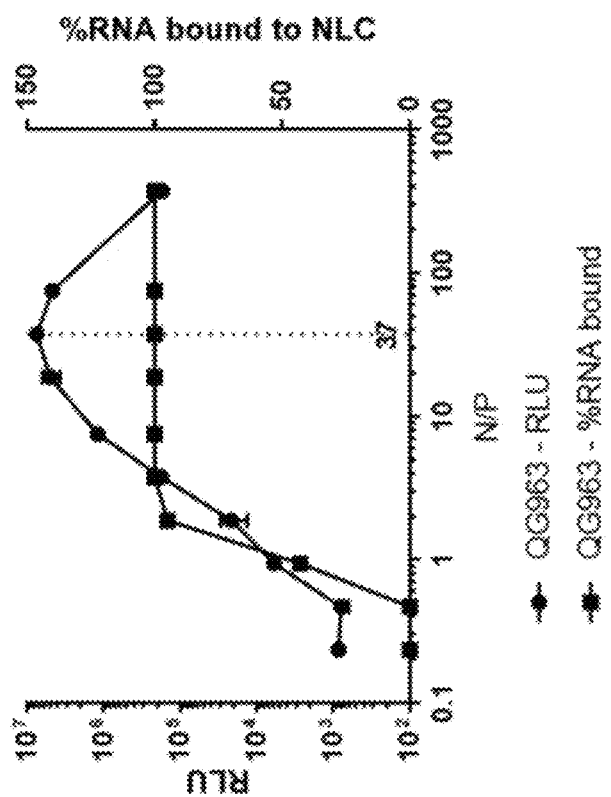
Figure 3B:
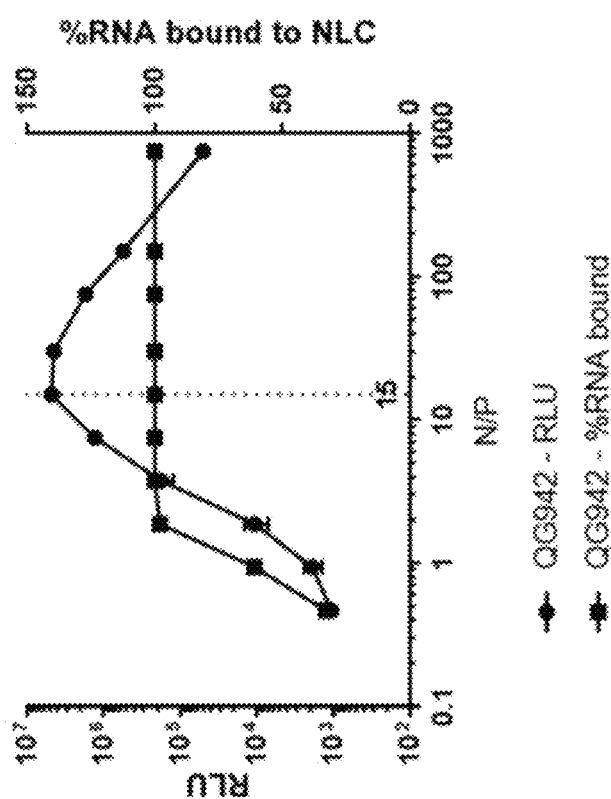
Figure 3E:
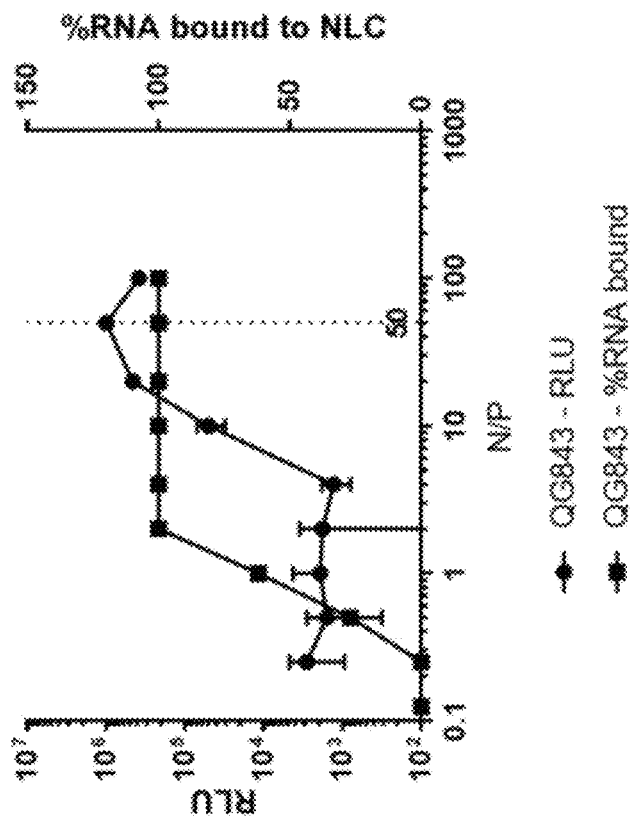
Figure 3D:
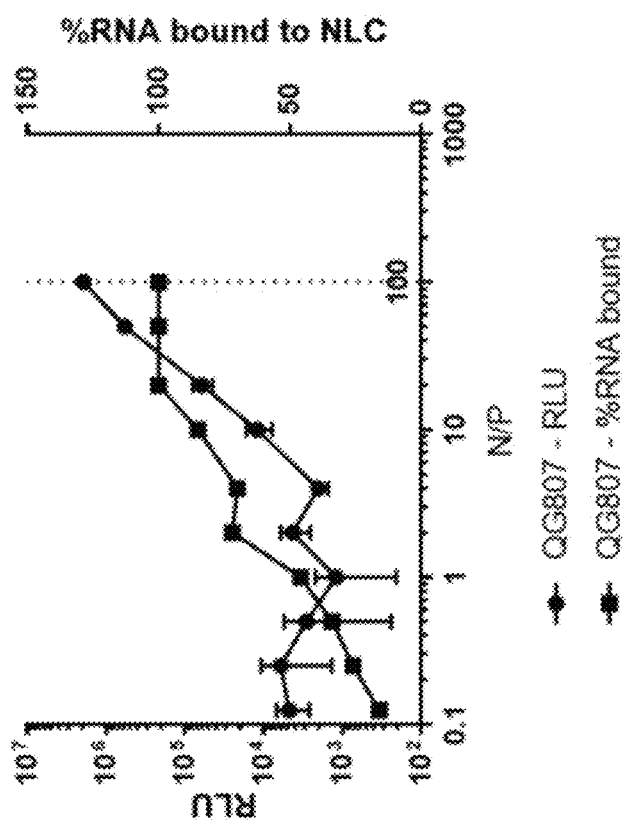

Furthermore, RNA binding to NLC as a function of the theoretical N/P is characterized using a gel retardation assay (GRA). RNA at 20 µg/ml was mixed 1:1 (v/v) with undiluted formulation or diluted formulation. The formulation dilution factor ranged from 1/2 to 1/1600. Depending on the starting DOTAP concentration, the N/P ratio ranged from 0.12—for instance, when complexing 20 µg/ml RNA with QG807 (0.4% w/v DOTAP) diluted 800-fold—to approximately 750—when complexing 20 µg/ml RNA with undiluted QG942 (3% w/v DOTAP). The RNA-NLC mixtures were allowed to complex for 30 minutes on ice and then electrophoresed at 120 V for about an hour in a 1% agarose gel. Optical densitometry analysis of RNA bands was performed to determine the relative amount of RNA bound to NLC formulation as a function of N/P (FIG. 3A). Except for QG807 and QG911, the % RNA bound to NLC undergoes a sharp transition from 0% below N/P of 1 to nearly 100% above 1. At N/P of 1, which is theoretically an equimolar positive and negative charges, approximately 50% RNA is bound to NLC. The latter suggests that the RNA-NLC binding reaction is at equilibrium around N/P of 1—a condition at which there is approximately an equal amount of bound versus unbound RNA.

In order to see how RNA-NLC binding correlates to delivery and expression, an in vitro experiment using a SEAP-expressing replicon was performed. The SEAP replicon was complexed with QG807, QG843, QG942 or QG963 formulation. The N/P ratio for each formulation was varied in the same manner as shown in FIG. 3A. The SEAP data in FIGS. 3B-3E, specifically for QG942, QG963 and QG843, shows that peak expression for each formulation is different despite the RNA-NLC binding curves being nearly identical.

Also, an in vitro experiment where various dilutions of $NLC_{v2}$ were complexed with 20 µg/ml SEAP rvRNA, resulting in a range of N:P molar ratios was performed. These RNA/formulation complexes were then physically and biologically characterized, by measuring in vitro SEAP expression, particle size, zeta potential and RNA binding (FIGS. 22A-D). The results indicate that there are N:P ratios that result in optimal SEAP expression levels corresponding with maximal RNA binding, and a constant positive zeta potential, but minimal increase in particle size. Given that, for the same formulation, there is a correlation between antigen expression and immunogenicity (see Pepini et al., J. Immunol. 1601877 (2017)), similar nAb titers at N:P ratios (region shaded in grey in FIG. 22) that corresponded to peak SEAP expression are expected.

To characterize NLCv2 in vivo in terms of protein expression, reactogenicity, and immunogenicity, 4 to 5 N:P ratios were tested, including those correlating with in vitro SEAP activity ≥5.8 Log 10 RLU (100, 37, 15, 5.6), and an N:P of 3, outside the hypothesized optimal zone. To characterize protein expression, C57BL/6 mice were injected IM with 1000, 100, and 10 ng doses of SEAP rvRNA at each N:P ratio. To characterize reactogenicity, 50 µg of rvRNA complexed with NLCv2 at each N:P were also injected via ID route in guinea pigs and flare diameter was measured. Twenty-four hours after injection, mice were bled to measure serum SEAP activity and guinea pig injection sites were measured (FIGS. 22E-H). To characterize immunogenicity, ZIKV rvRNA was complexed with NLCv2 at each N:P, and 1000 ng or 100 ng was delivered via the IM route in mice. Mice were then bled 14 days later to quantify nAb titers (FIGS. 22F and 22G).

Beginning with SEAP expression in vivo, optimal N:P ratios were dependent on dose, with optimal N:P of 15 for the 1000 ng dose, 37 for the 100 ng dose, and 100 for the 10 ng dose (FIG. 22E). As expected, immunogenicity appeared to correlate with SEAP expression at the two doses that were compared (FIGS. 22F and 22G). At the 1000 ng dose, significant differences in nAb titers were not detected with any of the N:P ratios tested, similar to SEAP activity at those N:P ratios (FIG. 22F). At the 100 ng dose, no significant difference in nAb titers between N:P ratios of 37 and 15 was observed and slight but insignificant differences in SEAP activity, however, a significant reduction in titer occurred between N:P ratios of 15 and 5.6 in a similar manner to SEAP activity (FIG. 22G). In terms of reactogenicity, a significant reduction in flare diameter when the N:P ratio was reduced 2.5 fold from 37 to 15 (FIG. 22H) was observed. Importantly, these data suggest that reducing the N:P 2.5 fold from 37 to 15 would significantly reduce reactogenicity but minimally impact antigen expression levels and subsequent immunogenicity, especially at higher rvRNA doses. In fact, at N:P values of 15 and 37, a dose-sparing effect was observed as there was not a significant difference in SEAP activity between 1000 and 100 ng doses (FIG. 22E). The largest differences in SEAP activity between doses was observed at low N:P ratios (FIG. 22E).

Figure 4A:
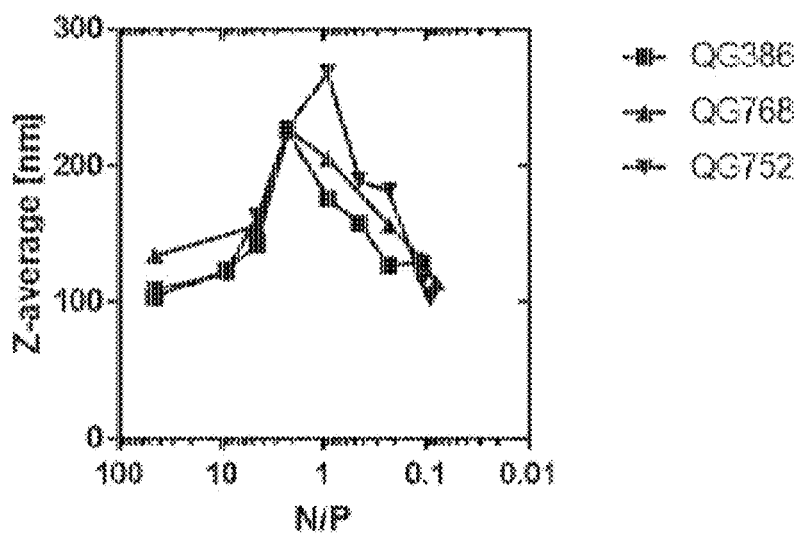
FIGS. 4A-C depict comparison of DLS particle size (Z-average, nm) of formulation-RNA complexes with varying nitrogen to phosphate (calculated) ratios (FIG. 4A), RNA to particle (theoretical) ratio (FIG. 4B), or DOTAP to RNA mass ratio (calculated) (FIG. 4C).
Figure 4B:
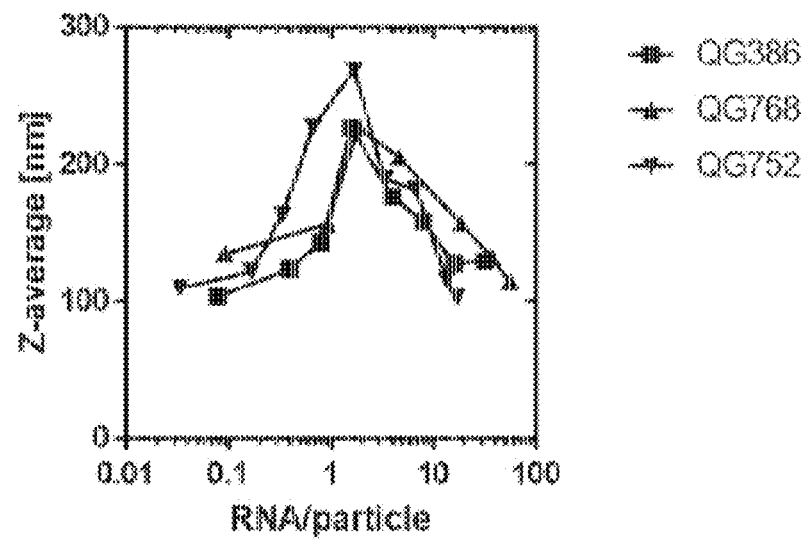
Figure 4C:
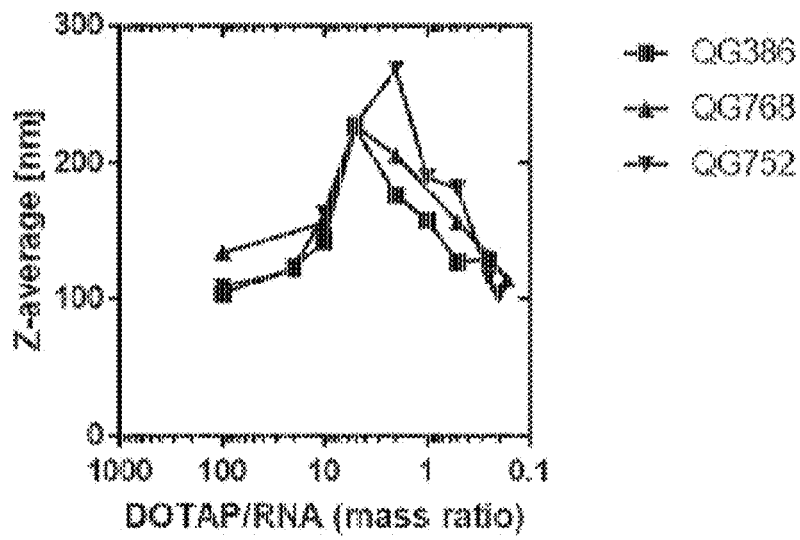
Figure 5:
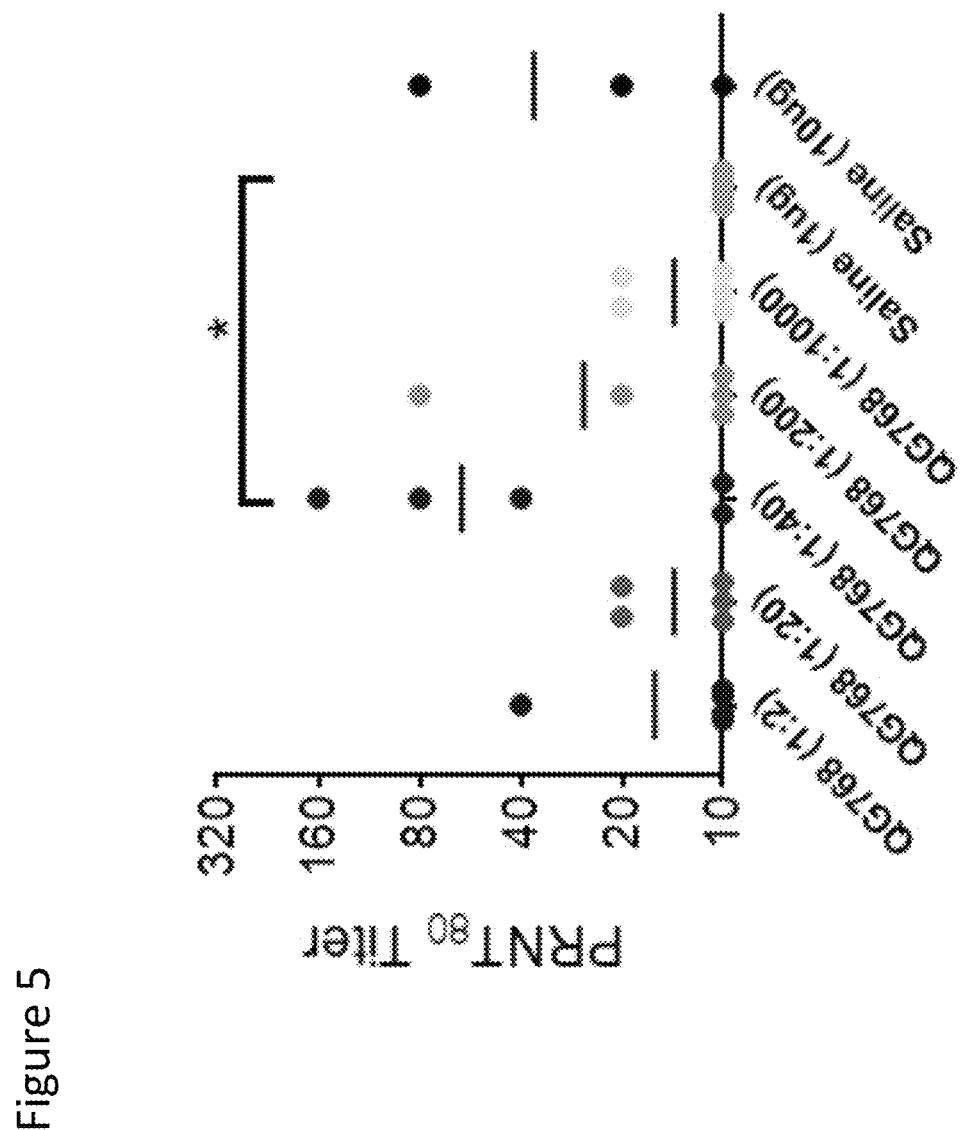
FIG. 5 depicts neutralizing antibody titers from mice (n=5/group) 14 days after a single IM administration of Zika antigen-expressing rvRNA complexed with different amounts of QG768 formulation. Neutralizing antibody titers were determined by 80% plaque reduction neutralization test ($PRNT_{80}$). Significance was determined by One-way ANOVA.
Figure 6:
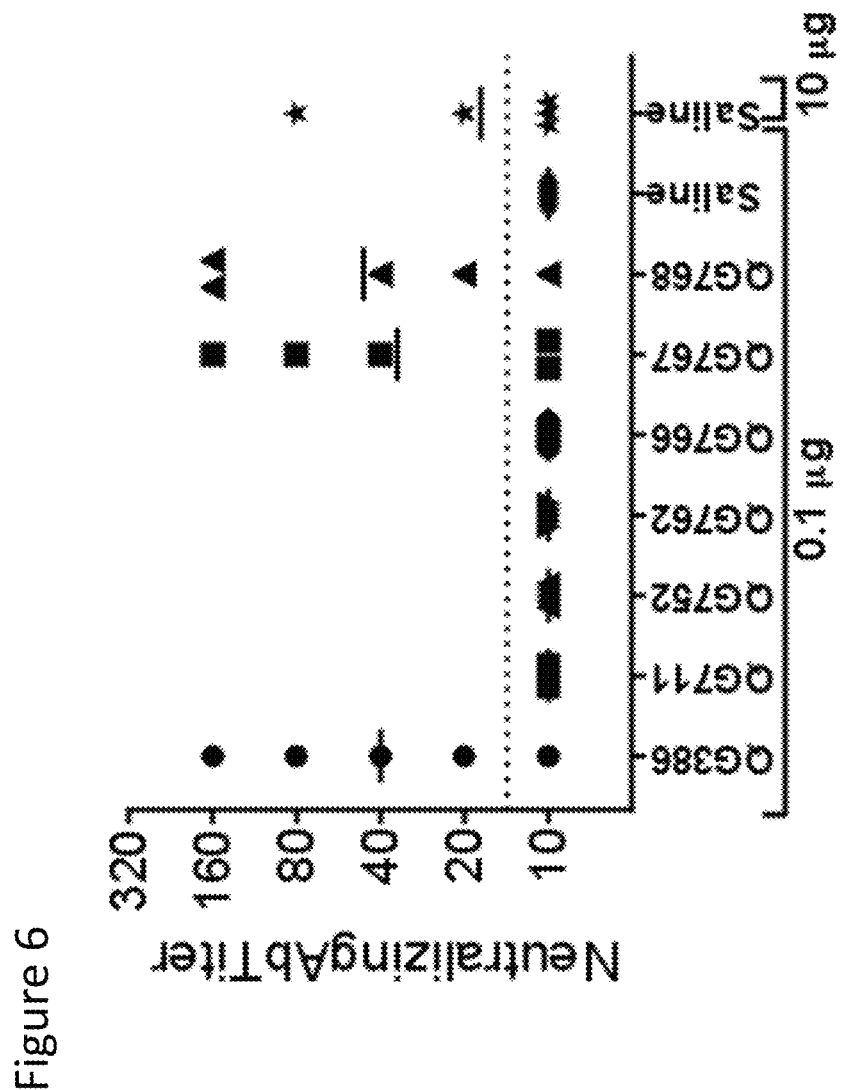
FIG. 6 depicts neutralizing antibody titers from mice (N=5/group) after intramuscularly (IM) administration with RNA either complexed with formulation (0.1 µg RNA mixed 1:1 (v/v) with formulation) or naked (0.1 µg or 10 µg RNA mixed 1:1 with saline). Neutralizing antibody titers were determined by 80% plaque reduction neutralization test ($PRNT_{80}$). Significance was determined by one-way ANOVA.

In order to evaluate whether the theoretical RNA/particle ratio is predictive of the physical state of the RNA-formulation complex, the hydrodynamic diameter (z-average; nm) of three formulations, QG752, QG768 and QG386, mixed in varying amounts with a fixed amount (1 µg) of a model 10 kb RNA was compared. The hydrodynamic size for all formulations exhibited an approximate bell curve-shaped profile with increasing formulation dilution, i.e. decreasing N/P (FIG. 4A) or increasing RNA/particle (FIG. 4B) or decreasing DOTAP/RNA (FIG. 4C). Despite all formulations containing identical amounts of DOTAP (0.4% w/v), the peak in particle size, potentially indicating clustered NLC particles cross-linked with RNA, is observed at different N/P ratios (FIG. 4A)—~3 for QG768 and QG386 (40-fold formulation dilution or 0.01% w/v DOTAP) and ~1 for QG752 (100-fold formulation dilution or 0.004% w/v DOTAP). This discrepancy is however reconciled after accounting for differences in the starting particle size and plotting Z-average as a function of RNA/particle ratio (FIG. 4B)—the peak particle size for all formulations is observed at approximately 1-2 RNA copies per NLC particle. Since the starting average particle size of QG752 (75 nm) is smaller than both QG386 and QG768 (~100 nm), it has a higher surface area/volume ratio, and thus requires more dilution (lower N/P) to obtain an RNA/particle ratio similar to QG386 and QG768. In general, if the chemical composition is held constant, decreasing particle size would increase the surface area/volume ratio and consequently increase the particle concentration. Arithmetically, the latter principle is summarized as follows: if formulations A and B share identical chemical composition and spherical geometry but different diameters dA and dB, respectively, and where dA>dB, then formulation B has a particle concentration greater than formulation A by a factor of (dA/dB)3.

Furthermore, this RNA-formulation particle size data correlates with a formulation's capacity to bind RNA as determined in a gel retardation assay (GRA). GRA is based on the principle that any unbound or free RNA will migrate and coincide with the control unformulated or naked RNA when separated in a gel under an applied voltage; thus, it evaluates the ability of formulation to bind and immobilize RNA in standard gel electrophoresis conditions. GRA was run in a self-contained pre-cast 1.2% agarose gel stained with ethidium bromide (EtBr) (E-gel®, 1.2% general purpose agarose, ThermoFisher Scientific). When RNA was complexed with NLC formulation QG768, it remained immobilized at all N/P ratios higher than 2.3, which corresponds to the ascending region (going from left to right) including the maximum of the RNA-formulation particle size profile for QG768 (FIG. 4A). The amount of unbound RNA gradually increased as the N/P ratio was 0.9 and lower, which corresponds to the descending region (going left to right) in FIG. 2A. Thus, particle size correlates with binding capacity, and can be used as a method to optimize RNA complexing and delivery using minimal formulation dose. In order to investigate how RNA/particle ratio impacts immunogenicity, mice (n=5/group) were injected IM with ZIKV rvRNA complexed with QG768 at different ratios and ZIKV neutralizing antibodies (PRNT80 titers) were measured 14 day later.

Example 4: Evaluation of NLC Formulations as Zika Vaccine Candidates

Lead candidate NLC formulations which demonstrated physical stability were combined with synthetic replicating viral RNA (rvRNA) derived from a strain of Venezuelan equine encephalitis virus (VEEV, strain TC83) where the VEEV structural genes were replaced with a ZIKV PrM-E cassette. RNA replicon systems were developed to facilitate heterologous prime-boost strategies. The formulated rvRNA may was administered via the intramuscular route using a conventional needle. Several NLC formulations promoted robust immune responses in vivo.

Materials and Methods

Cell Culture

C6/36 cells (American Type Culture Collection (ATCC), Rockville, Md.), derived from *A. albopictus* mosquitoes, were maintained at 29° C. with 5% C02 in Dulbecco's minimal essential medium (DMEM) containing 10% (V/V) heat-inactivated fetal bovine serum (FBS), sodium pyruvate (1 mM), penicillin (100 U/mL), streptomycin (100 µg/mL), and 1% (v/v) tryptose phosphate broth (Sigma, St. Louis, Mo.). Vero, BHK-21, and 293T cells (ATCC, Manassas, Va.) were propagated at 37° C. with 5% C02 in DMEM containing 10% (V/V) heat-inactivated FBS, sodium pyruvate (1 mM), penicillin (100 U/mL), and streptomycin (100 µg/mL). All cell lines were also tested for *mycoplasma* contamination.

Plasmid Constructs

A plasmid encoding an SP6 promoter followed by the 5' and 3' untranslated regions (UTRs) and nonstructural genes of Venezuelan equine encephalitis virus (VEEV) strain TC-83 (FIG. 21A) as well as enhanced GFP under the control of the VEEV subgenomic promoter, termed pSP6-VEE-Rep-GFP, was kindly provided by Dr. Scott Weaver. A control reporter rvRNA, encoding secreted human embryonic alkaline phosphatase (SEAP) was also designed (FIG. 21B).

The SP6 promoter was then replaced with a T7 promoter using standard cloning techniques, termed pT7-VEE-Rep-GFP. A fragment encoding codon-optimized prM and E genes from French Polynesian Zika virus (ZIKV) strain H/PF/2013 was synthesized and cloned into pUC57 (Genscript). Using a Q5 mutagenesis kit (New England Biolabs), a kozak sequence was then inserted and followed by either the heterotypic Japanese encephalitis virus (JEV) or upstream homotypic ZIKV signal sequence (ss) using the following primers: JEVss-FWD (gctggcctccctggctgtggtcattgcctgcgctggagca GCCGAGGTGACCAGGAGAGG; SEQ ID NO: 13), and JEVss-REV (cacatgattgatccggcactcctcttgcccatggcggcggc GTGAGCTGGCGGCGGGTG; SEQ ID NO: 14), or ZIKVss-FWD (ggaatcgtgggcctgctgctgaccacagcaatggca GCCGAGGTGACCAGGAGAGG; SEQ ID NO: 15), and ZIKVss-REV (cacggatgtgtctgctcctctccgcatggcg gcggcGTGAGCTGGCGGCGGGTG; SEQ ID NO: 16). This combined fragment encoding either the JEVss or ZIKVss followed by ZIKV prM and E genes was then PCR amplified with the primers ZIKV-prM-E-FWD (AATGGACTACgacatagtcgccgccgccatg; SEQ ID NO: 17) and ZIKV-prM-E-REV (GCGGTTTTTGACA ccgcggTCAGGCA-GACACGGCG; SEQ ID NO: 18) and cloned between PflFI and SacII sites in pT7-VEE-Rep-GFP, using infusion enzyme mix (Clontech), resulting in pT7-VEE-Rep-JEVss-ZIKV-prM-E or pT7-VEE-Rep-ZIKVss-ZIKV-prM-E plasmids. pT7-VEE-Rep-SEAP was constructed by PCR amplification and cloned between PflFI and SacII sites in pT7-VEE-Rep-GFP as described above (FIG. 21B). All plasmids were confirmed by Sanger-sequencing.

RNA Production

Following transformation and amplification in Top10 cells (Invitrogen) and isolation using maxi-prep kits (Qiagen), plasmids were linearized by restriction digest with NotI enzyme (New England Biolabs) and purified using phenol-chloroform. RNA was then transcribed in vitro using T7 megascript kit (Invitrogen), followed by lithium chloride precipitation and capping with a Vaccinia capping kit (New England Biolabs). Capped transcripts were then precipitated in lithium chloride and resuspended in nuclease-free water to a final concentration of 1 µg/µl and analyzed by agarose-gel electrophoresis. All RNA was aliquoted and stored at −80° C.

RNase Challenge Assay

ZIKV-rvRNA was complexed with NLCv1 and NLCv2 at N:P ratios of 50 and 15 respectively and placed on ice for 30 minutes. After diluting the NLCv2 complex using nuclease-free water, complexes containing 1 µg of rvRNA at 20 µg/mL were treated with 50 ng of RNase A (Thermo Scientific) for 30 minutes at room temperature, followed by an incubation with 5 µg of recombinant Proteinase K (Thermo Scientific) for 10 minutes at 55° C. RNA was then extracted using an equal volume of 25:24:1 phenol:chloroform:isoamyl alcohol (Invitrogen). After vortexing, samples were centrifuged at 17,000×g for 15 minutes. The supernatants were collected and mixed 1:1 with Glyoxal load dye (Invitrogen) and heated at 50° C. for 15 minutes. The equivalent of 200 ng of RNA were loaded and run on a denatured 150 mL 1% agarose gel in Northern Max Gly running buffer (Invitrogen) at 120 V for 45 minutes. Gels were imaged using a ChemiDoc™ MP imaging system (BioRad). The intensity of the intact rvRNA band was compared to phenol:chloroform:isoamyl extracted RNA from complexes that were not subjected to RNase and Proteinase K treatment. Additional controls included rvRNA alone with and without RNase and proteinaseK treatment at a 200 ng rvRNA load.

Complexing Conditions for In Vitro and In Vivo Experiments

In N:P optimization experiments, NLCv1 or NLCv2 was serially diluted in 10 mM citrate buffer and complexed 1:1 with rvRNA diluted to 20 µg/ml in a nuclease-free 10% sucrose solution (to maintain isotonicity without using an ionic agent such as saline). rvRNA was added to formulation and gently pipetted up and down to ensure complete mixing. The complex was incubated for 30 min on ice, resulting in a range of N:P molar ratios. These complexes were then further diluted in 10% sucrose to achieve the desired doses. For in vitro stimulation of human PBMCs, complexed formulations were diluted 1:125. For vaccination studies utilizing NLCv1 or CNE at an N:P of 50, rvRNA was diluted to 40 µg/ml in 10% sucrose and complexed 1:1 with formulation. For the guinea pig study where NLCv2 was utilized at an N:P of 37, rvRNA was diluted to 400 µg/ml in 10% sucrose and complexed 1:1 with formulation. For vaccine studies that utilized NLCv2 at an N:P of 15, rvRNA was diluted to 1000 µg/ml in 10% sucrose and complexed 1:1 with formulation. Complexes were then utilized neat or diluted in 10% sucrose for the desired doses.

ZIKV VLP Characterization

ZIKV-rvRNA was complexed with NLCv1 at an N:P of 50 and 100 ng was incubated on a monolayer of 293T cells in a 6-well plate in Optimem media for 4 hours, followed by replacement with complete media and a final 20 hour incubation. Supernatants were then harvested and overlaid onto a 20% sucrose solution and pelleted by ultracentrifugation at 100,000×g for 2 hrs at 10° C. (OPTIMA MAX-XP, Beckman, Indianapolis, Ind.). Pellets were then resuspended in PBS and analyzed by SDS-PAGE and western blot. To detect ZIKV proteins following transfer to nitrocellulose membrane, anti-ZIKV mouse immune ascitic fluids (WRCEVA, UTMB) were utilized at a 1:5000 dilution and a 1:4000 dilution of the secondary reagent, goat anti-mouse IgG-HRP (Southern Biotech), was utilized to visualize protein bands. For transmission electron microscopy (TEM) evaluation, the above 293T supernatants were pelleted through a 20% sucrose solution onto a 70% sucrose cushion by ultracentrifugation at 100,000×g for 2 hrs at 10° C. The interphase was then harvested and sucrose replaced with PBS by filtration through a 100-kDa Amicon filter (Millipore, Billerica, Mass.). To confirm that the rvRNAs encoding ZIKV prM/E were functional and induced the secretion of ZIKV virus-like particles (VLPs), a drop of undiluted filtrate was dried on a 300-mesh holey carbon grid, stained with uranyl acetate and examined in a 200 kV FEI TEM for the presence of ZIKV VLPs by Western blot (FIG. 21C) and electron microscopy (FIG. 21D).

SEAP Assay

To characterize protein expression from formulated rvRNA, a SEAP reporter system was used. Twenty-four hours after BHK cells were incubated with formulated SEAP rvRNA, supernatants were harvested and SEAP activity was measured by NovaBright™ Phospha-Light™ assay, per manufacturer's instructions (ThermoFisher). See FIG. 23D.

Neutralizing Antibody Titer

Eighty percent plaque-reduction neutralization tests (PRNT80) were performed on Vero cells as previously described (Beaty et al., Arboviruses, Diagnostic procedures for viral, rickettsial and chlamydial infections, Schmidt N J J, Emmons R W W, Eds., Am. Public Health Assoc., Washington, D.C., pp. 797-855 (1989)) using ZIKV strain FSS 13025 as the control virus. Briefly, a stock of ZIKV FSS 13025 was diluted to ~1×10³ plaque-forming units per milliliter (PFU/ml) and the titer was confirmed by plaque assay on Vero cells. Samples were heat-inactivated at 56° C. for 30 min then serially diluted in DMEM containing 1% FBS. All diluted samples were then diluted an additional 2-fold by the addition of ~200 PFU of ZIKV, mixed, and incubated at 37° C. for 1 hour, then transferred to 90% confluent monolayers of Vero cells in 6-well plates (Costar) and incubated at 37° C. for 1 hour. Overlay containing 1% agarose in DMEM with 1% non-essential amino acids, 1% L-glutamine, and 1% gentamycin, was then pipetted into each well and plates were incubated for 3 days at 37° C. Cells were then fixed in 10% formaldehyde and plaques visualized following crystal violet staining.

Figure 34A:
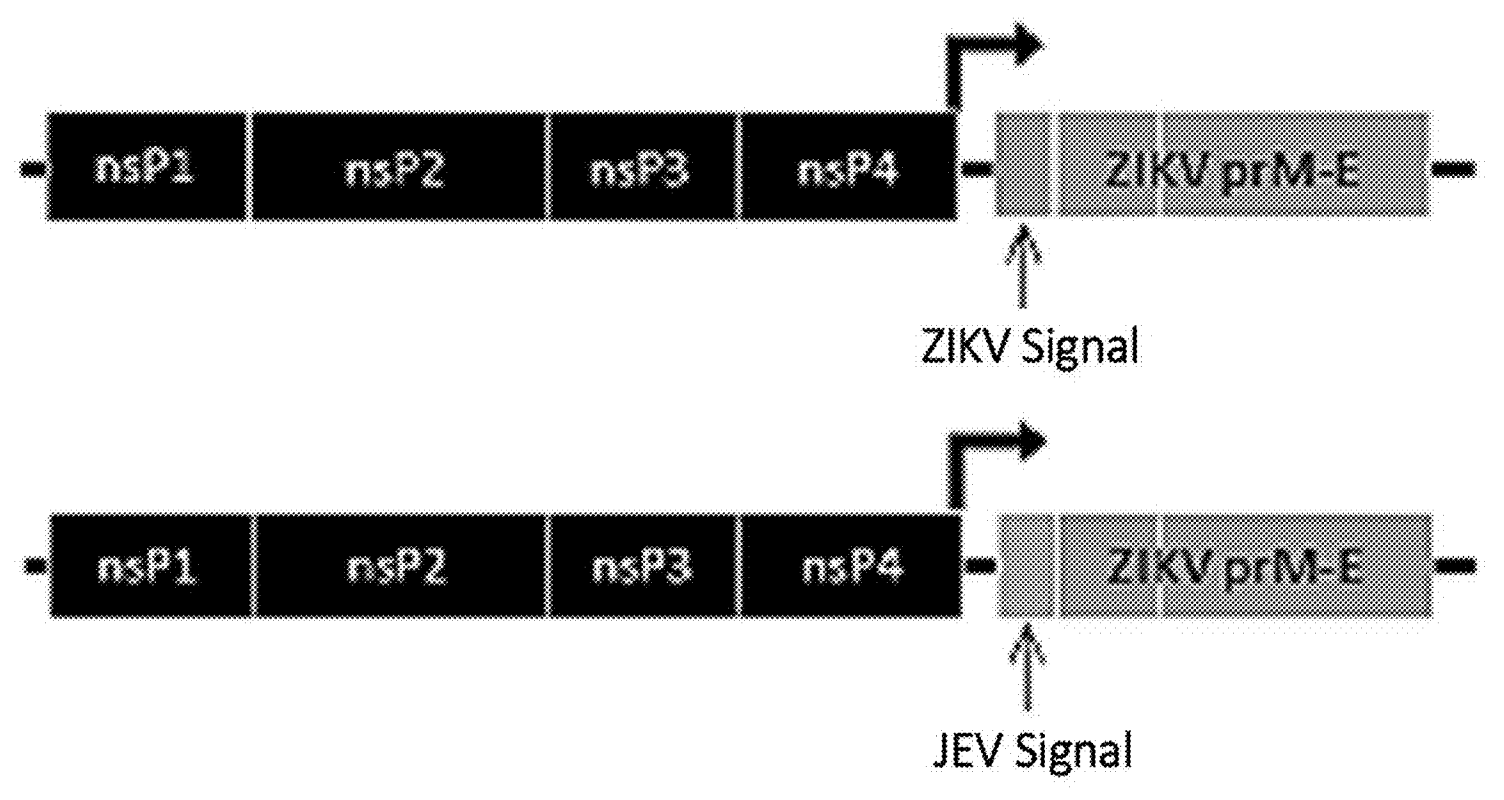
Figure 34B:
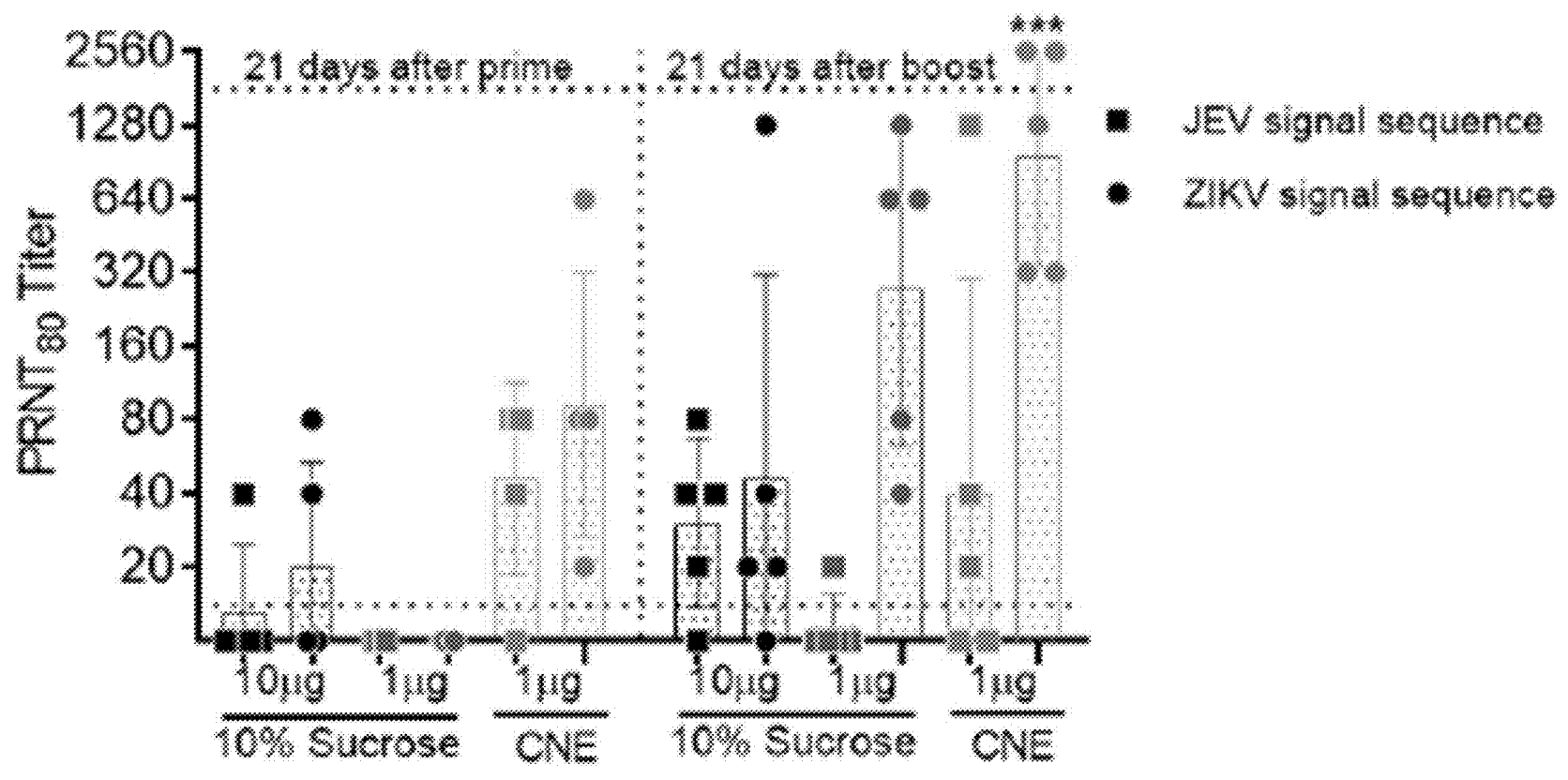

To down select a single ZIKV rvRNA construct for continued development, neutralizing antibody (nAb) responses between rvRNAs encoding ZIKV prM/E were compared with native as well as JEV signal sequences. The native ZIKV signal sequence construct induced 100% seroconversion after a single dose and significantly higher nAb titers after two doses compared to the rvRNA encoding the JEV signal sequence (FIGS. 34A-B).

Human Peripheral Blood Mononuclear Cell Assay

Studies involving human donors were approved by the Western Institutional Review Board. Heparinized whole blood was attained from 6 normal donors upon informed consent and peripheral blood mononuclear cells (PBMCs) were isolated as previously described. See Seubert et al., J Immunol. 180(8):5402-12 (2008). One million cells per 150 µl volume of serum-free RPMI were plated into U-bottom TC grade 96-well plates and formulation/rvRNA complexes were added to the cells in a 50 µl volume and incubated at 37° C. Twenty-four hours later, plates were centrifuged for 10 min at 1.8K rpm, and supernatants were harvested and stored at −20° C. Mip-1β ELISA was performed as previously described. See Seubert et al., J Immunol. 180(8):5402-12 (2008).

Animal Studies

All animal studies were approved by the Infectious Disease Research Institute Institutional Animal Care and Use Committee. The facility where animal studies were conducted is accredited by the Association for Assessment and Accreditation of Laboratory Animal Care, International and follows guidelines set forth by the Guide for the Care and Use of Laboratory Animals, National Research Council, 2011. All sample sizes were determined based on power analysis assuming LD100 challenge doses and subsequent survival rates of 0.99 versus 0.01 with $\alpha=0.05$ using a one-sided Fisher's exact test. Mice were non-specifically and blindly distributed into their respective groups. No exclusion criteria were established prior to beginning the studies.

To assess immunogenicity and tolerability in guinea pigs, 400-450 g Hartley guinea pigs (Charles River) were vaccinated IM or intradermally (ID) utilizing Nanopass Micronjet600 needles (Nanopass Technologies, Ltd.) with a 1:1 mixture containing NLC and rvRNA encoding ZIKV prM/E in the rear quadriceps muscle in a total volume of 250 μl. Twenty-four hours later, the diameter of the ID injection-site flare was measured. Blood was collected at the time points indicated in the figures via the femoral vein and serum was harvested following low-speed centrifugation and stored at −20° C. until PRNT80 titers were determined as described above.

Statistics

Statistical analysis was performed using GraphPad Prism software (version 7.0c) and RStudio (version 0.99.491). Data distribution and variance were evaluated for normality and similarity with or without transformation by qqplot and boxplot analyses. One-way and two-way ANOVAs with Tukey's multiple comparison test were used.

Example 5: Whole Blood Assay

In order to assess the ability of the NLC formulations to stimulate human whole blood cells to release chemokines, human whole blood assays were performed. Heparinized whole blood was obtained from eight normal donors. The indicated formulations (stock at 5% oil) were added to whole blood (0.4% oil final). Whole blood was incubated at 37° C.-CO2 for 24 hours. The plasma supernatant was aspirated and assayed for beta-chemokines CCL2 and CCL4 and neutrophil-recruiting chemokines CXCL1, CXCL5 and CXCL8. Q386 was found to be unstable in the presence of whole blood resulting in no data being collected. Human whole blood cells released higher levels of chemokines in response to QG768 as compared to the other formulations tested. (FIGS. 7A-E)

Example 6: Physical Characterization of NLC-rvRNA Complexes In Vitro rvRNA with NLCs of varying compositions were incubated in the presence or absence of RNase A and evaluated integrity of the extracted RNA using denaturing agarose gel electrophoresis. This test established that certain compositional requirements were essential for RNA protection; specifically, NLCs with a relatively high Tween 80 content (70% of total surfactant and cationic lipid mass) did not protect against RNase degradation (FIG. 36A) and could not deliver rvRNA in vivo (FIG. 36B). Conversely, NLCs with relatively lower Tween 80 fraction in the surfactant phase (35% of total surfactant and cationic lipid mass) protected rvRNA from degradation (FIG. 2D). As a result, subsequent studies were conducted with NLCs containing Tween 80 no greater than 35% of the total surfactant fraction, subsequently referred to as NLCv1. Next, the complexing conditions, as measured by the nitrogen (N) to phosphate (P) molar ratio (N:P), were optimized to maximize transfection in vitro. CNE or NLCv1 formulations were complexed with rvRNA encoding SEAP at a range of N:P values and 100 ng of each rvRNA complex was incubated with BHK cells overnight. SEAP expression as a function of N:P between NLCv1 and CNE (FIG. 2E) was compared. As N:P increased, levels of SEAP escalated with significantly higher expression with CNE compared to NLCv1 at N:P<50. However, at N:P~50, SEAP expression with CNE peaked, decreasing at N:P>50, potentially due to cytotoxicity evidenced by significant cellular detachment. Interestingly, at N:P~50, SEAP expression in the NLCv1 group was similar to CNE and continued to increase. For downstream comparison studies between NLCv1 and CNE, a N:P of 50 was utilized, which resulted in similar SEAP expression levels in vitro.

Example 7: Evaluation of Select Formulations for their Ability to Deliver rvRNA and Result in Protein Expression In data not shown, it was determined that formulations QG767 and QG768 could be improved by lowering the concentration of Tween. Observed antibody titers when using these formulations were variable with several non-responsive mice. Reduction of Tween in these formulations (to arrive at formulations QG807, 808 and 906) resulted in increased PRNT80 titers, and 100% seroconversion.

In work characterizing NLCv1 and NLCv2 a reduction of optimal N:P from >50 to 15 was observed (FIG. 23D). Concomitant with that reduction was increasing the S:O molar ratio from 0.18 to 1.68, which reduced the particle size from ~100 nm to ~40 nm (Table 2). Since the total oil content between NLCv1 and NLCv2 differs only slightly (~20%), in theory, reducing the particle size by approximately 2.5-fold amounts to approximately 12-fold increase in the number of nanoparticles, assuming spherical geometry. It is likely that the smaller size and theoretically higher number of nanoparticles in NLCv2 enables distribution of surface-bound rvRNA copies to a greater number of cells.

Figure 8A:
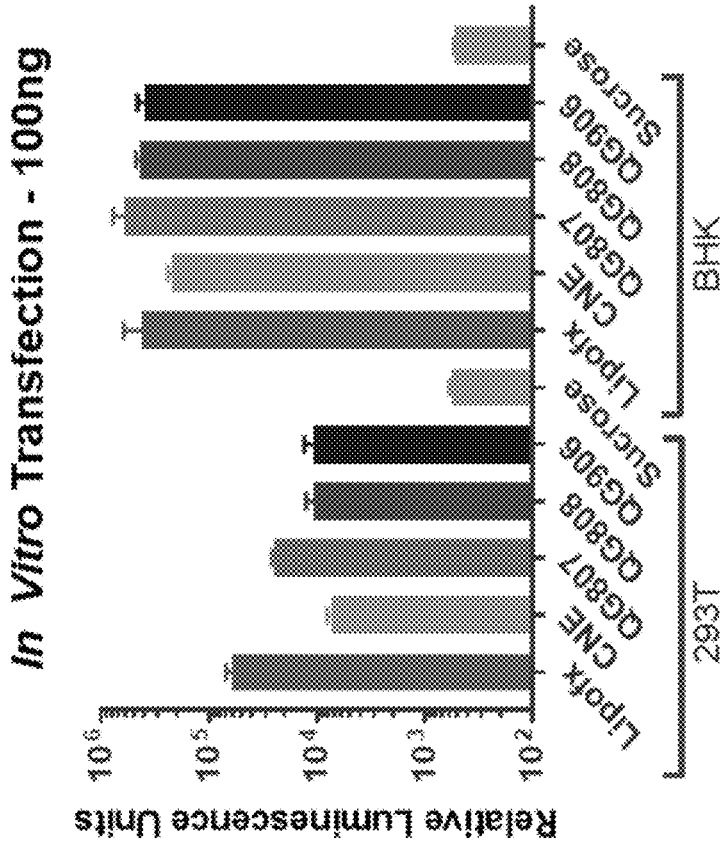
FIGS. 8A-B depict the ability of select formulations to deliver rvRNA in vitro. 293T or BHK cells were transfected with either 10 ng (FIG. 8A) or 100 ng (FIG. 8B) of rvRNA encoding SEAP using the indicated formulations as well as lipofectamine as a positive control and a 10% sucrose solution as a negative control. After transfection, supernatants were harvested and SEAP activity was measured using a luminescence assay.
Figure 8B:
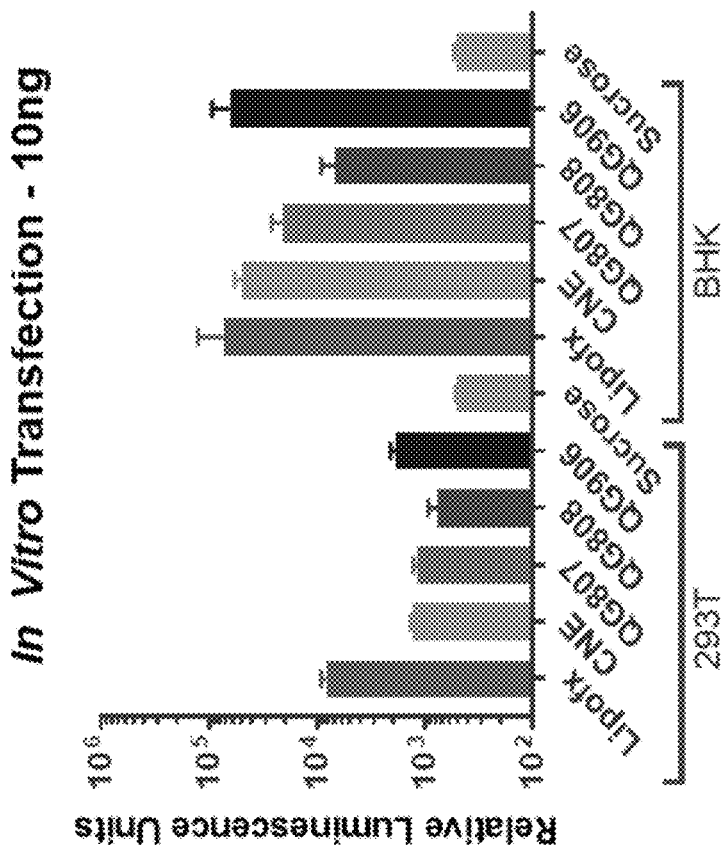

To evaluate various formulation compositions for their ability to deliver rvRNA in vitro, reporter rvRNA encoding secreted alkaline phosphatase (SEAP) was generated. 293T or BHK-21 cells were transfected with either 10 or 100 ng of rvRNA encoding SEAP, formulated with CNE, QG807, QG808, QG906, or with 10% sucrose or lipofectamine 2000 as negative and positive controls, respectively, and supernatant was harvested 24 hours after transfection and assayed for SEAP activity (FIGS. 8A-B). A cell- and dose-mediated effect on SEAP expression was observed across the various formulations with 293T cells being more refractory to transfection-mediated SEAP expression. In BHK cells, 100 ng of rvRNA formulated with QG807, QG808, or QG906 resulted in higher levels of SEAP expression compared to CNE while at the lower dose of RNA, CNE and QG906 formulations resulted in higher SEAP expression. SEAP activity was measured by NovaBright™ Phospha-Light™ assay, per manufacturer's instructions (ThermoFisher).

Figure 9:
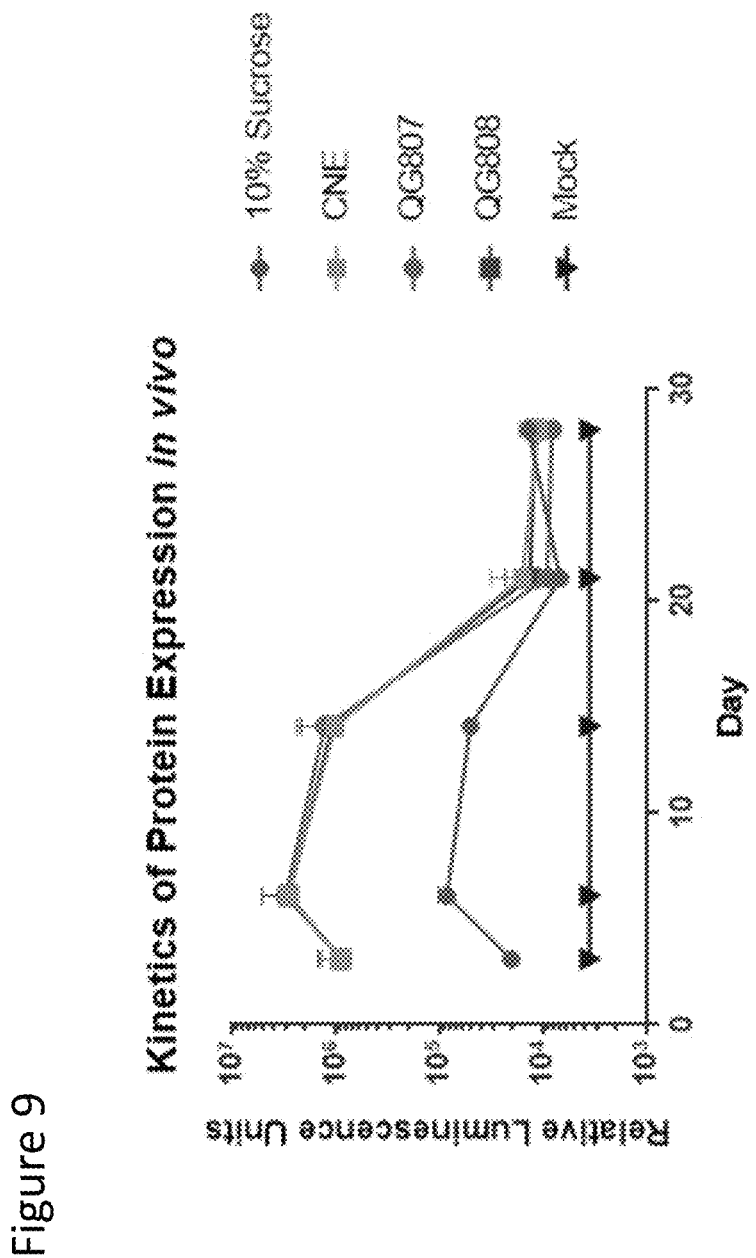
FIG. 9 depicts the kinetics of protein expression in vivo for select formulations. C57BL/6 mice were injected via the IM route with 1 µg rvRNA encoding SEAP and formulated in either 10% sucrose, CNE, QG807, or QG808. Saline-injected mice were utilized as a mock control. Serum was harvested at 3, 7, 14, 21, and 28 days after injection and SEAP activity was measured using a luminescence assay.

Next, the kinetics of protein expression in vivo was evaluated, following an intramuscular injection with rvRNA encoding SEAP formulated in CNE, QG807, QG808, or 10% sucrose and compared SEAP expression levels to mock-injected mice at various time points after injection (FIG. 9). RNA formulated in CNE, QG807, and QG808 demonstrated very similar expression profiles overtime with 33-to 36-fold higher SEAP activity compared to 10% sucrose-formulated RNA at the peak of 6 days following injection. By day 21, all groups returned to background levels of SEAP activity.

Figure 10:
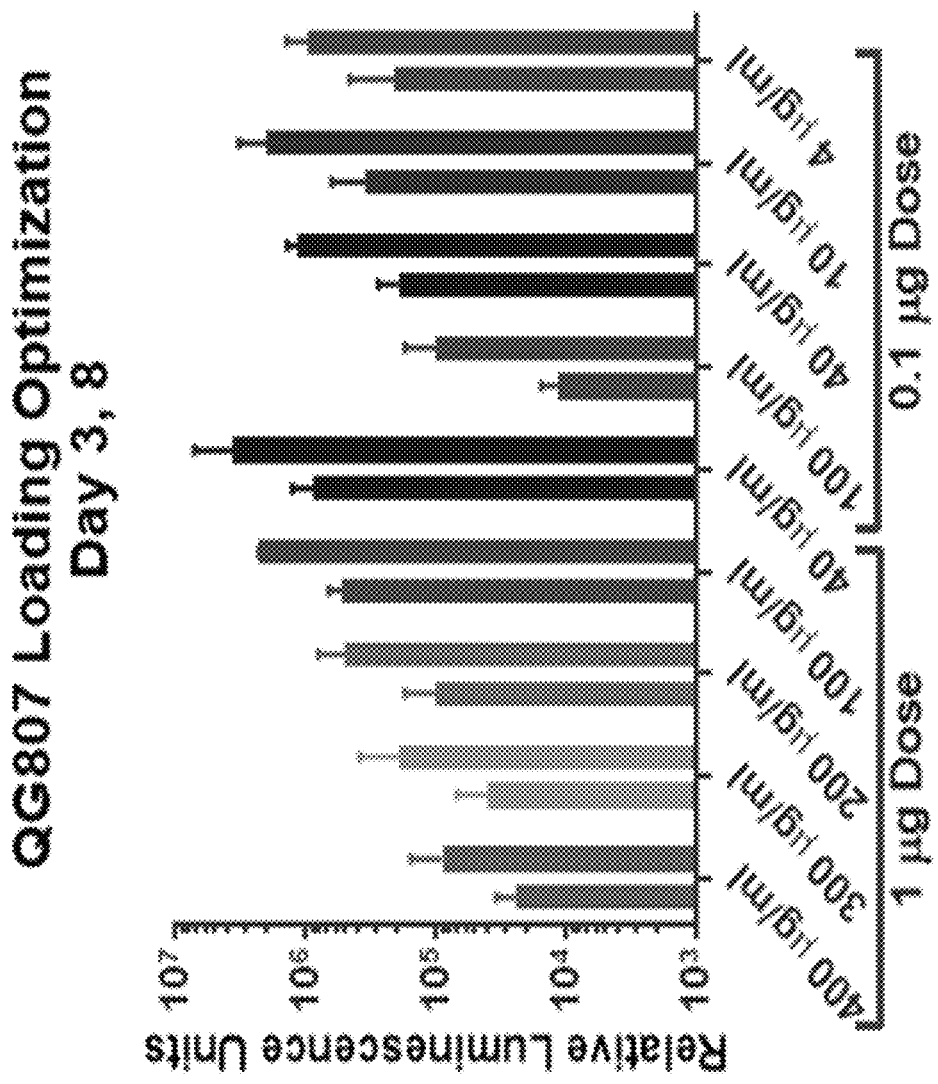
FIG. 10 depicts RNA loading optimization for the formulation, QG807. rvRNA encoding SEAP was diluted to various concentrations indicated on the x-axis in 10% sucrose and complexed at a 1:1 ratio with QG807. Formulated RNA was then diluted to achieve either a 1 µg or 0.1 µg dose in a 50 µl volume. C57BL/6 mice were then injected with each dose via the IM route and serum was harvested 3 and 8 days after injection. SEAP activity was then measured by luminescence assay.

Finally, the RNA loading capacity of QG807 was evaluated by complexing the formulation 1:1 with varied concentrations of rvRNA. Following the complexing reaction, formulated RNA was then diluted to a final concentration of 20 or 2 µg/ml and 50 µl of each was injected via the intramuscular route into C57BL/6 mice for final doses of 1 and 0.1 µg, respectively. Serum was then harvested on days 3 and 8 after injection and assayed for SEAP activity (FIG. 10). For the 1 µg dose, the lowest RNA concentration tested (40 µg/ml) resulted in the highest level of SEAP activity. Lower concentrations could not be tested at this dose due to injection volume constraints. The effect of lower concentrations could however be observed for the 0.1 µg doses. From this data it can be concluded that the optimal loading capacity is between 40 and 4 µg/ml of RNA.

Figure 11A:
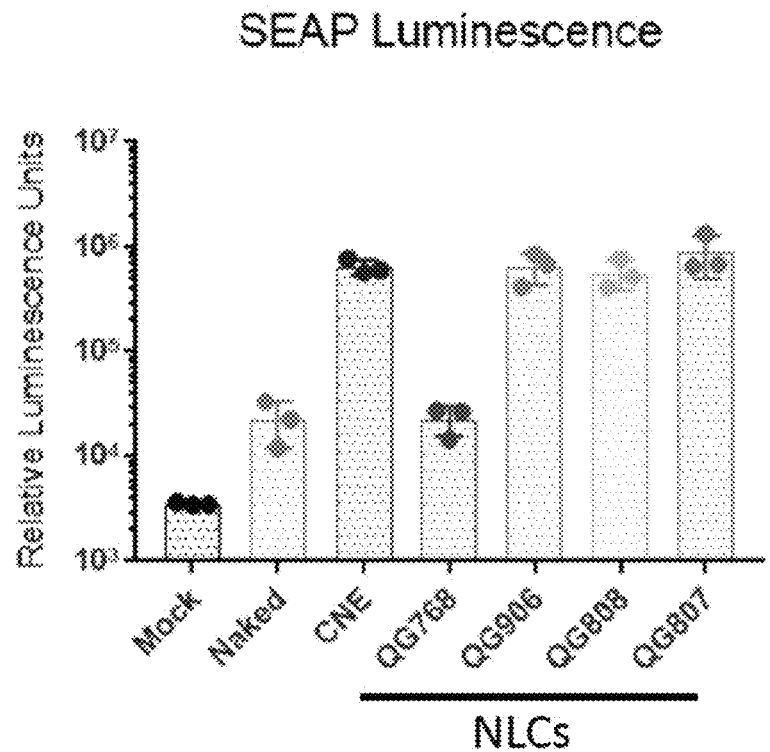
FIGS. 11A-C. For FIGS. 11A and 11B, mock=10% sucrose, naked=100 ng of SEAP rvRNA unformulated, CNE=SEAP rvRNA complexed with CNE (containing Span 85) QG768=NLC containing Span60, QG906=NLC containing Span80, QG808=NLC containing Span85, SQ807=NLC containing Span60.

Example 8: Formulations can be Modified to Enhance Immunogenicity Independent of Delivery Formulations can be modified to enhance immunogenicity independent of delivery and those enhancements are dependent on the presence of solid lipid. Based on the data from the in vitro whole blood chemokine release assays following stimulation with various high-percent hydrophilic surfactant-containing NLCs we hypothesized that different hydrophobic surfactants present in NLCs, with allow-percent hydrophilic surfactant composition, could differentially modulate immune responses in vivo. To test this hypothesis, one NLC with a high ratio of hydrophilic surfactant (2% tween 80), and three NLCs with a low ratio of hydrophilic surfactant (0.5% tween 80) and different types of hydrophobic surfactants (Span 85, Span 80, and Span 60), were complexed either with RNA encoding secreted alkaline phosphatase (SEAP) or with RNA encoding ZIKV prM and E genes. No detrimental effects on colloidal stability were observed as a result. A single 100 ng IM dose was administered to C57Bl/6 mice and compared with CNE-formulated or unformulated RNA (FIG. 11A). Protein expression, as measured by SEAP assay on serum harvested 3 days after injection, was enhanced over 25-fold in RNA-formulated NLCs containing low-percent hydrophilic surfactant (0.5% tween 80), but expression levels in serum were not different between RNA-formulated NLCs containing different hydrophobic surfactants or CNE-formulated RNA (FIG. 11A).

Figure 11B:
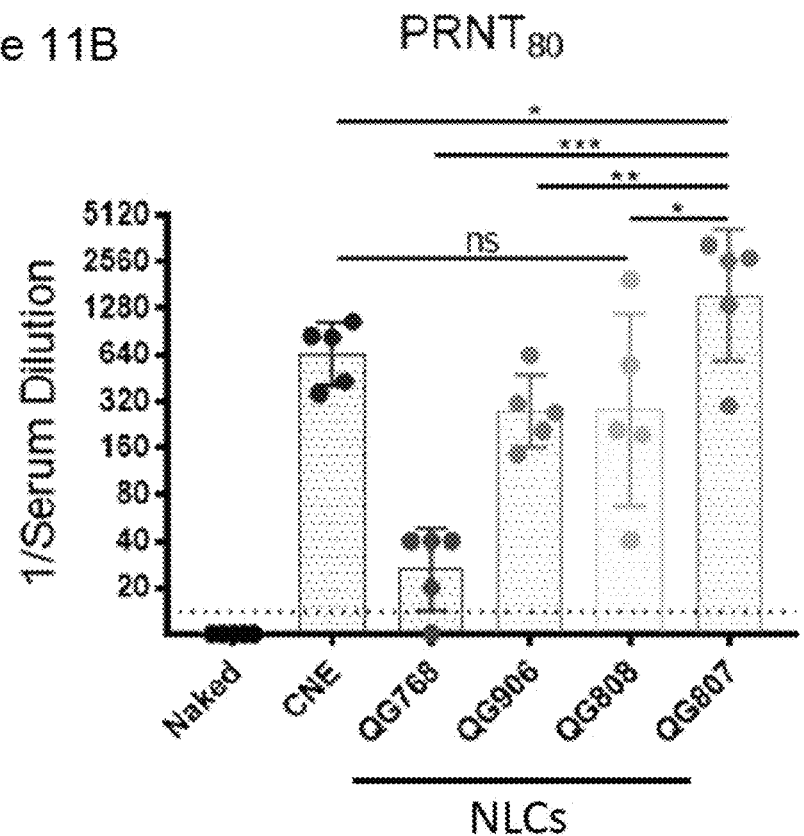
Figure 11C:
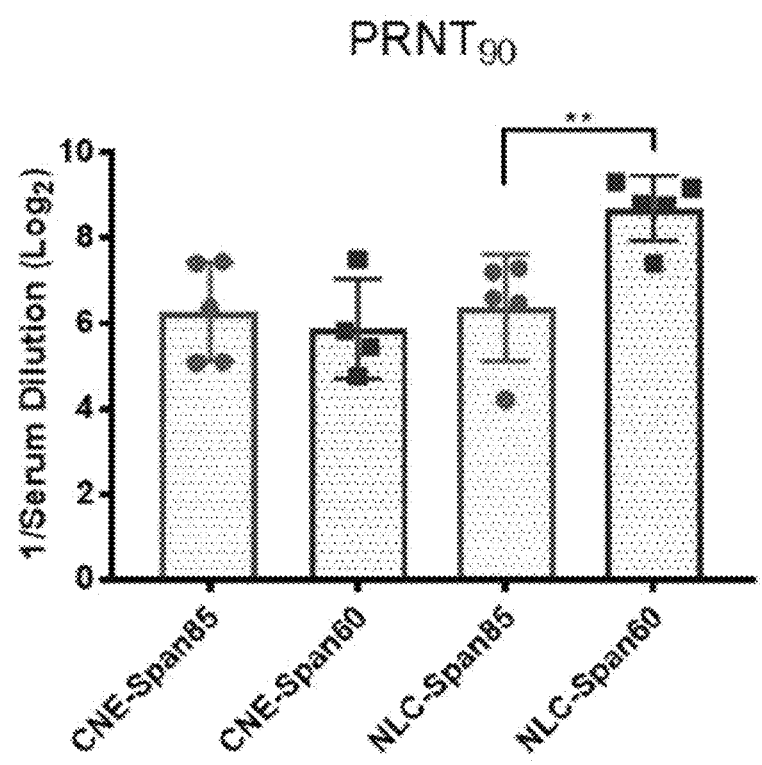

In contrast, there were significant differences in neutralizing antibody responses between each NLC-formulated RNA (FIG. 11B). While the low neutralizing antibody responses observed in mice immunized with RNA formulated with QG768 (containing 2% tween 80) could likely be attributed to low antigen expression levels, the differences observed between CNE and QG906, QG808, or QG807 are likely not due to differences in antigen expression. As QG906, QG808, and QG807 only differ in the hydrophobic surfactant composition, containing either Span 80, Span 85, or Span 60, respectively, the observed immunogenicity differences could be attributed to this component. Interestingly, CNE, which differs from NLCs in oil composition, where the former is only made up of squalene while the latter is composed of both squalene and dynasan, a solid lipid, was not significantly different than QG808, which contains the same hydrophobic surfactant as CNE (Span 85). As CNE and QG808 only differ in their oil composition with the latter having the addition of the solid lipid, dynasan, the effect of replacing Span 85 in CNE with Span 60 was tested, on immunogenicity of formulated RNA. CNEs with either Span 85 or Span 60 were complexed with RNA encoding ZIKV prM and E genes and compared to RNA formulated with NLCs composed of either Span 85 or Span 60 and administered to C57Bl/6 mice by a single 100 ng IM injection. By 14 days post-immunization, significant increases in neutralizing antibody (nAb) titers were only observed between NLCs when Span 85 was replaced with Span 60, indicating the importance of the solid oil component (FIG. 11C). Since SEAP expression levels between the different formulation groups were identical (FIG. 11A), differences in nAb titers were likely due to differences in the hydrophobic surfactant identity. To confirm that protein expression levels between CNE and NLCv1 were not changing over time, C57BL/6 mice were immunized with 100 ng of formulated or unformulated SEAP rvRNA and measured SEAP activity in serum harvested at days 3, 7, 14, 21, and 28 after injection (FIG. 25)—no significant differences were observed between CNE and NLCv1 groups.

Example 9: NLC-Formulated RNA Provides Single-Dose Immunogenicity and Efficacy

Figure 2A:
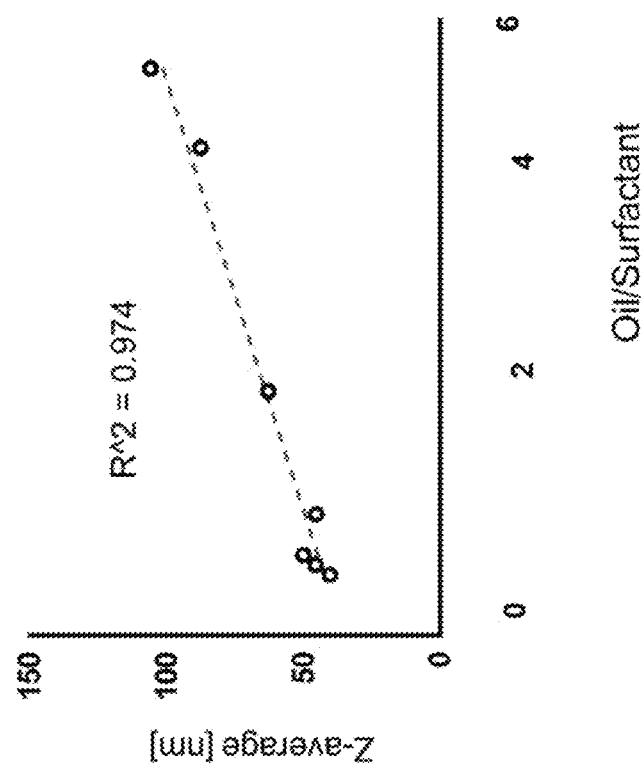

Based on the above data, all downstream experiments were performed with QG807 (Span60). To test the effectiveness of immune responses elicited by a single dose of NLC-formulated RNA, mice were immunized with 1 µg of either CNE- or NLC-formulated RNA and compared immunogenicity and efficacy to 10 µg or 1 µg of unformulated RNA. As observed in previous experiments there was a significantly higher neutralizing antibody response at 14 days after a single immunization in NLC-formulated groups compared to CNE-formulated or naked RNA groups (FIG. 2A). However, the 1 µg dose did reduce the overall neutralizing antibody titers compared to 0.1 µg doses seen in previous experiments (FIG. 11B). These findings are repeated in follow-up experiments.

For example, C57BL/6 were immunized with 1 or 0.1 µg of rvRNA formulated with NLCv1 (utilizing Span 60 as the hydrophobic surfactant) and compared to unformulated 10-fold higher doses in two separate experiments where one experiment assessed post-prime nAb titers while the other included a boost vaccination at day 28. Mice were periodically bled and nAb titers were assessed by PRNT80 (FIGS. 18A-B). In both experiments, showing peak nAb titers at day 14, with the 0.1 µg formulated doses inducing significantly higher titers than the 1 µg formulated doses. However, by day 88 and 156 after a single administration, the 0.1 µg formulated group exhibited a significant drop in nAb titers, compared to peak titers at day 14, in a similar manner to the 10 µg unformulated groups, while the 1 µg formulated group showed no significant change in titer (FIG. 18A). After boost immunization, significant nAb titer decay between day 14, 126, and 209 was present even with a booster immunization at day 28 in the 0.1 µg formulated group while the 1 µg formulated group showed no significant change in titer (FIG. 18B).

Figure 12A:
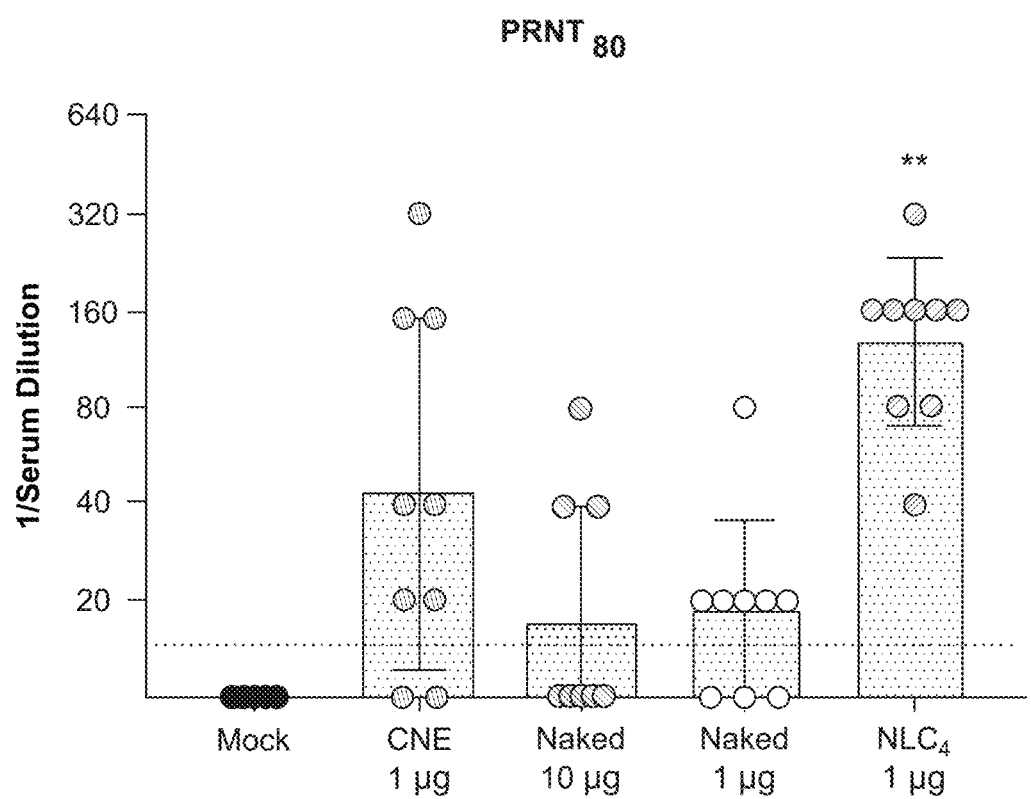
FIGS. 12A-H. C57Bl/6 mice (n=9/group) were immunized with a single IM injection of 1 µg CNE- or NLC-formulated RNA and compared to 10 or 1 µg unformulated RNA (FIG. 12A). Neutralizing antibodies were assessed 14 days after immunization, and then at 28 days, 3 mice per group were boosted with a second dose of each vaccine (FIGS. 12B-F). 46 days after the boost, spleens were harvested and stimulated with CD8 peptides corresponding to epitopes in ZIKV prM and E.
Figure 12B:
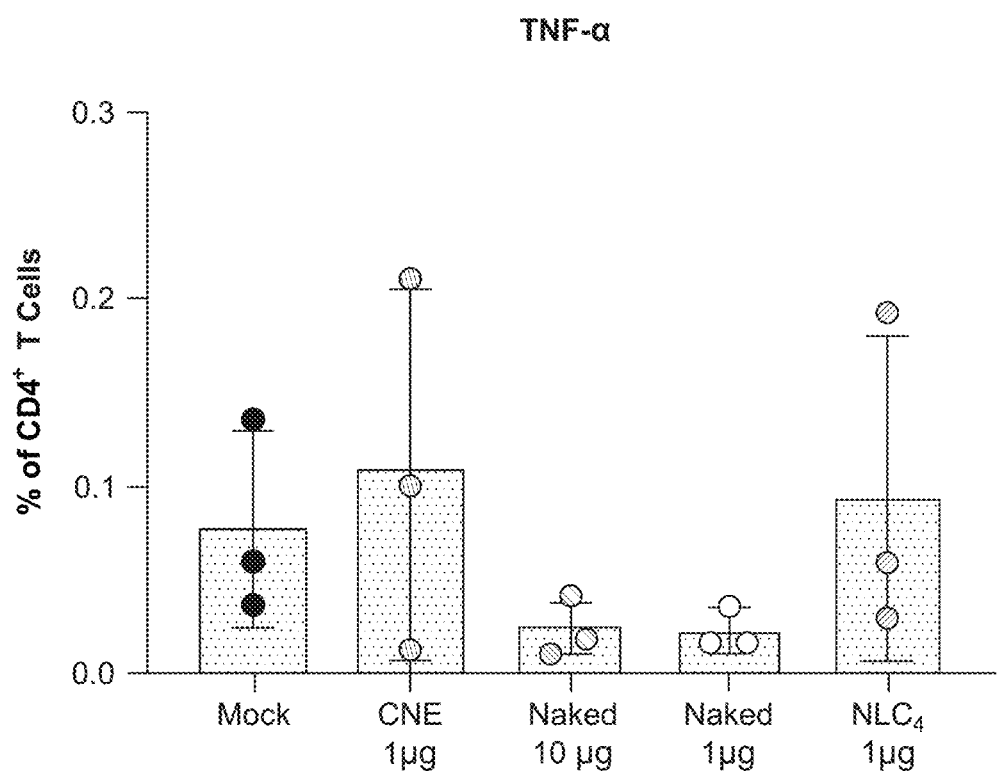
Figure 12C:
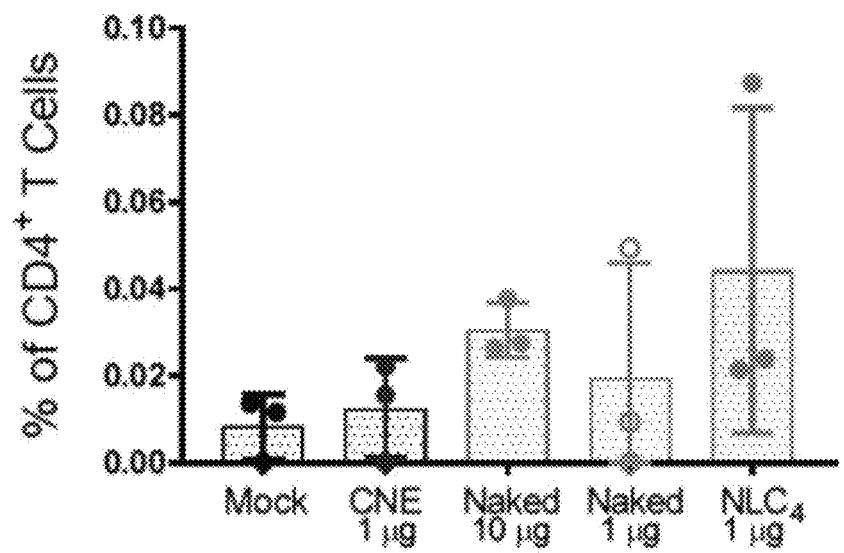
Figure 12D:
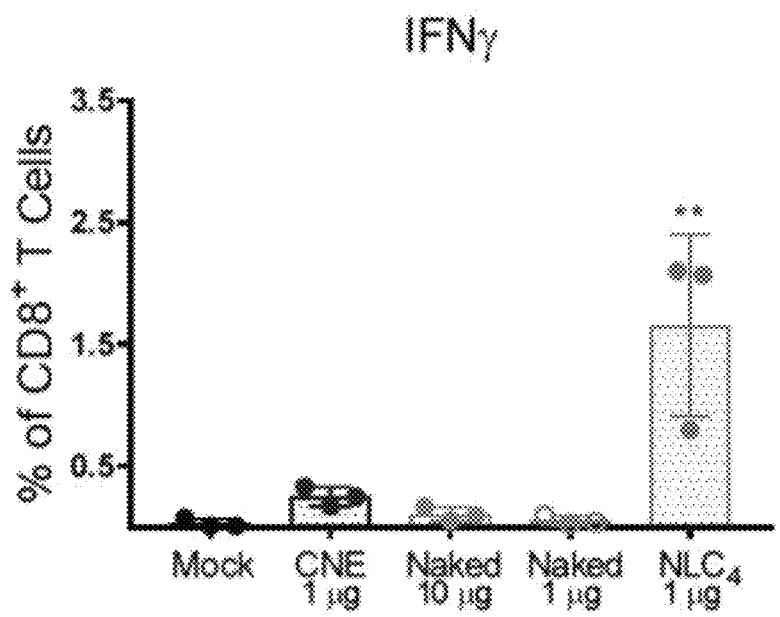
Figure 12E:
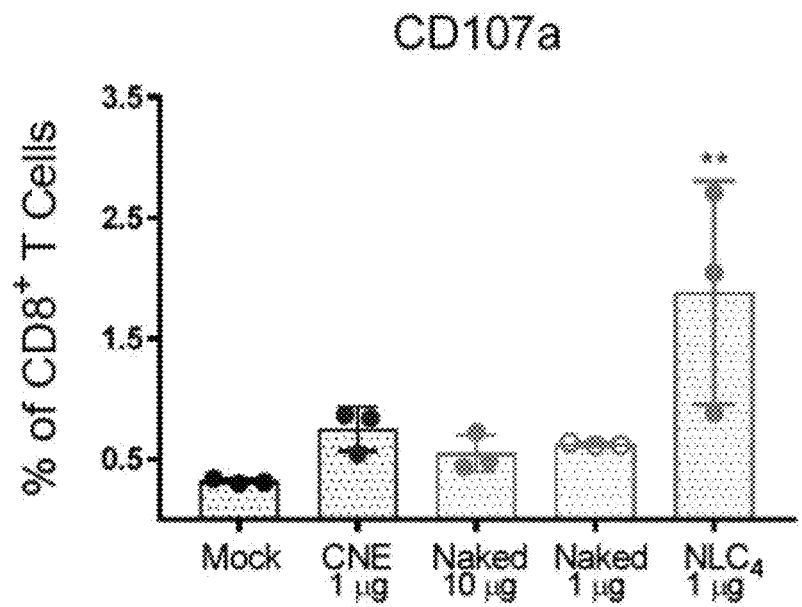
Figure 12F:
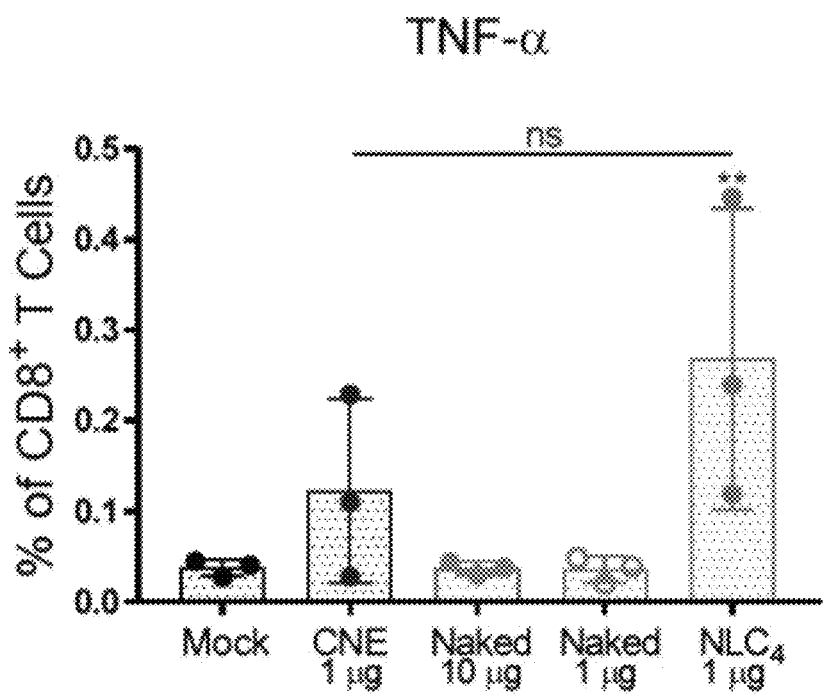

To assess post-contraction T cell responses after booster immunization, a subset of each group of mice was boosted with their respective vaccine formulations and harvested spleens 46 days later and stimulated splenocytes with a pool of peptides corresponding to CD8 epitopes in ZIKV prM and E (Muthumani et al., 2016; Elong Ngono et al., 2017) (FIGS. 12B-F). While significant differences were not observed for activated CD4 T cells (FIGS. 12B, 12C), NLC-formulated RNA induced significantly higher levels of IFNγ+ and CD107a+ CD8+ T cells compared to CNE- or un-formulated RNA (FIGS. 12D, 12E). While NLC-formulated RNA did not induce significantly higher levels of TNF-α+ CD8+ T cells compared to CNE-formulated RNA, levels of these activated CD8+ T cells were significantly higher than unformulated RNA groups (FIG. 12F). The remaining mice that were not boosted were then challenged at 30 days after a single immunization. The challenge model utilized was previously described (Smith et al., 2017) and involves the administration of an interferon alpha receptor (IFNAR) blocking monoclonal antibody 1 day before and 1 and 4 days after challenge in order to increase the susceptibility of these immunocompetent mice to ZIKV Dakar strain 41525.

Figure 28G:
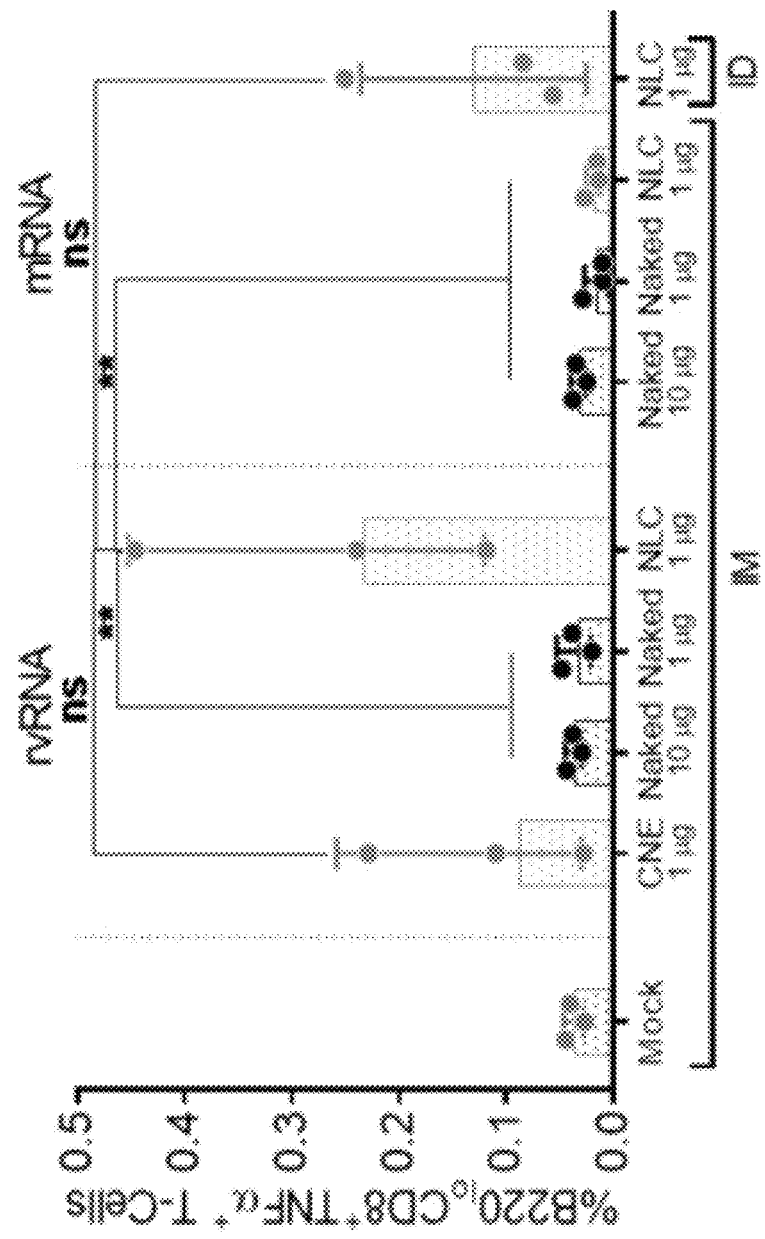

To assess immunogenicity and efficacy of the optimized vaccine platform, NLCv2 was complexed with rvRNA at a minimally reactive but immunogenic N:P ratio, and used to immunize C57BL/6 mice via the IM route with 100, 30, 10, and 3 ng complexed with NLCv2 at an N:P of 15 (n=14/group) and responses to mice immunized with 100 ng of NLCv1- (n=14) or CNE- (n=4) formulated rvRNA at the same N:P, which is suboptimal for their compositions, were compared. A separate study comparing NLCv1 and CNE at their optimal N:Ps is summarized in FIG. 28. Unformulated doses of 100 and 10 ng were administered along with mock vaccination as controls (n=14/group). Two weeks after a single administration, mice were bled to quantify nAb titers by PRNT80 and 4 mice per group were euthanized and splenocytes were isolated, stimulated with a pool of peptides corresponding to murine CD8+ T cell epitopes in ZIKV prM/E (34,50), and T-cell responses measured by flow cytometry (FIGS. 20A-B).

There was 100% seroconversion only in $NLC_{v2}$ formulated groups receiving 100, 30, and 10 ng doses with mean PRNT80 titers of 1:604, 1:302, and 1:113, respectively. There was 25% seroconversion in the 3 ng dose group, similar to the 100 ng NLCY group formulated at a suboptimal N:P ratio. The CNE-formulated group performed significantly better than NLCv1 at an N:P of 15, correlating with enhanced in vitro SEAP expression at lower N:P ratios (FIG. 3C), however, the same dose formulated with NLCv2 at the same N:P resulted in ~13-fold increase in nAb titers (mean PRNT80 of 1:604 vs 1:48, $p<0.0001$).

In terms of CD8+ T cell responses, there was significant percentages of B220loCD8+IFNγ+ T cells, compared to mock vaccination, in mice receiving a single dose of 100 and 30 ng formulated with NLCv2. These responses were significantly reduced compared to 2 doses of 1 μg formulated with NLCv1 at N:P of 50 (FIG. 28E), confirming that a prime-boost format can enhance cellular immune responses, as previously demonstrated. See Knudsen et al., J Virol. 88(21):12438-51 (2014).

Finally, the remaining 10 mice per group were challenged 30 days after a single administration, as described above, and bled 4 days later to quantify viremia by plaque assay (FIG. 20C). Mice were monitored daily for signs of disease and weight loss (FIGS. 20D-E). Any mice that lost more than 20% of their pre-challenge weight, or appeared moribund, were euthanized at the indicated time points (FIG. 20D). All mock and unformulated 100 ng vaccinated mice experienced high levels of viremia (between 2.6 and 5.8 log 10 PFU/ml) while 1 out of 10 mice in the 10 ng unformulated group was protected from detectable viremia (limit of detection=50 PFU/ml). In the NLCv2 groups, the 100, 30, and 10 ng doses were 100% protected from detectable viremia and the 3 ng dose protected 6 out of 10 mice. One animal out of 10 in the 100 ng NLCv1-formulated at the suboptimal N:P group was not protected from viremia. All NLCv1 and NLCv2 groups were protected from significant weight loss and death, including the 3 ng dose formulated with NLCv2. Unformulated groups experienced significant weight loss with only 10% and 20% surviving challenge up to 30 days post challenge in the 100 and 10 ng dose groups, respectively, compared to 100% death in the mock vaccination group after 10 days post challenge.

Figure 12G:
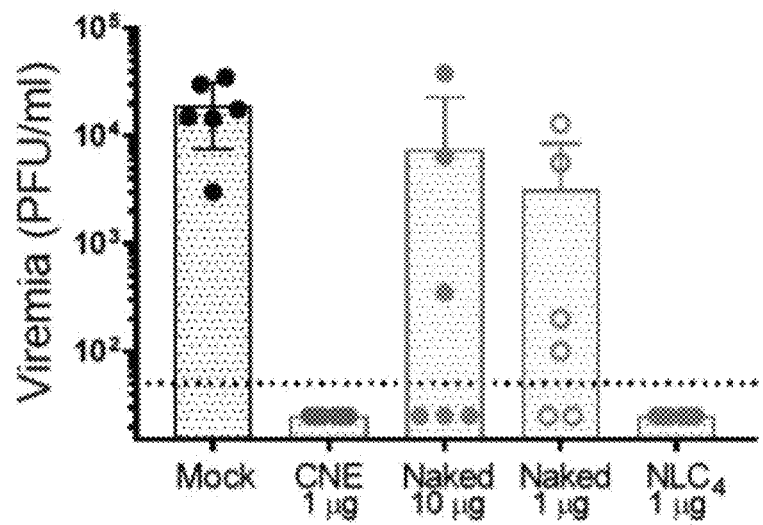
Figure 12H:
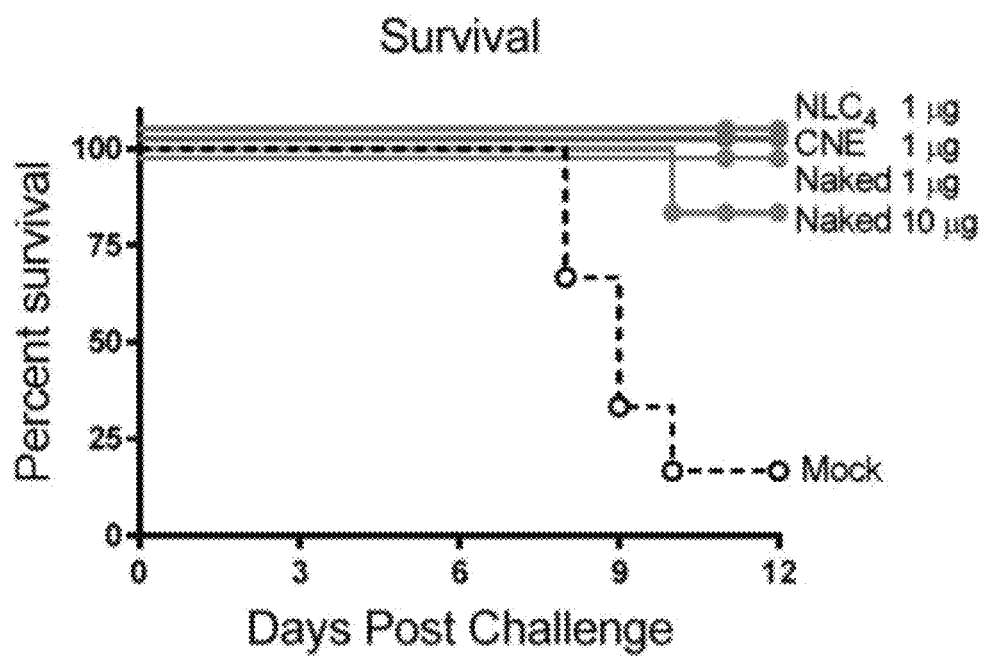

While unformulated RNA at both doses was unable to fully protect all mice from viremia, both CNE and NLC-formulated RNA demonstrated complete protection from detectable viremia (limit of detection=50 plaque forming units/ml) (FIG. 12G). In terms of survival, all 1 μg doses (unformulated, CNE-, or NLC-formulated) protected 100% of mice from death while 80% of 10 μg unformulated RNA vaccinated mice survived, compared to 17% survival in the mock-vaccinated mice.

Immunogenicity in Immunocompetent Mice

To assess protein expression or immunogenicity in an immunocompetent mouse model, five 4-week old female C57Bl/6 mice (Charles River) per group were vaccinated by intramuscular (IM) formulation in the rear quadriceps muscle with a 1:1 mixture containing RNA and in a total volume of 50 μl. At various time points, blood was collected via the retro-orbital route and serum was harvested following low-speed centrifugation and stored at −20° C. until PRNT80 titers were determined as described above. Following a single immunization intramuscular, mice injected with the formulations (/QG767 and/QG768) showed high titer ZIKV neutralizing antibody 14 days following immunization as measured by plaque reduction neutralization test (PRNT80) assays as compared to mice immunized with control or the other formulations lacking a sorbitan monoester (e.g., Span).

Figure 13A:
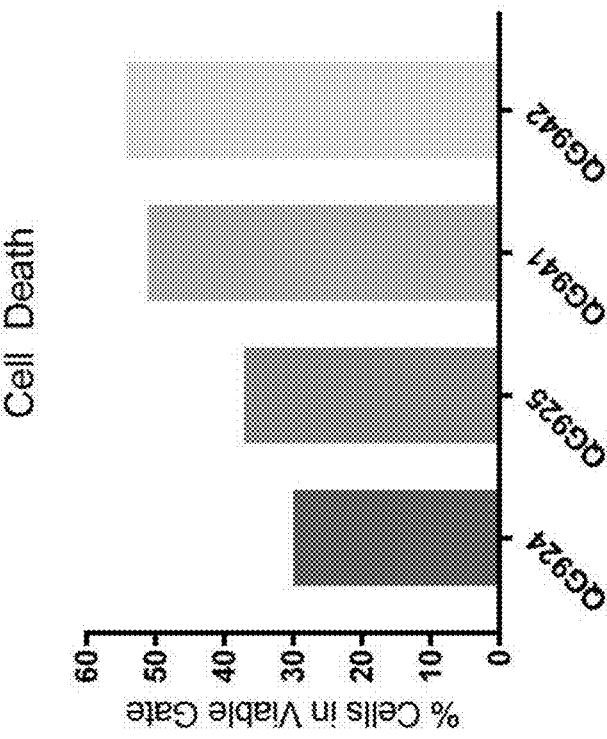
FIGS. 13A-B. C57BL/6 mice (n=3/group) were injected IM with 1 µg of SEAP RNA unformulated or formulated with QG807, QG924, QG925, QG941, or QG942 by complexing with RNA at 400 µg/ml and SEAP expression was compared to QG807 complexed at its optimal 40 µg/ml RNA concentration (FIG. 13A). BHK cells were incubated with a 1:20 dilution of each high RNA-load formulation for 4 hours and then stained with propidium iodide and annexin to detect cells that were dead or undergoing apoptosis. Flow cytometry was then used to quantify the proportion of cells that were not dead or undergoing apoptosis (FIG. 13B).

Example 10: Additional Modifications to NLCs to Enhance Loading Capacity and Delivery It has been previously demonstrated that squalene, the liquid oil component of NLCs, activates inflammatory pathways including caspase- and IL-18-dependent inflammasome activation (Desbien et al., 2015; unpublished data). As viral replication is negatively impacted by these events (Chen et al., 2015), reducing the squalene content while increasing DOTAP concentrations is expected to enhance the RNA-loading capacity of NLCs. To test this in vivo, 4 additional high RNA-load formulations were generated, QG924, QG925, QG941, and QG942 which all contain the same high concentration of DOTAP but higher than that of QG807 and reducing concentrations of squalene between each formulation. The SEAP-expressing replicon was complexed with QG807 at 40 μg/ml and compared SEAP expression at day 3 following a 1 μg IM dose to QG807, QG924, QG925, QG941, and QG942 complexed at a 10-fold higher RNA concentration, 400 μg/ml, and delivered at the same 1 μg IM dose (FIG. 13A). While QG807 complexed with RNA at 400 μg/ml was unable to deliver an effective 1 μg dose, as compared to QG807 complexed with RNA at 40 μg/ml, QG942 complexed with 400 μg/ml of RNA produced similar SEAP expression levels following a 1 μg dose compared to the same dose delivered with QG807 complexed at 40 μg/ml.

Figure 26:
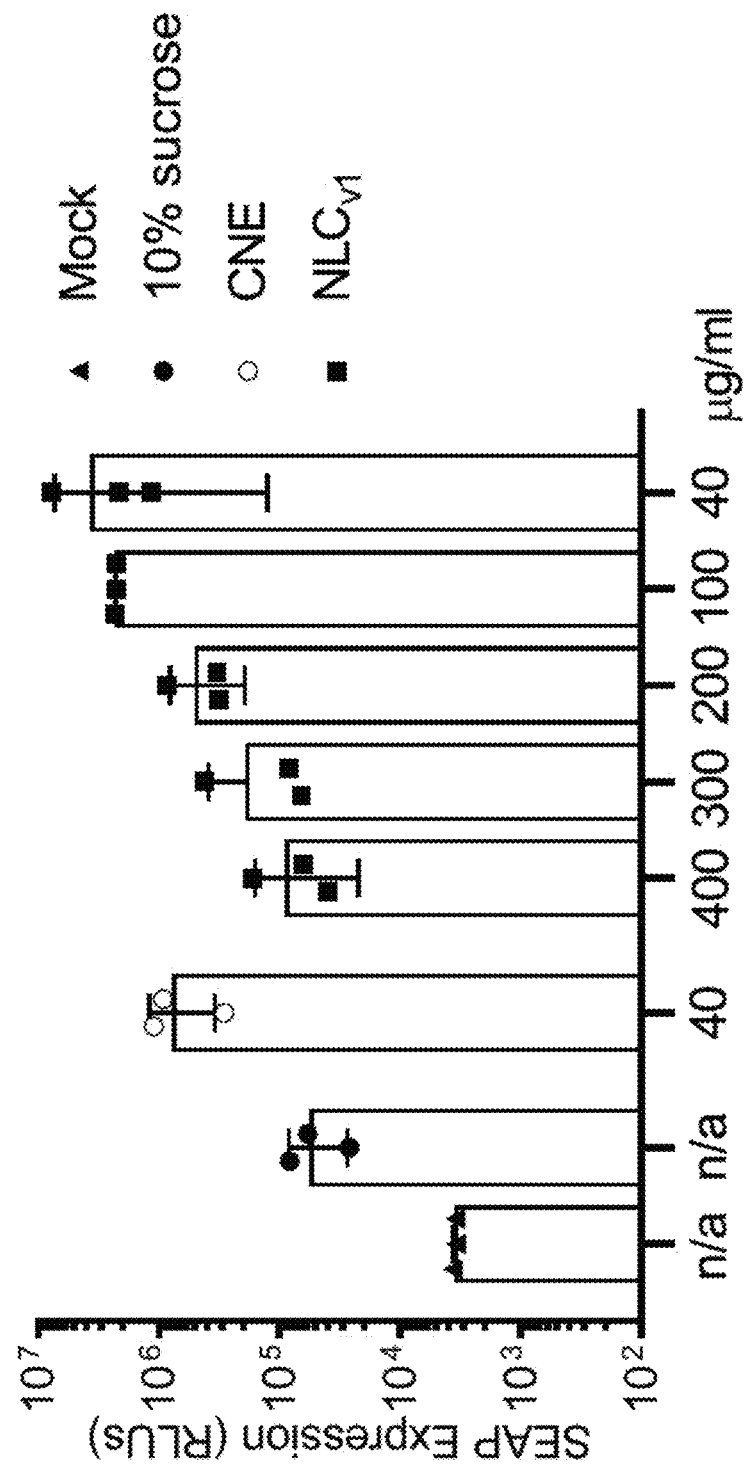
Figure 27:
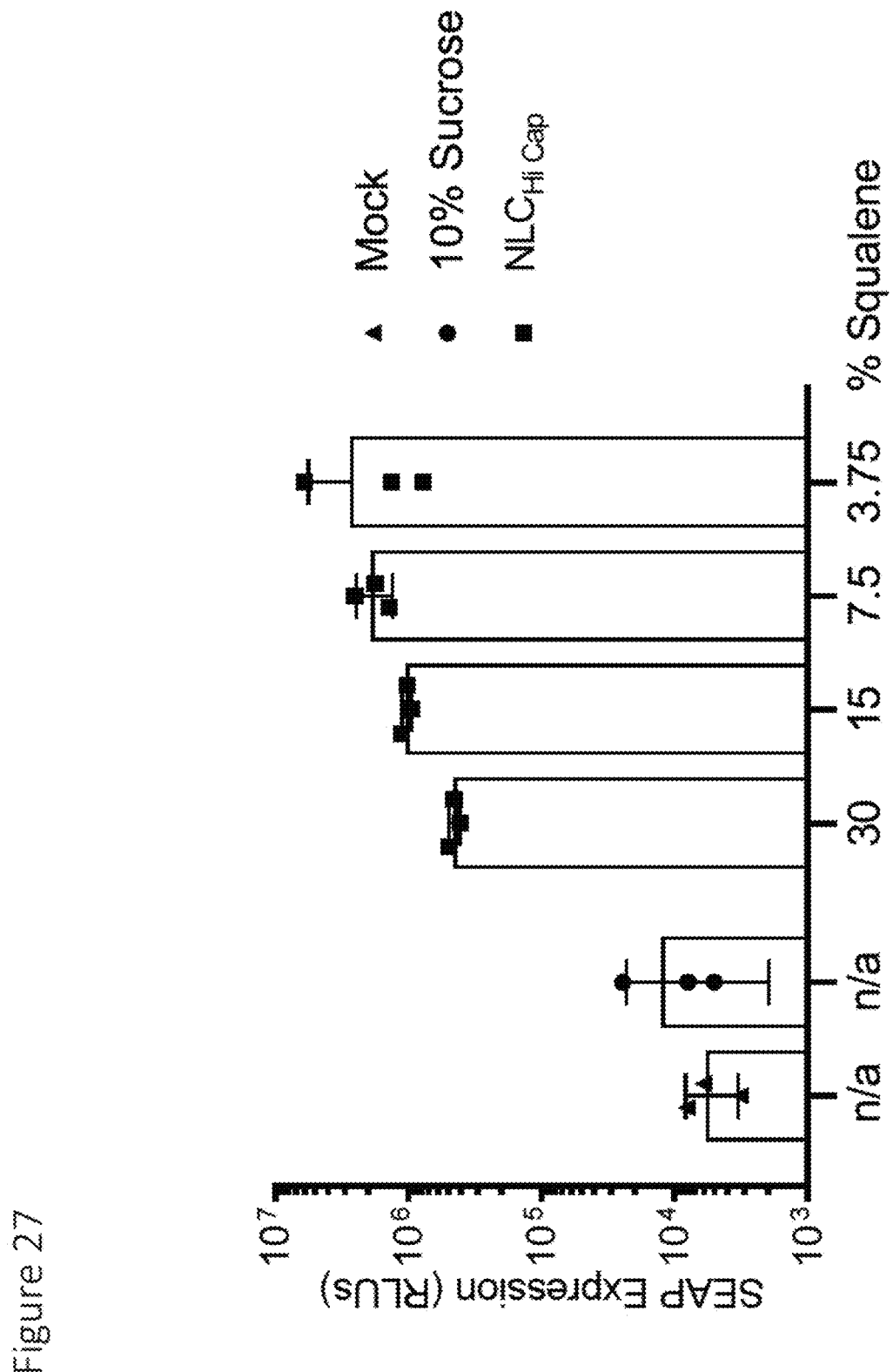

In the above experiments, NLCv1 or CNE was mixed 1:1 with 40 μg/ml RNA (N:P=50), which was the lowest concentration that 1) allowed for a 1 μg RNA dose in a 50 μl injection volume, and 2) resulted in optimal SEAP expression in vitro (FIG. 3C) and in vivo (FIG. 26). However, an N:P value of 50 translates to a relatively large excess of formulation, which poses formulation-associated tolerability risks with increasing dose requirements; emulsified squalene and DOTAP (cationic lipids in general) are immunostimulants, and high amounts can induce inflammatory and local reactogenicity. See Lv et al. J Control Release. 114(1):100-9 (2006); Desbien et al., Eur J Immunol. 45(2):407-17 (2015). As a result, an NLC formulation that can deliver high RNA dose at significantly lower N:P values was designed and synthesized. The resulting formulation was a derivative yet physicochemically distinct version of NLCv1, subsequently referred to as $NLC_{v2}$; physicochemical properties are summarized in Table 2. Prior to the inception of $NLC_{v2}$, highly concentrated versions of $NLC_{v1}$ were manufactured to increase RNA loading capacity—some containing as high as 30% w/v squalene and 1.8% w/v dynasan 114 but with identical S:O ratio. The latter allowed us to keep nanoparticle size and chemical composition constant while increasing RNA loading capacity by virtue of increased nanoparticle concentration. While this approach overcame the practical limitation of loading high amounts of RNA, it did not circumvent the use of excess formulation. As a result, in subsequent versions the amount of squalene and Dynasan 114 was reduced to as low as 3.75% w/v squalene and 0.24% dynasan 114, respectively, while keeping the total surfactant composition ([DOTAP]+[Span 60]+[Tween 80]) and ratio ([DOTAP]:[Span 60]:[Tween 80]) constant, effectively increasing the S:O ratio 9-fold (from 0.18 to 1.68) in NLCv2 relative to $NLC_{v1}$. Interestingly, when screened these formulations complexed were screed with SEAP rvRNA in vivo, increasing SEAP expression with decreasing squalene concentration (FIG. 27) was observed. Due to this relatively high S:O ratio, NLCv2 exhibited an average diameter of ~40 nm, a nearly 2-fold reduction in particle size compared to NLCv1 (FIG. 23A), as measured by DLS. Similar to NLCv1, NLCv2 protected rvRNA from RNase degradation (FIG. 23B). To confirm the increased loading capacity of NLCv2, escalating concentrations of rvRNA were complexed with NLCv1 or NLCv2 (1:1 by volume), and quantified unbound RNA by electrophoretic gel retardation assay (FIG. 23C). While 100% of RNA was bound to NLCv1 at rvRNA concentrations less than 100 μg/ml (N:P>20), NLCv2 exhibited 100% RNA-binding at rvRNA concentrations up to 10 mg/ml.

Figure 13B:
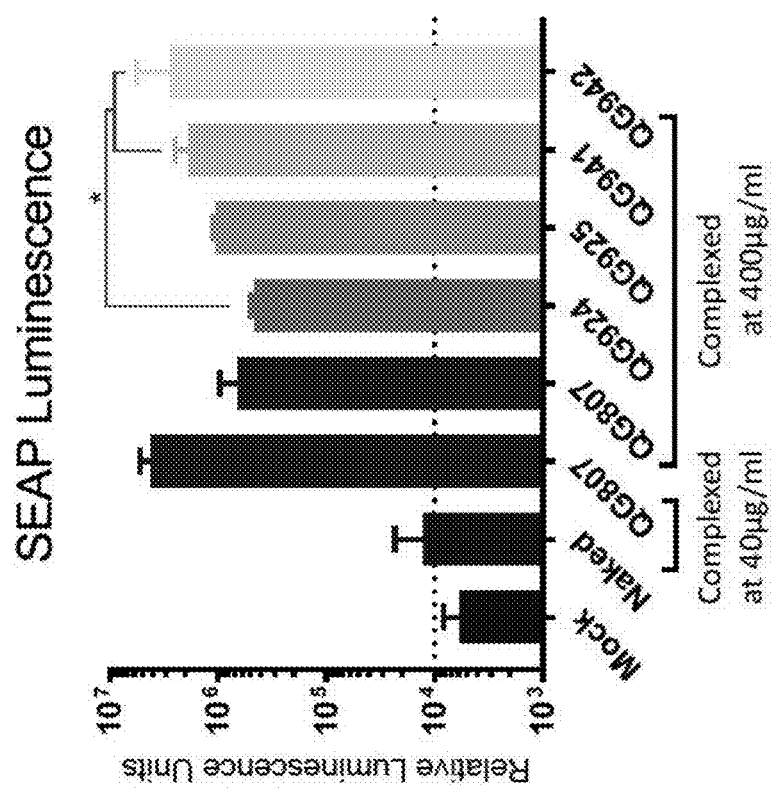

To test the effect of reducing squalene on cell death, BHK cells were incubated overnight with a 1:20 dilution of each high RNA-load formulation for 4 hours then assayed for cell death by propidium iodide (PI) and annexin staining to quantify live cells, by flow cytometry, that were not undergoing apoptosis (FIG. 13B). The highest amount of living cells were observed in the QG942 treated cells, which correlates with the lowest concentration of squalene while all other components between each formulation remained identical.

To evaluate the optimal N:P that would result in maximum SEAP expression in vitro, NLCv2 was complexed with SEAP-rvRNA at various N:P ratios and incubated 100 ng rvRNA doses with BHK cells overnight, as described above. At least a ~5-fold reduction in optimal N:P for NLCv2 compared to NLCv1 was observed, from >100 for NLCv1 to between 15 and 37 for NLCv2 (FIG. 23D). Interestingly, the maximum SEAP expression level for NLCv2 was also enhanced ~2.5 fold, compared to NLCv1. Finally, relative to CNE (FIG. 3C), NLCv2 provided nearly 10-fold increase in maximum SEAP expression at about ⅓ the N:P value.

Next, QG942 was moved into immunogenicity studies using 400-450 g Hartley guinea pigs (Charles River) to attempt to induce anti-ZIKV neutralizing antibodies in a large rodent model. In this study, QG942 (NLCv2) was loaded with RNA at a concentration of 400 μg/ml (a 10-fold higher concentration) and compared 50, 5, and 0.5 μg doses via IM or intradermally (ID) using Nanopass Micronjet600 needles (Nanopass Technologies, Ltd.) route to 5 and 0.5 μg doses of RNA loaded with QG807 at 40 μg/ml of RNA with a 1:1 mixture containing NLC and rvRNA encoding ZIKV prM/E in the rear quadriceps muscle in a total volume of 250 μl. Also, 50 μg of unformulated RNA was included as a control. Twenty-four hours later, the diameter of the IM/ID injection-site flare was measured. Blood was collected at the time points indicated in the figure legends via the femoral vein and serum was harvested following low-speed centrifugation and stored at −20° C. until PRNT80 titers were determined as described above. By 14 days after a single immunization, a dose-dependent neutralizing antibody response was observed indicating success at delivering the highest 50 μg dose of RNA which could not be achieved with QG807. Additionally, no significant differences between the 5 and 0.5 μg doses delivered by QG942 or QG807 was observed when assayed 28 days later, although a slight trend in the favor of QG942 may suggest that lowering squalene could be advantageous. A dose-response trend was observed, although there were no significant differences between doses, with the IM 50, 5, and 0.5 μg doses resulting in mean PRNT80 titers of 1:761, 1:452, and 1:226, respectively, while ID doses resulted in mean PRNT80 titers of 1:905, 1:380, and 1:269, respectively. See FIG. 23E. Interestingly, significant differences were observed between NLCv1- and NLCv2-formulated groups at 5 μg rvRNA dose, with NLCv2-formulated rvRNA inducing ~4- or ~8-fold higher nAb titers in ID or IM routes of administration, respectively. For reference, in vitro SEAP expression at these N:P ratios were enhanced ~8.4 fold (FIG. 23D) in NLCv2 compared to NLCv1. To characterize NLCv2 in vivo in terms of protein expression, reactogenicity, and immunogenicity, 4 to 5 N:P ratios were tested, including those correlating with in vitro SEAP activity 5.8 Log 10 RLU (100, 37, 15, 5.6), and an N:P of 3, outside the hypothesized optimal zone. To characterize protein expression, C57BL/6 mice were injected IM with 1000, 100, and 10 ng doses of SEAP rvRNA at each N:P ratio. To characterize reactogenicity, 50 μg of rvRNA complexed with NLCv2 at each N:P were also injected via ID route in guinea pigs and flare diameter was measured. Twenty-four hours after injection, mice were bled to measure serum SEAP activity and guinea pig injection sites were measured (FIGS. 22E-H). To characterize immunogenicity, ZIKV rvRNA was complexed with NLCv2 at each N:P, and 1000 ng or 100 ng was delivered via the IM route in mice. Mice were then bled 14 days later to quantify nAb titers (FIGS. 22F-G).

Beginning with SEAP expression in vivo, optimal N:P ratios were dependent on dose, with optimal N:P of 15 for the 1000 ng dose, 37 for the 100 ng dose, and 100 for the 10 ng dose (FIG. 22E). As expected, immunogenicity appeared to correlate with SEAP expression at the two doses that were compared (FIGS. 22F-G). At the 1000 ng dose, no significant differences in nAb titers with any of the N:P ratios tested were detected, similar to SEAP activity at those N:P ratios (FIG. 22F). At the 100 ng dose, no significant difference in nAb titers between N:P ratios of 37 and 15 was observed and slight but insignificant differences in SEAP activity was observed, however, a significant reduction in titer occurred between N:P ratios of 15 and 5.6 in a similar manner to SEAP activity (FIG. 22G). In terms of reactogenicity, there was a significant reduction in flare diameter when the N:P ratio was reduced 2.5 fold from 37 to 15 (FIG. 22H). Importantly, these data suggest that reducing the N:P 2.5-fold from 37 to 15 would significantly reduce reactogenicity but minimally impact antigen expression levels and subsequent immunogenicity, especially at higher rvRNA doses. In fact, at N:P values of 15 and 37, a dose-sparing effect was observed as there was not a significant difference in SEAP activity between 1000 and 100 ng doses (FIG. 22E). The largest differences in SEAP activity between doses was observed at low N:P ratios (FIG. 22E).

Example 11. Loading Capacity and RNA Delivery

Figure 14:
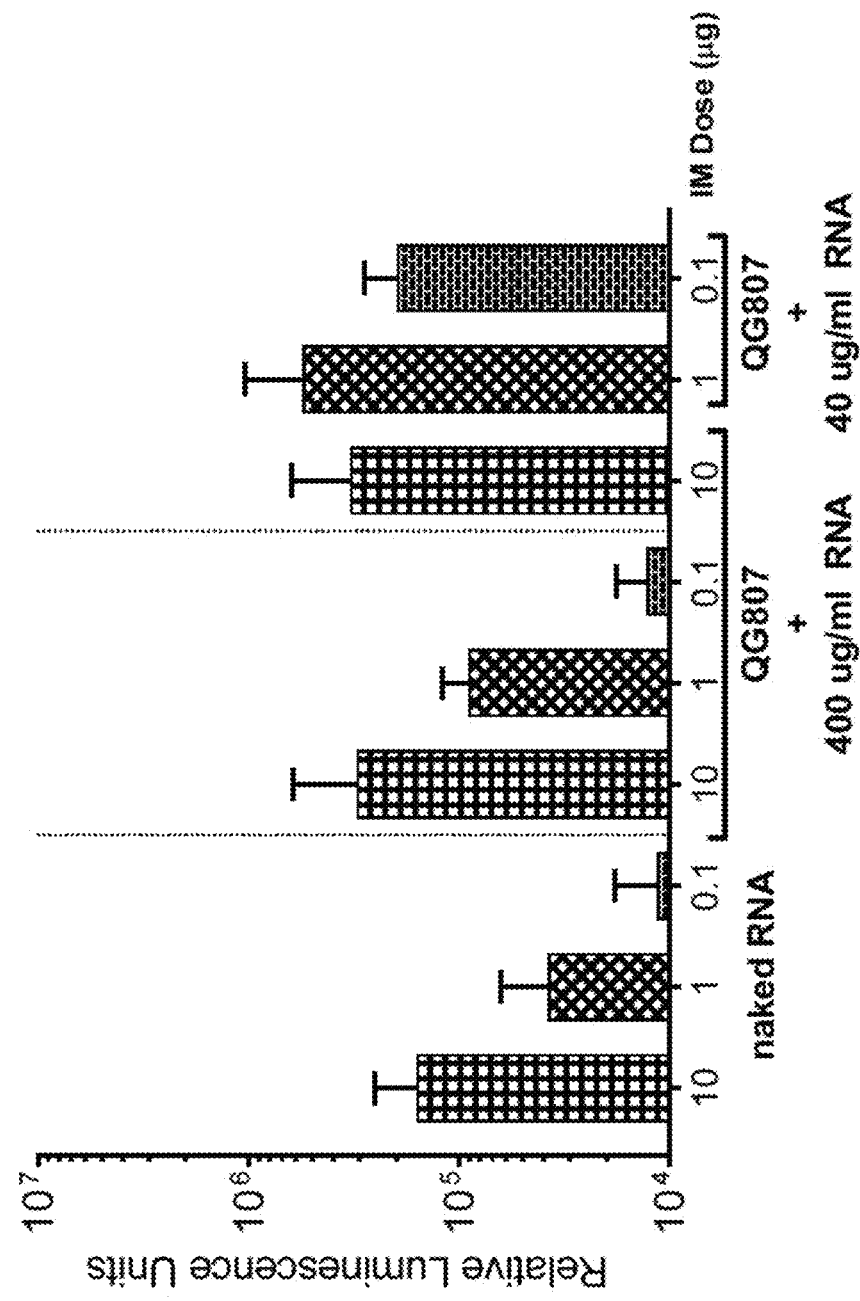
FIG. 14 depicts in vivo SEAP expression data comparing QG807 complexed with either 400 µg/ml or 40 µg/ml RNA.
Figure 15B:
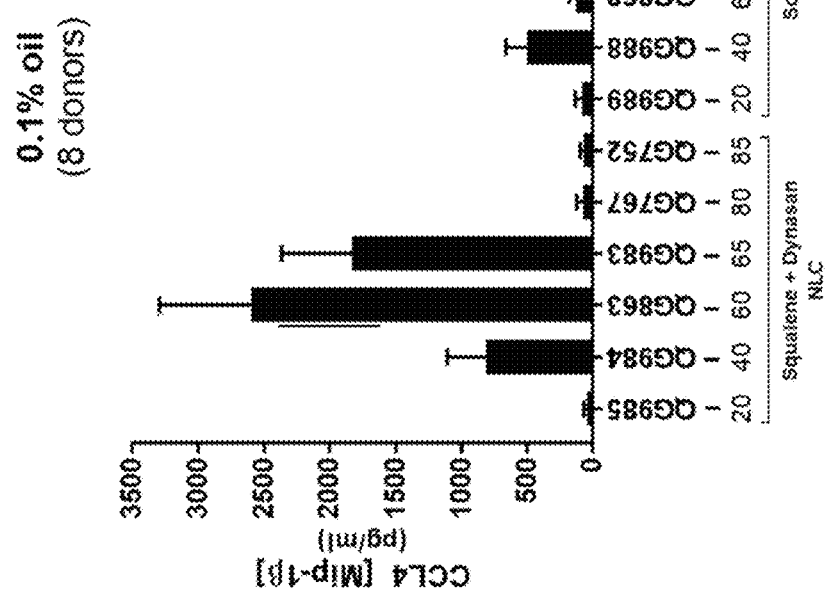
FIGS. 15A-D depict levels of chemokine release from human whole blood cells in the presence of the indicated formulations. Chemokine expression levels were determined by Luminex assay using a multiplex cytokine bead array.
Figure 15A:
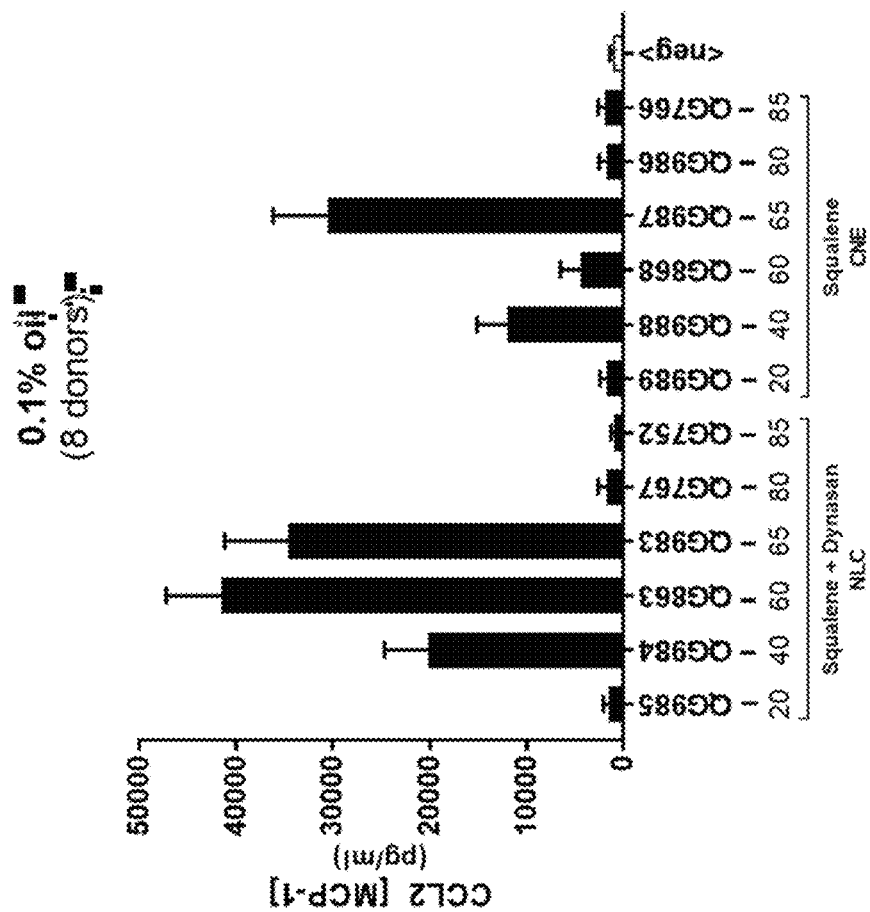
Figure 15D:
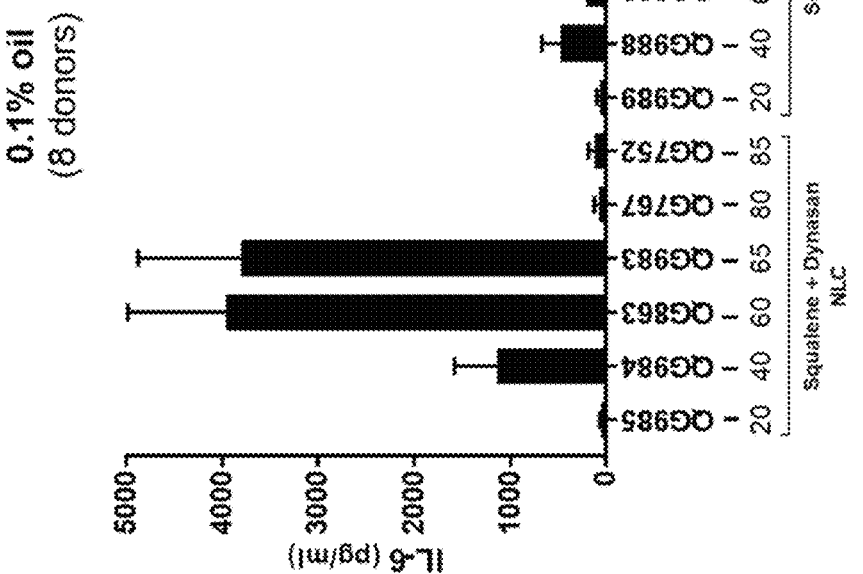
Figure 15C:
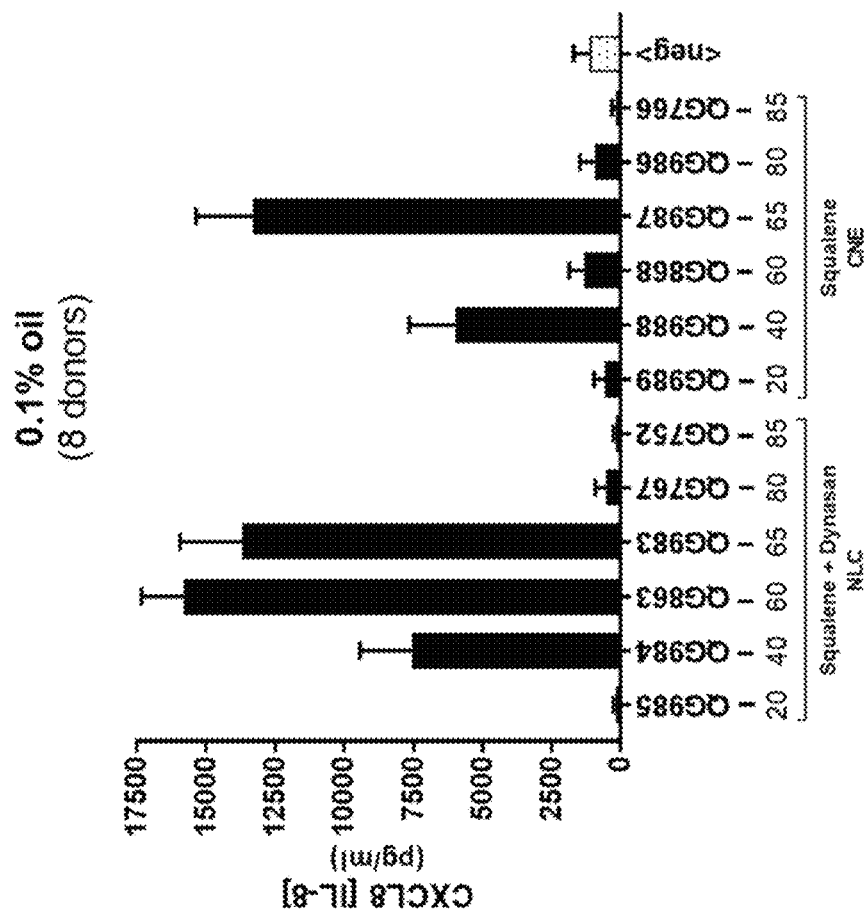

In order to deliver 10 µg RNA in a 50 µl injection volume (200 µg/ml RNA concentration), NLCs were made with increased loading capacity as compared to QG807. FIG. 14 shows that complexing 400 µg/ml RNA 1:1 (v/v) with QG807 (N/P~4.8) did not significantly improve in vivo SEAP expression relative to naked or unformulated RNA. On the other hand, QG807 does provide good SEAP expression when complexed with 1:1 (v/v) with 40 µg/ml RNA (N/P~48) at 1 or 0.1 µg RNA—10 µg dose. This suggested that in order to deliver 10 µg RNA the loading capacity of NLCs needed to increase.

To increase loading capacity, reducing average NLC particle size while keeping the total volume constant should theoretically increase the total number of NLC particles, thus translating to increase in RNA binding sites. As a result, QG911, which shares a relatively similar composition with QG807, except for 10 mM citrate that was added during manufacturing and it was microfluidized for 10 passes at 30,000 psi (compared to 5 passes at 30,000 psi for QG807) to attain a smaller average particle diameter. The final Z-average particle diameter of QG911 was 87 nm, which is ~17% smaller than QG807 (Z-average=105 nm).

To further decrease particle size, QG912 was manufactured with half the oil/surfactant ratio than QG911. Reducing the amount of oil relative to the total amount of surfactant increases the surface area (SA) to volume (V) ratio of NLC particles and thus reduces particle size. This principle is confirmed empirically in FIGS. 2A-B—NLCs with different oil/surfactant ratios were microfluidized for 10 passes at 30,000 psi. The lower oil/surfactant ratio of QG912 helped reduce the Z-average diameter to 63 nm.

In vitro SEAP expression data (data not shown) showed that both QG911 and QG912 promoted higher RNA loading capacity than QG807—optimum SEAP expression for QG911 and QG912 was around 100 µg/ml RNA compared to 40 µg/ml for QG807. In order to load more than 100 µg/ml RNA, the total NLC concentration was increased and QG924 (Z-average=110.6 nm) and QG925 (Z-average=58.6 nm) were manufactured. Both QG924 and QG925 share the same oil/surfactant ratio as QG911 and QG912, respectively, but are approximately 7.4 times more concentrated. In vitro SEAP expression showed that increasing NLC concentration 7.4 times led to further increase in RNA loading capacity (study N1006-214)—the optimal loading capacity for QG924 was around 200 µg/ml and QG925 was around 400 µg/ml or higher. Since QG925 has half the squalene and smaller average particle size than QG924, it is believed that reduction in either the squalene content or particle size or their combination was promoting higher expression. To further support this hypothesis, QG941 and QG942, which have 7.5% w/v squalene (oil/surfactant=1.2) and 3.75% w/v squalene (oil/surfactant=0.6), respectively were manufactured. In vivo SEAP expression experiment with QG924, QG925, QG941 and QG942 showed that reducing oil/surfactant correlates with increase in expression at 1 µg RNA dose.

Example 12. Whole Blood Assay with Various SPANs

Materials

| Name | Comments | Type |
|------|----------|------|
| QG752 | 4.75% Squalene, 0.25% Dynasan 114, 0.5% Span 85, 2% Tween 80 | Nanostructured Lipid Carrier |
| QG766 | 5% Squalene, 0.4% DOTAP, 0.5% Span 85, 2% Tween 80 | Emulsion |
| QG767 | 4.75% Squalene, 0.25% Dynasan 114, 0.4% DOTAP, 0.5% Span 80, 2% Tween 80 | Nanostructured Lipid Carrier |
| QG863 | 4.05% w/v squalene, 0.25% w/v Dynasan 114, 0.43% w/v DOTAP, 0.5% w/v span 60, 2% tween 80 | Nanostructured Lipid Carrier |
| QG868 | 5% Squalene, 0.4% DOTAP, 0.5% Span 60, 2% Tween 80 SLN | Emulsion |
| QG983 | 4.05% w/v squalene, 0.25% w/v dynasan 114, 0.4% w/v DOTAP, 0.5% w/v span 65, 2% w/v tween 80 | Nanostructured Lipid Carrier |
| QG984 | 4.05% w/v squalene, 0.25% w/v dynasan 114, 0.4% w/v DOTAP, 0.5% w/v span 40, 2% w/v tween 80 | Nanostructured Lipid Carrier |
| QG985 | 4.05% w/v squalene, 0.25% w/v dynasan 114, 0.4% w/v DOTAP, 0.5% w/v span 20, 2% w/v tween 80 | Nanostructured Lipid Carrier |
| QG986 | 4.05% w/v squalene, 0.4% w/v DOTAP, 0.5% w/v span 80, 2% w/v Tween 80 | Emulsion |
| QG987 | 4.05% w/v squalene, 0.4% w/v DOTAP, 0.5% w/v span 65, 2% w/v Tween 80 | Emulsion |
| QG988 | 4.05% w/v squalene, 0.4% w/v DOTAP, 0.5% w/v span 40, 2% w/v tween 80 | Emulsion |
| QG989 | 4.05% w/v squalene, 0.4% DOTAP, 0.5% span 20, 2% tween 80 | Emulsion |

Formulations were diluted 1:10 in irrigation-grade saline. 50 µl×16 of each dilution was plated into 96-well U-bottom tissue-grade culture plates. 200 µl of heparinized whole blood from 8 donors, in duplicate, was added to each formulation. After incubating for 24 h at 37° C.-CO2, plasma supernatants were removed and assayed for IL-6, IL-8 (CXCL8), MCP-1 (CCL2), and Mip-1b (CCL4).

The NLC formulation containing span 60 (sorbitan monostearate)—QG863—elicits significantly higher chemokines than all groups except QG983 (NLC with Span 65) and QG987 (CNE with Span 65) (p<0.0001; One-way ANOVA and Tukey's multiple comparisons test). Span 65 is sorbitan tristearate, which is the triacylated version of Span 60. The results suggest that sorbitan esters containing fully saturated C18 acyl chains (stearate groups) are most preferable, specifically the monoacylated version (Span 60) in a NLC composition, to promote the release of multiple chemokines (see FIGS. 15A-D).

Example 13. Evaluation of Single Immunization

VEEV Replicon RNA expressing ZIKV PrM-E was formulated with QG807 (1:1 mixture, RNA concentration 400 ng/μL), and used to immunize C57Bl/6 mice (n=5/group) via the intramuscular route (50 μL formulated RNA/injection/mouse). Serum was collected at indicated timepoints post injection and assayed for ZIKV neutralizing titer by PRNT assay.

Following a single injection, animals immunized with rvRNA alone (either 10 μg or 1 μg dose) had peak titers at D14 post-injection, which declined thereafter, and were undetectable at D85. In contrast, animals immunized with QG807 formulated rvRNA had persistent titers, which were measurable at D85, and in the case of animals receiving 1 μg of rvRNA, had not declined relative to titer measured at D14. A similar pattern was observed in animals receiving two injections of RNA; those receiving rvRNA alone (in 10% sucrose) showed boost of titers, which peaked at D42 and declined to undetectable levels by D120. In contrast, animals receiving QG807 formulated rvRNA had persistent titers, relative to those observed at D42 (FIGS. 18A-B).

Example 14. CD8 T-cell Induction

Mice were immunized with QG807 formulated VEEV-TC83 RNA expressing ZIKV PrM-E vaccine twice (D0, D28) via the intramuscular route. Mice (n=3/group) were euthanized 14 or 49 days post-boost, and splenocytes stained for ZIKV-specific CD8+ T-cells using flow cytometry. Induction of B220loCD8+ T-cells expressing interferon γ (IFNγ+) or CD107a was observed 14 days post-boost in all animals injected with rvRNA. At day 49, animals immunized with QG807 formulated RNA had significantly high levels of CD8+ T-cells compared with RNA-only immunization. (**** $p<0.0001$, one-way ANOVA, FIGS. 19A-B).

Example 15. Low-Dose RNA Protection

C57Bl/6 mice were immunized with replicating (rvRNA) expressing ZIKV-PrM-E. RNA was injected combined with QG942 or in 10% Sucrose at indicated doses. Twenty-eight days post injection, peripheral serum was assayed for ZIKV neutralizing antibody titers, and splenocytes were assayed for were assayed for the presence of antigen specific CD8+ T-cells following restimulation. Formulation dependent significant increases in titer could be observed at 100 ng RNA (One-way ANOVA); formulated RNA induced significantly higher neutralizing antibody and CD8+ T-cell titers than RNA alone at the same dose. Significant increases relative to mock immunized control animals could also be observed at 30 ng of RNA. Induction of antibodies was also observed at 10 ng, but these were not significant relative to controls (FIGS. 20A-B).

Example 16. Antibody Delivery

Antibody delivery clones in a replicon backbone were generated by insertion of antibody sequences downstream of a promoter. IgVH and IgVL variable and constant regions can be separated by either a 2A sequence or an internal ribosome entry site (IRES). Transfection of capped RNA containing antibody heavy and light chains resulted in functional binding antibody. These concentrations were observed with RNA doses/well between 10 μg and 100 μg.

Following detection of antibodies in vitro, an experiment in mice was performed. Briefly, an antibody construct wherein IgVH and IgVL genes were separated by an IRES was complexed with QG942 at and N:P ratio of 15. A dose of 5 μg or 50 μg was injected via intramuscular injection in a total volume of 100 uL (50 uL/1 eg). Serum was collected 7-days post-injection and assayed for antigen specific antibodies using a quantitative ELISA. Injection of 50 μg of QG942 formulated rvRNA resulted in greater antibody titers than injection of 5 μg of naked RNA.

Example 17: Neutralizing Antibodies and CD4+ T-cell Induction

The ID91 replicon (FIG. 29) combined with a prototype NLC formulation, QG807, was compared to a ID91+GLA-SE subunit vaccine in mice given a low dose aerosol of *Mycobacterium tuberculosis* (mtb) H37Rv. Cohorts of C57BL/6 mice (n=3/group) were immunized twice i.m., three weeks apart (prime/boost), with either a vaccine of 0.5 μg ID91 protein and 5 μg GLA-SE or a vaccine of 1 μg ID91-RNA on an Alpha virus backbone and QG807. Splenocytes were isolated two weeks after the last immunization and restimulated in vitro for 6 hours using medium only, ID91 whole protein, one of ten different ID91 peptides-pooled ID91 overlapping peptides, or P+I (total=16) for one full 96 well plate. See Table 4 below. ICS was then performed.

TABLE 4

| | 1<br>1-1 | 2<br>1-2 | 3<br>1-3 | 4<br>1-1 | 5<br>1-2 | 6<br>1-3 | 7<br>2-1 | 8<br>2-2 | 9<br>2-3 | 10<br>2-1 | 11<br>2-2 | 12<br>2-3 |
|---|---|---|---|---|---|---|---|---|---|---|---|---|
| A | Medium | | | Peptide pool #6 | | | Medium | | | Peptide pool #6 | | |
| B | P + I | | | Peptide pool #7 | | | P + I | | | Peptide pool #7 | | |
| C | ID91 protein | | | Peptide pool #8 | | | ID91 protein | | | Peptide pool #8 | | |
| D | Peptide pool #1 | | | Peptide pool #9 | | | Peptide pool #1 | | | Peptide pool #9 | | |
| E | Peptide pool #2 | | | Peptide pool #10 | | | Peptide pool #2 | | | Peptide pool #10 | | |
| F | Peptide pool #3 | | | Peptide pool #11 | | | Peptide pool #3 | | | Peptide pool #11 | | |
| G | Peptide pool #4 | | | Peptide pool #12 | | | Peptide pool #4 | | | Peptide pool #12 | | |
| H | Peptide pool #5 | | | Peptide pool #13 | | | Peptide pool #5 | | | Peptide pool #13 | | |

Mice immunized with rvRNA and protein ID91 vaccines induced CD8+ or CD4+ T cell responses (FIGS. 30A-B, 31A-D and 32A-D). Robust antigen expression with recognition of differential dominant ID91 epitopes was demonstrated depending on immunization with ID91 protein/GLA-SE adjuvant or ID91 rvRNA. Id. For ID91 protein/GLA-SE vaccine, both CD4 and CD8 epitopes were identified. Peptide pools #2, 4, 10, 12, and 13 induced good proliferating and cytokine-producing CD4+ T cells in ID91 protein/GLA-SE immunized C57BL/6 mice. Meanwhile, peptide pools #3, 4, 10, 11, and 12 induced good proliferating and cytokine-producing CD8+ T cells in ID91 protein/GLA-SE immunized C57BL/6 mice. The ID91 subunit Rv3478 may contain dominant epitopes for both CD4 and CD8 T cells. The ID91 RNA+QG807 vaccine generated mainly CD8 epitopes, rather than CD4 epitopes. Peptide pools #8, 9, 10, 12, 13 induced good proliferating and cytokine-producing CD8+ T cells in ID91 RNA+QG807 immunized C57BL/6 mice. ID91 subunit Rv1886 contains most dominant epitopes for CD8+ T cells.

Table 5 depicts epitope mapping of ID91 of 15mer with 8 amino acid sequences overlapping (the epitopes of SEQ ID NOs. 19-133, respectively).

TABLE 5

(see Table 1 for SEQ ID NOs).

| | |
|---|---|
| 1 | HMTINYQFGDVDAHG |
| 2 | FGDVDAHGAMIRAQA |
| 3 | GAMIRAQAGSLEAEH |
| 4 | AGSLEAEHQAIISDV |
| 5 | HQAIISDVLTASDFW |
| 6 | VLTASDFWGGAGSAA |
| 7 | WGGAGSAACQGFITQ |
| 8 | ACQGFITQLGRNFQV |
| 9 | QLGRNFQVIYEQANA |
| 10 | VIYEQANAHGQKVQA |
| 11 | AHGQKVQAAGNNMAQ |
| 12 | AAGNNMAQTDSAVGS |
| 13 | QTDSAVGSSWADDID |
| 14 | SSWADDIDWDAIAQC |
| 15 | DWDAIAQCESGGNWA |
| 16 | CESGGNWAANTGNGL |
| 17 | AANTGNGLYGGLQIS |
| 18 | LYGGLQISQATWDSN |
| 19 | SQATWDSNGGVGSPA |
| 20 | NGGVGSPAAASPQQQ |
| 21 | AAASPQQQIEVADNI |
| 22 | QIEVADNIMKTQGPG |
| 23 | IMKTQGPGAWPKCSS |
| 24 | GAWPKCSSCSQGDAP |
| 25 | SCSQGDAPLGSLTHI |
| 26 | PLGSLTHILTFLAAE |
| 27 | ILTFLAAETGGCSGS |
| 28 | ETGGCSGSRDDVVDF |
| 29 | SRDDVVDFGALPPEI |
| 30 | FGALPPEINSARMYA |
| 31 | INSARMYAGPGSASL |
| 32 | AGPGSASLVAAAKMW |
| 33 | LVAAAKMWDSVASDL |
| 34 | WDSVASDLFSAASAF |
| 35 | LFSAASAFQSVVWGL |
| 36 | FQSVVWGLTVGSWIG |
| 37 | LTVGSWIGSSAGLMA |
| 38 | GSSAGLMAAAASPYV |
| 39 | AAAASPYVAWMSVTA |
| 40 | VAWMSVTAGQAQLTA |
| 41 | AGQAQLTAAQVRVAA |
| 42 | AAQVRVAAAAYETAY |
| 43 | AAAYETAYRLTVPPP |
| 44 | YRLTVPPPVIAENRT |
| 45 | PVIAENRTELMTLTA |
| 46 | TELMTLTATNLLGQN |
| 47 | ATNLLGQNTPAIEAN |
| 48 | NTPAIEANQAAYSQM |
| 49 | NQAAYSQMWGQDAEA |
| 50 | MWGQDAEAMYGYAAT |
| 51 | AMYGYAATAATATEA |
| 52 | TAATATEALLPFEDA |
| 53 | ALLPFEDAPLITNPG |
| 54 | APLITNPGGLLEQAV |
| 55 | GGLLEQAVAVEEAID |
| 56 | VAVEEAIDTAAANQL |
| 57 | DTAAANQLMNNVPQA |
| 58 | LMNNVPQALQQLAQP |
| 59 | ALQQLAQPAQGVVPS |
| 60 | PAQGVVPSSKLGGLW |
| 61 | SSKLGGLWTAVSPHL |
| 62 | WTAVSPHLSPLSNVS |
| 63 | LSPLSNVSSIANNHM |
| 64 | SSIANNHMSMMGTGV |
| 65 | MSMMGTGVSMTNTLH |
| 66 | VSMTNTLHSMLKGLA |
| 67 | HSMLKGLAPAAAQAVE |

TABLE 5-continued (see Table 1 for SEQ ID NOs).

| | |
|---|---|
| 68 | PAAAQAVETAAENGV |
| 69 | ETAAENGVWAMSSLG |
| 70 | VWAMSSLGSQLGSSL |
| 71 | GSQLGSSLGSSGLGA |
| 72 | LGSSGLGAGVAANLG |
| 73 | AGVAANLGRAASVGS |
| 74 | GRAASVGSLSVPPAW |
| 75 | SLSVPPAWAAANQAV |
| 76 | WAAANQAVTPAARAL |
| 77 | VTPAARALPLTSLTS |
| 78 | LPLTSLTSAAQTAPG |
| 79 | SAAQTAPGHMLGGLP |
| 80 | GHMLGGLPLGHSVNA |
| 81 | PLGHSVNAGSGINNA |
| 82 | AGSGINNALRVPARA |
| 83 | ALRVPARAYAIPRTP |
| 84 | AYAIPRTPAAGFSRP |
| 85 | PAAGFSRPGLPVEYL |
| 86 | PGLPVEYLQVPSPSM |
| 87 | LQVPSPSMGRDIKVQ |
| 88 | MGRDIKVQFQSGGNN |
| 89 | QFQSGGNNSPAVYLL |
| 90 | NSPAVYLLDGLRAQD |
| 91 | LDGLRAQDDYNGWDI |
| 92 | DDYNGWDINTPAFEW |
| 93 | INTPAFEWYYQSGLS |
| 94 | WYYQSGLSIVMPVGG |
| 95 | SIVMPVGGQSSFYSD |
| 96 | GQSSFYSDWYSPACG |
| 97 | DWYSPACGKAGCQTY |
| 98 | GKAGCQTYKWETFLT |
| 99 | YKWETFLTSELPQWL |
| 100 | TSELPQWLSANRAVK |
| 101 | LSANRAVKPIGSAAI |
| 102 | KPTGSAAIGLSMAGS |
| 103 | IGLSMAGSSAMILAA |
| 104 | SSAMILAAYHPQQFI |
| 105 | AYHPQQFIYAGSLSA |
| 106 | IYAGSLSALLDPSQG |

TABLE 5-continued (see Table 1 for SEQ ID NOs).

| | |
|---|---|
| 107 | ALLDPSQGMGPSLIG |
| 108 | GMGPSLIGLAMGDAG |
| 109 | GLAMGDAGGYKAADM |
| 110 | GGYKAADMWGPSSDP |
| 111 | MWGPSSDPAWERNDP |
| 112 | PAWERNDPTQQIPKL |
| 113 | PTQQIPKLVANNTRL |
| 114 | LVANNTRLWVYCGNG |
| 115 | LWVYCGNGTPNELGG |
| 116 | GTPNELGGANIPAEF |
| 117 | GANIPAEFLENFVRS |
| 118 | FLENFVRSSNLKFQD |
| 119 | SSNLKFQDAYNAAGG |
| 120 | DAYNAAGGHNAVFNF |
| 121 | GHNAVFNFPPNGTHS |
| 122 | FPPNGTHSWEYWGAQ |
| 123 | SWEYWGAQLNAMKGD |
| 124 | QLNAMKGDLQSSLGA |
| 125 | AMKGDLQSSLGAGKL |

Figure 33A:
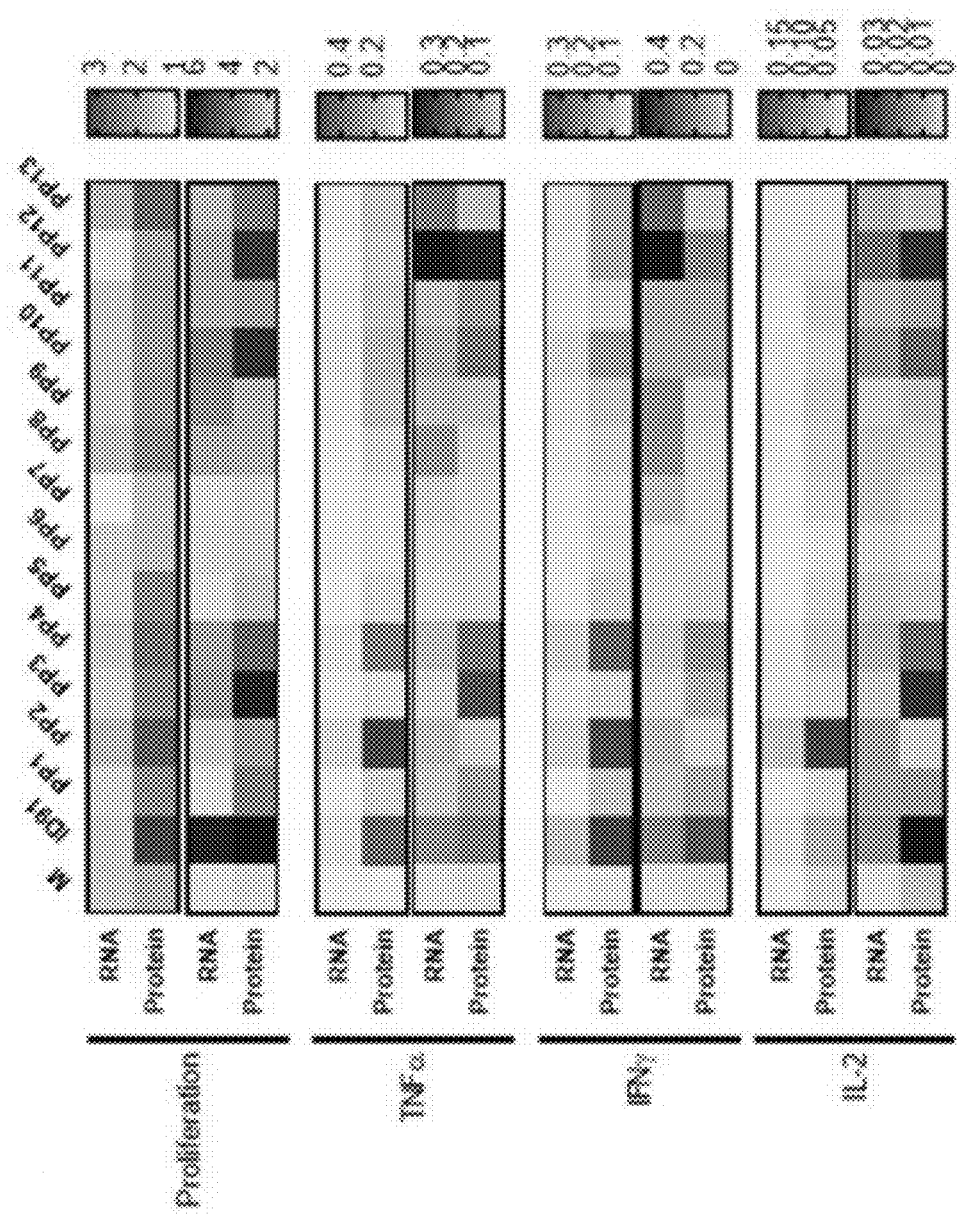

Cohorts of female C57BL/6 mice (n=4/group) were immunized by the i.m. route one time with saline, ID91+GLA-SE, or an ID91-RNA vaccine, and spleens were harvested 3 weeks later for assessment of T cell phenotypes. The results are represented as the percentage of CD4+/CD44+, or the percentage of CD8+ T cells expressing IFNg, IL-2, and TNF (FIG. 33A). Statistical significance of p<0.05 was analyzed using two-way ANOVA and is depicted by an asterisk. Following one immunization, the ID91+GLA-SE (protein) vaccine induced a TH1 CD4 T cell response, characterized by the induction of IFNα, TNF and IL-2, whereas the ID91-RNA vaccine was able to induce a significant CD4+ IL-2 response. Neither vaccine generated a significant CD8+ T cell response after one immunization in this experiment.

Figure 33B:
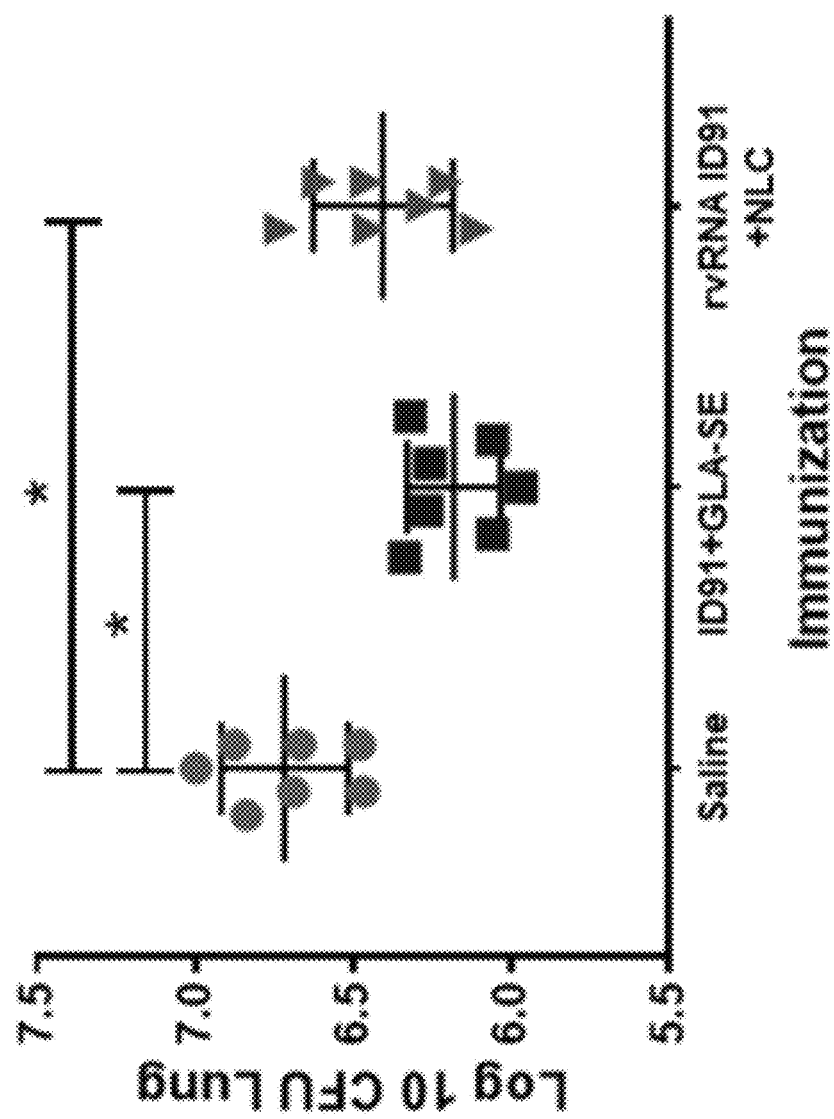

Efficacy against Mtb H37Rv was also demonstrated in vivo. Cohorts of female C57BL/6 mice (n=7/group) were immunized once with 1 µg of ID91+GLA-SE, ID91-RNA construct on an Alpha virus backbone, or saline, 3 weeks prior to challenge with Mtb H37Rv. Bacterial burden was assessed from lung homogenates 3 weeks post challenge with Mtb H37Rv (FIG. 33B). Results represent the Log 10 bacterial counts (colony forming units; CFU) within the lungs of mice 3 weeks after challenge. Significance of p<0.05 compared to Saline was analyzed using one-way ANOVA with Dunnetts multiple comparisons test and is depicted by an asterisk. Both ID91+GLA-SE and the ID91-RNA vaccine were effective after one immunization against infection with Mtb H37Rv, as measured by a reduction in bacterial load within the lung three weeks after infection.

Example 18. In Vitro Stimulation with NLC Formulated Ligands of Nucleic Acid Receptors Nucleic acid agonists engineered to mimic viral genetic material are potent innate immune stimulators and can drive a TH1-biased adaptive immune response against cancer and infectious diseases. See Temizoz et al., Curr Opin Pharmacol 41:104-113 (2018); Iurescia et al., Front Immunol 9:711 (2018); Reed et al., Nat Med 19(12):1597-608 (2013). Depending on the structure and location, nucleic acid agonists bind with either endosomal (TLR3, TLR7/8, TLR9) or cytosolic (RLRs, STING-I) sensors and stimulate interferon and other chemotactic cytokine production. TLR3 and RIG-1 sensors are also known to promote cross-presentation of antigens on MHC I proteins, thus activating CD8+ T cells that mature to form antigen-specific cytotoxic T lymphocytes (CTLs). See Jelinek et al., J Immunol 186(4):2422-9 (2011); Hochheiser et al., J Immunol 196(6):2439-43 (2016); Schmidt et al., Front Immunol 9:898 (2018). Here it is demonstrated that TLR3 (dsRNA) and RIG-1 (dsRNA with a triphosphate at the 5' end) agonists formulated with nanostructured lipid carriers (NLCs) significantly enhance in vitro chemokine induction relative to naked agonist in both primary, human PBMC-derived dendritic cells, and the mono-mac-6 (MM6) cell line.

Materials: poly(I:C):HMW is a synthetic dsRNA analog that can activate TLR3 and RIG-I/MDA5 pathways and was purchased from Invivogen. Riboxxol is a 50 bp synthetic TLR3 dsRNA agonist purchased from Riboxx GmBH. SEVDI (Sendai virus defective interfering) is a dsRNA RIG-1 agonist with a 5'-triphosphate terminal group and was synthesized according to a previously published protocol. Martinez-Gil et al., J Virol 87(3):1290-300 (2013). NLC formulation was manufactured by IDRI using commercially available reagents, including DOTAP (N-[1-(2,3-Dioleoyloxy)propyl]-N,N,N-trimethylammonium chloride) from Corden Pharma, Dynasan® 114 (glyceryl trimyristate) from Sasol Limited, and the following from Sigma-Aldrich: squalene, Span® 60 (sorbitan monostearate), Tween® 80 (ethoxylated sorbitan monooleate) and sodium citrate dihydrate.

NLC manufacturing method: An oil phase consisting squalene, the solid lipid glyceryl trimyristate (Dynasan® 114), the non-ionic surfactant sorbitan monostearate (Span® 60), and the cationic lipid DOTAP, was prepared in a 100 ml beaker and heated to 60° C. in a pre-heated water batch. The aqueous phase consisting 10 mM sodium citrate dihydrate and the non-ionic surfactant Tween® 80 was prepared in a separate 100 ml beaker and equilibrated to 60° C. Following complete dissolution of the solid components, the oil and aqueous phases were combined by adding the aqueous phase to the oil phase. The biphasic mixture was homogenized with a high-speed laboratory emulsifier (Silverson Machines, Inc.) to produce micron-sized NLC droplets. The crude NLC mixture was further processed in a M-110P microfluidizer (Microfluidics, Corp.) for 10 discrete passes at 30,000 psi. Final particle size, as measured by Dynamic Light Scattering (DLS), was between 40-50 nm (z-average diameter) with a polydispersity index (PDI) between 0.1-0.2. The microfluidized formulation was terminally filtered with a 0.2 μm polyethersulfone membrane syringe filter and stored at 2-8° C. Physicochemical properties of an exemplary NLC formulation (QG942) are provided in Table 6.

TABLE 6

| NLC Lot# | DOTAP [% w/v] | Span 60 [% w/v] | Tween 80 [% w/v] | Squalene [% w/v] | Dynasan 114 [% w/v] | Z-average [nm] (PDI) | Zeta potential [mV] | pH |
|---|---|---|---|---|---|---|---|---|
| QG942 | 3.0 | 3.7 | 3.7 | 3.75 | 0.25 | 40.55 (0.20) | 28.4 ± 1.27 | 5.78 |

PBMC-DCs stimulation method: RNA adjuvants were mixed with NLC at various nitrogen:phosphate (N:P) ratios and allowed to form an electrostatically-associated complex by incubation for 30 minutes on ice. Plated cells were stimulated with complexed material at various RNA doses to generate a dose response curve. In FIGS. 39A-E, PBMC-DCs from six human donors were stimulated with polyIC:HMW, Riboxxol or SEVDI, either formulated with NLC ("QG942 formulated") or naked ("unformulated"). Formulation-only control is labeled "media ctrl". After 24 hours incubation at 37° C. and 5% CO2 atmosphere, supernatants were assayed for concentration of innate immune markers using commercially available ELISA kits. Statistical analysis was performed by 2-way ANOVA with Sidak's multiple comparisons test. P-values: * $p<0.05$,  $p<0.005$, * $p<0.0005$, **** $p<0.0001$.

Formulation screen in MM6 cells: Riboxxol and pIC:HMW were complexed with exemplary cationic formulations of Table 7 at N:P of 15 and incubated overnight with MM6 cells after which supernatants were collected and assayed for IFNα/β (FIG. 40). MM6 cells stimulated with NLC formulated Riboxxol induced 20-30 times greater IFNα/β secretion relative to unstimulated control. A detailed analysis of IFNα/β induction by NLC formulated riboxxol is summarized in a heatmap (FIG. 41).

TABLE 7

| Name | Description | Z-average [nm] (PDI) at date of manufacturing |
|---|---|---|
| QG942 | Nanostructured Lipid Carrier | 40.55 (0.198) |
| QG843 | Cationic nanoemulsion (CNE) manufactured according to Brito et al | 95.04 (0.092) |
| QH007 | 4 mgCa/ml hydroxyapatite nanoparticles (Sigma-Aldrich catalog# 900194) stabilized with 2 mg/ml chitosan (Sigma catalog# 448877) | 101.3 (0.164) |
| QH005 | 4 mgCa/ml hydroxyapatite nanoparticles (Sigma-Aldrich catalog# 900194) stabilized with 2 mg/ml chitosan (Polysciences catalog# 21161) | 91.8 (0.177) |
| QH006 | 4 mgCa/ml hydroxyapatite nanoparticles (Sigma-Aldrich catalog# 900194) stabilized with 2 mg/ml chitosan (Sigma catalog# 448869) | 77.93 (0.184) |

TABLE 7-continued

| Name | Description | Z-average [nm] (PDI) at date of manufacturing |
|---|---|---|
| QH008 | 4 mgCa/ml hydroxyapatite nanoparticles (Sigma-Aldrich catalog# 900194) stabilized with 2 mg/ml chitosan (Sigma catalog# 419419) | 93.69 (0.186) |
| QH009 | 2 mgAl/ml Alhydrogel treated with phosphate buffer, then stabilized with 1 mg/ml chitosan (Polysciences catalog# 21161) | 294.1 (0.217) |
| QH142 | 2 mgAl/ml Alhydrogel treated with phosphate buffer, then stabilized with 1 mg/ml chitosan (Sigma catalog# 419419) | 304.8 (0.291) |
| QH141 | 2 mgAl/ml Alhydrogel treated with phosphate buffer, then stabilized with 1 mg/ml chitosan (Sigma catalog# 448877) | 318.3 (0.288) |
| QH140 | 2 mgAl/ml Alhydrogel treated with phosphate buffer, then stabilized with 1 mg/ml chitosan (Sigma catalog# 448869) | 347.4 (0.307) |
| QH115 | 9 mgAl/ml Alhydrogel stabilized with 7.5 mg/ml polyacrylic acid (Polysciences catalog# 06519) | 72.2 (0.200) |
| QH011 | 9 mgAl/ml Alhydrogel stabilized with 30 mg/ml polyacrylic acid (Sigma catalog# 535931) | 77.28 (0.144) |

Double-stranded RNA (dsRNA) adjuvants are enhanced by formulating with NLCs (WG942). Replicon RNA (ssRNA) encoding SEAP was co-formulated with dsRNA (dsRNA tested included Toil-like receptor 3 (TLR3) ligands such as Poly(IC) (synthetic 1.5-1.8 kb analog of dsRNA from Invivogen), Riboxxol (50 bp synthetic dsRNA from Riboxx, SEVDI (in vitro transcribed approximately 550 bp sendai virus defecting interfering RNA) or media control to evaluate the effect of adjuvant stimulation on protein expression (FIGS. 35A-E and 36A-D).

The dsRNA adjuvants were found to knock down SEAP expression in HEK293 cells. See, e.g., FIG. 37 (Venezuelan equine encephalitis virus (VEE) replicon (VEErep) encoding SEAP+TLR3 ligand+NLC). Further, VEErep translation in human DCs transfected in vitro in reduced 10% serum containing media demonstrated increased expression of SEAP and IP-10 (FIGS. 38A-B).

Example 19: Enhancement of Immunogenic Responses

Immunogenic responses to adjuvants, such as TLR3 ligands, may also be enhanced, separately or in addition to the use of NLC, by formulation with stable oil-in-water emulsions, such as emulsions comprising squalene. The following experiments examine the impact of formulation on the immunogenic responses supported by Hiltonol®. Hiltonol® (poly-ICLC) is a synthetic complex of carboxymethylcellulose, polyinosinic-polycytidylic acid double-stranded RNA, and poly-L-lysine.

5 mice per formulation group in Table 8 were used to generate antigen-specific antibody responses (expressed as endpoint titer) and antigen-specific recall of spleen cells (determined by 4 day incubation with antigen then cytokine ELISA). A synthetic lipid-A (SLA) derivative related to glucopyranosyl lipid A (GLA), was previously described in Coler et al., PloS one 6(1):e16333 (2011). SLA was combined with a stable oil-in-water emulsion (SE), see Van Hoeven et al., PLoS One. 11(2): e0149610 (2016), to form SLA-SE containing squalene.

TABLE 8

| Group | F2 protein | Hiltonol ® dose | Formulation (admixture) |
|---|---|---|---|
| 1 (protein control) | 1 µg | — | saline |
| 2 (baseline Hiltonol ® control) | 1 µg | 10 | saline |

TABLE 8-continued

| Group | F2 protein | Hiltonol ® dose | Formulation (admixture) |
|---|---|---|---|
| 3 (100 µg aluminum/mouse) | 1 µg | — | nanoAlum 2/PEG |
| 4 (100 µg aluminum/mouse) | 1 µg | 10 | nanoAlum 2/PEG |
| 5 | 1 µg | — | SE |
| 6 | 1 µg | 10 | SE |
| 7 (positive control) | 1 µg | — | SLA-SE |
| 8 (negative control) | — | — | — |

SLA = synthetic lipid A;
SE = stable emulsion;
nanoAlum2/PEG = nAlum PEG200-DSPE.

The stable emulsion (SE) of Table 8 above and Tables 10-13 below comprised the exemplary formulation in Table 9 below and was prepared as follows. SE consists of metabolizable oil (squalene) emulsified with dimyristoyl phosphatidylcholine and poloxamer. Emulsion droplets are ~100 nm in diameter and monodisperse. Preparing a 5× concentrate allows for mixing with vaccine antigen immediately prior to immunization. To manufacture SE, oil and aqueous phases were prepared separately. For the oil phase, 0.76 g of dimyristoyl phosphatidylcholine (DMPC) powder was added to 3.4 g of squalene. The bottle containing DMPC and oil was placed in a sonicating water bath heated to 70° C. until the DMPC was dispersed in the oil. For the aqueous phase, ammonium phosphate monobasic, ammonium phosphate dibasic, poloxamer 188, and glycerol were added to ultrapure water and sonicated to create an aqueous phase containing 27 mM ammonium phosphate buffer, 25 mg/mL glycerol, and 0.4 mg/mL poloxamer 188 with pH 6.25. The oil (10% by volume) and aqueous phases (90% by volume) were then combined and processed by high shear mixing for 10 min at 7,000-10,000 rpm (using a Silverson L5M-A with a ¾ in. tubular mixing assembly and square hole high shear screen mixing head) to create a crude emulsion. The crude emulsion was then processed by high pressure homogenization for 16 cycles at 30,000 psi (e.g. using a M-110P Microfluidics® processor) and water-cooled with a recirculating chiller set to 10° C. The final formulation was filtered under constant flow via a peristaltic pump through a 0.2-µm PVDF membrane and filled into vials. Characterization included quantitation of squalene by gas chromatography, quantitation of DMPC by HPLC with charged aerosol detection, measurement of particle size by dynamic light scattering, measurement of pH, and assessment of visual appearance. All values were within expected ranges. The formulation was diluted from 10% to 2% for injection.

TABLE 9

| Ingredient | Concentration |
| --- | --- |
| Aqueous phase | 90.0% v/vol |
| Glycerol | 1.8% v/vol |
| Ammonium phosphate monobasic | 23.67 mM |
| Ammonium phosphate dibasic | 1.296 mM |
| Squalene | 10.0% v/vol |
| Poloxamer 188 (copolymer of polyoxyethylene and polyoxypropylene) | 0.09% w/vol |
| 1,2-dimyristoyl-sn-glycero-3-phosphocholine (DMPC) | 1.9% w/vol |

Mice were immunized with of recombinant LEISH-F2 protein plus adjuvant formulation in a total volume of 0.1 ml. The mice were immunized subcutaneously two times with an interval of three weeks between injections. Injection was at the base of the tail of a total of 1 µg/dose protein and 10 µg/dose Hiltonol®. After immunizations, blood was collected, serum prepared and analyzed for antigen-specific antibody responses to determine if immunization elicited a response. Serum from immunized mice was titrated to find endpoint titer (last optical density (OD) value greater than a threshold determined by sera from unimmunized mice). The antigen-specific antibody response was analyzed for total IgG against the specific antigen, and also IgG2 and IgG1 isotypes to reveal any immune bias (given that IFNγ stimulates IgG2a/c responses while IL-4/5 stimulate IgG1 responses) (FIG. 45).

Figure 47B:
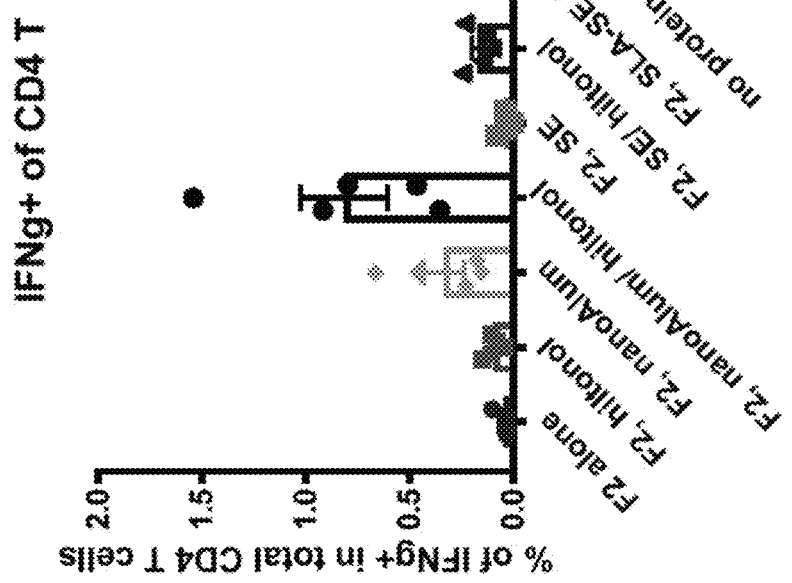
Figure 47A:
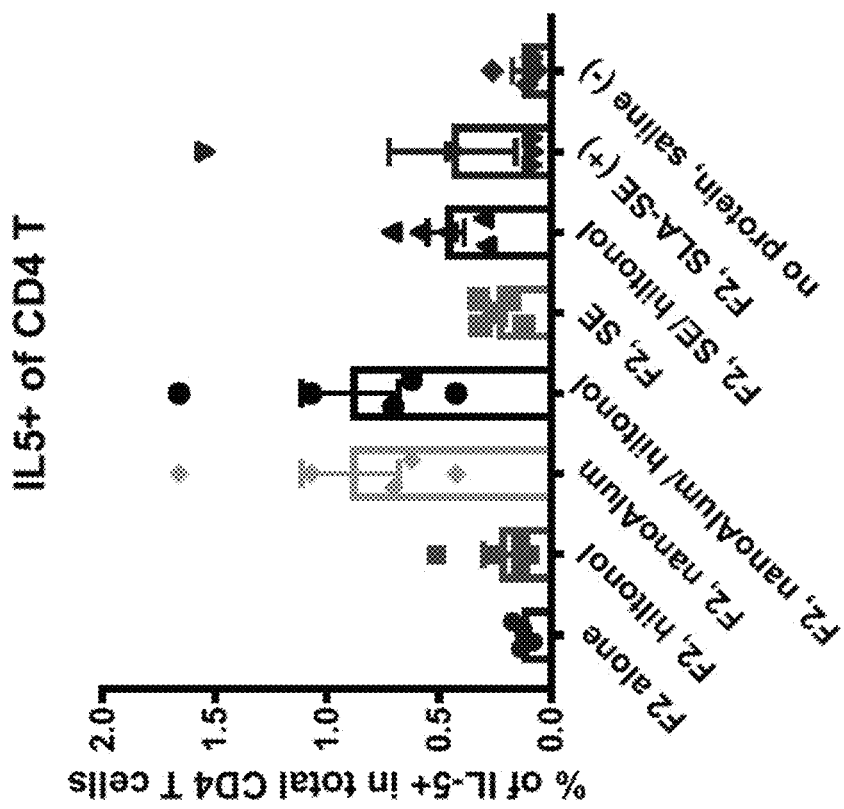
Figure 47C:
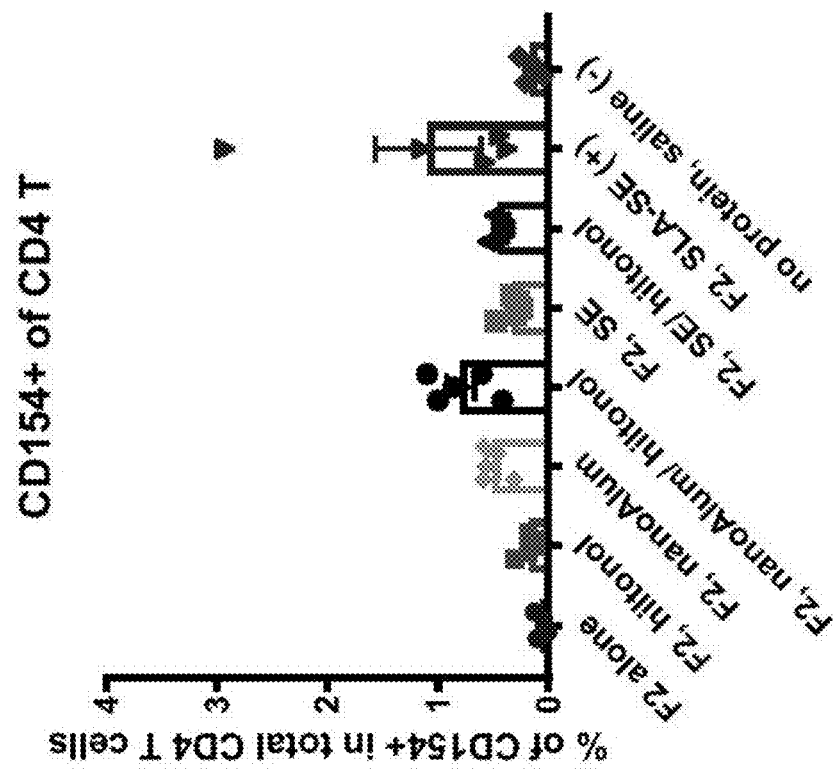
Figure 47D:
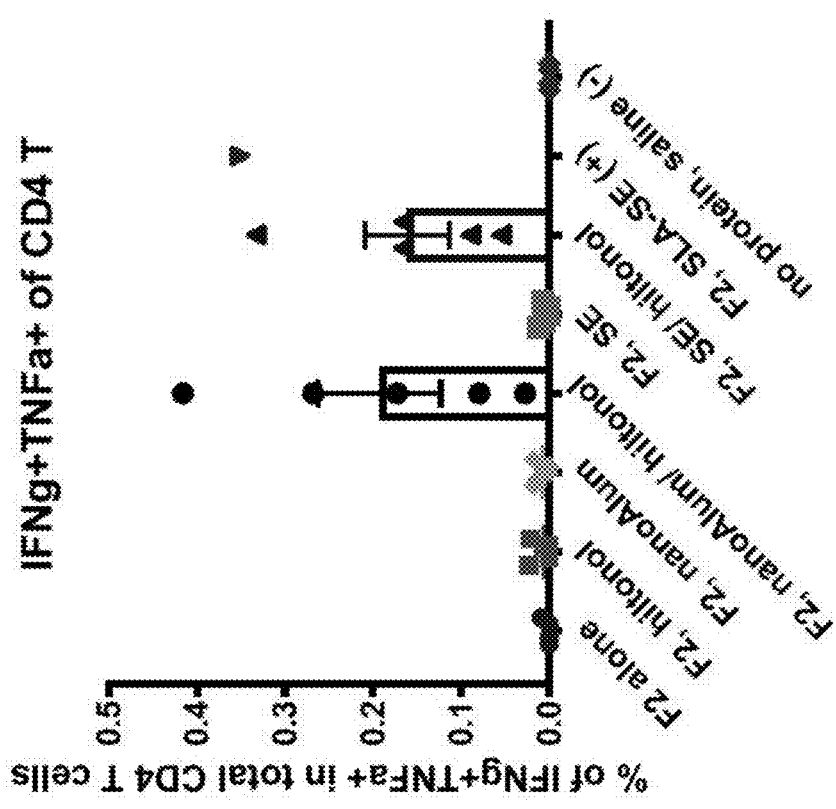
Figure 47E:
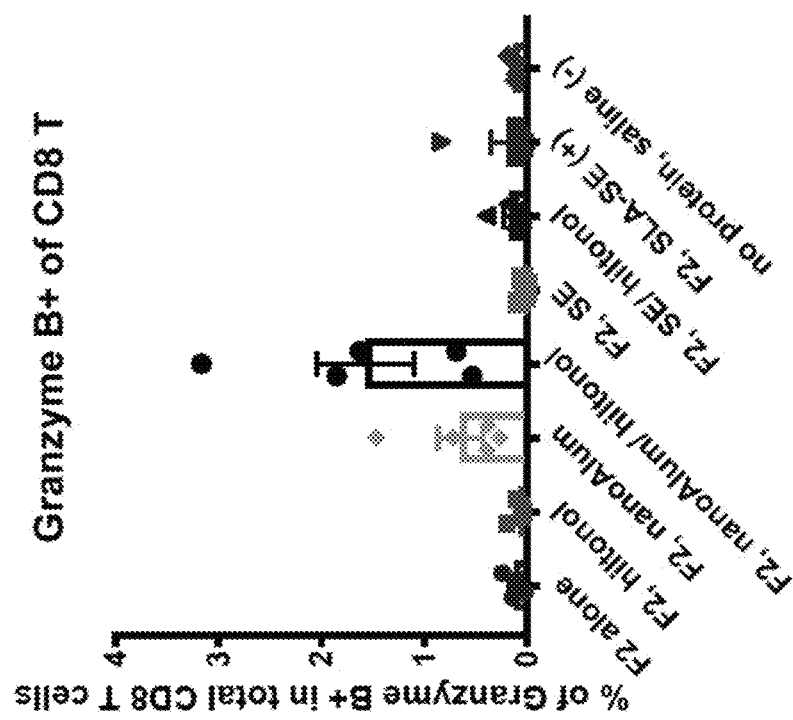

Twenty-one days after the final immunization, animals were killed and their spleens removed. Single cell suspensions are prepared and 2×105 cells/well incubated with 10 mg/ml recombinant antigen (LEISH-F2 antigen) to assess antigen-specific recall responses. The secretion of cytokines into the culture supernatant after 4 days was determined by cytokine ELISA according to the manufacturer's instructions (eBioScience)). See IL-5 in FIG. 46A and FIG. 47A. The Thelper1 profile is characterized by IFNγ secretion (FIG. 46B and FIG. 47B). See also IFNγ+TNFa+ in FIG. 47C, CD154+ in FIG. 47C, and Granzyme B+ in FIG. 47E.

After a prime, unlike Hiltonol® alone, the admixture formulation of Hiltonol® in SE or nanoalum elicited antigen-specific antibodies. After a boost, Hiltonol®/SE provided the strongest antigen-specific IgG2c responses. Further, the admixture formulation of Hiltonol® in SE or nanoalum elicited antigen-specific IFNγ recall responses.

Similar results were demonstrated in another study with 7 female mice per formulation group in Table 10 used to generate antigen-specific antibody responses (expressed as endpoint titer) and antigen-specific recall of spleen cells (determined by 4 day incubation with antigen then cytokine ELISA). (data not shown)

TABLE 10

| Group | F2 protein (µl) | Hiltonol ® dose (µl) | Formulation (µl) | Saline (µl) |
| --- | --- | --- | --- | --- |
| 1 (protein control) | 14 | 0 | 0 | 686 |
| 2 (baseline Hiltonol ® control) | 14 | 35 | 0 | 651 |
| 3 | 14 | 0 | 350 Alum | 336 |
| 4 | 14 | 35 | 350 Alum | 301 |
| 5 | 14 | 0 | 175 nan0Alum | 511 |
| 6 | 14 | 35 | 175 nanoAlum | 476 |
| 7 | 14 | 0 | 140 SE | 546 |
| 8 | 14 | 35 | 140 SE | 511 |
| 9 | 14 | 0 | 140 SLA-SE | 546 |
| 10 (negative control) | 0 | 0 | 0 | 700 |

Hiltonol ® (10 µg) 2 mg/ml, Alum = (100 µg) AL007 2 mg/ml, nanoAlum = (100 µg) nAlum PEG2000-DSPE 4 mg/ml.

C75BL/6 mice (5 per group) were also immunized with recombinant LEISH-F3+ protein plus adjuvant formulation in a total volume of 0.1 ml. The mice were immunized subcutaneously once by injection of 100 µl to the scruff of their neck with a total of 1 mg/dose protein and either 50, 10 or 2 mg/dose Hiltonol® in various formulations in Table 9.

TABLE 11

| Group | F3+ (NSDC) protein | Hiltonol ® dose | Formulation (admixture) |
| --- | --- | --- | --- |
| 1 (negative control) | — | — | — |
| 2 (protein control) | 1 µg | — | saline |
| 3 (top Hiltonol ® control) | 1 µg | 50 | saline |
| 4 (mid Hiltonol ® control) | 1 µg | 10 | saline |
| 5 (low Hiltonol ® control) | 1 µg | 2 | saline |
| 6 | 1 µg | 10 | nanoAlum 2, PEG |
| 7 | 1 µg | 2 | nanoAlum 2, PEG |
| 8 (formulation control) | 1 µg | — | nanoAlum 2, PEG |
| 9 | 1 µg | 10 | SE |
| 10 | 1 µg | 2 | SE |
| 11 (formulation control) | 1 µg | — | SE |

After immunization, blood was collected, serum prepared and analyzed for antigen-specific antibody responses to determine if immunization has elicited a response. Serum from immunized mice was titrated to find end point titer (last optical density (GD) value greater than a threshold determined by sera from unimmunized mice). The antigen-specific antibody response is analyzed for total IgG against the LEISH-F3+ antigen (FIGS. 48-49).

After a prime, the admixture formulation of Hiltonol® in SE or nanoalum elicited a greater antigen-specific antibody response than Ag Hiltonol® alone, and the admixture formulation of Hiltonol® in SE enhanced the antigen-specific IFNg recall responses over ag in Hiltonol® and Ag/Hiltonol®/nanoalum. The study also demonstrated that CD8 T cells can be generated by prime with Ag/Hiltonol®/SE, dose-sparing appears >25 fold, and 2 µg Hiltonol® in SE elicits responses >50 µg unformulated Hiltonol® (FIGS. 48-51).

In another study, the impact of antigen vaccine delivery on immunogenic responses was examined with a single administration (prime) of a formulation of Table 10 to C75BL/6 mice. See FIG. 50.

TABLE 12

| Group | F3+ (NSDC) protein | TLR3 agonist | TLR3 agonist dose (µg) | Formulation (admixture) |
|---|---|---|---|---|
| 1 (negative control) | — | — | — | — |
| 2 (protein control) | 1 µg | — | — | saline |
| 3 | 1 µg | PolyI:C LMW | 10 | saline |
| 4 | 1 µg | PolyI:C LMW | 10 | SE |
| 5 (poly:C HMW control) | 1 µg | PolyI:C HMW | 10 | saline |
| 6 | 1 µg | PolyI:C HMW | 10 | SE |
| 7 (poly I:C low dose) | 1 µg | PolyI:C LMW | 2 | SE |
| 8 (poly I:C low dose) | 1 µg | PolyI:C HMW | 2 | SE |
| 9 (formulation control) | 1 µg | — | — | SE |

In another study, C75BL/6 mice (5 per group, 5 for immune responses after prime, 5 for after boost) were administered one of the formulations of Table 12 to examine the impact of antigen vaccine delivery on the immunogenic responses.

TABLE 13

| Group | F3+ (NSDC) protein | TLR3 agonist | TLR3 agonist dose (µg) | Formulation (admixture) |
|---|---|---|---|---|
| 1 (negative control) | — | — | — | — |
| 2 (protein control) | 1 µg | — | — | Saline |
| 3 (top Hiltonol ® control) | 1 µg | Hiltonol ® | 50 | saline |
| 4 (mid Hiltonol ® control) | 1 µg | Hiltonol ® | 10 | saline |
| 5 (low Hiltonol ® control) | 1 µg | Hiltonol ® | 2 | saline |
| 6 | 1 µg | Hiltonol ® | 10 | SE |
| 7 | 1 µg | Hiltonol ® | 2 | SE |
| 8 (poly:C LMW control) | 1 µg | PolyI:C LMW | 10 | saline |
| 9 | 1 µg | PolyI:C LMW | 10 | SE |
| 10 | 1 µg | PolyI:C LMW | 2 | SE |
| 11 (poly:C HMW control) | 1 µg | PolyI:C HMW | 10 | saline |
| 12 | 1 µg | PolyI:C HMW | 10 | SE |
| 13 | 1 µg | PolyI:C HMW | 2 | SE |
| 14 (formulation control) | 1 µg | — | — | SE |

SE formulation of Hiltonol® led to dose-sparing for antigen-specific IFNγ induction, with suppression of IL-5 response (FIGS. 51-52). Responses to MHC I-restricted peptides (C+B) were not observed (FIGS. 52C-D).

What is claimed is:

1. A composition comprising nanostructured lipid carrier (NLC) particles for delivery of a bioactive agent to a cell, wherein the NLC particles comprise:
   (a) an oil core comprising a mixture of a liquid phase lipid and a solid phase lipid that is trimyristin;
   (b) a cationic lipid;
   (c) a sorbitan ester;
   (d) a hydrophilic surfactant; and
   (e) the bioactive agent,
   wherein relative amounts and specific components of the composition are selected such that when the bioactive agent is replicating viral RNA (rvRNA) encoding secreted alkaline phosphatase (SEAP), the highest peak expression of the bioactive agent occurs at a N:P molar ratio of 15 as measured by an in vitro SEAP expression assay using a SEAP-expressing replicon and measured by relative luminescence units (RLUs).

2. The composition of claim 1, wherein the sorbitan ester is sorbitan monostearate.

3. The composition of claim 1, wherein the bioactive agent is not encapsulated by the NLC particles and is associated with the surface of the NLC particles.

4. The composition of claim 1, wherein the bioactive agent is a protein, encodes a protein, is a protein antigen, encodes a protein antigen, is RNA, is DNA, is mRNA, is oncolytic viral RNA, is non-coding RNA, or is an adjuvant.

5. The composition of claim 1, wherein the average polydispersity index of the NLC particles is from 0.1 to about 0.5.

6. The composition of claim 1, wherein the z-average diameter of the NLC particles is from about 40 nm to about 80 nm.

7. The composition of claim 1, having an oil to surfactant molar ratio of about 0.5 to about 12.

8. The composition of claim 7, having an oil to surfactant molar ratio of about 0.5.

9. The composition of claim 1, having a hydrophilic surfactant to cationic component ratio of about 0.6.

10. A method of making the composition of claim 1, comprising:

(a) mixing the solid phase lipid, the liquid phase lipid, the cationic lipid, and the sorbitan ester to form an oil phase mixture;
(b) mixing the hydrophilic surfactant and water to form an aqueous phase mixture; and
(c) mixing the oil phase mixture with the aqueous phase mixture to form the NLC particles.

11. A method of generating or enhancing an immune response comprising administering to a subject in need thereof a therapeutically effective amount of the composition of claim 1, wherein the bioactive agent is an antigen or encodes an antigen.

12. The composition of claim 1, further comprising a citrate buffer.

13. The composition of claim 1, wherein the amount of hydrophilic surfactant is no greater than about 35% of the sum of the mass of the hydrophilic surfactant, sorbitan ester, and cationic lipid.

14. A composition comprising nanostructured lipid carrier (NLC) particles for delivery of a bioactive agent to a cell, wherein the NLC particles comprise:

(a) an oil core comprising a mixture of a liquid phase lipid that is squalene and a solid phase lipid that is trimyristin;
(b) a cationic lipid that is DOTAP;
(c) a sorbitan ester that is sorbitan monostearate;
(d) a hydrophilic surfactant that is polysorbate 80; and
(e) the bioactive agent, wherein the NLC particles comprise about 3.75% w/v liquid phase lipid, about 0.25% w/v solid phase lipid, about w/v 3% cationic lipid, about 3.7% w/v sorbitan ester, and about 3.7% w/v hydrophilic surfactant.

15. The composition of claim 14, wherein the bioactive agent is not encapsulated by the NLC particles and is associated with the surface of the NLC particles.

16. The composition of claim 14, wherein the bioactive agent is a protein, encodes a protein, is a protein antigen, encodes a protein antigen, is RNA, is DNA, is mRNA, is oncolytic viral RNA, is non-coding RNA, or is an adjuvant.

17. The composition of claim 14, wherein the average polydispersity index of the NLC particles is from 0.1 to about 0.5.

18. The composition of claim 14, wherein the z-average diameter of the NLC particles is from about 40 nm to about 80 nm.

19. The composition of claim 14, having an oil to surfactant molar ratio of about 0.5 to about 12.

20. The composition of claim 19, having an oil to surfactant molar ratio of about 0.5.

21. The composition of claim 14, having a hydrophilic surfactant to cationic lipid ratio of about 0.2 to about 1.5.

22. The composition of claim 21, having a hydrophilic surfactant to cationic component ratio of about 0.6.

23. A method of making the composition of claim 14, comprising:

(a) mixing the solid phase lipid, the liquid phase lipid, the cationic lipid, and the sorbitan ester to form an oil phase mixture;
(b) mixing the hydrophilic surfactant and water to form an aqueous phase mixture; and (c) mixing the oil phase mixture with the aqueous phase mixture to form the NLC particles.

24. A method of generating or enhancing an immune response comprising administering to a subject in need thereof a therapeutically effective amount of the composition of claim 14, wherein the bioactive agent is an antigen or encodes an antigen.

25. The composition of claim 14, further comprising a citrate buffer.

26. A composition comprising nanostructured lipid carrier (NLC) particles for delivery of a bioactive agent to a cell, wherein the NLC particles comprise:
(a) an oil core comprising a mixture of a liquid phase lipid that is squalene and a solid phase lipid that is trimyristin;
(b) a cationic lipid that is DOTAP;
(c) a sorbitan ester that is sorbitan monostearate;
(d) a hydrophilic surfactant that is polysorbate 80; and
(e) the bioactive agent,
wherein a hydrophilic surfactant to cationic lipid molar ratio is about 0.2 to about 1.5.

27. The composition of claim 26, wherein the bioactive agent is not encapsulated by the NLC particles and is associated with the surface of the NLC particles.

28. The composition of claim 26, wherein the bioactive agent is a protein, encodes a protein, is a protein antigen, encodes a protein antigen, is RNA, is DNA, is mRNA, is oncolytic viral RNA, is non-coding RNA, or is an adjuvant.

29. The composition of claim 26, wherein the average polydispersity index of the NLC particles is from 0.1 to about 0.5.

30. The composition of claim 26, wherein the z-average diameter of the NLC particles is from about 40 nm to about 80 nm.

31. The composition of claim 26, having an oil to surfactant molar ratio of about 0.5 to about 12.

32. The composition of claim 31, having an oil to surfactant molar ratio of about 0.5.

33. The composition of claim 26, having a hydrophilic surfactant to cationic component ratio of about 0.6.

34. A method of making the composition of claim 26, comprising:
(a) mixing the solid phase lipid, the liquid phase lipid, the cationic lipid, and the sorbitan ester to form an oil phase mixture;
(b) mixing the hydrophilic surfactant and water to form an aqueous phase mixture; and
(c) mixing the oil phase mixture with the aqueous phase mixture to form the NLC particles.

35. A method of generating or enhancing an immune response comprising administering to a subject in need thereof a therapeutically effective amount of the composition of claim 26, wherein the bioactive agent is an antigen or encodes an antigen.

36. The composition of claim 26, further comprising a citrate buffer.

37. The composition of claim 26, wherein the amount of hydrophilic surfactant is no greater than about 35% of the sum of the mass of the hydrophilic surfactant, sorbitan ester, and cationic lipid.

38. A composition comprising nanostructured lipid carrier (NLC) particles for delivery of a bioactive agent to a cell, wherein the NLC particles comprise:
(a) an oil core comprising a mixture of a liquid phase lipid and a solid phase lipid that is trimyristin;
(b) a cationic lipid;
(c) a sorbitan ester;
(d) a hydrophilic surfactant; and
(e) the bioactive agent,
wherein the composition is formulated such that when administered to mice in which the bioactive agent is rvRNA encoding ZIKV prM/E from a Venezuelan equine encephalitis virus (VEEV) plasmid, the composition induces mean $PRNT_{80}$ titers of between about 1:110 and about 1:2560 when loaded with about 30 ng to about 100 ng of the rvRNA at a N:P molar ratio of about 15.

39. The composition of claim 38, wherein the bioactive agent is not encapsulated by the NLC particles and is associated with the surface of the NLC particles.

40. The composition of claim 38, wherein the bioactive agent is a protein, encodes a protein, is a protein antigen, encodes a protein antigen, is RNA, is DNA, is mRNA, is oncolytic viral RNA, is non-coding RNA, or is an adjuvant.

41. The composition of claim 38, wherein the average polydispersity index of the NLC particles is from 0.1 to about 0.5.

42. The composition of claim 38, wherein the z-average diameter of the NLC particles is from about 40 nm to about 80 nm.

43. The composition of claim 38, having an oil to surfactant molar ratio of about 0.5 to about 12.

44. The composition of claim 43, having an oil to surfactant molar ratio of about 0.5.

45. The composition of claim 38, having a hydrophilic surfactant to cationic component ratio of about 0.6.

46. A method of making the composition of claim 38, comprising:
(a) mixing the solid phase lipid, the liquid phase lipid, the cationic lipid, and the sorbitan ester to form an oil phase mixture;
(b) mixing the hydrophilic surfactant and water to form an aqueous phase mixture; and
(c) mixing the oil phase mixture with the aqueous phase mixture to form the NLC particles.

47. A method of generating or enhancing an immune response comprising administering to a subject in need thereof a therapeutically effective amount of the composition of claim 38, wherein the bioactive agent is an antigen or encodes an antigen.

48. The composition of claim 38, further comprising a citrate buffer.

49. The composition of claim 38, wherein the amount of hydrophilic surfactant is no greater than about 35% of the sum of the mass of the hydrophilic surfactant, sorbitan ester, and cationic lipid.

\* \* \* \* \*

SEQUENCE LISTING

```
<160> NUMBER OF SEQ ID NOS: 143

<210> SEQ ID NO 1
<211> LENGTH: 877
<212> TYPE: PRT
<213> ORGANISM: Artificial Sequence
<220> FEATURE:
<223> OTHER INFORMATION: Fusion protein ID91

<400> SEQUENCE: 1

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala Asp Asp
```

-continued

```
                85                  90                  95
Ile Asp Trp Asp Ala Ile Ala Gln Cys Glu Ser Gly Gly Asn Trp Ala
                100                 105                 110
Ala Asn Thr Gly Asn Gly Leu Tyr Gly Gly Leu Gln Ile Ser Gln Ala
                115                 120                 125
Thr Trp Asp Ser Asn Gly Gly Val Gly Ser Pro Ala Ala Ser Pro
    130                 135                 140
Gln Gln Gln Ile Glu Val Ala Asp Asn Ile Met Lys Thr Gln Gly Pro
145                 150                 155                 160
Gly Ala Trp Pro Lys Cys Ser Ser Cys Ser Gln Gly Asp Ala Pro Leu
                165                 170                 175
Gly Ser Leu Thr His Ile Leu Thr Phe Leu Ala Ala Glu Thr Gly Gly
                180                 185                 190
Cys Ser Gly Ser Arg Asp Asp Val Val Asp Phe Gly Ala Leu Pro Pro
                195                 200                 205
Glu Ile Asn Ser Ala Arg Met Tyr Ala Gly Pro Gly Ser Ala Ser Leu
                210                 215                 220
Val Ala Ala Lys Met Trp Asp Ser Val Ala Ser Asp Leu Phe Ser
225                 230                 235                 240
Ala Ala Ser Ala Phe Gln Ser Val Val Trp Gly Leu Thr Val Gly Ser
                245                 250                 255
Trp Ile Gly Ser Ser Ala Gly Leu Met Ala Ala Ala Ser Pro Tyr
                260                 265                 270
Val Ala Trp Met Ser Val Thr Ala Gly Gln Ala Gln Leu Thr Ala Ala
                275                 280                 285
Gln Val Arg Val Ala Ala Ala Tyr Glu Thr Ala Tyr Arg Leu Thr
                290                 295                 300
Val Pro Pro Val Ile Ala Glu Asn Arg Thr Glu Leu Met Thr Leu
305                 310                 315                 320
Thr Ala Thr Asn Leu Leu Gly Gln Asn Thr Pro Ala Ile Glu Ala Asn
                325                 330                 335
Gln Ala Ala Tyr Ser Gln Met Trp Gly Gln Asp Ala Glu Ala Met Tyr
                340                 345                 350
Gly Tyr Ala Ala Thr Ala Ala Thr Ala Thr Glu Ala Leu Leu Pro Phe
                355                 360                 365
Glu Asp Ala Pro Leu Ile Thr Asn Pro Gly Gly Leu Leu Glu Gln Ala
                370                 375                 380
Val Ala Val Glu Glu Ala Ile Asp Thr Ala Ala Ala Asn Gln Leu Met
385                 390                 395                 400
Asn Asn Val Pro Gln Ala Leu Gln Gln Leu Ala Gln Pro Ala Gln Gly
                405                 410                 415
Val Val Pro Ser Ser Lys Leu Gly Gly Leu Trp Thr Ala Val Ser Pro
                420                 425                 430
His Leu Ser Pro Leu Ser Asn Val Ser Ser Ile Ala Asn Asn His Met
                435                 440                 445
Ser Met Met Gly Thr Gly Val Ser Met Thr Asn Thr Leu His Ser Met
                450                 455                 460
Leu Lys Gly Leu Ala Pro Ala Ala Gln Ala Val Glu Thr Ala Ala
465                 470                 475                 480
Glu Asn Gly Val Trp Ala Met Ser Ser Leu Gly Ser Gln Leu Gly Ser
                485                 490                 495
Ser Leu Gly Ser Ser Gly Leu Gly Ala Gly Val Ala Ala Asn Leu Gly
                500                 505                 510
```

Arg Ala Ala Ser Val Gly Ser Leu Ser Val Pro Pro Ala Trp Ala Ala
                515                 520                 525

Ala Asn Gln Ala Val Thr Pro Ala Arg Ala Leu Pro Leu Thr Ser
        530                 535                 540

Leu Thr Ser Ala Ala Gln Thr Ala Pro Gly His Met Leu Gly Gly Leu
545                 550                 555                 560

Pro Leu Gly His Ser Val Asn Ala Gly Ser Gly Ile Asn Asn Ala Leu
                565                 570                 575

Arg Val Pro Ala Arg Ala Tyr Ala Ile Pro Arg Thr Pro Ala Ala Gly
        580                 585                 590

Phe Ser Arg Pro Gly Leu Pro Val Glu Tyr Leu Gln Val Pro Ser Pro
        595                 600                 605

Ser Met Gly Arg Asp Ile Lys Val Gln Phe Gln Ser Gly Gly Asn Asn
        610                 615                 620

Ser Pro Ala Val Tyr Leu Leu Asp Gly Leu Arg Ala Gln Asp Asp Tyr
625                 630                 635                 640

Asn Gly Trp Asp Ile Asn Thr Pro Ala Phe Glu Trp Tyr Tyr Gln Ser
                645                 650                 655

Gly Leu Ser Ile Val Met Pro Val Gly Gly Gln Ser Ser Phe Tyr Ser
                660                 665                 670

Asp Trp Tyr Ser Pro Ala Cys Gly Lys Ala Gly Cys Gln Thr Tyr Lys
        675                 680                 685

Trp Glu Thr Phe Leu Thr Ser Glu Leu Pro Gln Trp Leu Ser Ala Asn
        690                 695                 700

Arg Ala Val Lys Pro Thr Gly Ser Ala Ala Ile Gly Leu Ser Met Ala
705                 710                 715                 720

Gly Ser Ser Ala Met Ile Leu Ala Ala Tyr His Pro Gln Gln Phe Ile
                725                 730                 735

Tyr Ala Gly Ser Leu Ser Ala Leu Leu Asp Pro Ser Gln Gly Met Gly
                740                 745                 750

Pro Ser Leu Ile Gly Leu Ala Met Gly Asp Ala Gly Gly Tyr Lys Ala
        755                 760                 765

Ala Asp Met Trp Gly Pro Ser Ser Asp Pro Ala Trp Glu Arg Asn Asp
770                 775                 780

Pro Thr Gln Gln Ile Pro Lys Leu Val Ala Asn Asn Thr Arg Leu Trp
785                 790                 795                 800

Val Tyr Cys Gly Asn Gly Thr Pro Asn Glu Leu Gly Gly Ala Asn Ile
                805                 810                 815

Pro Ala Glu Phe Leu Glu Asn Phe Val Arg Ser Ser Asn Leu Lys Phe
        820                 825                 830

Gln Asp Ala Tyr Asn Ala Ala Gly Gly His Asn Ala Val Phe Asn Phe
        835                 840                 845

Pro Pro Asn Gly Thr His Ser Trp Glu Tyr Trp Gly Ala Gln Leu Asn
850                 855                 860

Ala Met Lys Gly Asp Leu Gln Ser Ser Leu Gly Ala Gly
865                 870                 875

<210> SEQ ID NO 2
<211> LENGTH: 94
<212> TYPE: PRT
<213> ORGANISM: Mycobacterium tuberculosis

<400> SEQUENCE: 2

Met Thr Ile Asn Tyr Gln Phe Gly Asp Val Asp Ala His Gly Ala Met

```
                1               5                      10                      15
        Ile Arg Ala Gln Ala Gly Ser Leu Glu Ala Glu His Gln Ala Ile Ile
                                20                      25                      30
        Ser Asp Val Leu Thr Ala Ser Asp Phe Trp Gly Gly Ala Gly Ser Ala
                                35                      40                      45
        Ala Cys Gln Gly Phe Ile Thr Gln Leu Gly Arg Asn Phe Gln Val Ile
                50                              55                      60
        Tyr Glu Gln Ala Asn Ala His Gly Gln Lys Val Gln Ala Ala Gly Asn
        65                              70                      75                      80
        Asn Met Ala Gln Thr Asp Ser Ala Val Gly Ser Ser Trp Ala
                                85                      90

<210> SEQ ID NO 3
<211> LENGTH: 105
<212> TYPE: PRT
<213> ORGANISM: Mycobacterium tuberculosis

<400> SEQUENCE: 3

Asp Asp Ile Asp Trp Asp Ala Ile Ala Gln Cys Glu Ser Gly Gly Asn
        1               5                      10                      15
        Trp Ala Ala Asn Thr Gly Asn Gly Leu Tyr Gly Gly Leu Gln Ile Ser
                                20                      25                      30
        Gln Ala Thr Trp Asp Ser Asn Gly Gly Val Gly Ser Pro Ala Ala Ala
                                35                      40                      45
        Ser Pro Gln Gln Gln Ile Glu Val Ala Asp Asn Ile Met Lys Thr Gln
                50                              55                      60
        Gly Pro Gly Ala Trp Pro Lys Cys Ser Ser Cys Ser Gln Gly Asp Ala
        65                              70                      75                      80
        Pro Leu Gly Ser Leu Thr His Ile Leu Thr Phe Leu Ala Ala Glu Thr
                                85                      90                      95
        Gly Gly Cys Ser Gly Ser Arg Asp Asp
                                100                     105

<210> SEQ ID NO 4
<211> LENGTH: 393
<212> TYPE: PRT
<213> ORGANISM: Mycobacterium tuberculosis

<400> SEQUENCE: 4

Val Val Asp Phe Gly Ala Leu Pro Pro Glu Ile Asn Ser Ala Arg Met
        1               5                      10                      15
        Tyr Ala Gly Pro Gly Ser Ala Ser Leu Val Ala Ala Lys Met Trp
                                20                      25                      30
        Asp Ser Val Ala Ser Asp Leu Phe Ser Ala Ala Ser Ala Phe Gln Ser
                                35                      40                      45
        Val Val Trp Gly Leu Thr Val Gly Ser Trp Ile Gly Ser Ser Ala Gly
                50                              55                      60
        Leu Met Ala Ala Ala Ser Pro Tyr Val Ala Trp Met Ser Val Thr
        65                              70                      75                      80
        Ala Gly Gln Ala Gln Leu Thr Ala Ala Gln Val Arg Val Ala Ala Ala
                                85                      90                      95
        Ala Tyr Glu Thr Ala Tyr Arg Leu Thr Val Pro Pro Val Ile Ala
                                100                     105                     110
        Glu Asn Arg Thr Glu Leu Met Thr Leu Thr Ala Thr Asn Leu Leu Gly
                                115                     120                     125
        Gln Asn Thr Pro Ala Ile Glu Ala Asn Gln Ala Ala Tyr Ser Gln Met
```

```
                130                 135                 140
Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Ala Ile
            180                 185                 190

Asp Thr Ala Ala Ala Asn Gln Leu Met Asn Asn Val Pro Gln Ala Leu
                195                 200                 205

Gln Gln Leu Ala Gln Pro Ala Gln Gly Val Val Pro Ser Ser Lys Leu
                210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
                260                 265                 270

Ala Ala Gln Ala Val Glu Thr Ala Ala Glu Asn Gly Val Trp Ala Met
                275                 280                 285

Ser Ser Leu Gly Ser Gln Leu Gly Ser Ser Leu Gly Ser Ser Gly Leu
290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
                340                 345                 350

Ala Pro Gly His Met Leu Gly Gly Leu Pro Leu Gly His Ser Val Asn
                355                 360                 365

Ala Gly Ser Gly Ile Asn Asn Ala Leu Arg Val Pro Ala Arg Ala Tyr
                370                 375                 380

Ala Ile Pro Arg Thr Pro Ala Ala Gly
385                 390

<210> SEQ ID NO 5
<211> LENGTH: 285
<212> TYPE: PRT
<213> ORGANISM: Mycobacterium tuberculosis

<400> SEQUENCE: 5

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
                20                  25                  30

Ser Pro Ala Val Tyr Leu Leu Asp Gly Leu Arg Ala Gln Asp Asp Tyr
                35                  40                  45

Asn Gly Trp Asp Ile Asn Thr Pro Ala Phe Glu Trp Tyr Tyr Gln Ser
            50                  55                  60

Gly Leu Ser Ile Val Met Pro Val Gly Gly Gln Ser Ser Phe Tyr Ser
65              70                  75                  80

Asp Trp Tyr Ser Pro Ala Cys Gly Lys Ala Gly Cys Gln Thr Tyr Lys
                85                  90                  95

Trp Glu Thr Phe Leu Thr Ser Glu Leu Pro Gln Trp Leu Ser Ala Asn
                100                 105                 110
```

```
Arg Ala Val Lys Pro Thr Gly Ser Ala Ala Ile Gly Leu Ser Met Ala
            115                 120                 125
Gly Ser Ser Ala Met Ile Leu Ala Ala Tyr His Pro Gln Gln Phe Ile
    130                 135                 140
Tyr Ala Gly Ser Leu Ser Ala Leu Leu Asp Pro Ser Gln Gly Met Gly
145                 150                 155                 160
Pro Ser Leu Ile Gly Leu Ala Met Gly Asp Ala Gly Tyr Lys Ala
                165                 170                 175
Ala Asp Met Trp Gly Pro Ser Ser Pro Ala Trp Glu Arg Asn Asp
            180                 185                 190
Pro Thr Gln Gln Ile Pro Lys Leu Val Ala Asn Asn Thr Arg Leu Trp
            195                 200                 205
Val Tyr Cys Gly Asn Gly Thr Pro Asn Glu Leu Gly Gly Ala Asn Ile
    210                 215                 220
Pro Ala Glu Phe Leu Glu Asn Phe Val Arg Ser Ser Asn Leu Lys Phe
225                 230                 235                 240
Gln Asp Ala Tyr Asn Ala Ala Gly Gly His Asn Ala Val Phe Asn Phe
                245                 250                 255
Pro Pro Asn Gly Thr His Ser Trp Glu Tyr Trp Gly Ala Gln Leu Asn
            260                 265                 270
Ala Met Lys Gly Asp Leu Gln Ser Ser Leu Gly Ala Gly
        275                 280                 285

<210> SEQ ID NO 6
<211> LENGTH: 880
<212> TYPE: PRT
<213> ORGANISM: Artificial Sequence
<220> FEATURE:
<223> OTHER INFORMATION: pET29 vector

<400> SEQUENCE: 6

His Met Thr Ile Asn Tyr Gln Phe Gly Asp Val Asp Ala His Gly Ala
1               5                   10                  15
Met Ile Arg Ala Gln Ala Gly Ser Leu Glu Ala Glu His Gln Ala Ile
            20                  25                  30
Ile Ser Asp Val Leu Thr Ala Ser Asp Phe Trp Gly Gly Ala Gly Ser
        35                  40                  45
Ala Ala Cys Gln Gly Phe Ile Thr Gln Leu Gly Arg Asn Phe Gln Val
    50                  55                  60
Ile Tyr Glu Gln Ala Asn Ala His Gly Gln Lys Val Gln Ala Ala Gly
65                  70                  75                  80
Asn Asn Met Ala Gln Thr Asp Ser Ala Val Gly Ser Ser Trp Ala Asp
                85                  90                  95
Asp Ile Asp Trp Asp Ala Ile Ala Gln Cys Glu Ser Gly Gly Asn Trp
            100                 105                 110
Ala Ala Asn Thr Gly Asn Gly Leu Tyr Gly Gly Leu Gln Ile Ser Gln
        115                 120                 125
Ala Thr Trp Asp Ser Asn Gly Gly Val Gly Ser Pro Ala Ala Ala Ser
    130                 135                 140
Pro Gln Gln Gln Ile Glu Val Ala Asp Asn Ile Met Lys Thr Gln Gly
145                 150                 155                 160
Pro Gly Ala Trp Pro Lys Cys Ser Ser Cys Ser Gln Gly Asp Ala Pro
                165                 170                 175
Leu Gly Ser Leu Thr His Ile Leu Thr Phe Leu Ala Ala Glu Thr Gly
            180                 185                 190
```

-continued

```
Gly Cys Ser Gly Ser Arg Asp Asp Val Val Asp Phe Gly Ala Leu Pro
            195                 200                 205
Pro Glu Ile Asn Ser Ala Arg Met Tyr Ala Gly Pro Gly Ser Ala Ser
    210                 215                 220
Leu Val Ala Ala Ala Lys Met Trp Asp Ser Val Ala Ser Asp Leu Phe
225                 230                 235                 240
Ser Ala Ala Ser Ala Phe Gln Ser Val Val Trp Gly Leu Thr Val Gly
                245                 250                 255
Ser Trp Ile Gly Ser Ser Ala Gly Leu Met Ala Ala Ala Ala Ser Pro
            260                 265                 270
Tyr Val Ala Trp Met Ser Val Thr Ala Gly Gln Ala Gln Leu Thr Ala
        275                 280                 285
Ala Gln Val Arg Val Ala Ala Ala Tyr Glu Thr Ala Tyr Arg Leu
    290                 295                 300
Thr Val Pro Pro Pro Val Ile Ala Glu Asn Arg Thr Glu Leu Met Thr
305                 310                 315                 320
Leu Thr Ala Thr Asn Leu Leu Gly Gln Asn Thr Pro Ala Ile Glu Ala
                325                 330                 335
Asn Gln Ala Ala Tyr Ser Gln Met Trp Gly Gln Asp Ala Glu Ala Met
            340                 345                 350
Tyr Gly Tyr Ala Ala Thr Ala Ala Thr Ala Thr Glu Ala Leu Leu Pro
        355                 360                 365
Phe Glu Asp Ala Pro Leu Ile Thr Asn Pro Gly Gly Leu Leu Glu Gln
    370                 375                 380
Ala Val Ala Val Glu Glu Ala Ile Asp Thr Ala Ala Ala Asn Gln Leu
385                 390                 395                 400
Met Asn Asn Val Pro Gln Ala Leu Gln Gln Leu Ala Gln Pro Ala Gln
                405                 410                 415
Gly Val Val Pro Ser Ser Lys Leu Gly Gly Leu Trp Thr Ala Val Ser
            420                 425                 430
Pro His Leu Ser Pro Leu Ser Asn Val Ser Ser Ile Ala Asn Asn His
        435                 440                 445
Met Ser Met Met Gly Thr Gly Val Ser Met Thr Asn Thr Leu His Ser
450                 455                 460
Met Leu Lys Gly Leu Ala Pro Ala Ala Gln Ala Val Glu Thr Ala
465                 470                 475                 480
Ala Glu Asn Gly Val Trp Ala Met Ser Ser Leu Gly Ser Gln Leu Gly
                485                 490                 495
Ser Ser Leu Gly Ser Ser Leu Gly Ala Gly Val Ala Ala Asn Leu
            500                 505                 510
Gly Arg Ala Ala Ser Val Gly Ser Leu Ser Val Pro Pro Ala Trp Ala
        515                 520                 525
Ala Ala Asn Gln Ala Val Thr Pro Ala Ala Arg Ala Leu Pro Leu Thr
    530                 535                 540
Ser Leu Thr Ser Ala Ala Gln Thr Ala Pro Gly His Met Leu Gly Gly
545                 550                 555                 560
Leu Pro Leu Gly His Ser Val Asn Ala Gly Ser Gly Ile Asn Asn Ala
                565                 570                 575
Leu Arg Val Pro Ala Arg Ala Tyr Ala Ile Pro Arg Thr Pro Ala Ala
            580                 585                 590
Gly Phe Ser Arg Pro Gly Leu Pro Val Glu Tyr Leu Gln Val Pro Ser
        595                 600                 605
Pro Ser Met Gly Arg Asp Ile Lys Val Gln Phe Gln Ser Gly Gly Asn
```

|  |  |  | 610 |  |  |  | 615 |  |  |  | 620 |  |
|--|--|--|--|--|--|--|--|--|--|--|--|--|

Asn Ser Pro Ala Val Tyr Leu Leu Asp Gly Leu Arg Ala Gln Asp Asp
625 630 635 640

Tyr Asn Gly Trp Asp Ile Asn Thr Pro Ala Phe Glu Trp Tyr Tyr Gln
　　　　　　　645　　　　　　　　650　　　　　　　　655

Ser Gly Leu Ser Ile Val Met Pro Val Gly Gly Gln Ser Ser Phe Tyr
　　　　　660　　　　　　　　665　　　　　　　　670

Ser Asp Trp Tyr Ser Pro Ala Cys Gly Lys Ala Gly Cys Gln Thr Tyr
　　675　　　　　　　　680　　　　　　　　685

Lys Trp Glu Thr Phe Leu Thr Ser Glu Leu Pro Gln Trp Leu Ser Ala
690　　　　　　　　695　　　　　　　　700

Asn Arg Ala Val Lys Pro Thr Gly Ser Ala Ala Ile Gly Leu Ser Met
705　　　　　　　　710　　　　　　　　715　　　　　　　　720

Ala Gly Ser Ser Ala Met Ile Leu Ala Ala Tyr His Pro Gln Gln Phe
　　　　　725　　　　　　　　730　　　　　　　　735

Ile Tyr Ala Gly Ser Leu Ser Ala Leu Leu Asp Pro Ser Gln Gly Met
　　　　740　　　　　　　　745　　　　　　　　750

Gly Pro Ser Leu Ile Gly Leu Ala Met Gly Asp Ala Gly Gly Tyr Lys
　　　　755　　　　　　　　760　　　　　　　　765

Ala Ala Asp Met Trp Gly Pro Ser Ser Asp Pro Ala Trp Glu Arg Asn
770　　　　　　　　775　　　　　　　　780

Asp Pro Thr Gln Gln Ile Pro Lys Leu Val Ala Asn Asn Thr Arg Leu
785　　　　　　　　790　　　　　　　　795　　　　　　　　800

Trp Val Tyr Cys Gly Asn Gly Thr Pro Asn Glu Leu Gly Gly Ala Asn
　　　　　805　　　　　　　　810　　　　　　　　815

Ile Pro Ala Glu Phe Leu Glu Asn Phe Val Arg Ser Ser Asn Leu Lys
　　　　820　　　　　　　　825　　　　　　　　830

Phe Gln Asp Ala Tyr Asn Ala Ala Gly Gly His Asn Ala Val Phe Asn
　　　　835　　　　　　　　840　　　　　　　　845

Phe Pro Pro Asn Gly Thr His Ser Trp Glu Tyr Trp Gly Ala Gln Leu
　　　　850　　　　　　　　855　　　　　　　　860

Asn Ala Met Lys Gly Asp Leu Gln Ser Ser Leu Gly Ala Gly Lys Leu
865　　　　　　　　870　　　　　　　　875　　　　　　　　880

<210> SEQ ID NO 7
<211> LENGTH: 2637
<212> TYPE: DNA
<213> ORGANISM: Artificial Sequence
<220> FEATURE:
<223> OTHER INFORMATION: Fusion protein ID91

<400> SEQUENCE: 7

```
accatcaact atcaattcgg ggacgtcgac gctcacggcg ccatgatccg cgctcaggcc      60
gggtcgctgg aggccgagca tcaggccatc atttctgatg tgttgaccgc gagtgacttt     120
tggggcggcg ccggttcggc ggcctgccag gggttcatta cccagctggg ccgtaacttc     180
caggtgatct acgagcaggc caacgcccac gggcagaagg tgcaggctgc cggcaacaac     240
atggcacaaa ccgacagcgc cgtcggctcc agctgggccg acgacatcga ttgggacgcc     300
atcgcgcaat gcgaatccgg cggcaattgg cggccaacac ccgtaacgg gttatacggt     360
ggtctgcaga tcagccaggc gacgtgggat ccaacggtg tgtcgggtc gccggcggcc     420
gcgagtcccc agcaacagat cgaggtcgca gacaacatta tgaaaaccca aggcccgggt     480
gcgtggccga aatgtagttc ttgtagtcag ggagacgcac cgctgggctc gctcacccac     540
atcctgacgt tcctcgcggc cgagactgga ggttgttcgg ggagcaggga cgatgtggtg     600
```

```
gatttcgggg cgttaccacc ggagatcaac tccgcgagga tgtacgccgg cccgggttcg    660
gcctcgctgg tggccgccgc gaagatgtgg gacagcgtgg cgagtgacct gttttcggcc    720
gcgtcggcgt ttcagtcggt ggtctggggt ctgacggtgg ggtcgtggat aggttcgtcg    780
gcgggtctga tggcggcggc ggcctcgccg tatgtggcgt ggatgagcgt caccgcgggg    840
caggcccagc tgaccgccgc ccaggtccgg gttgctgcgg cggcctacga gacagcgtat    900
aggctgacgg tgcccccgcc ggtgatcgcc gagaaccgta ccgaactgat gacgctgacc    960
gcgaccaacc tcttggggca aaacacgccg gcgatcgagg ccaatcaggc cgcatacagc   1020
cagatgtggg gccaagacgc ggaggcgatg tatggctacg ccgccacggc ggcgacggcg   1080
accgaggcgt tgctgccgtt cgaggacgcc ccactgatca ccaaccccgg cgggctcctt   1140
gagcaggccg tcgcggtcga ggaggccatc gacaccgccg cggcgaacca gttgatgaac   1200
aatgtgcccc aagcgctgca acagctggcc cagccagcgc agggcgtcgt accttcttcc   1260
aagctgggtg gctgtggac ggcggtctcg ccgcatctgt cgccgctcag caacgtcagt   1320
tcgatagcca acaaccacat gtcgatgatg ggcacgggtg tgtcgatgac caacaccttg   1380
cactcgatgt tgaagggctt agctccggcg cggctcagg ccgtggaaac cgcggcggaa   1440
aacggggtct gggcgatgag ctcgctgggc agccagctgg gttcgtcgct gggttcttcg   1500
ggtctgggcg ctggggtggc cgccaacttg ggtcggcgg cctcggtcgg ttcgttgtcg   1560
gtgccgccag catgggccgc ggccaaccag gcggtcaccc cggcggcgcg ggcgctgccg   1620
ctgaccagcc tgaccagcgc cgcccaaacc gcccccggac acatgctggg cgggctaccg   1680
ctggggcact cggtcaacgc cggcagcggt atcaacaatg cgctgcgggt gccggcacgg   1740
gcctacgcga tacccgcac accgccgcc ggattctccc ggccggggct gccggtcgag   1800
tacctgcagg tgccgtcgcc gtcgatgggc cgcgacatca aggttcagtt ccagagcggt   1860
gggaacaact cacctgcggt ttatctgctc gacggcctgc cgcgccaaga cgactacaac   1920
ggctgggata tcaacacccc ggcgttcgag tggtactacc agtcgggact gtcgatagtc   1980
atgccggtcg gcgggcagtc cagcttctac agcgactggt acagcccggc ctgcggtaag   2040
gctggctgcc agacttacaa gtgggaaacc ttcctgacca gcgagctgcc gcaatggttg   2100
tccgccaaca gggccgtgaa gcccaccggc agcgctgcaa tcggcttgtc gatggccggc   2160
tcgtcggcaa tgatcttggc cgcctaccac ccccagcagt tcatctacgc cggctcgctg   2220
tcggccctgc tggacccctc tcaggggatg gggcctagcc tgatcggcct cgcgatgggt   2280
gacgccggcg gttacaaggc cgcagacatg tggggtccct cgagtgaccc ggcatgggag   2340
cgcaacgacc ctacgcagca gatccccaag ctggtcgcaa acaacacccg gctatgggtt   2400
tattgcggga acggcacccc gaacgagttg ggcggtgcca acatacccgc cgagttcttg   2460
gagaacttcg ttcgtagcag caacctgaag ttccaggatg cgtacaacgc cgcgggcggg   2520
cacaacgccg tgttcaactt cccgcccaac ggcacgcaca gctgggagta ctggggcgct   2580
cagctcaacg ccatgaaggg tgacctgcag agttcgttag gcgccggctg aaagctt     2637
```

<210> SEQ ID NO 8
<211> LENGTH: 279
<212> TYPE: DNA
<213> ORGANISM: Mycobacterium tuberculosis

<400> SEQUENCE: 8

```
accatcaact atcaattcgg ggacgtcgac gctcacggcg ccatgatccg cgctcaggcc     60
```

```
gggtcgctgg aggccgagca tcaggccatc atttctgatg tgttgaccgc gagtgacttt    120
tggggcggcg ccggttcggc ggcctgccag gggttcatta cccagctggg ccgtaacttc    180
caggtgatct acgagcaggc caacgcccac gggcagaagg tgcaggctgc cggcaacaac    240
atggcacaaa ccgacagcgc cgtcggctcc agctgggcc                           279

<210> SEQ ID NO 9
<211> LENGTH: 315
<212> TYPE: DNA
<213> ORGANISM: Mycobacterium tuberculosis

<400> SEQUENCE: 9
gacgacatcg attgggacgc catcgcgcaa tgcgaatccg gcggcaattg gcggccaac     60 accggtaacg ggttatacgg tggtctgcag atcagccagg cgacgtggga ttccaacggt    120
ggtgtcgggt cgccggcggc cgcgagtccc cagcaacaga tcgaggtcgc agacaacatt    180
atgaaacccc aaggcccggg tgcgtggccg aaatgtagtt cttgtagtca gggagacgca    240
ccgctgggct cgctcacccca catcctgacg ttcctcgcgg ccgagactgg aggttgttcg    300
gggagcaggg acgat                                                    315

<210> SEQ ID NO 10
<211> LENGTH: 1179
<212> TYPE: DNA
<213> ORGANISM: Mycobacterium tuberculosis

<400> SEQUENCE: 10
gtggtggatt tcggggcgtt accaccggag atcaactccg cgaggatgta cgccggcccg    60
ggttcggcct cgctggtggc cgccgcgaag atgtgggaca gcgtggcgag tgacctgttt    120
tcggccgcgt cggcgtttca gtcggtggtc tggggtctga cggtgggggtc gtggataggt    180 tcgtcggcgg gtctgatggc ggcggcggcc tcgccgtatg tggcgtggat gagcgtcacc    240
gcggggcagg cccagctgac cgccgcccag gtccgggttg ctgcggcggc ctacgagaca    300
gcgtataggc tgacggtgcc cccgccggtg atcgccgaga accgtaccga actgatgacg    360
ctgaccgcga ccaacctctt ggggcaaaac acgccggcga tcgaggccaa tcaggccgca    420
tacagccaga tgtggggcca agacgcggag gcgatgtatg gctacgccgc cacggcggcg    480
acggcgaccg aggcgttgct gccgttcgag gacgccccac tgatcaccaa ccccggcggg    540
ctccttgagc aggccgtcgc ggtcgaggag gccatcgaca ccgccgcggc gaaccagttg    600
atgaacaatg tgccccaagc gctgcaacag ctggcccagc cagcgcaggg cgtcgtacct    660
tcttccaagc tgggtgggct gtggacggcg gtctcgccgc atctgtcgcc gctcagcaac    720
gtcagttcga tagccaacaa ccacatgtcg atgatgggca cggtgtgtc gatgaccaac    780 accttgcact cgatgttgaa gggcttagct ccggcggcgg ctcaggccgt ggaaaccgcg    840
gcggaaaacg gggtctgggc gatgagctcg ctgggcagcc agctgggttc gtcgctgggt    900
tcttcgggtc tgggcgctgg ggtggccgcc aacttgggtc gggcggcctc ggtcggttcg    960
ttgtcggtgc cgccagcatg ggccgcggcc aaccaggcgg tcaccccggc ggcgcgggcg   1020
ctgccgctga ccagcctgac cagcgccgcc caaaccgccc ccggacacat gctgggcggg   1080
ctaccgctgg ggcactcggt caacgccggc agcggtatca acaatgcgct gcgggtgccg   1140
gcacgggcct acgcgatacc ccgcacaccg gccgccgga                          1179

<210> SEQ ID NO 11
<211> LENGTH: 855
```

```
<212> TYPE: DNA
<213> ORGANISM: Mycobacterium tuberculosis

<400> SEQUENCE: 11
ttctcccggc cggggctgcc ggtcgagtac ctgcaggtgc cgtcgccgtc gatgggccgc      60
gacatcaagg ttcagttcca gagcggtggg aacaactcac ctgcggttta tctgctcgac    120
ggcctgcgcg cccaagacga ctacaacggc tgggatatca caccccggc gttcgagtgg     180 tactaccagt cgggactgtc gatagtcatg ccggtcggcg ggcagtccag cttctacagc    240
gactggtaca gcccggcctg cggtaaggct ggctgccaga cttacaagtg ggaaaccttc    300
ctgaccagcg agctgccgca atggttgtcc gccaacaggg ccgtgaagcc caccggcagc    360
gctgcaatcg gcttgtcgat ggccggctcg tcggcaatga tcttggccgc ctaccacccc    420
cagcagttca tctacgccgg ctcgctgtcg gccctgctgg acccctctca ggggatgggg    480
cctagcctga tcggcctcgc gatgggtgac gccggcggtt acaaggccgc agacatgtgg    540
ggtccctcga gtgacccggc atgggagcgc aacgacccta cgcagcagat ccccaagctg    600
gtcgcaaaca cacccggct atgggtttat tgcgggaacg gcaccccgaa cgagttgggc     660
ggtgccaaca tacccgccga gttcttggag aacttcgttc gtagcagcaa cctgaagttc    720
caggatgcgt acaacgccgc gggcgggcac aacgccgtgt tcaacttccc gcccaacggc    780
acgcacagct gggagtactg gggcgctcag ctcaacgcca tgaagggtga cctgcagagt    840
tcgttaggcg ccggc                                                      855

<210> SEQ ID NO 12
<211> LENGTH: 2643
<212> TYPE: DNA
<213> ORGANISM: Artificial Sequence
<220> FEATURE:
<223> OTHER INFORMATION: pET29 vector

<400> SEQUENCE: 12
catatgacca tcaactatca attcggggac gtcgacgctc acggcgccat gatccgcgct     60
caggccgggt cgctggaggc cgagcatcag gccatcattt ctgatgtgtt gaccgcgagt    120
gacttttggg gcggcgccgg ttcggcggcc tgccaggggt tcattaccca gctgggccgt    180
aacttccagg tgatctacga gcaggccaac gccacgggc agaaggtgca ggctgccggc    240
aacaacatgg cacaaaccga cagcgccgtc ggctccagct gggccgacga catcgattgg    300
gacgccatcg cgcaatgcga atccggcggc aattgggcgg ccaacaccgg taacgggtta    360
tacggtggtc tgcagatcag ccaggcgacg tgggattcca acggtggtgt cgggtcgccg    420
gcggccgcga gtccccagca acagatcgag gtcgcagaca acattatgaa aacccaaggc    480
ccgggtgcgt ggccgaaatg tagttcttgt agtcagggag acgcaccgct gggctcgctc    540
acccacatcc tgacgttcct cgcggccgag actggaggtt gttcggggag cagggacgat    600
gtggtggatt tcggggcgtt accaccgag atcaactccg cgaggatgta cgccggcccg     660
ggttcggcct cgctggtggc cgccgcgaag atgtgggaca gcgtggcgag tgacctgttt    720
tcggccgcgt cggcgtttca gtcggtggtc tggggtctga cggtggggtc gtggataggt    780 tcgtcggcg gtctgatggc ggcggcggcc tcgccgtatg tggcgtggat gagcgtcacc    840
gcggggcagg cccagctgac cgccgcccag gtccgggttg ctgcggcggc ctacgagaca    900
gcgtataggc tgacggtgcc cccgccggtg atcgccgaga accgtaccga actgatgacg    960
ctgaccgcga ccaacctctt ggggcaaaac acgccggcga tcgaggccaa tcaggccgca   1020
```

| | |
|---|---|
| tacagccaga tgtggggcca agacgcggag gcgatgtatg gctacgccgc cacggcggcg | 1080 |
| acggcgaccg aggcgttgct gccgttcgag gacgccccac tgatcaccaa ccccggcggg | 1140 |
| ctccttgagc aggccgtcgc ggtcgaggag gccatcgaca ccgccgcggc gaaccagttg | 1200 |
| atgaacaatg tgccccaagc gctgcaacag ctggcccagc cagcgcaggg cgtcgtacct | 1260 |
| tcttccaagc tgggtgggct gtggacggcg gtctcgccgc atctgtcgcc gctcagcaac | 1320 |
| gtcagttcga tagccaacaa ccacatgtcg atgatgggca cgggtgtgtc gatgaccaac | 1380 |
| accttgcact cgatgttgaa gggcttagct ccggcggcgg ctcaggccgt ggaaaccgcg | 1440 |
| gcggaaaacg gggtctgggc gatgagctcg ctgggcagcc agctgggttc gtcgctgggt | 1500 |
| tcttcgggtc tgggcgctgg ggtggccgcc aacttgggtc gggcggcctc ggtcggttcg | 1560 |
| ttgtcggtgc cgccagcatg gccgcggcc aaccaggcgg tcaccccggc ggcgcgggcg | 1620 |
| ctgccgctga ccagcctgac cagcgccgcc caaaccgccc ccggacacat gctgggcggg | 1680 |
| ctaccgctgg ggcactcggt caacgccggc agcggtatca acaatgcgct gcgggtgccg | 1740 |
| gcacgggcct acgcgatacc ccgcacaccg gccgccggat tctcccggcc ggggctgccg | 1800 |
| gtcgagtacc tgcaggtgcc gtcgccgtcg atgggccgcg acatcaaggt tcagttccag | 1860 |
| agcggtggga caactcacc tgcggtttat ctgctcgacg gcctgcgcgc ccaagacgac | 1920 |
| tacaacggct gggatatcaa caccccggcg ttcgagtggt actaccagtc gggactgtcg | 1980 |
| atagtcatgc cggtcggcgg gcagtccagc ttctacagcg actggtacag cccggcctgc | 2040 |
| ggtaaggctg gctgccagac ttacaagtgg gaaaccttcc tgaccagcga gctgccgcaa | 2100 |
| tggttgtccg ccaacagggc cgtgaagccc accggcagcc tgcaatcgg cttgtcgatg | 2160 |
| gccggctcgt cggcaatgat cttggccgcc taccacccc agcagttcat ctacgccggc | 2220 |
| tcgctgtcgg ccctgctgga ccctctcag gggatgggc ctagcctgat cggcctcgcg | 2280 |
| atgggtgacg ccggcggtta caaggccgca gacatgtggg gtccctcgag tgacccggca | 2340 |
| tgggagcgca acgaccctac gcagcagatc cccaagctgg tcgcaaacaa cacccggcta | 2400 |
| tgggtttatt gcgggaacgg caccccgaac gagttgggcg gtgccaacat acccgccgag | 2460 |
| ttcttggaga acttcgttcg tagcagcaac ctgaagttcc aggatgcgta caacgccgcg | 2520 |
| ggcgggcaca acgccgtgtt caacttcccg cccaacggca cgcacagctg ggagtactgg | 2580 |
| ggcgctcagc tcaacgccat gaagggtgac ctgcagagtt cgttaggcgc cggctgaaag | 2640 |
| ctt | 2643 |

<210> SEQ ID NO 13
<211> LENGTH: 60
<212> TYPE: DNA
<213> ORGANISM: Artificial Sequence
<220> FEATURE:
<223> OTHER INFORMATION: JEVss-FWD

<400> SEQUENCE: 13
gctggcctcc ctggctgtgg tcattgcctg cgctggagca gccgaggtga ccaggagagg      60

<210> SEQ ID NO 14
<211> LENGTH: 59
<212> TYPE: DNA
<213> ORGANISM: Artificial Sequence
<220> FEATURE:
<223> OTHER INFORMATION: JEVss-REV

<400> SEQUENCE: 14
cacatgattg atccggcact cctcttgccc atggcggcgg cgtgagctgg cggcgggtg       59

<210> SEQ ID NO 15
<211> LENGTH: 56
<212> TYPE: DNA
<213> ORGANISM: Artificial Sequence
<220> FEATURE:
<223> OTHER INFORMATION: ZIKVss-FWD

<400> SEQUENCE: 15
ggaatcgtgg gcctgctgct gaccacagca atggcagccg aggtgaccag gagagg     56

<210> SEQ ID NO 16
<211> LENGTH: 54
<212> TYPE: DNA
<213> ORGANISM: Artificial Sequence
<220> FEATURE:
<223> OTHER INFORMATION: ZIKVss-REV

<400> SEQUENCE: 16
cacggatgtg tctgctcctc tccgcatggc ggcggcgtga gctggcggcg ggtg       54

<210> SEQ ID NO 17
<211> LENGTH: 31
<212> TYPE: DNA
<213> ORGANISM: Artificial Sequence
<220> FEATURE:
<223> OTHER INFORMATION: ZIKV-prM-E-FWD

<400> SEQUENCE: 17
aatggactac gacatagtcg ccgccgccat g                                31

<210> SEQ ID NO 18
<211> LENGTH: 35
<212> TYPE: DNA
<213> ORGANISM: Artificial Sequence
<220> FEATURE:
<223> OTHER INFORMATION: ZIKV-prM-E-REV

<400> SEQUENCE: 18
gcggtttttg acaccgcggt caggcagaca cggcg                            35

<210> SEQ ID NO 19
<211> LENGTH: 15
<212> TYPE: PRT
<213> ORGANISM: Artificial Sequence
<220> FEATURE:
<223> OTHER INFORMATION: Id91 epitope 1

<400> SEQUENCE: 19

His Met Thr Ile Asn Tyr Gln Phe Gly Asp Val Asp Ala His Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Id91 epitope 2

<400> SEQUENCE: 20

Phe Gly Asp Val Asp Ala His Gly Ala Met Ile Arg Ala Gln Ala
1               5                   10                  15

<210> SEQ ID NO 21
<211> LENGTH: 15
<212> TYPE: PRT

```
<213> ORGANISM: Artificial Sequence
<220> FEATURE:
<223> OTHER INFORMATION: Id91 epitope 3

<400> SEQUENCE: 21

Gly Ala Met Ile Arg Ala Gln Ala Gly Ser Leu Glu Ala Glu His
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Id91 epitope 4

<400> SEQUENCE: 22

Ala Gly Ser Leu Glu Ala Glu His Gln Ala Ile Ile Ser Asp Val
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Id91 epitope 5

<400> SEQUENCE: 23

His Gln Ala Ile Ile Ser Asp Val Leu Thr Ala Ser Asp Phe Trp
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Id91 epitope 6

<400> SEQUENCE: 24

Val Leu Thr Ala Ser Asp Phe Trp Gly Gly Ala Gly Ser Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Id91 epitope 7

<400> SEQUENCE: 25

Trp Gly Gly Ala Gly Ser Ala Ala Cys Gln Gly Phe Ile Thr Gln
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Id91 epitope 8

<400> SEQUENCE: 26

Ala Cys Gln Gly Phe Ile Thr Gln Leu Gly Arg Asn Phe Gln Val
1               5                   10                  15

<210> SEQ ID NO 27
<211> LENGTH: 15
<212> TYPE: PRT
<213> ORGANISM: Artificial Sequence
```

```
<220> FEATURE:
<223> OTHER INFORMATION: Id91 epitope 9

<400> SEQUENCE: 27

Gln Leu Gly Arg Asn Phe Gln Val Ile Tyr Glu Gln Ala Asn Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Id91 epitope 10

<400> SEQUENCE: 28

Val Ile Tyr Glu Gln Ala Asn Ala His Gly Gln Lys Val Gln Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Id91 epitope 11

<400> SEQUENCE: 29

Ala His Gly Gln Lys Val Gln Ala Ala Gly Asn Asn Met Ala Gln
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Id91 epitope 12

<400> SEQUENCE: 30

Ala Ala Gly Asn Asn Met Ala Gln Thr Asp Ser Ala Val Gly Ser
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Id91 epitope 13

<400> SEQUENCE: 31

Gln Thr Asp Ser Ala Val Gly Ser Ser Trp Ala Asp Asp Ile Asp
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Id91 epitope 14

<400> SEQUENCE: 32

Ser Ser Trp Ala Asp Asp Ile Asp Trp Asp Ala Ile Ala Gln Cys
1               5                   10                  15

<210> SEQ ID NO 33
<211> LENGTH: 15
<212> TYPE: PRT
<213> ORGANISM: Artificial Sequence
<220> FEATURE:
```

```
<223> OTHER INFORMATION: Id91 epitope 15

<400> SEQUENCE: 33

Asp Trp Asp Ala Ile Ala Gln Cys Glu Ser Gly Gly Asn Trp Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Id91 epitope 16

<400> SEQUENCE: 34

Cys Glu Ser Gly Gly Asn Trp Ala Ala Asn Thr Gly Asn Gly Leu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Id91 epitope 17

<400> SEQUENCE: 35

Ala Ala Asn Thr Gly Asn Gly Leu Tyr Gly Gly Leu Gln Ile Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Id91 epitope 18

<400> SEQUENCE: 36

Leu Tyr Gly Gly Leu Gln Ile Ser Gln Ala Thr Trp Asp Ser Asn
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Id91 epitope 19

<400> SEQUENCE: 37

Ser Gln Ala Thr Trp Asp Ser Asn Gly Gly Val Gly Ser Pro Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Id91 epitope 20

<400> SEQUENCE: 38

Asn Gly Gly Val Gly Ser Pro Ala Ala Ala Ser Pro Gln Gln Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Id91 epitope 21
```

```
<400> SEQUENCE: 39

Ala Ala Ala Ser Pro Gln Gln Gln Ile Glu Val Ala Asp Asn Ile
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Id91 epitope 22

<400> SEQUENCE: 40

Gln Ile Glu Val Ala Asp Asn Ile Met Lys Thr Gln Gly Pro Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Id91 epitope 23

<400> SEQUENCE: 41

Ile Met Lys Thr Gln Gly Pro Gly Ala Trp Pro Lys Cys Ser Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Id91 epitope 24

<400> SEQUENCE: 42

Gly Ala Trp Pro Lys Cys Ser Ser Cys Ser Gln Gly Asp Ala Pro
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Id91 epitope 25

<400> SEQUENCE: 43

Ser Cys Ser Gln Gly Asp Ala Pro Leu Gly Ser Leu Thr His Ile
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Id91 epitope 26

<400> SEQUENCE: 44

Pro Leu Gly Ser Leu Thr His Ile Leu Thr Phe Leu Ala Ala Glu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Id91 epitope 27
```

```
<400> SEQUENCE: 45

Ile Leu Thr Phe Leu Ala Ala Glu Thr Gly Gly Cys Ser Gly Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Id91 epitope 28

<400> SEQUENCE: 46

Glu Thr Gly Gly Cys Ser Gly Ser Arg Asp Asp Val Val Asp Phe
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Id91 epitope 29

<400> SEQUENCE: 47

Ser Arg Asp Asp Val Val Asp Phe Gly Ala Leu Pro Pro Glu Ile
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Id91 epitope 30

<400> SEQUENCE: 48

Phe Gly Ala Leu Pro Pro Glu Ile Asn Ser Ala Arg Met Tyr Ala
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Id91 epitope 31

<400> SEQUENCE: 49

Ile Asn Ser Ala Arg Met Tyr Ala Gly Pro Gly Ser Ala Ser Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Id91 epitope 32

<400> SEQUENCE: 50

Ala Gly Pro Gly Ser Ala Ser Leu Val Ala Ala Ala Lys Met Trp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Id91 epitope 33

<400> SEQUENCE: 51
```

```
Leu Val Ala Ala Ala Lys Met Trp Asp Ser Val Ala Ser Asp Leu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Id91 epitope 34

<400> SEQUENCE: 52

Trp Asp Ser Val Ala Ser Asp Leu Phe Ser Ala Ala Ser Ala Phe
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Id91 epitope 35

<400> SEQUENCE: 53

Leu Phe Ser Ala Ala Ser Ala Phe Gln Ser Val Val Trp Gly Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Id91 epitope 36

<400> SEQUENCE: 54

Phe Gln Ser Val Val Trp Gly Leu Thr Val Gly Ser Trp Ile Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Id91 epitope 37

<400> SEQUENCE: 55

Leu Thr Val Gly Ser Trp Ile Gly Ser Ser Ala Gly Leu Met Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Id91 epitope 38

<400> SEQUENCE: 56

Gly Ser Ser Ala Gly Leu Met Ala Ala Ala Ser Pro Tyr Val
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Id91 epitope 39

<400> SEQUENCE: 57
```

```
Ala Ala Ala Ala Ser Pro Tyr Val Ala Trp Met Ser Val Thr Ala
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Id91 epitope 40

<400> SEQUENCE: 58

Val Ala Trp Met Ser Val Thr Ala Gly Gln Ala Gln Leu Thr Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Id91 epitope 41

<400> SEQUENCE: 59

Ala Gly Gln Ala Gln Leu Thr Ala Ala Gln Val Arg Val Ala Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Id91 epitope 42

<400> SEQUENCE: 60

Ala Ala Gln Val Arg Val Ala Ala Ala Ala Tyr Glu Thr Ala Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Id91 epitope 43

<400> SEQUENCE: 61

Ala Ala Ala Tyr Glu Thr Ala Tyr Arg Leu Thr Val Pro Pro Pro
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Id91 epitope 44

<400> SEQUENCE: 62

Tyr Arg Leu Thr Val Pro Pro Pro Val Ile Ala Glu Asn Arg Thr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Id91 epitope 45

<400> SEQUENCE: 63

Pro Val Ile Ala Glu Asn Arg Thr Glu Leu Met Thr Leu Thr Ala
```

<210> SEQ ID NO 64
<211> LENGTH: 15
<212> TYPE: PRT
<213> ORGANISM: Artificial Sequence
<220> FEATURE:
<223> OTHER INFORMATION: Id91 epitope 46

<400> SEQUENCE: 64

Thr Glu Leu Met Thr Leu Thr Ala Thr Asn Leu Leu Gly Gln Asn
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Id91 epitope 47

<400> SEQUENCE: 65

Ala Thr Asn Leu Leu Gly Gln Asn Thr Pro Ala Ile Glu Ala Asn
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Id91 epitope 48

<400> SEQUENCE: 66

Asn Thr Pro Ala Ile Glu Ala Asn Gln Ala Ala Tyr Ser Gln Met
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Id91 epitope 49

<400> SEQUENCE: 67

Asn Gln Ala Ala Tyr Ser Gln Met Trp Gly Gln Asp Ala Glu Ala
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Id91 epitope 50

<400> SEQUENCE: 68

Met Trp Gly Gln Asp Ala Glu Ala Met Tyr Gly Tyr Ala Ala Thr
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Id91 epitope 51

<400> SEQUENCE: 69

Ala Met Tyr Gly Tyr Ala Ala Thr Ala Thr Ala Thr Glu Ala
1               5                   10                  15

```
<210> SEQ ID NO 70
<211> LENGTH: 15
<212> TYPE: PRT
<213> ORGANISM: Artificial Sequence
<220> FEATURE:
<223> OTHER INFORMATION: Id91 epitope 52

<400> SEQUENCE: 70

Thr Ala Ala Thr Ala Thr Glu Ala Leu Leu Pro Phe Glu Asp Ala
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Id91 epitope 53

<400> SEQUENCE: 71

Ala Leu Leu Pro Phe Glu Asp Ala Pro Leu Ile Thr Asn Pro Gly
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Id91 epitope 54

<400> SEQUENCE: 72

Ala Pro Leu Ile Thr Asn Pro Gly Gly Leu Leu Glu Gln Ala Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Id91 epitope 55

<400> SEQUENCE: 73

Gly Gly Leu Leu Glu Gln Ala Val Ala Val Glu Glu Ala Ile Asp
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Id91 epitope 56

<400> SEQUENCE: 74

Val Ala Val Glu Glu Ala Ile Asp Thr Ala Ala Ala Asn Gln Leu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Id91 epitope 57

<400> SEQUENCE: 75

Asp Thr Ala Ala Ala Asn Gln Leu Met Asn Asn Val Pro Gln Ala
1               5                   10                  15
```

<210> SEQ ID NO 76
<211> LENGTH: 15
<212> TYPE: PRT
<213> ORGANISM: Artificial Sequence
<220> FEATURE:
<223> OTHER INFORMATION: Id91 epitope 58

<400> SEQUENCE: 76

Leu Met Asn Asn Val Pro Gln Ala Leu Gln Gln Leu Ala Gln Pro
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Id91 epitope 59

<400> SEQUENCE: 77

Ala Leu Gln Gln Leu Ala Gln Pro Ala Gln Gly Val Val Pro Ser
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Id91 epitope 60

<400> SEQUENCE: 78

Pro Ala Gln Gly Val Val Pro Ser Ser Lys Leu Gly Gly Leu Trp
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Id91 epitope 61

<400> SEQUENCE: 79

Ser Ser Lys Leu Gly Gly Leu Trp Thr Ala Val Ser Pro His Leu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Id91 epitope 62

<400> SEQUENCE: 80

Trp Thr Ala Val Ser Pro His Leu Ser Pro Leu Ser Asn Val Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Id91 epitope 63

<400> SEQUENCE: 81

Leu Ser Pro Leu Ser Asn Val Ser Ser Ile Ala Asn Asn His Met
1               5                   10                  15

```
<210> SEQ ID NO 82
<211> LENGTH: 15
<212> TYPE: PRT
<213> ORGANISM: Artificial Sequence
<220> FEATURE:
<223> OTHER INFORMATION: Id91 epitope 64

<400> SEQUENCE: 82

Ser Ser Ile Ala Asn Asn His Met Ser Met Met Gly Thr Gly Val
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Id91 epitope 65

<400> SEQUENCE: 83

Met Ser Met Met Gly Thr Gly Val Ser Met Thr Asn Thr Leu His
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Id91 epitope 66

<400> SEQUENCE: 84

Val Ser Met Thr Asn Thr Leu His Ser Met Leu Lys Gly Leu Ala
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Id91 epitope 67

<400> SEQUENCE: 85

His Ser Met Leu Lys Gly Leu Ala Pro Ala Ala Ala Gln Ala Val Glu
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Id91 epitope 68

<400> SEQUENCE: 86

Pro Ala Ala Ala Gln Ala Val Glu Thr Ala Ala Glu Asn Gly Val
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Id91 epitope 69

<400> SEQUENCE: 87

Glu Thr Ala Ala Glu Asn Gly Val Trp Ala Met Ser Ser Leu Gly
1               5                   10                  15

<210> SEQ ID NO 88
```

```
<211> LENGTH: 15
<212> TYPE: PRT
<213> ORGANISM: Artificial Sequence
<220> FEATURE:
<223> OTHER INFORMATION: Id91 epitope 70

<400> SEQUENCE: 88

Val Trp Ala Met Ser Ser Leu Gly Ser Gln Leu Gly Ser Ser Leu
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Id91 epitope 71

<400> SEQUENCE: 89

Gly Ser Gln Leu Gly Ser Ser Leu Gly Ser Ser Gly Leu Gly Ala
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Id91 epitope 72

<400> SEQUENCE: 90

Leu Gly Ser Ser Gly Leu Gly Ala Gly Val Ala Ala Asn Leu Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Id91 epitope 73

<400> SEQUENCE: 91

Ala Gly Val Ala Ala Asn Leu Gly Arg Ala Ala Ser Val Gly Ser
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Id91 epitope 74

<400> SEQUENCE: 92

Gly Arg Ala Ala Ser Val Gly Ser Leu Ser Val Pro Pro Ala Trp
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Id91 epitope 75

<400> SEQUENCE: 93

Ser Leu Ser Val Pro Pro Ala Trp Ala Ala Asn Gln Ala Val
1               5                   10                  15

<210> SEQ ID NO 94
<211> LENGTH: 15
```

```
<212> TYPE: PRT
<213> ORGANISM: Artificial Sequence
<220> FEATURE:
<223> OTHER INFORMATION: Id91 epitope 76

<400> SEQUENCE: 94

Trp Ala Ala Ala Asn Gln Ala Val Thr Pro Ala Ala Arg Ala Leu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Id91 epitope 77

<400> SEQUENCE: 95

Val Thr Pro Ala Ala Arg Ala Leu Pro Leu Thr Ser Leu Thr Ser
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Id91 epitope 78

<400> SEQUENCE: 96

Leu Pro Leu Thr Ser Leu Thr Ser Ala Ala Gln Thr Ala Pro Gly
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Id91 epitope 79

<400> SEQUENCE: 97

Ser Ala Ala Gln Thr Ala Pro Gly His Met Leu Gly Gly Leu Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Id91 epitope 80

<400> SEQUENCE: 98

Gly His Met Leu Gly Gly Leu Pro Leu Gly His Ser Val Asn Ala
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Id91 epitope 81

<400> SEQUENCE: 99

Pro Leu Gly His Ser Val Asn Ala Gly Ser Gly Ile Asn Asn Ala
1               5                   10                  15

<210> SEQ ID NO 100
<211> LENGTH: 15
<212> TYPE: PRT
```

```
<213> ORGANISM: Artificial Sequence
<220> FEATURE:
<223> OTHER INFORMATION: Id91 epitope 82

<400> SEQUENCE: 100

Ala Gly Ser Gly Ile Asn Asn Ala Leu Arg Val Pro Ala Arg Ala
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Id91 epitope 83

<400> SEQUENCE: 101

Ala Leu Arg Val Pro Ala Arg Ala Tyr Ala Ile Pro Arg Thr Pro
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Id91 epitope 84

<400> SEQUENCE: 102

Ala Tyr Ala Ile Pro Arg Thr Pro Ala Ala Gly Phe Ser Arg Pro
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Id91 epitope 85

<400> SEQUENCE: 103

Pro Ala Ala Gly Phe Ser Arg Pro Gly Leu Pro Val Glu Tyr Leu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Id91 epitope 86

<400> SEQUENCE: 104

Pro Gly Leu Pro Val Glu Tyr Leu Gln Val Pro Ser Pro Ser Met
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Id91 epitope 87

<400> SEQUENCE: 105

Leu Gln Val Pro Ser Pro Ser Met Gly Arg Asp Ile Lys Val Gln
1               5                   10                  15

<210> SEQ ID NO 106
<211> LENGTH: 15
<212> TYPE: PRT
<213> ORGANISM: Artificial Sequence
```

```
<220> FEATURE:
<223> OTHER INFORMATION: Id91 epitope 88

<400> SEQUENCE: 106

Met Gly Arg Asp Ile Lys Val Gln Phe Gln Ser Gly Gly Asn Asn
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Id91 epitope 89

<400> SEQUENCE: 107

Gln Phe Gln Ser Gly Gly Asn Asn Ser Pro Ala Val Tyr Leu Leu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Id91 epitope 90

<400> SEQUENCE: 108

Asn Ser Pro Ala Val Tyr Leu Leu Asp Gly Leu Arg Ala Gln Asp
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Id91 epitope 91

<400> SEQUENCE: 109

Leu Asp Gly Leu Arg Ala Gln Asp Asp Tyr Asn Gly Trp Asp Ile
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Id91 epitope 92

<400> SEQUENCE: 110

Asp Asp Tyr Asn Gly Trp Asp Ile Asn Thr Pro Ala Phe Glu Trp
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Id91 epitope 93

<400> SEQUENCE: 111

Ile Asn Thr Pro Ala Phe Glu Trp Tyr Tyr Gln Ser Gly Leu Ser
1               5                   10                  15

<210> SEQ ID NO 112
<211> LENGTH: 15
<212> TYPE: PRT
<213> ORGANISM: Artificial Sequence
<220> FEATURE:
```

<223> OTHER INFORMATION: Id91 epitope 94

<400> SEQUENCE: 112

Trp Tyr Tyr Gln Ser Gly Leu Ser Ile Val Met Pro Val Gly Gly
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Id91 epitope 95

<400> SEQUENCE: 113

Ser Ile Val Met Pro Val Gly Gly Gln Ser Ser Phe Tyr Ser Asp
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Id91 epitope 96

<400> SEQUENCE: 114

Gly Gln Ser Ser Phe Tyr Ser Asp Trp Tyr Ser Pro Ala Cys Gly
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Id91 epitope 97

<400> SEQUENCE: 115

Asp Trp Tyr Ser Pro Ala Cys Gly Lys Ala Gly Cys Gln Thr Tyr
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Id91 epitope 98

<400> SEQUENCE: 116

Gly Lys Ala Gly Cys Gln Thr Tyr Lys Trp Glu Thr Phe Leu Thr
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Id91 epitope 99

<400> SEQUENCE: 117

Tyr Lys Trp Glu Thr Phe Leu Thr Ser Glu Leu Pro Gln Trp Leu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Id91 epitope 100

```
<400> SEQUENCE: 118

Thr Ser Glu Leu Pro Gln Trp Leu Ser Ala Asn Arg Ala Val Lys
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Id91 epitope 101

<400> SEQUENCE: 119

Leu Ser Ala Asn Arg Ala Val Lys Pro Thr Gly Ser Ala Ala Ile
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Id91 epitope 102

<400> SEQUENCE: 120

Lys Pro Thr Gly Ser Ala Ala Ile Gly Leu Ser Met Ala Gly Ser
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Id91 epitope 103

<400> SEQUENCE: 121

Ile Gly Leu Ser Met Ala Gly Ser Ser Ala Met Ile Leu Ala Ala
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Id91 epitope 104

<400> SEQUENCE: 122

Ser Ser Ala Met Ile Leu Ala Ala Tyr His Pro Gln Gln Phe Ile
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Id91 epitope 105

<400> SEQUENCE: 123

Ala Tyr His Pro Gln Gln Phe Ile Tyr Ala Gly Ser Leu Ser Ala
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Id91 epitope 106
```

```
<400> SEQUENCE: 124

Ile Tyr Ala Gly Ser Leu Ser Ala Leu Leu Asp Pro Ser Gln Gly
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Id91 epitope 107

<400> SEQUENCE: 125

Ala Leu Leu Asp Pro Ser Gln Gly Met Gly Pro Ser Leu Ile Gly
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Id91 epitope 108

<400> SEQUENCE: 126

Gly Met Gly Pro Ser Leu Ile Gly Leu Ala Met Gly Asp Ala Gly
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Id91 epitope 109

<400> SEQUENCE: 127

Gly Leu Ala Met Gly Asp Ala Gly Gly Tyr Lys Ala Ala Asp Met
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Id91 epitope 110

<400> SEQUENCE: 128

Gly Gly Tyr Lys Ala Ala Asp Met Trp Gly Pro Ser Ser Asp Pro
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Id91 epitope 111

<400> SEQUENCE: 129

Met Trp Gly Pro Ser Ser Asp Pro Ala Trp Glu Arg Asn Asp Pro
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Id91 epitope 112

<400> SEQUENCE: 130
```

Pro Ala Trp Glu Arg Asn Asp Pro Thr Gln Gln Ile Pro Lys Leu
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Id91 epitope 113

<400> SEQUENCE: 131

Pro Thr Gln Gln Ile Pro Lys Leu Val Ala Asn Asn Thr Arg Leu
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Id91 epitope 114

<400> SEQUENCE: 132

Leu Val Ala Asn Asn Thr Arg Leu Trp Val Tyr Cys Gly Asn Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Id91 epitope 115

<400> SEQUENCE: 133

Leu Trp Val Tyr Cys Gly Asn Gly Thr Pro Asn Glu Leu Gly Gly
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Id91 epitope 116

<400> SEQUENCE: 134

Gly Thr Pro Asn Glu Leu Gly Gly Ala Asn Ile Pro Ala Glu Phe
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Id91 epitope 117

<400> SEQUENCE: 135

Gly Ala Asn Ile Pro Ala Glu Phe Leu Glu Asn Phe Val Arg Ser
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Id91 epitope 118

<400> SEQUENCE: 136

```
Phe Leu Glu Asn Phe Val Arg Ser Ser Asn Leu Lys Phe Gln Asp
1               5                   10                  15
```

<210> SEQ ID NO 137
<211> LENGTH: 15
<212> TYPE: PRT
<213> ORGANISM: Artificial Sequence
<220> FEATURE:
<223> OTHER INFORMATION: Id91 epitope 119

<400> SEQUENCE: 137

```
Ser Ser Asn Leu Lys Phe Gln Asp Ala Tyr Asn Ala Ala Gly Gly
1               5                   10                  15
```

<210> SEQ ID NO 138
<211> LENGTH: 15
<212> TYPE: PRT
<213> ORGANISM: Artificial Sequence
<220> FEATURE:
<223> OTHER INFORMATION: Id91 epitope 120

<400> SEQUENCE: 138

```
Asp Ala Tyr Asn Ala Ala Gly Gly His Asn Ala Val Phe Asn Phe
1               5                   10                  15
```

<210> SEQ ID NO 139
<211> LENGTH: 15
<212> TYPE: PRT
<213> ORGANISM: Artificial Sequence
<220> FEATURE:
<223> OTHER INFORMATION: Id91 epitope 121

<400> SEQUENCE: 139

```
Gly His Asn Ala Val Phe Asn Phe Pro Pro Asn Gly Thr His Ser
1               5                   10                  15
```

<210> SEQ ID NO 140
<211> LENGTH: 15
<212> TYPE: PRT
<213> ORGANISM: Artificial Sequence
<220> FEATURE:
<223> OTHER INFORMATION: Id91 epitope 122

<400> SEQUENCE: 140

```
Phe Pro Pro Asn Gly Thr His Ser Trp Glu Tyr Trp Gly Ala Gln
1               5                   10                  15
```

<210> SEQ ID NO 141
<211> LENGTH: 15
<212> TYPE: PRT
<213> ORGANISM: Artificial Sequence
<220> FEATURE:
<223> OTHER INFORMATION: Id91 epitope 123

<400> SEQUENCE: 141

```
Ser Trp Glu Tyr Trp Gly Ala Gln Leu Asn Ala Met Lys Gly Asp
1               5                   10                  15
```

<210> SEQ ID NO 142
<211> LENGTH: 15
<212> TYPE: PRT
<213> ORGANISM: Artificial Sequence
<220> FEATURE:
<223> OTHER INFORMATION: Id91 epitope 124

<400> SEQUENCE: 142

Gln Leu Asn Ala Met Lys Gly Asp Leu Gln Ser Ser Leu Gly Ala

```
                1               5              10              15

<210> SEQ ID NO 143
<211> LENGTH: 15
<212> TYPE: PRT
<213> ORGANISM: Artificial Sequence
<220> FEATURE:
<223> OTHER INFORMATION: Id91 epitope 125

<400> SEQUENCE: 143

Ala Met Lys Gly Asp Leu Gln Ser Ser Leu Gly Ala Gly Lys Leu
1               5                   10                  15
```